(12) United States Patent
Elgebaly

(10) Patent No.: US 11,654,134 B2
(45) Date of Patent: May 23, 2023

(54) CYCLOCREATINE PHOSPHATE: A NOVEL BIOENERGETIC THERAPY TO PREVENT AND TREAT ISCHEMIA-INDUCED AND AGING-RELATED CARDIOVASCULAR AND NEURODEGENERATIVE DISEASES

(71) Applicant: Nour Heart, Inc., Vienna, VA (US)

(72) Inventor: Salwa A. Elgebaly, Vienna, VA (US)

(73) Assignee: NOUR HEART, INC., Vienna, VA (US)

( * ) Notice: Subject to any disclaimer, the term of this patent is extended or adjusted under 35 U.S.C. 154(b) by 144 days.

(21) Appl. No.: 16/948,235

(22) Filed: Sep. 9, 2020

(65) Prior Publication Data

US 2020/0397757 A1    Dec. 24, 2020

Related U.S. Application Data

(63) Continuation-in-part of application No. 16/719,723, filed on Dec. 18, 2019, now Pat. No. 10,859,573, which is a continuation-in-part of application No. 16/252,402, filed on Jan. 18, 2019, now Pat. No. 10,895,572, application No. 16/948,235 is a continuation-in-part of application No. 16/719,723, filed on Dec. 18, 2019, now Pat. No. 10,859,573.

(60) Provisional application No. 62/686,184, filed on Jun. 18, 2018, provisional application No. 63/002,179, filed on Mar. 30, 2020.

(51) Int. Cl.
| | |
|---|---|
| C07H 21/02 | (2006.01) |
| C07H 21/04 | (2006.01) |
| A61K 31/4168 | (2006.01) |
| G01N 33/68 | (2006.01) |
| A61K 31/137 | (2006.01) |
| A61K 9/00 | (2006.01) |

(52) U.S. Cl.
CPC ........ *A61K 31/4168* (2013.01); *A61K 31/137* (2013.01); *G01N 33/6893* (2013.01); *A61K 9/0019* (2013.01)

(58) Field of Classification Search
CPC .................................................. A61K 31/137
See application file for complete search history.

(56) References Cited

U.S. PATENT DOCUMENTS

| | | |
|---|---|---|
| 5,091,404 A | 2/1992 | Elgebaly |
| 7,659,091 B2 | 2/2010 | Elgebaly |
| 8,288,350 B2 | 10/2012 | Elgebaly et al. |
| 2006/0063199 A1 | 3/2006 | Elgebaly et al. |
| 2015/0119437 A1 | 4/2015 | Clark et al. |
| 2019/0383809 A1 | 12/2019 | Elgebaly et al. |
| 2020/0109454 A1 | 4/2020 | Elgebaly |
| 2020/0400684 A1 | 12/2020 | Elgebaly |

FOREIGN PATENT DOCUMENTS

| | | |
|---|---|---|
| WO | WO94026261 A1 | 11/1994 |
| WO | WO2007038341 A2 | 4/2007 |

OTHER PUBLICATIONS

Matthews et al. (Experimental Neurology, 157, 142-149, 1999).*
Ono et al. (International Journal of Cardiology, 209, 216, 196-205).*
Stergiopoulos et al. (JAMA Internal Medicine, 2014, 174, 2, 232-240).*
(Turner, Om et al.) Enhanced Ability of Skeletal Muscle Containing Cyclocreatine Phosphate 1-13 to Sustain ATP Levels during Ischemia following beta-Adrenergic Stimulation. Journal of Biological Chemistry. May 15, 1987, vol. 262, No. 14; pp. 6605-6609.
(Jacobstein, Md et al.) Myocardial Protection During Ischemia by Prior Feeding With the Creatine Analog: Cyclocreatine. Journal of the American College of Cardiology. Jul. 1989, vol. 14, No. 1; pp. 246-251; DOI 10.1016/0735-1097(89)90081-8.
(Kumarswamy, R et al.) Circulating Long Noncoding RNA, LIPCAR, Predicts Survival in 1-19 Patients With Heart Failure. Circulation Research, 2014, vol. 114, Issue 10, pp. 1569-1575;pp. 1570-1572; figure 1; DOI: 10.1161/CIRCRESAHA.114.303915.
(Wang, C et al.) Non-coding RN as as biomarkers for acute myocardial infarction. Acta 1-19 Pharmacologica Sinica, 2018, vol. 39, Issue 7, pp. 1110-1119; abstract; DOI: 10.1038/aps.2017.205.
Zhenbing Liu et al. LncRNA GAS5 exacerbatesmyocardial ischemia-reperfusion injury through regulating serpina3 by targeting miR-137. May 1, 2020.
M Zhang et al. miR-137 alleviates focal cerebral ischemic injury in rats by regulating JAK1/STAT1 signaling pathway miR-137 alleviates focal cerebral ischemic injury. Jan. 21, 2020.
Yuuichi Arakawa et al. Transgenic mice overexpressing miR-137 in the brain show schizophrenia-associated behavioral deficits and transcriptome profiles. Jul. 30, 2019.

(Continued)

*Primary Examiner* — Amy H Bowman

(57) ABSTRACT

The present invention provides methods and composition of a novel mechanism using the bioenergetic Cyclocreatine Phosphate as a potent cardioprotective drug by preserving cellular energy source, preventing ischemic injury, rejuvenating organ function, thus, maintaining normal physical activity. Cyclocreatine Phosphate can be used as a new therapeutic approach to prevent disease development and progression, and to treat ischemia-induced diseases in ischemic heart disease patients, including: coronary artery disease, unstable angina, acute myocardial infarction, heart failure, atrial fibrillation, and Takotsubo cardiomyopathy, as well as provides cardioprotection during cardiac procedures and surgeries. The invention further provides methods and composition to prevent and treat aging-related neurodegenerative diseases where hypoxia/ischemia play a key role in the development and progression of the disease. More specifically, the present invention provides Cyclocreatine Phosphate as a new therapeutic approach to prevent disease development and progression, as well as to treat patients with brain ischemia (stroke) and Alzheimer's disease.

8 Claims, 100 Drawing Sheets

Specification includes a Sequence Listing.

(56) References Cited

OTHER PUBLICATIONS

Haiyan Li et al. MicroRNA-137 regulates hypoxia-induced retinal ganglion cell apoptosis through Notch1. Dec. 12, 2017.
Fenghui Chen et al. LncRNA GAS5 regulates ischemic stroke as a competing endogenous RNA for miR-137 to regulate the Notch1 signaling pathway. Jan. 29, 2018.
Naveet Pannu et al. Resveratrol: from enhanced biosynthesis and bioavailability to multitargeting chronic diseases. Jan. 2019.
Marit Wiersma et al. Mitochondrial Dysfunction Underlies Cardiomyocyte Remodeling in Experimental and Clinical atrial Fibrillation. Oct. 5, 2019.
Sufang Li et al. Circulating microRNAs as potential biomarkers for coronary plaque rupture. May 30, 2017.
Jun Liu et al. Circulating microRNAs as potential biomarkers for unstable angina. Aug. 1, 2017.
Alessandro Valli et al. Hypoxia metabolism in ageing. Jul. 2015.
O. O. Ogunshola et al. Contribution of hypoxia to Alzheimer's disease: is HIF-1a a mediator of neurodegeneration? Sep. 11, 2019.
Muhammad Shahzeb Khan et al. Targeting Mitochondrial Function in Heart Failure. Apr. 2019.
Christophe Bauters et al. Circulating miR-133a and miR-423-5p fail as biomarkers for left ventricular remodeling after myocardial infarction. Jan. 24, 2013.
E Mahmoudi et al. MiR-137: an important player in neural development and neoplastic transformation. Sep. 13, 2016.
E. Nabialek et al. Circulating microRNAs (miR-423-5p, miR-208a and miR-1) in acute myocardial infarction and stable coronary heart disease. Dec. 2013.
Shan-shan Zhou et al. miRNAS in cardiovascular diseases: potential biomarkers, therapeutic targets and challenges. Jun. 7, 2018.
Christian Mueller et al. Heart Failure Association of the European Society of Cardiology practical guidance on the use of natriuretic peptide concentralions. Jun. 20, 2019.
Jana S. Burchfield et al. Pathological Ventricular Remodeling. Jul. 23, 2013.
Giuseppe Lippi et al. Risk assessment of post-infarction heart failure. Systematic review on the role of emerging biomarkers. Jan. 9, 2014.
Sheryl L. Chow et al. Role of Biomarkers for the Prevention, Assessment, and Management of Heart Failure: A Scientific Statement From the American Heart Association. May 30, 2017.
Saumya Das et al. Noncoding RNAs in Cardiovascular Disease: Current Knowledge, Tools and Technologies for nvestigation, and Future Directions. Jun. 29, 2020.
Yao-Meng Huang et al. The diagnostic value of circulating microRNAs in heart failure. Jan. 15. 2019.
D.J. Maron et al. Initial Invasive or Conservative Strategy for Stable Coronary Disease. Mar. 30, 2020.
Salwa A. Elgebaly et al. Cyclosporin H: a Novel Anti-Inflammatory Therapy for Influenza Flu Patients. Apr. 2017.
S Nilsson et al. Chest pain and ischaemic heart disease in primary care. May 2003.
J. Hector Pope et al. Missed Diagnoses of Acute Cardiac Ischemia in the Emergency Department. Apr. 20, 2000.
Salwa A. Elgebaly et al. Cyclocreatine protects against ischemic injury and enhances cardiac recovery during eariy reperfusion. Sep. 17, 2019.
Zhihua Liu et al. MiR-106b and MiR-15b Modulate Apoptosis and Angiogenesis in Myocardial Infarction. May 11, 2012.
Anke J. Tijsen et al. Circulating microRNAs as diagnostic biomarkers for cardiovascular diseases. Aug. 31, 2012.
Solenne Paiva et al. MiRroring the Multiple Potentials of MicroRNAs in Acute Myocardial infarction. Nov. 20, 2017.
Chen Wang et al. Non-coding RNAs as biomarkers for acute myocardial infarction. Apr. 26, 2018.
Joost Petrus Gerardus Sluijter et al. Extracellular vesicles in diagnostics and therapy of the ischaemic heart: Position Paper from the Working Group on Cellular Biology of the Heart of the European Society of Cardiology. Nov. 2, 2017.
Zhang Jing et al. Role of miR-106b-5p in the regulation of gene profiles in endothelial cells. Feb. 2019.
J. Bogaert et al., Ischemic Heart Disease. Clinical Cardiac MRI, Medical Radiology. Diagnostic Imaging (2012) DOI: 10.1007/174_2011_336.

\* cited by examiner ferritin heavy polypeptide-like 17 [HOMO Sapiens]
SequenceID: NP_114100.1 Length: 183 Number of Matches:1

▽ Next Match △ Previous Match

Range 1: 19 to 24 Genpept Graphics

| Score | Expect | Identities | Positives | Gaps |
|---|---|---|---|---|
| 21.4 bits(43) | 62 | 6/6(100%) | 6/6(100%) | 0/6(0%) |

```
Query  9  AAINSH  14
          AAINSH
Sbjct  19 AAINSH  24
```

| | Ensembl Gene Id | miRNA name | miTG score | Also Predicted |
|---|---|---|---|---|
| 1 | ENSG00000132445 (FTHL17) | hsa-miR-548ar-3p | 0.977695557050703 | |
| 2 | ENSG00000132445 (FTHL17) | hsa-miR-589-5p | 0.977113273205747 | |
| 3 | ENSG00000132445 (FTHL17) | hsa-miR-548e-3p | 0.958778553040087 | |
| 4 | ENSG00000132445 (FTHL17) | hsa-miR-4766-5p | 0.953774408116615 | |
| 5 | ENSG00000132445 (FTHL17) | hsa-miR-137 | 0.916733991921927 | |
| 6 | ENSG00000132445 (FTHL17) | hsa-miR-548a-3p | 0.858381214044193 | |
| 7 | ENSG00000132445 (FTHL17) | hsa-miR-548az-3p | 0.845149519537714 | |
| 8 | ENSG00000132445 (FTHL17) | hsa-miR-548f-3p | 0.837928897852551 | |
| 9 | ENSG00000132445 (FTHL17) | hsa-miR-4639-5p | 0.816317602779086 | |

FIG. 6

| name | mirAccession | geneName | targetSites | bioComplex | clipReadNum | CancerNum |
|---|---|---|---|---|---|---|
| hsa-miR-137 | MIMAT0000429 | RP11-206L10.11 | 1 | 1 | 6 | NoData |
| hsa-miR-137 | MIMAT0000429 | RP11-3782.1 | 1 | 1 | 99 | NoData |
| hsa-miR-137 | MIMAT0000429 | RP11-14886.1 | 1 | 1 | 9 | NoData |
| hsa-miR-137 | MIMAT0000429 | OIP5-AS1 | 3 | 13 | 836 | NoData |
| hsa-miR-137 | MIMAT0000429 | AF127936.7 | 1 | 1 | 12 | NoData |
| hsa-miR-137 | MIMAT0000429 | CTB-89H12.4 | 1 | 2 | 1378 | NoData |

FIG. 7

```
caaatgccat tgaaaccgct agtcttattt cctttctact tttctttggc actcttactg      60
cctgtaagga gtagaactgt tagggcacac tgttgctata cagtttaact cccattttca     120
tgttttgtct ttcttttccc atttctgggg cttacctcct gatacctgct tactttctgg     180
aagtagtggg caagtaagat ttggctcttg gttctaatt tttaaatttc tgaatactgc      240
cctagtctga actggcctt tatagattaa tctttgcttc acattttag tgttgtattt       300 aaactatttt ataatttaaa aatagattct aatctgaaga tacttttcaa gaaatattat    360
taactgatgt catcctcatc ccagcagctc atctgttagg aatgaagttg agatgcttct    420
attccatgtt tttgtatttg ggaaggattc aaagttgaag gtttattgtc gttgggtttt    480
tcagatggtg acatgtaaac tcaggatagc aaaccctaat gttcacacag tgctctgcct    540
ctgcatctca gttgggatag ttgctccttt tgagtgtttt aatcatcgta taactaatca    600
tagtgccaag aagttcataa tgtgttatgt agctaatgtc actgaaaaac agtcctacca    660
ttttaggtaa gaccaaacag agtctctaac ccaggactt gttacacctg acaacctata    720
gtatatttgc ttttctcac aaaatgaaac caatttgcc gaaagctagc tgggataata    780
ggatcatcac aagttgcagt ttctataact aaaattagat tgaaatctct tctgacctag    840
aacattttac ttcaggcatt cagcagattt cagaaagaat tacctta ttt taagttagtt    900 tctttgttag tttactgtgt gtctcttatt caataaacaa gcagaatttg tgtcctgccc    960
```

FIG. 15A

```
tatccatgtc ttaaagatga gaagttggat ccactgagtt agtttcattg gggcggggga    1020
aagaactgta attaaacttg tttaatcctt attttgtatt gtagctattt tttgtaaaag    1080
caacttaaaa tcttttaaaa attttatagt gacattagag acaatggtca tacaaattat    1140
cacataaaca tggacttgaa aaattaggct tttcataaaa cacatcacat gtcattgact    1200 gcttttaga aatacacttc caaggcagta catctgtatt gctactgaaa agtgccattt     1260
cacagaacac agacttcttt ttgctctttg acatcttgaa aacatctgtt tttcttttt     1320 aatacaaaac tttgtgctca agacaaatct tacatgaaac tctcataaac catgaaaatg    1380
tagctggcct tcgggcctta ggcatgaaat aagcatgagg aacatattcc cctaacttct    1440 accccagcc cagcaagtta tcctttaaga aatctcctag gaattctgga gtttgaaaac     1500
aattgctcta tgttattcct gcttccagtc tctaagtaac aagggcattt aaaagcatag    1560
tctcttaagg tccactatag tggttcttta tttaaggaat aactcagctg ggtgcagtgg    1620
ctcacgcctg ttatcccagc actttgagag gctgaggcaa gcagatcact tgaggccagg    1680
agttcgagag tctggccaac atggtggaaa cccatctcta caaaaaatac aaaaattagc    1740
caggtgtggt ggcgtgcacc tatggtccca gctatttggg aggctgaggc aggagaattg    1800
cttgaacctg ggaggtggag gttgcagtga gccaagattg tgccgctgca ctccagcctg    1860
ggtgacagag tgagactctg tctcaaaaaa aaaaaaaaaa ggaactcata cagctcaatg    1920
```

FIG. 15B

```
attcattgat cccaataata aatcgtttta ataatgatga aaacatccta ctggggtttt      1980
cttgttaaaa actttaggac aggcgcagtg gctcatgcct gttattccaa cacatttggg      2040
aggctgaggt gggagaattg cttgaccota ggagttctag acttgcctgg gccacatagt      2100 aagacootgt cccagctccc tccaacatcg tccccaaccc ccccccccc aaaaaaaaa        2160 agcgccaggc gcagtagtga gtgcctgtga tcccagctgt gttgggaggc tgaggtggga      2220
gtatcacctg agcctggag gttgaggctg caatgagagc tgtgatcatg ccactgcact       2280
ccagcctggg caacagatga gacctgtgt cacaacaagg aattttaga aggtgctttt        2340 tatattactc ttcacagagt taaattttca gaggatttag tattattgaa ctaagtttca      2400
taagtgtatt ttaagcaagt aaatctctaa tgtaggaaaa tccccaaaat ggtagcattt      2460
actaatgttt tatatggtaa tttttgaaaa atatatctga tatttcttca gtaaaaatgg      2520
tgttgtttta ataacttaat aagaatgttt aaagattctt taagtctggc ttatctagct      2580
aatgtgggcc tattaaataa taggcagact tctgccttcc ttatattctt tagatctttt      2640
caaatactcc attccaatat ccatcaaaag acttctcttt atgccactta ttatctatac      2700
tagtttttaa tgttcaatta ctacaagatt ataattactg tttttattca tgttcccaag      2760
aaaaatacat aagattcaca cccaacacac ttcgaaattt atttcactcc ctttgactat      2820
atgtgattat caaaaagta tttttcaaga tattaaaaat aagtaaagga aaatgaaata       2880
```

FIG. 15C

```
tttttaggac attcaaaatc taatgaagtt cagtgtttct ttaattgagg gcaggcagag      2940 gtggggaga atttcagaag gtagtgaacc caaaggtgga ttcttggata attctactat       3000
tctgtactct catcatctta acccatctgt ttactaccct aaccatagtt actaagcaga      3060
gttttatcat aataatatag acagctctca aagtattgac attcagaggg gattacaaat     3120 attattttc tatcatattg acctaccatg tccacagtct tccttgaatt accttccagt      3180
tttactgggc tgcatctacc gtttatgtct agtttgactt tttctgagtt caccaattgc    3240
tgctaggaat gtgctggtca ctcagcagca cacccacatc acaggggaag attttgaaat    3300
acctggacag tctgaacaca ctgctctgaa tacactcaat tctaagaagt accagggaac    3360
cgcatcttct tgctgaaatc ttgaatttt gtcagctttt tttttactg tggacagtaa      3420 agctggaaag atctaaataa cccaacagga aatgcggatg aaagtgcaag agttggtttg    3480
tggtcatctg gagtccatgt ctccaagact gctggacctt caaattctgc aacttgttag   3540
atcatctgga tgatagcaca actgttagaa gacctagaag aatacagcgt tgctatgact    3600
cagtggtgtt gaatgcagac catctaccag ctggggaaag aatcaattat aaacaggaat    3660
aaagggattc attcctcatt ttaactgatg ttacagtgaa gatgggttct tgaactcttg    3720
gaagcctgga tgagccacct aatctgcaag ataaaaacca agaccaatg cgtattgggg    3780 aaaagaatgc ttagtactgc aagactgttg aatacctgtt gaatattcct attgaggttt    3840
```

FIG. 15D

```
tttcctaaac atacttcagt aacatcttag gacaattcac tggagaaatg ttgatccctg    3900
gctggaatgt cataccattg acccatttga agagttaaag ctggatttga ctgctctatt    3960
ctaccaggaa tattgttagg gtagcctttt accagtttct aaacaattgt aatcatttat    4020
tgactcagca attcctcaga taacaggtca aaagatgtac agatacattc tgaagttttc    4080
ttgctattaa aggcacaaga gtttccttgt attttgactg acaatgtagc atgtttccat    4140
tttagtttgt tagtgatggt ggttttccct ttgaaagcca tttggtatat tcaccataac    4200
aattagttta atatgattac ataagaaaac tatgataaaa cccagcaatt ttagtagttg    4260
tgaaaatacg ttttttaaat catgtttaag aagaattgca agacttgaaa ccaaatcctg    4320 atggggaat tctgtttaat cctgtttaat ctgtttaatt tctgtttaat ccttagtttc    4380
ttaacctgca tagcttatcc tgtattgtac ttttttcctt tttaaactc ccaaacaaga    4440 agcttgaaac ttttcctgta ttttaaaatt gaaatttggt cacagggtat agtcagattt    4500
ttattaaggt ttggtttgac aacctttaaa agaaaggttt acctcgctaa tacttcttaa    4560
taacatgcat caaatgatat tccctatggt gaagtatatt ctcaaagtta tgttatcttt    4620
catttttggc atttggtgct tatggactta gtacccaggc aacaaagatc tattatgcac    4680
ctactctctt gtatgttcgc tattatttcc caaaaaaaaa aagggcata tatgcataag    4740 aaataaatat tagaattatt ttgtttctcc cacaaagccc atggagatg gcccaacaaa    4800
```

FIG. 15E

```
tgttaaaaa gtaaagaag ctgggcacgg tggctccac ctgtaacccc cacactttgg      4860
gaggccatgg cgggtggatc acgaggtcag gagtttgaga ccagcctggc caacacagtg      4920
aaactgtgtc tctactataa atacaaaaat tagccaggca tggtggcagg cacctatagt      4980
cccagctact caggaggctg aggcaggaga atcgcttgaa cccaggaggc agaggttgcg      5040
gtgagccaag atcatgccac tgcctccag cctgggtgac agagcgagac tgtctccaaa      5100 aaaaagaaa aagaactaa agaaaagga gcagtttatg attgaagaaa acatgacctg      5160
ggctgaagaa gtgaggattg attggagtgg gctagaatga gctatagttt ctagctcatt      5220
tgtaaggagg tagacaaagg agcattggtg cctcagagtg ggtgtctggt gagaggaaaa      5280
acggtgctta agagattttc aggctattgc tgtgggacag gcatattttc tccctttgcc      5340
tttagctgta gataaagtgt ggttatgacc tgaggcttct tgtattcaaa cttggcctag      5400
ggcctatgta gaggccctag ggtctacttg tggtggagga gggaagtatt tgtagaatgt      5460
gtaggcttga gaagtaaata aagccaaaaa agcatcactt gcttacattt ttaaatgagt      5520
cacaaaacaa tctttctaat gcggccggta aagaagtttt aaaggtctaa ggtttctcta      5580
cagaaattac atgcttctca ggtctttgtt tagtaaaata atacagataa ttatgctttg      5640
aatgcattta ttattaaagc taaccgtttt aatttgtgtc agaaataatt tgtgcctatg      5700
gtaggattaa aattgtattc tttagttaaa gcaaagcaat ctgttttca ttgatttgat      5760
```

FIG. 15F

```
aaatatgtga atgcctaata tgttctgcat atgtaaaaat gcagaaacat gctcatttga    5820
attactaata attattttag tatgctgaga ggctttgaat tcactgtacc actccttcct    5880
agagtcattc aaaacagaaa aaattagttt taagtataga ttcatgtttt tctgttttaa    5940
aaagttgagc taatactttt cacaagagac gaaataacat gagccactat aattattggc    6000
tcagttccac ccaatttcca tattttgggt gtaatttaaa attttgact tggaatttta     6060 actttttttt tgttttgatt ttttaccagg tttctaagca tgaattgagg aacagaagaa    6120
gcagagcaga tgatcggagc agcatttgtt tctccccaaa tctagaaatt ttagttcata    6180
tgtacactag ccagtggttg tggacaacca tttacttggt gtaaagaact taatttcagt    6240
ataaactgac tctgggcagc attggtgatg ctgtatcctg agttgtagcc tctgtaattg    6300
tgaatattaa ctgagatagt gaaacatggt gtccggtttt ctattgcatt ttttcaagtg    6360
gaaaagttaa ctaaatggtt gacacacaaa aattggtgga gaaattgtgc atatgccaat    6420 ttttttgttaa aaccttttgt tttgaactat actgctttga gatctcattt cagaagaacg    6480
gcatgaacag tcttcagcca cagttgtgat ggttgttaaa tgctcacaat tgtgcattct    6540
tagggttttt ccatccctgg ggtttgcaag ttgttcactt aaaacattct taaaatggtt    6600
ggcttcttgt ctgcaagcca gctgatatgg tagcaaccaa agattccagt gtttgagcat    6660
atgaaagact ctgcctgctt aattgtgcta gaaataacag catctaaagt gaagacttaa    6720
```

FIG. 15G

```
gaaaaactta gtgactacta gattatcctt aggactctgc attaactcta taatgttctt    6780
ggtattaaaa aaaagcata tttgtcacag aaatttagtt aacatcttac aactgaacat    6840
gtatgtatgt tgcttagata aatgtaatca ctgtaaacat ctatatgatc tgggattttg    6900
tttttatttt gaaatgggag ctttttgtt tacaagttca ttaaaaacta aaaactgttt    6960
ctgtaaggaa atgagatttt ttttaaacaa caaaaatgc cttgctgact cactattaaa    7020 taaaatctc cccaattttt tgatagacta cttcaagcca tttgttacat ggtattcctt    7080
tgcaagtcaa tttaggtttc gtgttataac ttttcctctt tttttaagaa aaatgaaaaa    7140
agtaattctt ttgtctgaag gggaaaggca ttctttcatt tttttctttt tttttttttt    7200
tttttatgac ttgcaggcac aatatctagt actgcaactg ccagaacttg gtattgtagc    7260
tgctgcccgc tgactagcag ctggactgat tttgaataaa aatgaaagca ttaaagggtt    7320
tccctacaaa acatttttct ttaaaatact tttgaaatgg ctataagcag ttgactttca    7380
cccttggaga gcatcacact gtgtgaggtt cagtgattgt tgaccctccc cagcccctcc    7440
tgcttcttta agttatctgt gtgcgtgcgc ttcctctcaa tcttctttgc acgctcattt    7500
ctttttctct gacccatgag aaaggaaaac ttactgatga taattttaa atagtgtaat    7560 ttattcattt atagcatgtc aggataaatt aaaagaacat ttgtctggaa atgctgccgg    7620
gagcctattg tgtaaatgta ggtattttgt aaaataacct tgaaattgta aattgacacg    7680
```

FIG. 15H

```
tgtttggtca gattgtgtca agtttaattt gttttgtttt cttttttctt tttttattt      7740 gaaaactact ttagcaataa ttaattccat gattatcaca ttctgccatt aagggatatt     7800
agtaccgtaa tactgaagaa attttattaa gtctgaactt ctggggtagg cagcttcttt     7860
gtttcttttc tatccaccct tgtcggttga ggtatttgtt tcttgactaa taaaccctt      7920 gatacttttg ccagaaatc agtctcataa agctatttt gagtatagtt tgtgtaaaat      7980
aaaaatgttt agctttggta ataacttcca agctgaactc cctctagcaa gatattttc     8040 agtgctttta ttactatgc acttagacta tgcactttt ctgaaatatt tttgtaacac      8100
ttttttgtat ttttgccatt tgaaaaggtt gtggtgtagt tggtctgtaa ttaagttgca    8160
gatttaaaac tgctgttagc tttgtaaatc aaaatatagg tgttttttgt cctggtatat    8220
cgtcattcca tctgcagctg gagctggaat cccattgatc ttctagctac cattcatttt    8280
cttcactgtt cacaaaagaa gagtgtgaaa ttcagtgaat gctgttacta atcctgttac    8340
gagatgaatc tcatttcacc aaaattaaat tatgttttc cgctaaaatg atgatacaag     8400
ttgaagacac atcactctga aattggaaga cctcaccact taaggctcca cagtggctta    8460
ctcagctgaa ctctaggtta ctactcttta ctttgttcac ccattggggg gtgcagtttt    8520
tttaaaatgt tgggagatgg ccattctaac tactgttgaa tgtctctgtt tgggaaggt    8580 ataacaagaa ataaaaaga atatatatga agggagagac tggttatctc ctccca         8636
```

FIG. 15I

| Groups | No | miR-106b expression [log$^{10}$] | | miR-137 expression [log$^{10}$] | |
|---|---|---|---|---|---|
| | | Median (range) | Statistics | Median (range) | Statistics |
| A) Healthy vs CAD | | | | | |
| Healthy Control | 16 | 1.1 (0.2 – 3.6) | $\chi^2$: 37.0 | 1.1 (0.1 – 3.7) | $\chi^2$: 37.0 |
| CAD group | 63 | 283 (16.7 – 2504) | P=0.001 | 1911 (230 – 9878) | P=0.001 |
| B) Angina vs AMI | | | | | |
| Angina | 47 | 203.7 (168 – 613) | $\chi^2$: 30.0 | 1296 (230.7 – 6841) | $\chi^2$: 13.0 |
| AMI | 16 | 952.8 (30.6-2504) | P=0.001 | 3163 (936 – 9878) | P=0.001 |
| C) Angina Time | | | | | |
| *Early Angina* | 29 | 164 (17 – 304) | $\chi^2$: 14.0 | 861 (230 – 6841) | $\chi^2$: 8.2 |
| *Late Angina* | 18 | 313 (81 – 613) | P=0.001 | 2033 (613 – 5113) | P=0.004 |
| D) Suspected Angina | | | | | |
| Negative (Stress ECHO/Treadmill) | 7 | 3.3 (1.8 – 8.6) | $\chi^2$: 9.8 | 4.4 (1.3 – 8.6) | $\chi^2$: 10 |
| Positive (Stress ECHO/Treadmill) | 7 | 452 (336 – 832) | P=0.002 | 1458 (803 – 3848) | P=0.002 |

CAD: Coronary artery disease "cases of angina and AMI"; Early angina: time of sample collection is a 1 – 10 hours after onset of chest pain; Late angina: time of sample collection is 24 – 72 hours after onset of chest pain. $\chi^2$: Chi-square value of non-parametric Kruskal Wallis test, p value <0.01 considered a high statistical significance, p value ≤0.05 considered a significant difference between both groups.

FIG. 16

| Groups | Cut-off | AUC | Asymptotic 95% Confidence Interval (lower-upper) bound | Biomarker sensitivities (%) | Biomarker specificity (%) |
|---|---|---|---|---|---|
| miR-106b[log¹⁰] CAD vs Healthy control | 3.5 | 1.0 | 1.0 – 1.0 | 100 | 94 |
| miR-137[log¹⁰] CAD vs Healthy control | 3.5 | 1.0 | 1.0 – 1.0 | 100 | 95 |
| miR-106b[log¹⁰] Angina vs AMI | 372 | 0.9 | 0.9 – 1.0 | 87 | 79 |
| miR-137[log¹⁰] Angina vs AMI | 2488 | 0.8 | 0.7 – 0.9 | 75 | 72 |
| miR-106b[log¹⁰] Early vs late Angina | 283 | 0.85 | 0.72 – 0.97 | 72 | 96 |
| miR-137[log¹⁰] Early vs late Angina | 1240 | 0.75 | 0.62 – 0.88 | 78 | 70 |
| miR-106b[log¹⁰] Negative / Positive stress test | 172 | 1.0 | 1.0 – 1.0 | 100 | 85 |
| miR-137[log¹⁰] Negative / Positive stress test | 8.0 | 0.98 | 1.0 – 1.0 | 100 | 85 |

AUC: area under the curve, ROC: receiving operating characteristics.

FIG. 18

| Groups | No | FTHL-17 expression [log¹⁰] | | ANAPC11 expression [log¹⁰] | |
|---|---|---|---|---|---|
| | | Median (range) | Statistics | Median (range) | Statistics |
| A) Healthy vs CAD | | | | | |
| Healthy Control | 16 | 0.58 (0.12 – 5.7) | $\chi^2$: 19.2 | 0.86 (0.1 – 3.9) | $\chi^2$: 26.3 |
| CAD group | 63 | 4.0 (0.23 – 71.5) | P=0.001 | 6.0 (1.2 – 25.0) | P=0.001 |
| B) Angina vs AMI | | | | | |
| Angina | 47 | 3.3 (0.2 – 13) | $\chi^2$: 35.6 | 4.0 (1.2 – 21.3) | $\chi^2$: 8.4 |
| AMI | 16 | 50.4 (32.4 – 71.5) | P=0.001 | 8.4 (4.5 – 25.0) | P=0.004 |
| C) Angina Time | | | | | |
| Early Angina | 29 | 3.9 (1.1 – 13.0) | $\chi^2$: 13.0 | 7.4 (1.2 – 22.0) | $\chi^2$: 18.2 |
| Late Angina | 18 | 1.5 (0.23 – 4.6) | P=0.001 | 1.7 (1.3 – 6.4) | P=0.001 |
| D) Suspected Angina | | | | | |
| Negative (Stress ECHO/Treadmill) | 7 | 2.0 (0.17 – 4.6) | $\chi^2$: 9.8 | 0.2 (0.15 – 1.7) | $\chi^2$: 10.2 |
| Positive (Stress ECHO/Treadmill) | 7 | 130 (49 – 228) | P=0.002 | 12 (5.4 – 18) | P=0.002 |

CAD: Coronary artery disease "cases of Angina and AMI", Early Angina: time of sample collection is a 1 to 10 hours after onset of chest pain, Late Angina: time of sample collection is 24 to 72 hours after onset of chest pain. $\chi^2$: Chi-square value of non-parametric Kruskal Wallis test, p value <0.01 considered a high statistical significance, p value ≤0.05 considered a significant difference between both groups.

FIG. 20

| Groups | No | Lnc-CTB89H12.4 expression [log^10] | |
|---|---|---|---|
| | | Median (range) | Statistics |
| A) Healthy vs CAD | | | |
| Healthy Control | 16 | 1.0 (0.6 – 1.8) | $\chi^2$: 38.0 |
| CAD group | 63 | 0.09 (0.0 – 0.5) | P=0.001 |
| B) Angina vs AMI | | | |
| Angina | 47 | 0.13 (0.01 – 0.5) | $\chi^2$: 22.6 |
| AMI | 16 | 0.02 (0 – 0.16) | P=0.001 |
| C) Angina Time | | | |
| Early Angina | 29 | 0.08 (0.01 – 0.4) | $\chi^2$: 20.5 |
| Late Angina | 18 | 0.2 (0.07 – 0.5) | P=0.001 |
| D) Suspected Angina | | | |
| Negative (Stress ECHO/Treadmill) | 7 | 0.84 (0.5 – 1.0) | $\chi^2$: 10.0 |
| Positive (Stress ECHO/Treadmill) | 7 | 0.07 (0.02 – 0.1) | P=0.002 |

FIG. 21

| Groups | Cut-off | AUC | Asymptotic 95% Confidence Interval (lower-upper) bound | Biomarker sensitivities (%) | Biomarker specificity (%) |
|---|---|---|---|---|---|
| FTHL-17 [log¹⁰] CAD vs Healthy control | 2.3 | 0.85 | 0.75 – 0.95 | 72 | 81 |
| ANAPC11 [log¹⁰] CAD vs Healthy control | 3.8 | 0.91 | 0.84 – 0.98 | 65 | 93 |
| lnc-CTB89H12.4 [log¹⁰] CAD vs Healthy control | 0.27 | 0.88 | 0.71 – 1.0 | 84 | 88 |
| FTHL-17 [log¹⁰] Angina vs AMI | 10.8 | 1.0 | 1.0 – 1.0 | 100 | 86 |
| ANAPC11 [log¹⁰] Angina vs AMI | 7.8 | 0.7 | 0.62 – 0.86 | 68 | 70 |
| lnc-CTB89H12.4 [log¹⁰] Angina vs AMI | 0.04 | 0.89 | 0.8 – 0.98 | 75 | 87 |
| FTHL-17 [log¹⁰] Early vs late Angina | 10.8 | 0.8 | 0.68 – 0.93 | 100 | 96 |
| ANAPC11 [log¹⁰] Early vs late Angina | 6.0 | 0.8 | 0.76 – 0.97 | 68 | 62 |
| lnc-CTB89H12.4 [log¹⁰] Early vs late Angina | 0.04 | 0.9 | 0.80 – 0.98 | 75 | 87 |
| FTHL-17 [log¹⁰] Negative / Positive stress test | 2.3 | 1.0 | 1.0 – 1.0 | 80 | 65 |
| ANAPC11 [log¹⁰] Negative / Positive stress test | 3.7 | 1.0 | 1.0 – 1.0 | 80 | 89 |
| lnc-CTB89H12.4 [log¹⁰] Negative / Positive stress test | 0.13 | 1.0 | 1.0 – 1.0 | 80 | 84 |

AUC: area under the curve, ROC: receiving operating characteristics

FIG. 23

| Variables | ACS (n=46) |
|---|---|
| miR-137 vs FTHL17 | r: 0.53; p=0.0005 [HS] |
| miR-137 vs lnc_CTB8912.4 | r: -0.34; p=0.02 [S] |

| Variables | ACS (n=46) |
|---|---|
| miR-106b vs ANAPCII | r: 0.35; p=0.02[S] |
| miR-106b vs lnc_CTB8912.4 | r: -0.6; p=0.0001 [HS] |

After 6h Preservation

| Treatment | Rat# | Incubation Time (hours) | Dose (g/kg) | ECHO Analysis Wall Thickness and Left Ventricular Mass | Heart Beating Score | Potential Graft Survival |
|---|---|---|---|---|---|---|
| Saline | 1 | 22 | -- | Loss | 1+ | Poor |
| | 2 | 24 | -- | Partial Loss | 1+-2+ | Poor |
| | 3 | 24 | -- | Loss | 1+-2+ | Poor |
| | 4 | 22 | -- | Loss | 1+ | Very Poor |
| | 5 | 22 | -- | Loss | 1+ | Poor |
| CCrP | 6 | 22 | 1.5 | Preservation | 3+ | Excellent |
| | 7 | 22 | 1.2 | Preservation | 4+ | Excellent |
| | 8 | 24 | 0.5 | Partial Preservation | 2+ | Average |
| | 9 | 24 | 0.5 | Preservation | 3+ | Very Good |
| | 10 | 22 | 0.8 | Preservation | 4+ | Excellent |
| | 11 | 22 | 0.8 | Partial Preservation | 2+ | Very Good |

FIG. 43

```
<210> SEQ ID NO 11
<211> LENGTH, 3
<212> TYPE, PRT
<213> ORGANISM, Artificial Sequence
<220> FEATURE,
<223> OTHER INFORMATION, Synthetic peptide

<400> SEQUENCE, 11

Met Leu Phe
1
```

FIG. 52

CYCLOCREATINE PHOSPHATE: A NOVEL BIOENERGETIC THERAPY TO PREVENT AND TREAT ISCHEMIA-INDUCED AND AGING-RELATED CARDIOVASCULAR AND NEURODEGENERATIVE DISEASES

CROSS REFERENCE TO RELATED APPLICATIONS

The current application is a continuation-in-part of the U.S. patent application Ser. No. 16/252,402 filed Jan. 18, 2019 which claims benefit of the U.S. Provisional Patent Application 62/686,184 filed Jun. 18, 2018. The current application is a continuation-in-part of the U.S. patent application Ser. No. 16/719,723 filed Dec. 18, 2019 which is a continuation-in-part of the U.S. patent application Ser. No. 16/252,402 filed Jan. 18, 2019, wherein U.S. patent application Ser. No. 16/252,402 claims benefit of U.S. Provisional Patent Application 62/686,184 filed Jun. 18, 2018. The current application claims benefit of U.S. Provisional Patent Application 63/002,179 filed Mar. 30, 2020.

SEQUENCE LISTING

The instant application contains a Sequence Listing which has been submitted electronically in ASCII format and is hereby incorporated by reference in its entirety. Said ASCII copy, created on Aug. 23, 2020, is named TUP58988 Seq List_ST25.txt and is 20,480 bytes in size.

FIELD OF THE INVENTION

The present invention generally relates to the fields of medicine, physiology, biochemistry, molecular, prevention, medical treatments, procedures and surgeries. The present invention particularly relates to the use of the novel bioenergetic drug, Cyclocreatine Phosphate (CCrP) as a potent cardioprotective drug by preserving cellular ATP energy source, preventing ischemic injury, rejuvenating organ function, thus, maintaining normal physical activity. Cyclocreatine Phosphate can be used as a new therapeutic approach to prevent disease development and progression, and to treat ischemia-induced, as well as aging-related cardiovascular and neurodegenerative diseases. More specifically, the present invention provides methods to prevent and treat patients with ischemic heart disease, including coronary artery disease, unstable angina, acute myocardial infarction, heart failure, atrial fibrillation, and Takotsubo cardiomyopathy, and provides cardioprotection during cardiac procedures and surgeries, as well as aging-related diseases, including stroke and Alzheimer.

BACKGROUND OF THE INVENTION

Cardiovascular disease is the leading cause of mortality in the United States and in westernized countries with "ischemic" heart disease accounting for the majority of these deaths. Acute coronary syndrome (ACS) is a term used to describe a range of conditions associated with sudden, reduced, or blocked blood flow (ischemia) to the heart. Myocardial ischemia or myocardial ischemic injury occurs when blood flow to the heart muscle (myocardium) is obstructed by a partial or complete blockage of a coronary artery by a buildup of plaques (atherosclerosis). Unstable plaque is the root cause of ACS is in coronary artery disease patients. If the plaques rupture, it develops into a heart attack or myocardial infarction. If reduction of blood flow is brief (less than 15 minutes), the ischemic injury is reversible, as seen in unstable angina (UA) patients. But if reduced blood flow is persistent for an extended period of time (more than 15 minutes), irreversible necrotic damage (cell death) occurs which leads to acute myocardial infarction (AMI i.e., heart attack). In the present disclosure, ACS patients are composed of UA and AMI patients, which in turn consists of STEMI and NSTEMI patients.

Currently, Troponin test is the "Gold Standard" for determining if a patient has had a heart attack but, no laboratory blood test exists that can specifically and accurately identify myocardial ischemic injury and diagnose UA patients who produce a negative Troponin test. Current Troponin tests, which are a biomarker of "cell death" for heart attack patients cannot be done until several hours (two to six hours) after presentation of symptoms in a patient in order to allow enough substances to be released in the blood from the dead heart tissue. Similarly, no simple blood test exists that can diagnose stable coronary artery disease (CAD) patients and identify and predict patients who will develop ACS and heart failure due to myocardial ischemic events. Currently, invasive coronary angiography procedures are used to diagnose CAD.

Heart disease is the leading cause of death in women and men worldwide according to the World Health Organization and it is predicted to persist as one of the main causes of illness due to the progressive aging of population. Chest pain affects 20% to 40% of the general population during their lifetime. Each year, approximately 1.5% of the population consults a primary care physician for symptoms of chest pain. The rate is even higher at the Emergency Departments (ED), where more than 5% of visits and up to 40% to 60% of admissions are because of chest pain. In the United States, ACS accounts for approximately 9% of all the cases with acute chest pain presenting to the ED. In a British study, angina pectoris or a history of possible AMI was reported in 14% of all cases with chest pain while a further 24% suffered from atypical chest pain. Data from the United States showed that in patients with chest pain, 17% ultimately met the criteria for cardiac ischemia and 8% had myocardial infarction. The non-acute myocardial infarction patients constitute a heterogeneous group with several diagnostic possibilities, for e.g. unstable and stable angina pectoris (includes, squeezing, pressure, heaviness, tightness, or pain in the chest caused by reduced blood flow to the heart muscles), non-atherosclerotic cardiac pain, and non-cardiac pain. Chest pain due to causes other than ischemic heart disease is frequent and often clinically indistinguishable from classic angina pectoris. Paradoxically, the improvements in the medical and surgical treatments of ACS are one of the leading factors underlying an increasing number of survivors' post-treatment developing heart failure.

One person dies every 37 seconds in the United States from cardiovascular disease (conditions that include diseased vessels, structural problems and blood clots and involve narrowed or blocked blood vessels that can lead to a heart attack, chest pain (angina) or stroke). About 647,000 Americans die from heart disease each year—that is 1 in every 4 deaths. Heart disease costs the United States about $219 billion each year from 2014 to 2015 (American Heart Association). Coronary heart disease (CHD, coronary arteries narrow, limiting blood flow to the heart) is the most common type of heart disease, that killed 365,914 people in 2017. About 18.2 million adults aged 20 and older have CAD (about 6.7% of the total). About 2 in 10 deaths from CAD happen in adults less than 65 years old (Centers of Disease Control and Prevention).

Myocardial ischemia is a major denominator of many cardiac diseases, including: CAD, UA, AMI and HF. These diseases and syndromes represent a continuum of ischemic disease ranging from UA, AMI, to large areas of heart cell death. Each year in the United States, between 6 to 10 million individuals present annually to the ED with clinical signs and symptoms of ACS including chest pain. Of the 6 to 10 million patients presenting annually to the ED with chest pain, up to 90% do not have a heart-associated cause for their symptoms. In the United States, the high rate of chest pain admissions of non-heart origin is as high as 60%. Accordingly, there is an urgent need for an early and accurate diagnosis of ACS patients to warrant immediate medical care, which would reduce mortality and improve prognosis, while also preventing diversion of attention away from such patients to non-critical, non-cardiac patients and otherwise heart-healthy subjects. A quick blood test is further needed that can accurately "rule in or rule out" the approximate 10% of ACS heart patients, who are also equally divided (50:50) between UA and heart attack. As such, currently, there is no biomarker or blood test to identify patients with UA seen in the ED with chest pain. The misdiagnosis of UA patients in the ED is one of the highest sources of medical malpractice lawsuits in the United States.

Heart failure (HF) is a clinical diagnosis when the heart fails to provide sufficient circulatory force to meet the body's metabolic requirements. It is one of the major causes of mortality in the United States, responsible for ~30% of patient deaths annually. HF is the final manifestation of cardiovascular disease (CVD) and cardiac injury. The lifetime risk for HF is substantial. It is strongly age dependent, with incidence rates of <1% below the age of 50 years and up to 30% at advanced ages (>80 years). According to the American Heart Association's Heart and Stroke Facts, the prevalence of HF will increase ≈50% between 2012 and 2030, resulting in >8 million people at ≥18 years of age with HF. This daunting future reflects the increased prevalence of HF as the population ages, AMI survival improves, and HF survival itself increases at rates that exceed the scientific and medical our impact to prevent the development of HF.

HF is becoming an increasing concern to healthcare worldwide because of the increasing disease burden and economic impact. It is the only cardiovascular disorder that continues to increase in both prevalence and incidence, and as the population continues to age, it is expected that the prevalence of this disease will continue to rise. Admissions for acute heart failure continue to increase but, to date, no new therapies have improved clinical outcomes.

HF has primarily been recognized as a disease of the elderly population (>60 years) and is reported to affect about 2% to 3% of people in the United States. Of these include 10% of males and 8% of females. Unfortunately, these numbers are on a gradual increase due to the on-going prevalence of HF with increasing age. In the United States itself, about more than three million physician visits per year have been accounted for patients with HF as the primary health issue. In 2013, the total number of HF patients were 5.1 million, and direct costs were equal to $32 billion; and this cost is being projected to increase by about three-fold by 2030. As of 2011, the estimated lifetime cost of HF per individual patient was $110,000/year, with more than three-fourths of this cost consumed by 'in-hospital care'. It is predicted that as the population ages, the direct medical costs of all cardiovascular diseases (including hypertension, coronary heart disease, stroke, and heart failure) will triple, reaching $818 billion in 2030.

Natriuretic peptide [NP; B-type NP (BNP), N-terminal proBNP (NT-proBNP), and mid regional proANP (MR-proANP)] concentrations are the known quantitative plasma biomarkers for the presence and severity of hemodynamic cardiac stress and HF. NPs are used in conjunction with all other clinical information and they are surrogates for intra-cardiac volumes and filling pressures. NPs are measured in patients presenting with symptoms suggestive of HF such as dyspnea (difficulty breathing) and/or fatigue, as their use facilitates the early diagnosis and risk stratification of HF and they have very high diagnostic accuracy in discriminating HF from other causes of dyspnea: the higher the NP, the higher the likelihood that dyspnea is caused by HF.

However, limitations of Natriuretic peptides, include:
1) The grey zone levels: BNP is indicative of only stress and muscle stretch, but not cell injury, thus, it needs to be combined with concomitant clinical features: such as a history of HF, jugular venous pressure and prior diuretic use.
2) Patients with acute and chronic ischemia: Natriuretic peptides do not seem to provide added diagnostic information on top of clinical judgement and/or Troponin measurements in the detection of inducible myocardial ischemia.
3) Renal impairment: it affects NPs level.

Thus, there is still an unmet clinical need related to HF patients since physicians' face challenges in identification and treatment of patients with myocardial ischemia who may be exposed to a higher risk of adverse outcomes such as re-infarction, early cardiac dysfunction, HF, and death. The current approaches for stratifying the risk of cardiac dysfunction in patients with AMI is based on clinical judgment, echocardiographic findings, and measurement of some selected biomarkers, namely cardio-specific Troponins and natriuretic peptides. Diagnostic imaging of the heart by means of echocardiography or magnetic resonance imaging (MRI) is commonplace, but only allows a physician to capture a sporadic and virtually instantaneous picture of cardiac function that, without serial monitoring, does not provide an absolute perception of the future risk for developing HF.

Therefore, there is a need for new biomarkers, specifically:
1) a biomarker that measures early ischemic injury before necrosis;
2) predictive biomarkers that would address important late complications and allow for the precocious identification—importantly immediately after AMI—of those patients at greater risk for HF and other adverse outcomes;
3) a biomarker that aids in risk stratification of new-onset HF in patients with AMI that occur during the acute phase of HF or AMI itself;
4) the ability to monitor the progression of disease (or its improvement);
5) the possibility to be easily and affordably measured in most clinical laboratories, and the capacity to be standardized in order to allow for universal application of diagnostic protocols;
6) the interpretation should not replicate data already available from clinic assessment and diagnostic imaging; and
7) should preferably be independent from information provided by other consolidated biomarkers such as cardio specific Troponins and natriuretic peptides.

Gene expression profiles and regulatory RNA networks are novel diagnostic and prognostic biomarkers for multiple human diseases due to their remarkably high stability in body fluids. They are also easy to obtain through non-invasive methods, are highly sensitive to early detection and have high specificity to different disease entities. In the cardiovascular system, regulatory RNAs including miRNAs play a significant role in its development and physiology. They control basic functions in all cell types of the cardiovascular system (endothelial cells, cardiac muscle, smooth muscle, inflammatory cells) and have been identified in all stages of cardiac tissue development. Thus, they are crucial in the search for new solutions in diagnosis, prognosis and therapy.

The present invention, therefore, presents the regulatory function of Nourin-related hsa-miR-137 (interchangeably referred to as miR-137 herein) and hsa-miR-106b (interchangeably referred to as miR-106b herein) as diagnostic and prognostic biomarkers in ischemia-induced diseases, including: CAD, UA, AMI (STEMI and NSTEMI), as well as HF, and identified their signaling pathways of lncR-CTB9H12.4 (interchangeably referred to as lnc-RNA-CTB9H12.4), mRNA-FTLH-17 (interchangeably referred to as mRNA FTLH-17 and FTLH-17 mRNA herein) and mRNA-ANAPC11 (interchangeably referred to as mRNA ANAPC11 and ANAPC11 mRNA herein) that regulate miR-137 and miR-106b in these ischemic heart diseases. Unlike BNP which is indicative of only stress and muscle stretch, Nourin-dependent gene-based RNA network are "cardiac specific" and are expressed only in response to "ischemic" cardiac injury and inflammation, and are not expressed in healthy hearts. Furthermore, since the level of Nourin reflects the severity of myocardial injury and inflammation, it will accurately predict AMI patients who would progress to develop HF. High level of Nourin is indicative of high probability of development of HF, while low level of Nourin is indicative of low probability of HF. Thus, Nourin will have the advantage over BNP of independently monitoring the progression of AMI patients for the development of HF.

Further, it is known in the art that AMI is associated with the release of proteins and nucleotides (RNAs) as a result of ischemic damage to cardiac tissue. As aforesaid, Nourin is a 3 KDa N-formyl peptide rapidly released within 5 minutes by reversible ischemic myocardial tissue, such as in the case of CAD, UA and by necrotic myocardial tissue, such as in the case of AMI. The formylated peptide Nourin is a potent inflammatory mediator which stimulates leukocyte chemotaxis, adhesion and activation to release a number of cytokine and chemokine mediators, adhesion molecules, digestive enzymes and free radicals. In vivo, the injection of human cardiac Nourin into rabbit skin resulted in an acute inflammatory response within the first 30 minutes characterized by a significant neutrophil infiltration. Nourin can, thus, be characterized as an Alarmin that promotes the innate immune response since it is rapidly released by local myocardial tissues following ischemia and contributes to the initiation and amplification of post-reperfusion myocardial inflammation. As such, Nourin can be an important diagnostic and therapeutic target. Nourin works as a ligand on leukocyte formyl peptide receptors (FPR) that are important potential therapeutic targets to control early and late post-reperfusion inflammation and injury. The cardiac-derived Nourin was purified from cardioplegic solutions collected during cardiac arrest (i.e., reversible ischemia) from patients who underwent cardiopulmonary bypass surgery for coronary revascularization. The amino acid sequence of Nourin released by reversibly ischemic human hearts is formyl substituted-MIINHNLAAINSHRSPGAD-GNGGEAMPGGGR (SEQ ID NO:15) confirmed by mass spectrometry analysis.

Using both the functional leukocyte chemotaxis assay and the ELISA immunoassay, studies demonstrated that the cardiac-derived Nourin peptide is rapidly released by ischemic heart tissue while it is still "viable" before cells are dead, as well as by necrotic hearts. Consistent results showing the "early" release of Nourin by ischemic hearts were demonstrated using various species (human, dog, rat and cow) as well as several models of ischemic injury to include (1) AMI (necrotic), (2) global cardiac arrest (necrotic), (3) cardiopulmonary bypass surgery (reversible) and (4) heart transplantation (reversible). Unlike Troponin, Nourin was detected in fresh blood samples collected from ACS patients as well as from frozen samples stored at −70° C. for 3 years.

Currently, Troponin released by necrotic heart tissue is the most widely used biomarker for AMI. However, Troponin is a marker of cell death and have certain drawbacks. For example, the Troponin complex is not highly stable as an extracellular protein, and thus its usefulness as a marker for AMI is diminished in samples that have been stored. Troponin also has low specificity where 50% of the time the elevated levels of Troponin give false positives for non-ischemic heart attack patients such as renal failure and non-ischemic heart failure.

Although the Troponin test is currently the "Gold Standard" for determining if a patient has had a heart attack, it is a marker of "cell death" and requires three to six hours of waiting after the onset of chest pain in order for Troponin to appear in enough quantities to be measured in blood samples. At this stage, however, a delay is a missed treatment to save ischemic heart tissues and that a critical delay could lead to permanent cardiac damage and higher incidence of heart failure or death. Although the cardiac Troponin level is dependent on infarct size following reperfusion therapy, the actual Troponin level can be misleading due to the washout phenomenon. Moreover, truly elevated Troponin levels have also been detected in tachyarrhythmias, hypertension, myocarditis and patients with chronic renal failure (CRF). Thus, a multi-marker approach incorporating both biomarkers and clinical scores may improve the diagnostic accuracy.

Therefore, a need exists in the art for a better test to diagnose unstable angina and myocardial infarction that is "earlier" and more "specific" using a "non-invasive" laboratory test at a lower cost than current standard invasive procedures. Since coronary artery disease is a leading health care threat to human lives, early and accurate diagnosis warrant immediate medical care, which would reduce mortality and improve prognosis.

Additionally, there is a need for a biomarker of ischemic injury without concomitant cell death that can detect sub-clinical or silent myocardial ischemia without infarction, as well as low-grade myocardial ischemia without cell death. This biomarker could also be used to monitor cardiac disease progression and predict drug therapy response in clinical trials.

Furthermore, since 40% to 60% of patients presenting with chest pain to ED are admitted, there is a need for a simple good negative test to accurately diagnose non-ACS chest pain patients and reduce health care expenses by eliminating unnecessary hospital admissions.

Additionally, since the misdiagnosis of unstable angina patients in the ED is the highest source of medical malpractice lawsuits in the United States, there is a need for a simple good positive test to accurately diagnose unstable angina patients and avoid the common misdiagnosis of this patient population by progressing to AMI.

Despite declines in heart failure morbidity and mortality with current therapies, re-hospitalization rates remain distressingly high, impacting substantially on individuals, society, and the economy. As a result, the need for new therapeutic advances and novel medical devices is urgent. Since AMI is the most common cause of HF and that ischemic injury plays a key role in the pathogenesis of HF, biomarkers that can detect myocardial cell injury before necrosis, are crucial.

Cardiac myocytes carry out the contractile function of the myocardium, and they are largely incapable of replication; hence, their survival is crucial. After myocardial injury, cardiac myocytes undergoing necrosis lyse and release intracellular contents, some of which can be detected in the blood and used as markers of necrosis (for e.g., creatine kinase-MB, cardiac Troponins).

The present invention, therefore, presents the regulatory function of Nourin gene-based RNA molecular network of biomarkers related to the Nourin peptide sequence comprising, *Homo sapiens* micro RNA-137 (hsa-miR-137) and *Homo sapiens* micro RNA-106b (hsa-miR-106b) as diagnostic and prognostic biomarkers in ischemia-induced cardiac diseases, including: CAD, UA, AMI (STEMI and NSTEMI), as well as HF, and identifies the RNA-based signaling pathways comprising, long non-coding intergenic RNA (lnc-RNA-CTB89H12.4), ferritin heavy chain like polypeptide mRNA-17 (mRNA-FTHL-17), and anaphase promoting complex subunit mRNA-11 (mRNA-ANAPC11) that regulate hsa-miR-137 and hsa-miR-106b in ischemic heart diseases and in turn relate to the levels of Nourin gene and consequently, Nourin protein expression. Importantly, by monitoring the Nourin gene and protein expression along with its related RNA molecular network of biomarkers with known pathophysiology it is not just a new biomarker for CAD, UA, AMI and HF patient diagnosis and prognosis but, it further provides a fertile therapeutic target in a method for prevention and treatment of ischemic diseases and aging-related disorders involving ischemia-induced injury providing with the following benefits:

1. Since Nourin is "early" released in response to injury by ischemic myocardium "before necrosis", it will be earlier than Troponin and CK-MB which are biomarkers of necrosis. Specifically, elevated level of miR-137 as a marker of cell injury will permit crucial therapy to save cardiac muscles and reduce the development of HF.
2. Since Nourin is also a potent inflammatory mediator, elevated level of miR-106b as a marker of inflammation, will provide essential information regarding the severity of tissue inflammatory response to ischemic injury.
3. Each Nourin-dependent miRNA (miR-137 and miR-106b) has its specific role in myocardial ischemia, miR-137 as a marker of cell injury and miR-106b as marker of inflammation. Thus, using both markers with different mode of actions gives more diagnostic accuracy.
4. Nourin can detect the degree of cell injury associated with ischemia and haemodynamic cardiac stress which is currently measured by BNP, and thus it will have a significant add value in understanding the patients' cardiac "injury" and response to treatments.
5. Nourin can identify patients at increased risk of developing HF due to ischemia, and, therefore, will permit early crucial therapeutic strategy to alleviate ischemic injury. Targeted therapy would include revascularization (e.g., bypass surgery) and/or medical treatment such as the bioenergetic drug, Cyclocreatine Phosphate (CCrP).
6. Nourin can monitor the heart health before and after medical and surgical treatments of CAD patients.
7. Nourin can have medical value for the diagnostic evaluation of suspected HF.
8. Nourin can facilitate the early diagnosis and risk stratification of HF.

SUMMARY OF THE INVENTION

Generally, in one aspect of the present invention, a novel Nourin gene-based RNA molecular network is disclosed for the early diagnosis of and differentiation between diseases or disorders using molecular network for the detection of RNAs released as a result of certain cardiac events, such as stable and unstable angina patients with negative Troponin, and it reflects the disease progression and severity of heart damage. In another aspect of the present invention, a method for the early diagnosis, prognosis and differentiation of ischemic cardiac events in myocardial ischemia by a Nourin gene-based RNA molecular network of biomarkers related to the Nourin peptide sequence is provided comprising: obtaining a sample from a subject; and assaying the sample for one or more of a Nourin gene-based RNA molecular network of biomarkers related to the Nourin peptide sequence, comprising: i) anaphase promoting complex subunit mRNA-11 (mRNA-ANAPC11) gene, ii) ferritin heavy chain like polypeptide mRNA-17 (mRNA-FTHL-17) gene, iii) *Homo sapiens* micro RNA-106b (hsa-miRNA-106b), iv) *Homo sapiens* micro RNA-137 (hsa-miRNA-137), v) Nourin gene mRNA, and vi) long non-coding intergenic RNA (lnc-RNA-CTB89H12.4), wherein, hsa-miRNA-137 is a marker of cell damage, wherein, hsa-miRNA-106b is a marker of cardiovascular inflammation, wherein, hsa-miRNA-137 and hsa-miRNA-106b regulate the expression of Nourin gene and are linked to myocardial ischemia and ischemic cardiac events, wherein, hsa-miRNA-137 and hsa-miRNA-106b are upregulated after ischemic cardiac events in myocardial ischemia and are linked to overexpression of mRNA-FTHL-17 and mRNA-ANAPC11, wherein, hsa-miRNA-137 and hsa-miRNA-106b are upstream regulated by lnc-RNA-CTB89H12.4, wherein, lnc-RNA-CTB89H12.4 is downregulated after ischemic cardiac events in myocardial ischemia and is linked to higher levels of hsa-miRNA-137 and hsa-miRNA-106b, and to overexpression of mRNA-FTHL-17 and mRNA-ANAPC11, wherein, lnc-RNA-CTB89H12.4 is downregulated after ischemic cardiac events in myocardial ischemia and is linked to increased translation and production of high levels of Nourin protein, wherein, hsa-miRNA-137, hsa-miRNA-106b, mRNA-FTHL-17, mRNA-ANAPC11, Nourin gene, and Nourin protein show extremely low or no expression in the samples from healthy, non-ischemic, non-cardiac subject, and wherein, lnc-RNA-CTB89H12.4 is upregulated in the samples from healthy, non-ischemic, non-cardiac subject.

In yet another aspect of the present invention, the novel Nourin gene-based RNA molecular network of biomarkers related to the Nourin peptide sequence is composed of lncRNA-CTB89H12.4, hsa-miRNA-137, hsa-miRNA-106b, mRNA-FTHL-17, and mRNA-ANAPC11 and said RNAs can be utilized individually and/or together for early diagnosis and prognosis of various cardiovascular ischemia-induced diseases, including: CAD, UA, AMI (STEMI and NSTEMI), as well as HF in patients presenting with chest pain to hospital ED and in outpatient clinics to allow for quick crucial intervention. Bioinformatics analysis revealed that the two miRNAs related to Nourin gene hsa-miRNA-106b and hsa-miRNA-137 regulate the expression of Nourin protein via sponging of Nourin gene. The invention also allows for the Nourin gene-based RNA molecular network of biomarkers to: (a) diagnose angina in patients with history of chest pain suspected of angina, (b) differentiate between positive angina patients from symptomatic non-angina patients and healthy subjects, (c) diagnose symptomatic UA and AMI patients, (d) differentiate between UA and AMI patients, as well as symptomatic non-cardiac and healthy subjects, and (e) diagnose heart failure and differentiate the diseases from healthy non-ischemic.

In another aspect of the present invention, the molecular pathway by which hsa-miRNA-106b (miR-106b) and hsa-miRNA-137 (miR-137) regulates the expression of Nourin gene are evident in coronary artery diseases and are strongly linked to myocardial ischemia. The present invention demonstrates that the downregulation of Nourin gene-associated lncR-CTB9H12.4 in coronary artery disease patients compared to non-cardiac and healthy controls, is significantly associated with upregulation of hsa-miR-106b and hsa-miR-137 resulting in overexpression of mRNA-ANAPC11 and mRNA-FTHL-17; respectively.

In another aspect of the present invention, the novel Nourin-related molecular network provides a non-invasive good positive test to diagnose angina patients, which is also a good negative test to accurately exclude non-angina patients.

In another aspect of the present invention, the novel molecular network has a high stability and is often present in tissue disease association expression and can be measured with high sensitivity and specificity.

In another aspect of the present invention, the novel Nourin molecular network disclosed therein is composed of lnc-RNA-CTB89H12.4, hsa-miRNA-106b, hsa-miRNA-137, mRNA-ANAPC11 and mRNA-FTHL-17 can be utilized alone, and in combination with the Nourin protein.

Additionally, early diagnosis of acute coronary syndromes (ACS) angina patients presenting with chest pain to hospital Emergency Department (ED) and outpatient clinics will permit crucial intervention. Early intervention of ischemic heart patients can, thus, abort infarction and save heart muscles. The molecular Nourin RNA network alone and in combination with the Nourin protein can also diagnose AMI patients earlier than Troponin; differentiate cardiac from non-cardiac patients presenting with chest pain to hospital ED and in outpatient clinics; monitor disease progression; and predict drug therapy response (myocardial cell damage) in clinical trials.

In another aspect of the present invention, the novel Nourin molecular network disclosed therein and Nourin protein have the potential to additionally diagnose subclinical or silent myocardial ischemia without infarction, as well as low-grade myocardial ischemia without cell death; microvascular angina that could not be diagnosed by coronary angiography, screen CAD coronary artery patients for risk assessment to predict which patients are at risk for developing AMI; screen heart transplantation patients' blood samples for cardiac allograft inflammation, thus, reduce the invasive heart biopsies; and determine the risk level of heart patients experiencing chest pain who present to hospital ED and in outpatient clinics and provide risk stratification of AMI patients.

In another aspect of the present invention, a method for screening, diagnosing, and predicting therapy response with an agent in ischemic diseases and aging-related disorders, the method comprising the steps of:
a) administering Isoproterenol with or without an agent to be screened for therapy for ischemic diseases and aging-related disorders to cause myocardial injury for inducing ischemia-induced heart failure, wherein myocardial injury is evident within the first 24 hours after administration;

b) assaying a sample obtained after 14 days of the administration in step (a) for gene expression level of a Nourin gene-based RNA molecular network biomarkers related to the Nourin peptide sequence, the biomarkers comprising a group of genes selected from anaphase promoting complex subunit mRNA-11 (mRNA-ANAPC11) gene, ferritin heavy chain like polypeptide mRNA-17 (mRNA-FTHL-17) gene, *Homo sapiens* micro RNA-106b (hsa-miRNA-106b), *Homo sapiens* micro RNA-137 (hsa-miRNA-137), Nourin gene mRNA;
c) assaying the sample for gene expression level of lncR-CTB89H12.4, a Nourin gene-based RNA molecular network of biomarkers related to the Nourin peptide sequence;
d) assaying the sample for gene expression level of the cardiac marker CK-MB;
e) assessing the subject for amount of collagen deposition;
f) assessing the subject for amount of fibrosis;
g) assessing the subject for heart weight;
h) assessing the subject for amount of ejection fraction;
i) assessing the subject for physical activity level;
j) assessing normal subject for heart function;
k) correlating the gene expression level of step (b) with the gene expression level of the lncR-CTB89H12.4 of step (c);
l) correlating the gene expression level of step (b) with the level of the cardiac marker CK-MB of step (d);
m) correlating the gene expression level of step (b) with the amount of collagen deposition of step (e);
n) correlating the gene expression level of step (b) with the amount of fibrosis of step (f);
o) correlating the gene expression level of step (b) with the heart weight of step (g);
p) correlating the gene expression level of step (b) with the amount of ejection fraction of step (h);
q) correlating the gene expression level of step (b) with the physical activity level of step (i);
r) correlating the gene expression level of step (b) with the heart function of step (j);
s) analyzing the gene expression level of step (b) 14 days after the administration of step (a); and
t) identifying subjects responding to medical treatment with the agent as responders,
wherein the subjects having a drop in gene expression level in step (s) are responders, whereas the subjects having an increase in gene expression level in step (s) are non-responders for the agent,
and wherein, a high gene expression level after just Isoproterenol administration is a marker of Isoproterenol induced cardiotoxicity and myocardial injury, an increase in gene expression level after combined administration of Isoproterenol and the agent is a marker of Isoproterenol induced cardiotoxicity and myocardial injury with no effect of the agent,
a drop in gene expression level to normal non-ischemic level after combined administration of Isoproterenol and the agent is a marker of prevention of ischemic injury by the agent, when CK-MB level is not elevated,
a drop in gene expression level to normal non-ischemic level after combined administration of Isoproterenol and the agent is a marker of prevention of development of heart failure by the agent,
a drop in gene expression level to normal non-ischemic level after combined administration of Isoproterenol and the agent is a marker of prevention of development of heart failure by the agent, when there is no increase in fibrosis, collagen deposition and heart weight,
a drop in gene expression level to normal non-ischemic level after combined administration of Isoproterenol and the agent is a marker of prevention of development of heart failure by the agent, when there is an increase in ejection fraction and physical activity, a drop in gene expression level to normal non-ischemic level after combined administration of Isoproterenol and the agent is a marker of prevention of development of heart failure by the agent, wherein there is an up-regulation of lncR-CTB89H12.4 and a downregulation of hsa-miRNA-137 and hsa-miRNA-106b with no change in mRNA-FTHL-17 and mRNA-ANAPC11 gene expression level, a drop in gene expression level to normal non-ischemic level after combined administration of Isoproterenol and the agent is a marker of prevention of development of heart failure by the agent which is indicative of improvements of heart health, a drop of gene expression level to normal non-ischemic level after combined administration of Isoproterenol and the agent is a marker of prevention of development of heart failure by the agent, when there is no change in heart function which is indicative of absence of toxicity, a drop in gene expression level to normal non-ischemic level after combined administration of Isoproterenol and the agent is a marker of prevention of development of heart failure by the agent in a dose response manner, wherein the amount of the agent is in the range of 0.4 g/kg/day, 0.8 g/kg/day, and 1.2 g/kg/day, an up-regulation of hsa-miRNA-137, hsa-miRNA-106b, mRNA-FTHL-17 and mRNA-ANAPC11, and a downregulation of lncR-CTB89H12.4 are new biomarkers for left ventricular remodeling, wherein their levels are indicator of the degree of remodeling, and predictive of heart failure diseases, and a downregulation of hsa-miRNA-137, hsa-miRNA-106b, mRNA-FTHL-17 and mRNA-ANAPC11, and an up-regulation of lncR-CTB89H12.4 after medical treatment and drug-testing is indicative of successful therapy and lack of cardiac toxicity.

In another aspect of the present invention, it describes a novel non-invasive blood test for Nourin protein and its RNA regulatory network for early diagnosis and prognosis of:

1. symptomatic unstable angina patients and acute myocardial infarction (STEMI and NSTEMI) patients at presentation to hospital ED, and differentiates between unstable angina and acute myocardial infarction patients.
2. acute coronary syndrome (ACS) patients and differentiates ACS patients from symptomatic non-cardiac patients and healthy individuals.
3. angina disease in suspected patients with history of chest pain, and differentiates angina patients from non-angina chest pain patients and healthy individuals.
4. heart failure and provides a prognostic value for "new-onset" heart failure and risk prediction of disease progression and deterioration, as well as monitoring patients' response to treatments.

In another aspect of the present invention, it also indicates that the downregulation of Nourin-dependent lncR-CTB9H12.4 in ischemic heart disease patients compared to non-cardiac and healthy controls, is significantly associated with upregulation of miR-137 (marker of cell damage) and miR-06b (marker of cardiovascular inflammation), resulting in overexpression of mRNA-FTHL-17 and mRNA-ANAPC11, respectively.

In another aspect of the present invention, it further indicates high expression of Nourin RNA network (miR-137, miRNA-106b, mRNA-FTHL-17 and mRNA-ANAPC11, and lncR-CTB89H12.4) in the Isoproterenol (ISO) rat model of HF. The administration of the bioenergetic drug, Cyclocreatine Phosphate (CCrP) prevented both ischemic injury and gene expression of Nourin RNA network (miR-137, miRNA-106b, mRNA-FTHL-17 and mRNA-ANAPC11, and lncR-CTB89H12.4) in ISO HF rats.

Specifically, CCrP administration in ISO rat model of HF prevented the development of HF by:
1. preventing ischemic injury as indicated by normal level of the cardiac biomarker CK-MB after 24 hours;
2. preventing cardiac remodeling by reducing fibrosis and collagen deposition;
3. preventing gain in heart weight; and
4. restoring normal left ventricular ejection fraction and cardiac function, thus, restored high physical activity.

In summary, CCrP not only prevented ischemia-induced myocardial injury by 24 hours after ISO administration, but also protected cardiac tissue from remodeling and prevented the "progression" of myocardial injury to acute heart failure at day 14. Thus, the bioenergetic CCrP is a promising first-in-class novel mechanism of cardioprotection that prevents ischemic injury, prevents development and progression of heart failure, resulting in rejuvenation of cardiac function and restoration of normal physical activity.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWING

The accompanying drawings are included to provide a further understanding of the invention, and are incorporated in and constitute a part of the present invention and, together with the description, serve to explain the principle of the invention.

Bioinformatic analysis was done using BLAST program to retrieve relevant gene to the Nourin peptide sequence formyl substituted-MIINHNLAAINSHR (SEQ ID NO:16) that is the N-terminus portion of the Nourin peptide sequence and relevant to AMI based on previous microarray studies coronary artery disease based on previous microarray studies. Two novel competing endogenous RNA network that were related to Nourin protein expression were retrieved to assess their potentiality as early diagnostic and prognostic biomarkers for ischemic cardiac disease. A gene ontology analysis using Kyoto Encyclopedia of Genes and Genomes (KEGG) indicated that the downregulation of lncRNA-CTB89H12.4 (SEQ ID NO:19) upregulates the expression of hsa-miR-106b (SEQ ID NO:21) and hsa-miR-137 (SEQ ID NO:22). Furthermore, and subsequently, hsa-miR-106b (SEQ ID NO:21) and hsa-miR-137 (SEQ ID NO:22) regulate the expression of ferritin heavy polypeptide like 17 (mRNA-FTHL-17) (SEQ ID NO:03) and Anaphase Promoting Complex Subunit 11 (mRNA-ANAPC11) (SEQ ID NO:20), and those miRNAs network were involved in Nourin autophagy signaling pathways in response to hypoxia and ischemia.

In the drawings,

Figure 1:
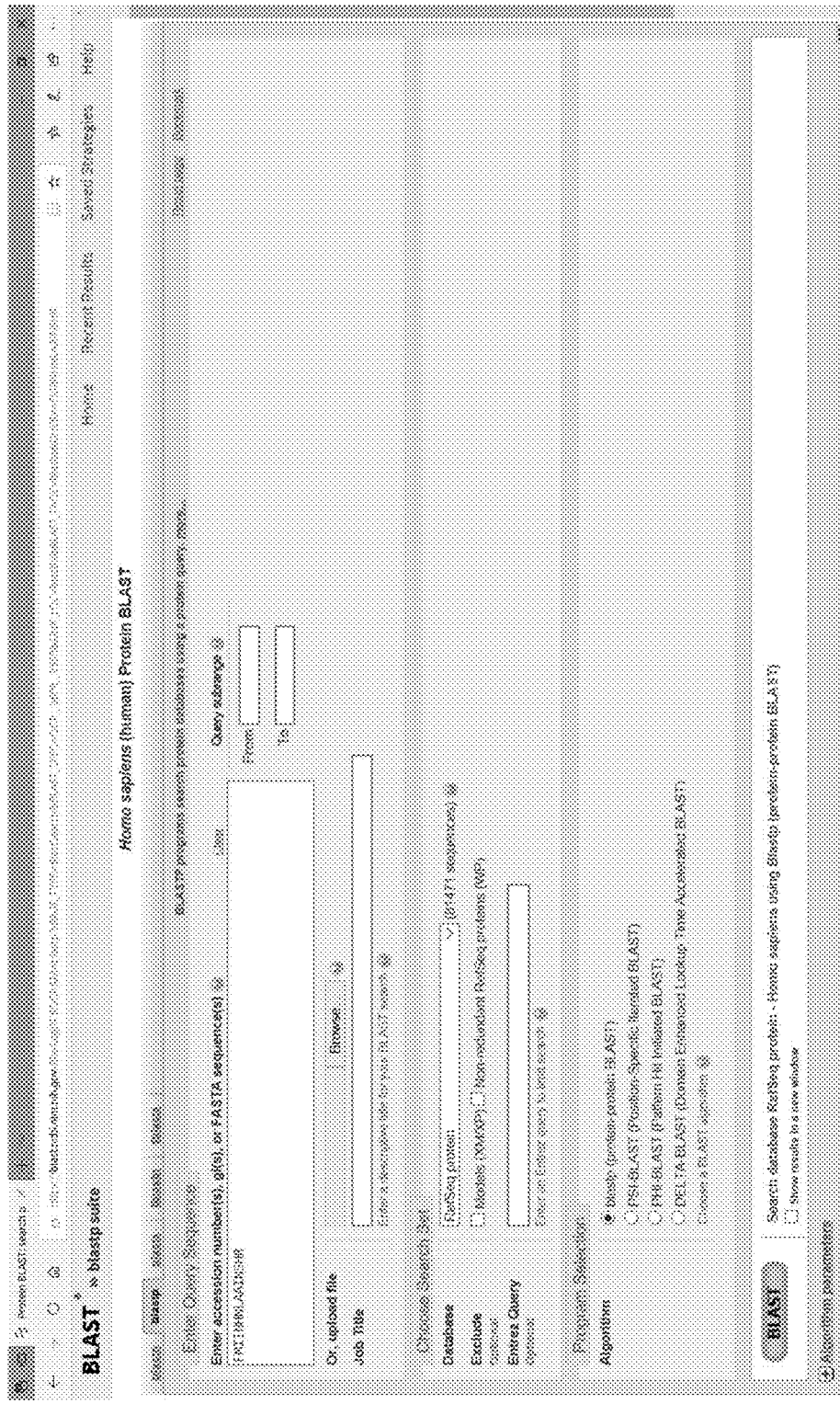

FIG. 1 indicates a snapshot of expression of Atlas database showing retrieving target gene involved relevant to the Nourin-1 peptide sequence formyl-MIINHNLAAINSHR. https://blast.ncbi.nlm.nih.gov/Blast.cgi?PROGRAM= blastp&PAGE_TYPE=BlastSearch&BLAST_SPEC=OGP_

9606_9558&LINK_LOC=blasttab&LAST_PAGE=blastn&QUERY=FMIINHNLAAINSHR

FIG. 2 indicates a print screen showing BLAST alignment of mRNA-FTHL-17 with Nourin also refer to as Nourin-1 peptide sequence formyl-MIINHNLAAINSHR, available at: https://blast.ncbi.nlm.nih.gov/Blast.cgi?PROGRAM=blastp&PAGE_TYPE=BlastSearch&BLAST_SPEC=OGP_9606_9558&LINK_LOC=blasttab&LAST_PAGE=blastn&QUERY=FMIINHNLAAINSHR https://blast.ncbi.nlm.nih.gov/Blast.cgi#300244535

FIG. 3 indicates a snapshot showing gene ontology of mRNA-FTHL-17. https://www.ncbi.nlm.nih.gov/gene/53940

Figure 4:
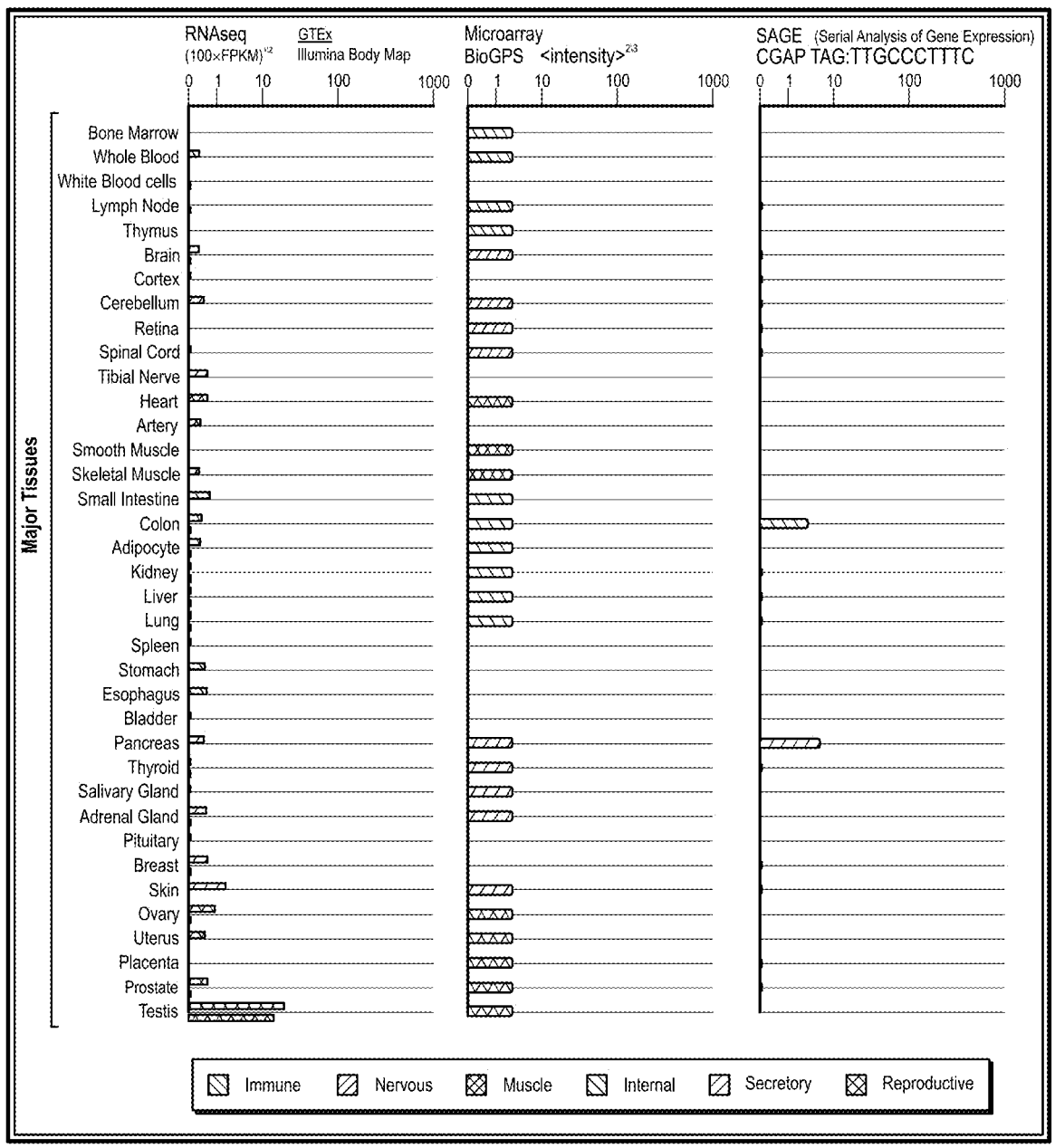

FIG. 4 indicates a snapshot showing minimal gene expression of mRNA-FTHL-17 in normal tissues confirming the low level of Nourin-related mRNA-FTHL-17 and Nourin protein detected in serum and plasma samples collected from healthy subjects. https://www.genecards.org/cgi-bin/carddisp.pl?gene=FTHL17&keywords=FTHL17

Figure 5:
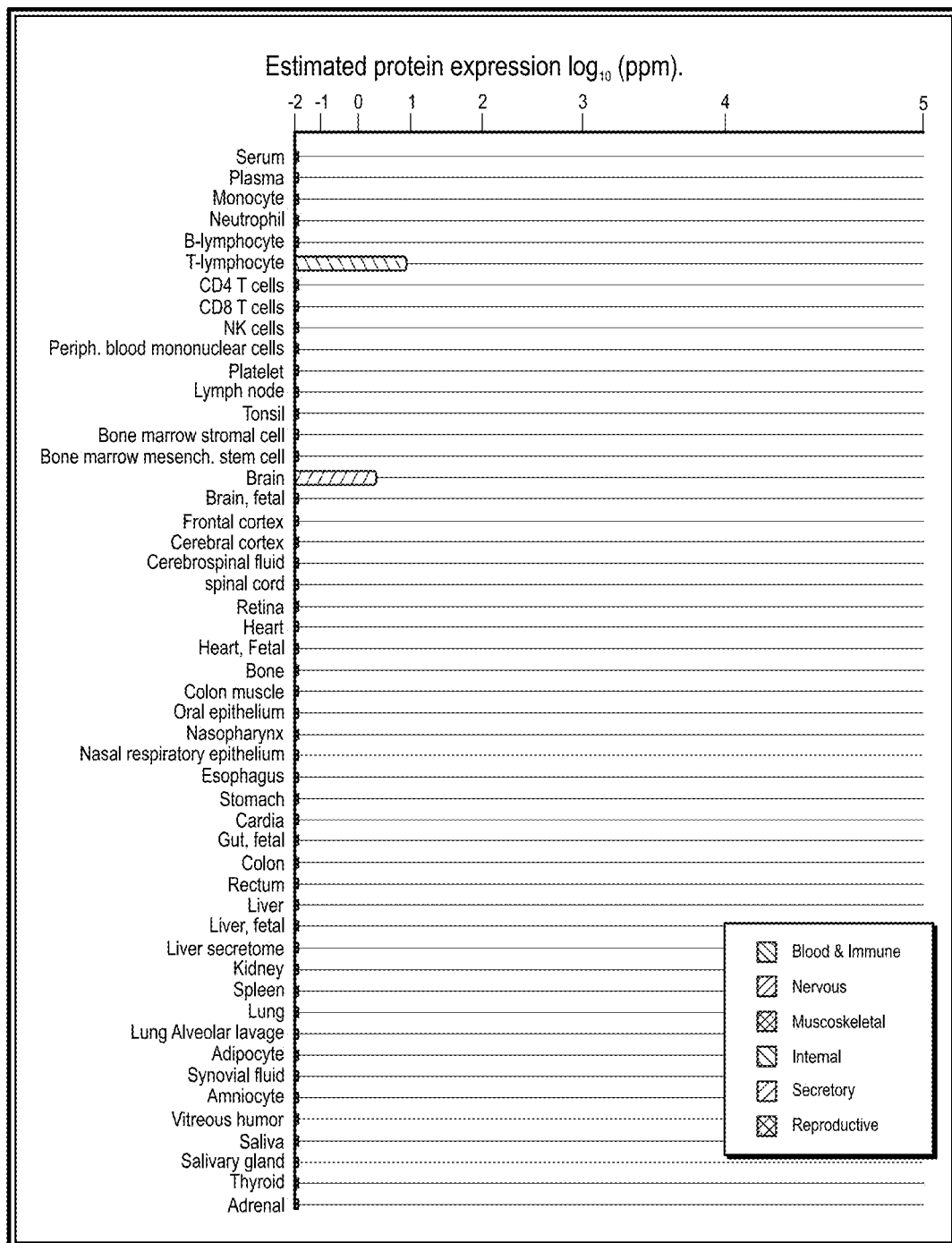

FIG. 5 indicates a continuation of the snapshot showing minimal gene expression of mRNA-FTLH17 in normal tissues confirming the low level of Nourin mRNA-FTLH17 and Nourin protein detected in serum and plasma samples collected from healthy subjects. https://www.genecards.org/cgi-bin/carddisp.pl?gene=FTHL17&keywords=FTHL17

FIG. 6 indicates a print screen showing hsa-miRNA-137 targeting mRNA-FTHL-17 and it is available at: http://diana.imis.athenainnovation.gr/DianaTools/index.php?r=microT_CDS/results&keywords=ENSG00000132446&genes=ENSG00000132446%20&mirnas=&descr=&threshold=0.7

FIG. 7 indicates a print screen showing the interaction between hsa-miRNA-137 and lncRNA-CTB89H12.4. Available at star base database.

Figure 8:
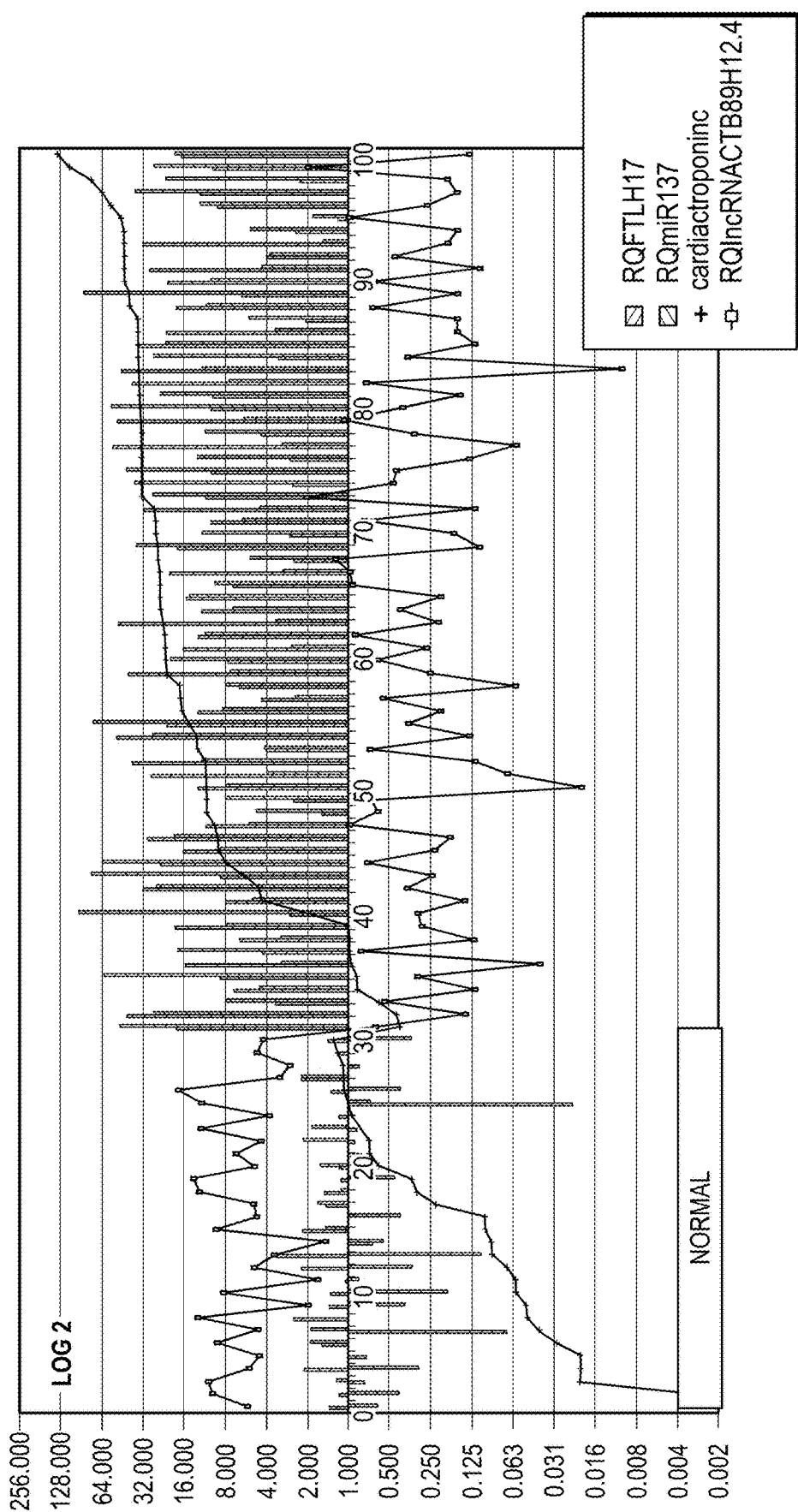

FIG. 8 indicates the expression pattern and level of the Nourin-based molecular biomarker panel of mRNA-FTHL-17, hsa-miRNA-137 and lncRNA-CTB89H12.4 in comparison to Troponin I measured in the same serum samples collected from AMI patients and healthy volunteers. Results revealed that the two-log analysis of the three RNAs-based biomarker network long non-coding intergenic RNA (lncRNA-CTB89H12.4), Homo sapiens microRNA-137 (hsa-miRNA-137), and mRNA-FTHL-17, had high sensitivity and specificity for discriminating AMI patients from healthy controls. While the AMI group had a higher expression of mRNA-FTHL-17 and hsa-miRNA-137 as well as elevated levels of Troponin I in comparison to the healthy control group, there is concomitant lower expression of lncRNA-CTB89H12.4 in AMI patients and higher expression in the healthy control group.

Figure 9:
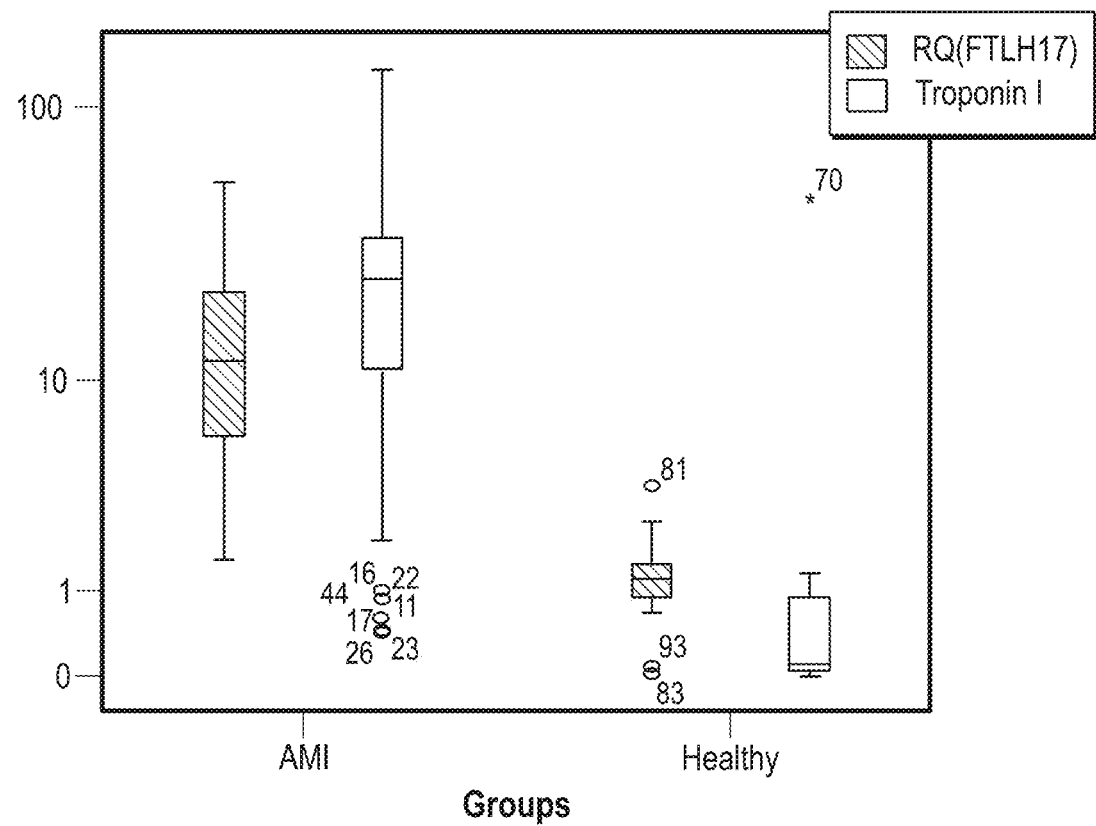

FIG. 9 indicates the expression level of the Nourin-based molecular biomarker mRNA-FTHL-17 in comparison to Troponin I measured in serum samples of AMI patients and healthy volunteers. Highly significant difference by the independent t test (P<0.001).

Figure 10:
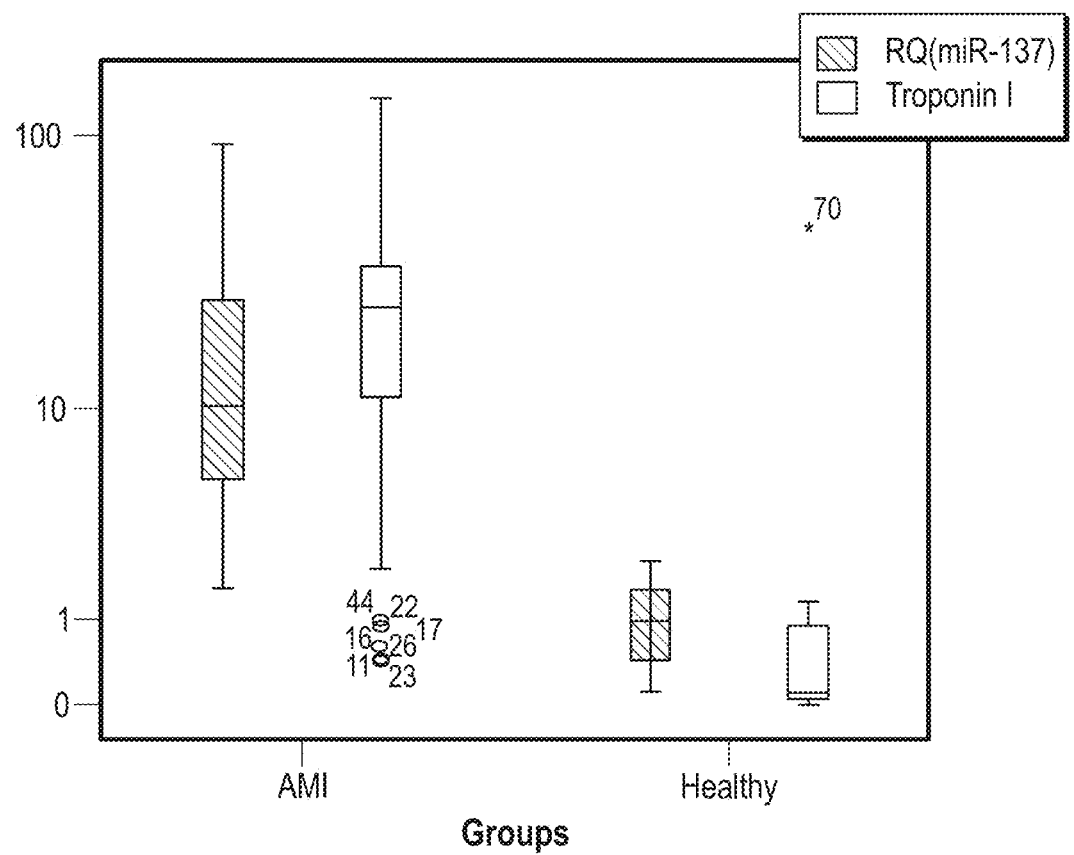

FIG. 10 indicates the expression level of the Nourin-based molecular biomarker hsa-miRNA-137 in comparison to Troponin I measured in serum samples of AMI patients and healthy volunteers. Highly significant difference by the independent t test (P<0.001).

Figure 11:
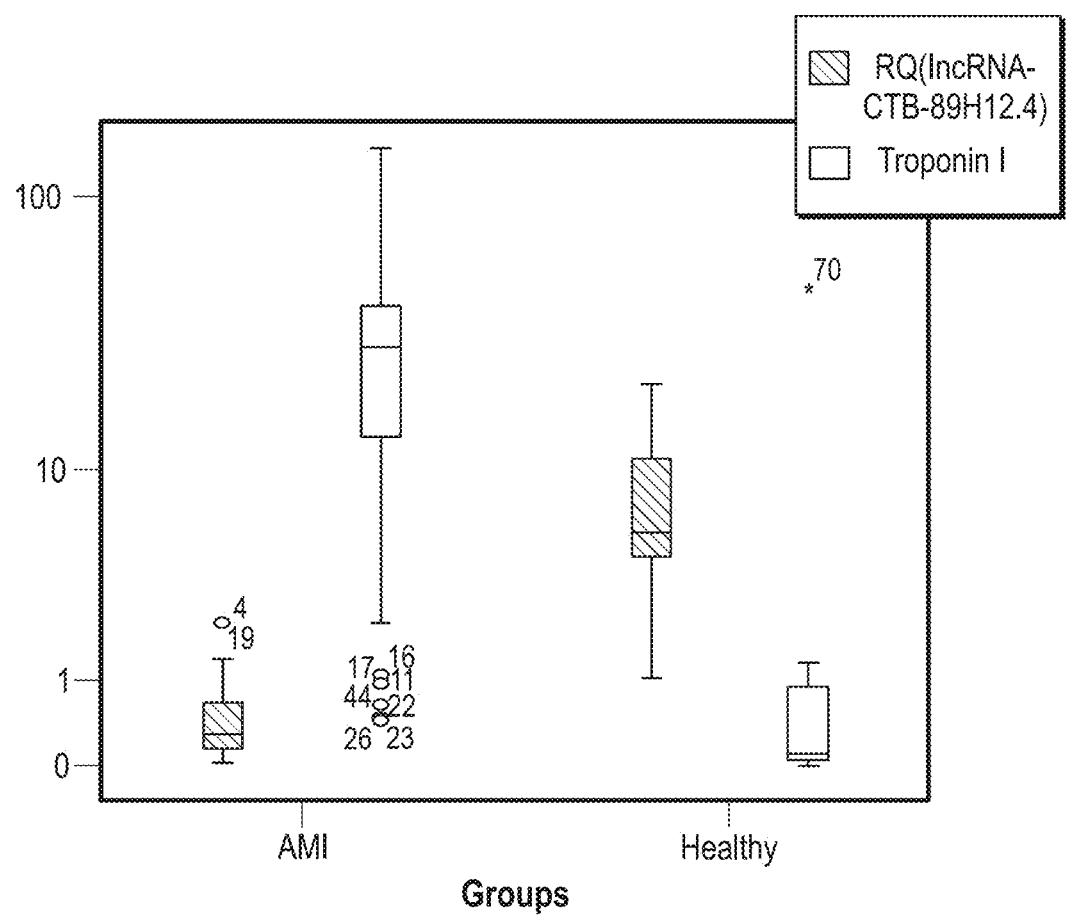

FIG. 11 indicates the expression level of the Nourin-based molecular biomarker lncRNA-CTB89H12.4 in comparison to Troponin I measured in serum samples of AMI patients.

Figure 12:
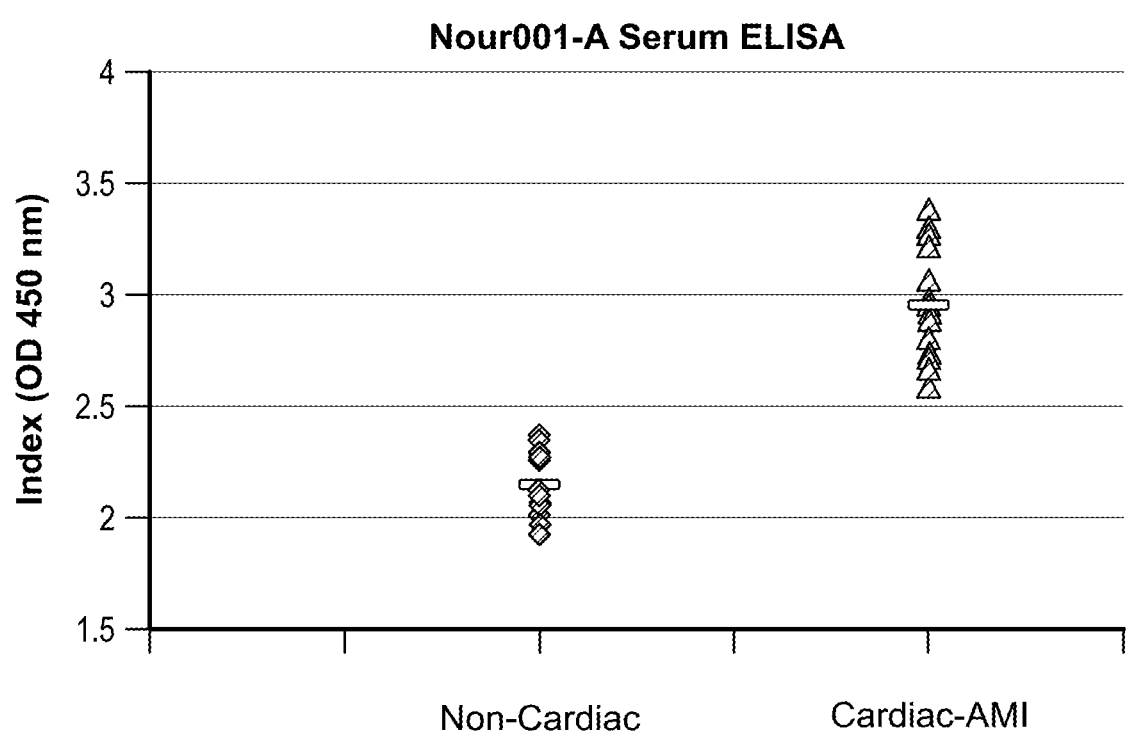

FIG. 12 indicates the differential level of the Nourin protein measured with the ELISA immunoassay in "Cardiac-AMI" patients presenting to hospital ED with chest pain and non-cardiac patients also complaining of chest pain. The ELISA immunoassay measured antibodies (hereinafter referred to as "Nour001-A") developed against Nourin polypeptide comprising of the epitope sequence N-f-MII moiety. Troponin negative (−) samples (labeled "Non-Cardiac) showed an average OD reading of approximately 2.2, whereas the Troponin positive (+) samples (labeled "Cardiac AMI") showed an average OD reading of approximately 2.9, with no overlap between individual samples of the two types. The Nour001-A antibody assay showed a statistical significance difference (P=0.0001) between samples from "Cardiac-AMI" patients and Non-Cardiac patients with chest pain. When the same samples were stored for one month at −20° C. then thawed and subjected to the same ELISA test procedure, the data was similar to and confirmed the results obtained using fresh samples, showing a difference between Troponin (+) samples and Troponin (−) samples. In this repeat frozen-sample study, Troponin (+) samples showed an average OD of approximately 2.4, whereas the Troponin (−) samples showed an average OD of approximately 1.8. The lack of stability of Troponin is a significant drawback to its use as a marker for AMI in stored samples, which is overcome by the Nourin assay. Thus, the Nour001-A antibody binding profile correlates well with Troponin level profile. As such, the Nour001-A antibody is well suited as a detection reagent for AMI and can differentiate between patients suffering AMI and patients complaining of chest pain, but not suffering AMI. The Nour001-A antibody, thus, can be used in diagnostic assay to differentiate AMI patients from symptomatic non-cardiac.

Figure 13:
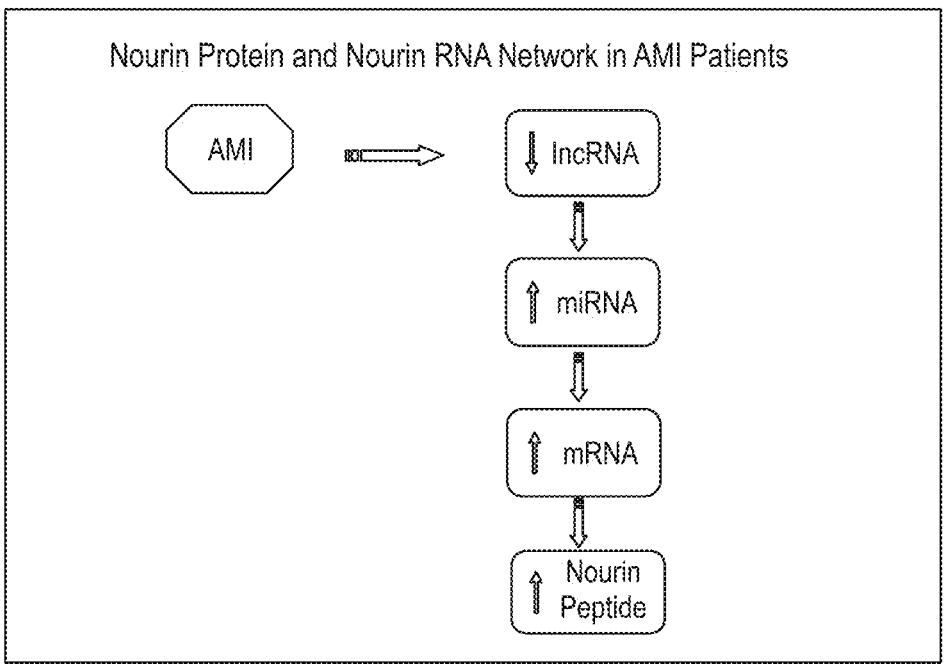

FIG. 13 indicates the down-regulation of lncRNA-CTB89H12.4 after an AMI event resulted in up-regulation of hsa-miRNA-137 and activation of mRNA-FTHL-17 with an increased translation and production of high levels of Nourin protein. There is none to a minimal gene expression of mRNA-FTHL-17 in normal non-stressed tissues. lncRNA-CTB89H12.4 is related to cardiomyocyte regeneration and angiogenesis and it is down-regulated after myocardial injury. FIG. 13 also indicates that the clinical application of the Nourin-based molecular biomarker panel composed of mRNA-FTHL-17, hsa-miRNA-137 and lncRNA-CTB89H12.4 can be used individually and in combination with the protein-based biomarker Nourin for better and faster diagnosis of AMI patients presenting with chest pain at the ED and in outpatient clinics.

Figure 14:
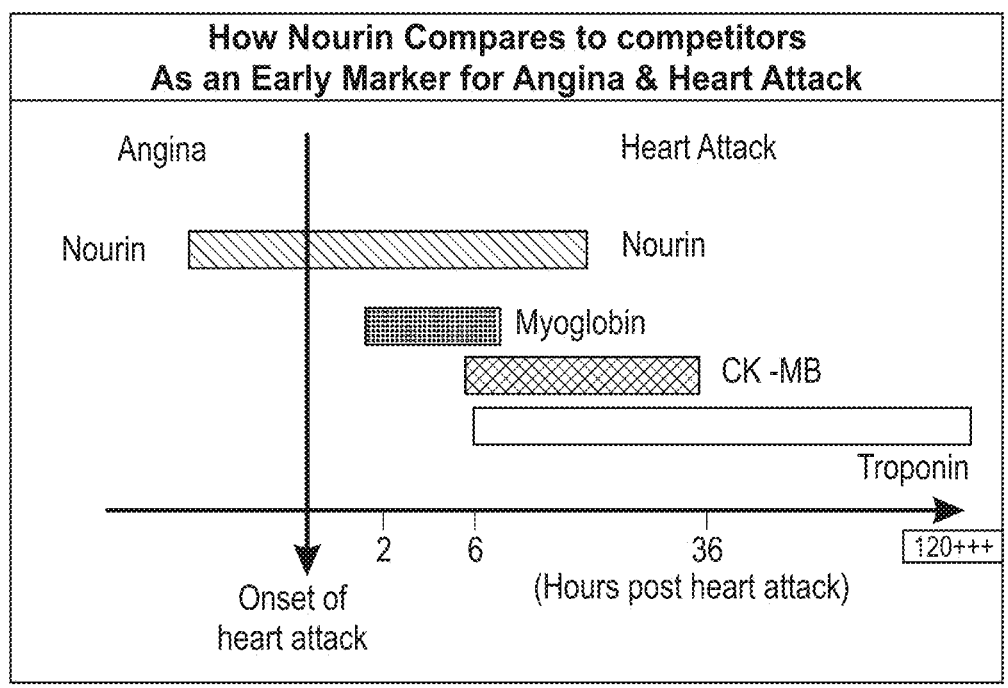
Figure 17A:
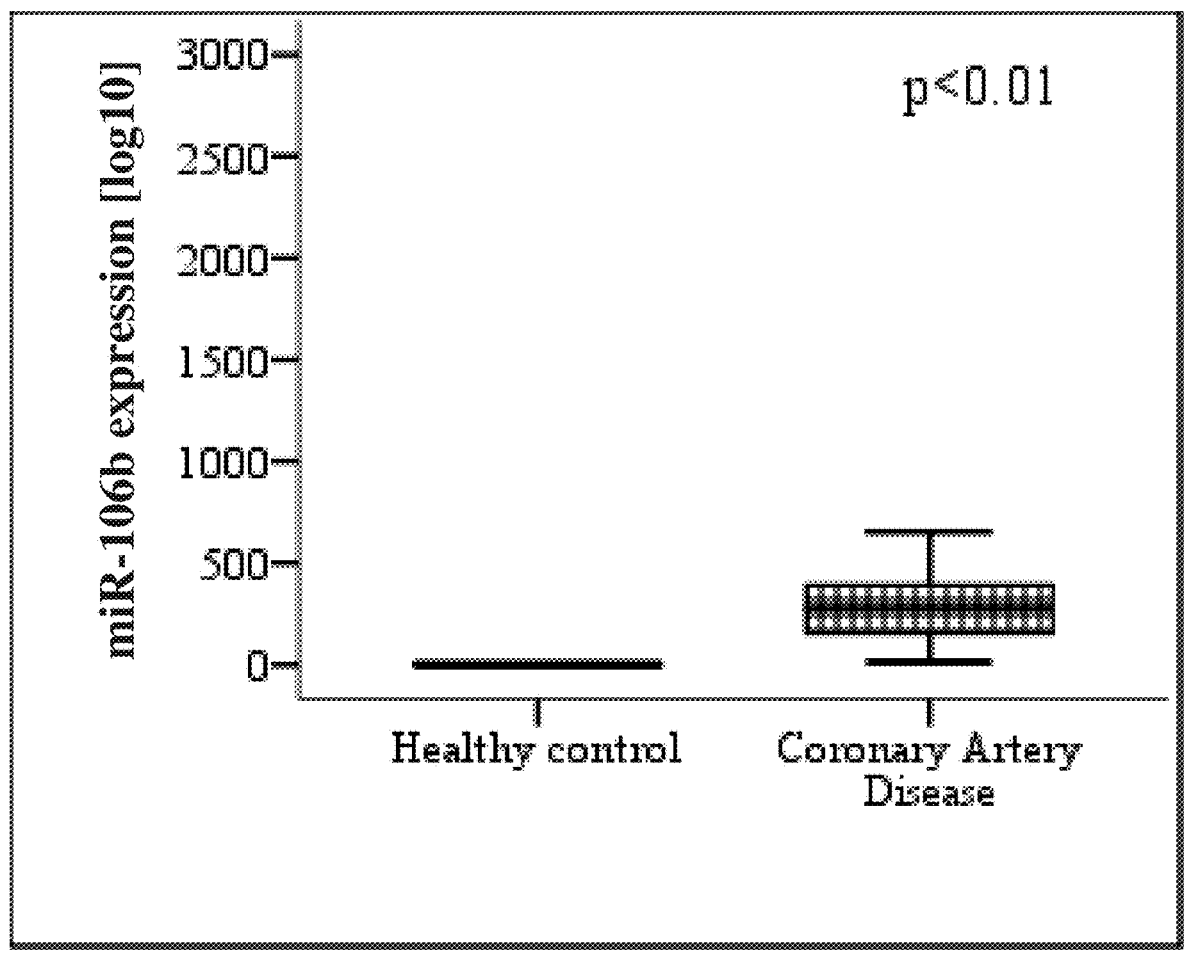
Figure 17B:
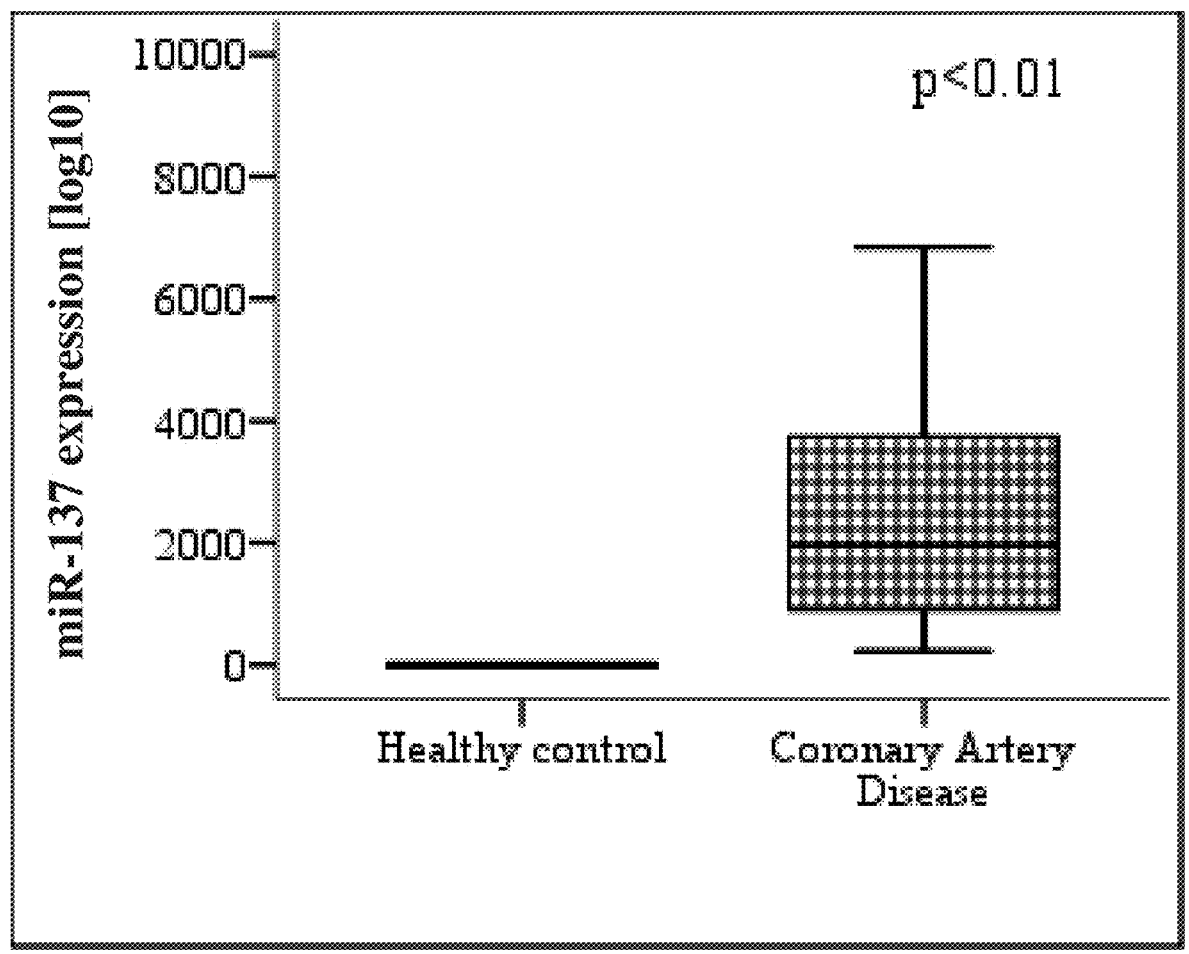
Figure 17C:
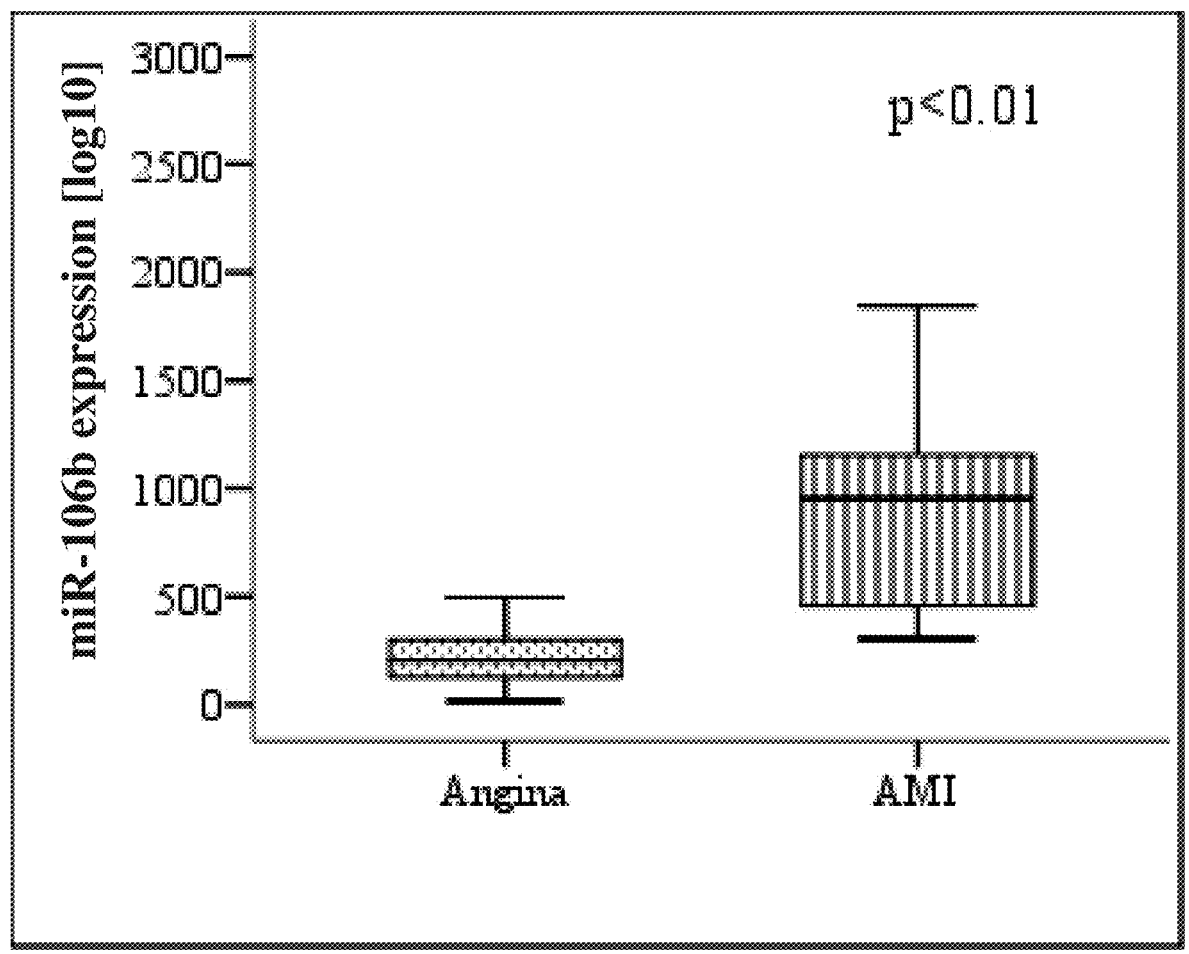
Figure 17D:
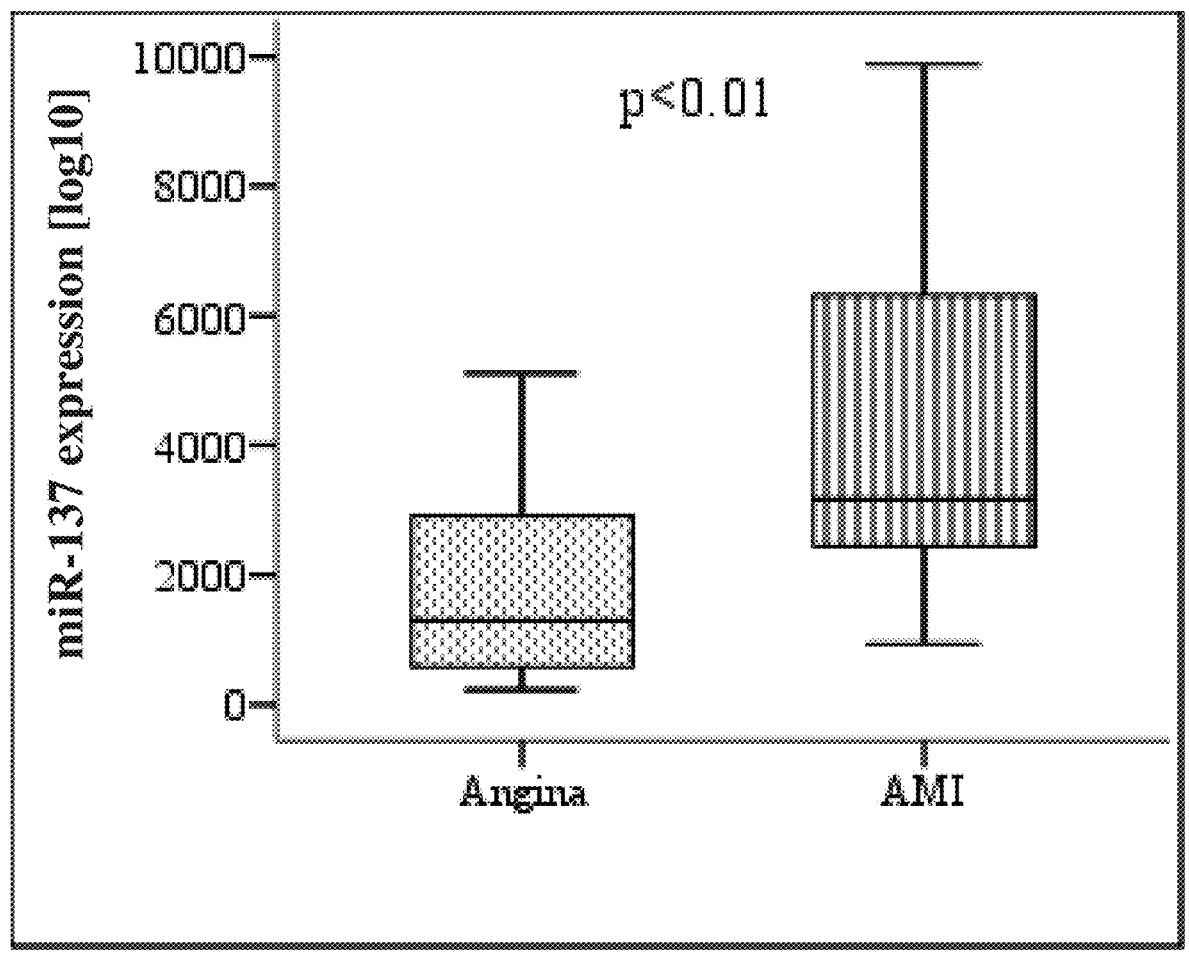
Figure 17E:
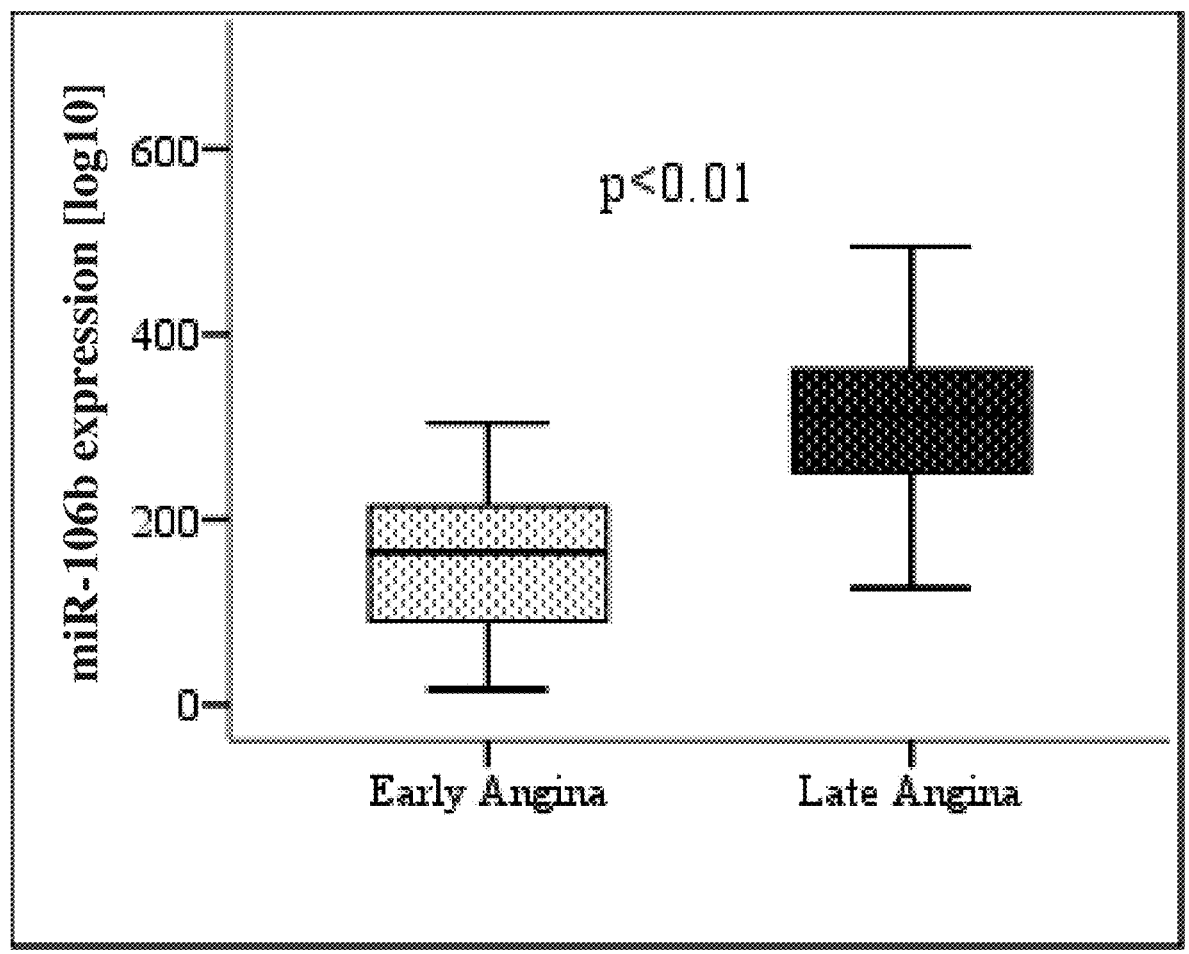
Figure 17F:
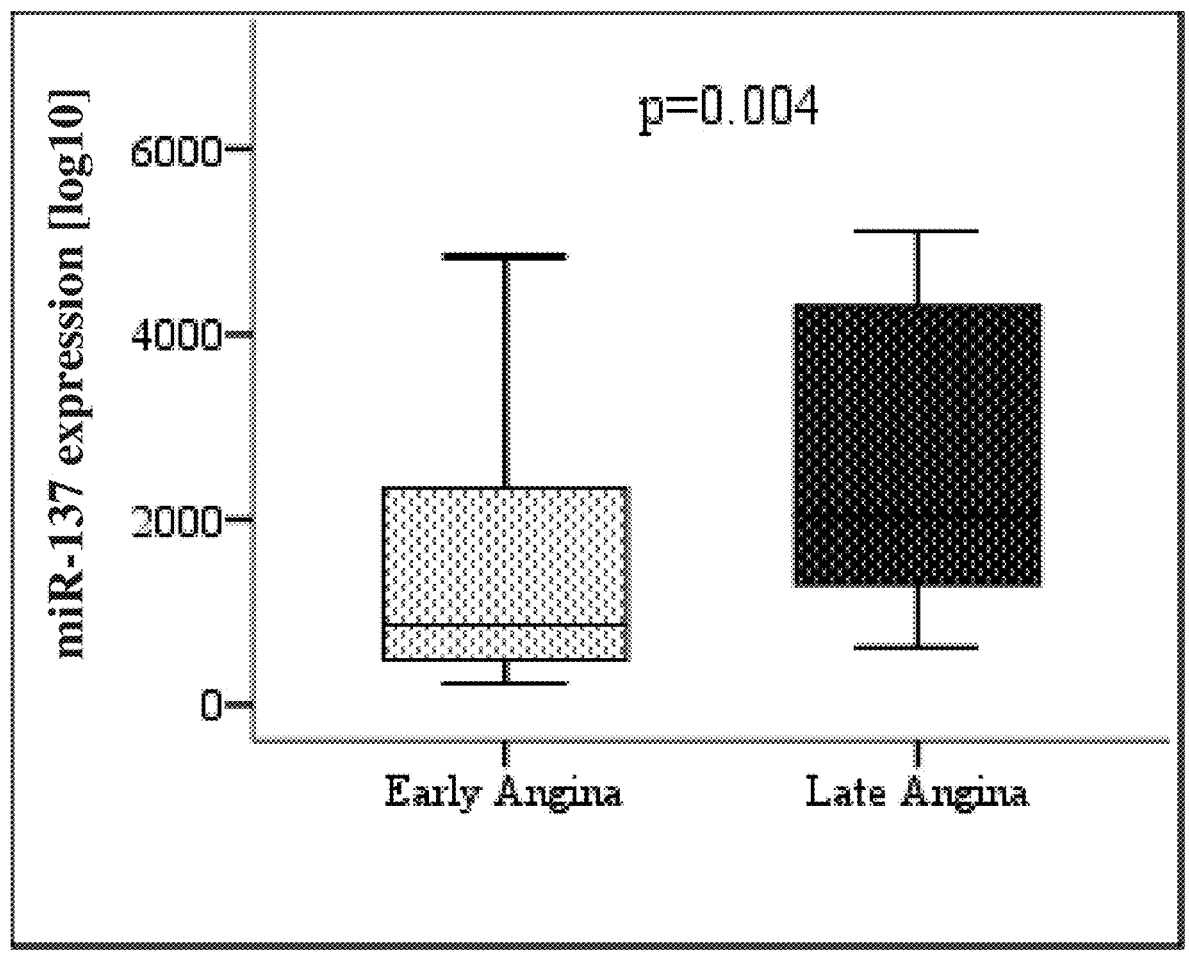
Figure 17G:
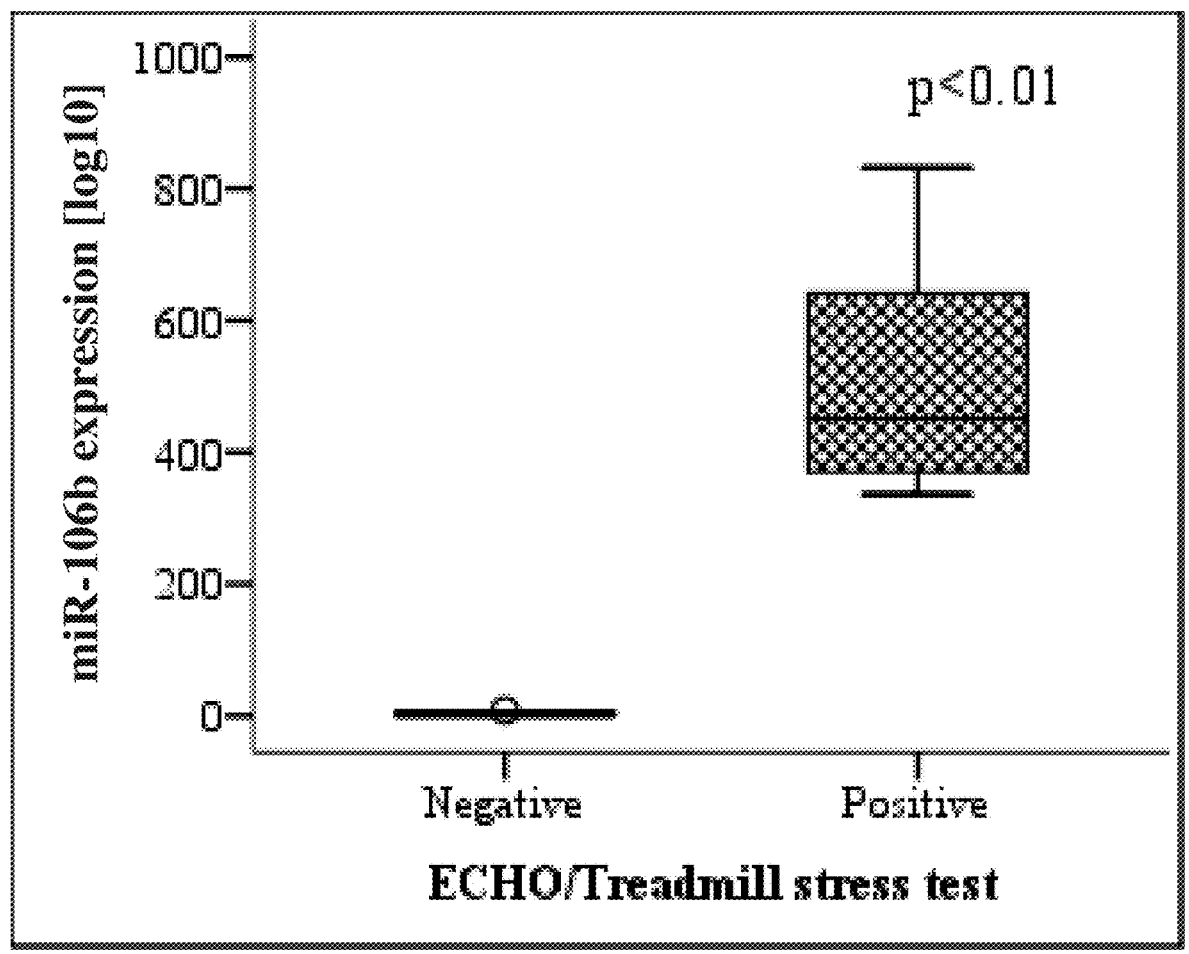
Figure 17H:
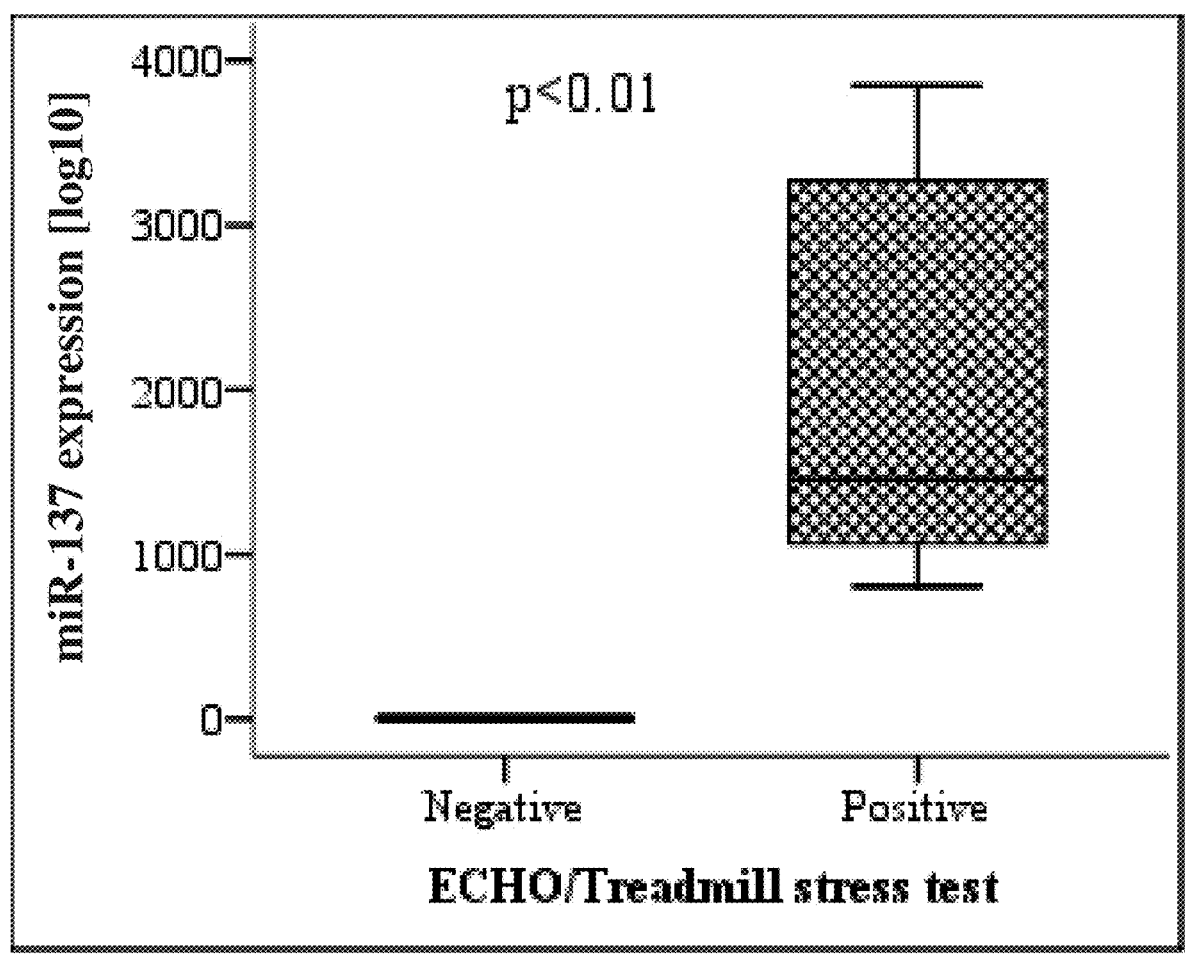
Figure 19A:
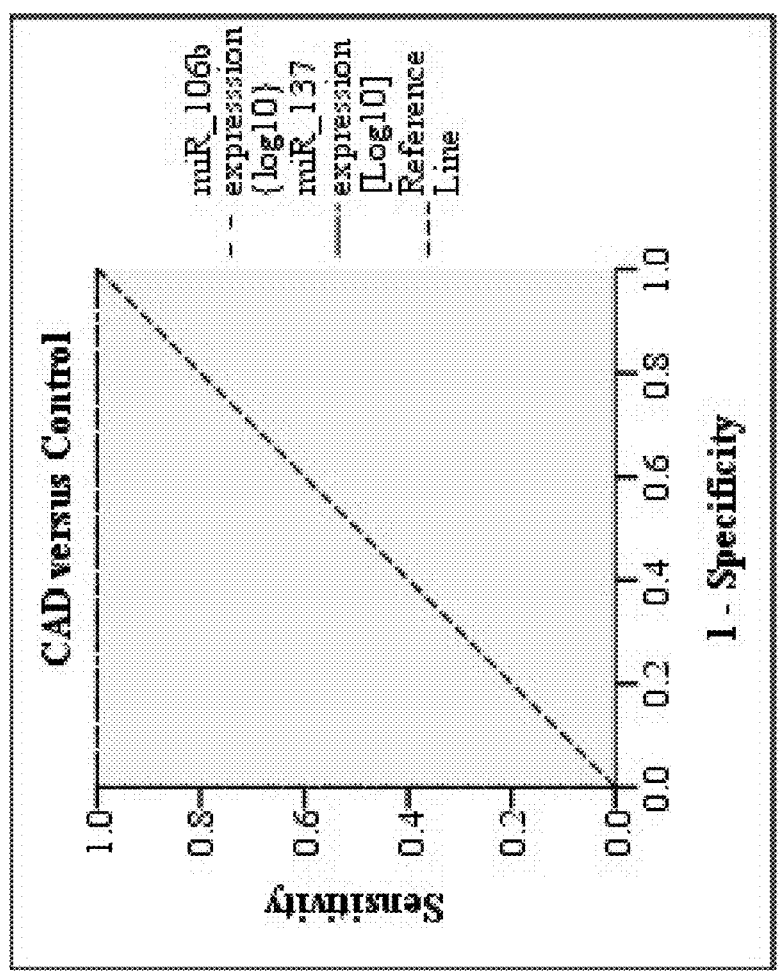
Figure 19B:
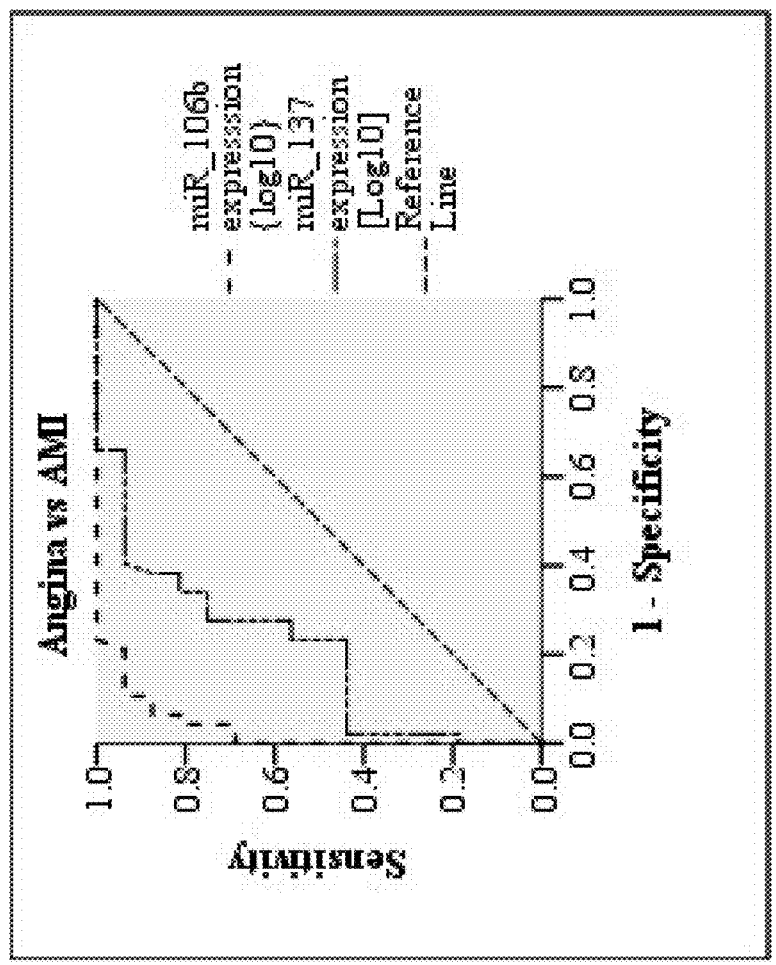
Figure 19C:
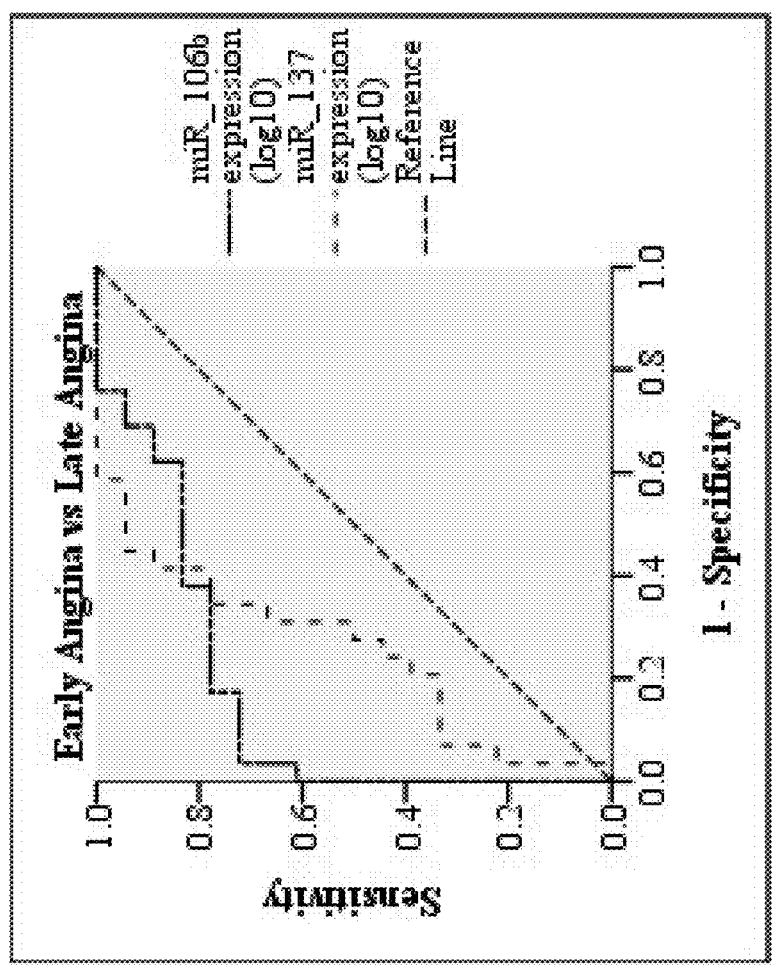
Figure 19D:
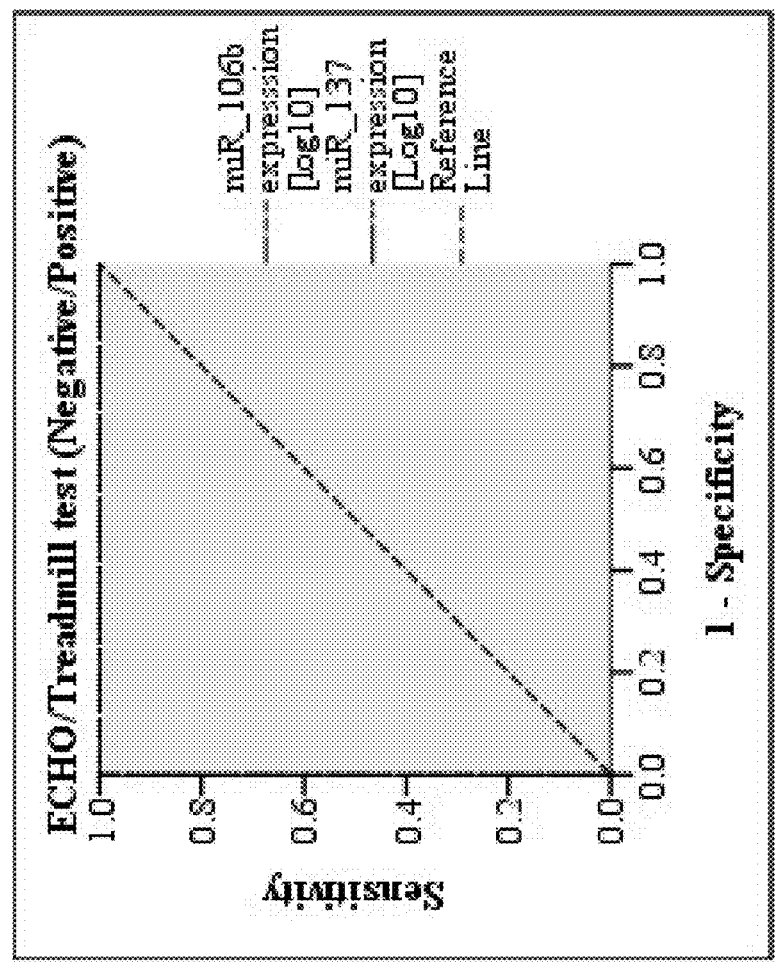

FIG. 14 indicates the timeframe under which various assays for angina and AMI are useful and the absence of biomarkers for angina patients, while several are available for AMI patients. Specifically, the present Nourin assay can diagnose angina prior to proceeding to a heart attack and it can be detected immediately after the initiation of AMI and up to at least 32 hours after an event. The Nourin protein was not tested beyond 32 hours after the onset of chest pain in AMI patients. The present Nourin assay is capable of diagnosing angina in patients, regardless of whether or not they ultimately suffer a heart attack. The myoglobin assay known in the art cannot detect angina and can detect AMI only between about 2 hours and 8 hours after AMI. The CK-MB assay known in the art likewise cannot detect angina, and is useful only between 6 hours and 36 hours after a heart attack. The Troponin assay is likewise limited to use only after 6 to 8 hours post-heart attack, although it can be detected up to 120 hours or more after an ischemic onset. Recent Troponin assays shortened the early detection time to 2 to 6 hours after the initiation of myocardial injury.

FIG. 15A to FIG. 15I indicate the sequence listing of the gene sequences for lncRNA-CTB89H12.4 by PatentIn software. Long non-coding intergenic RNA-(lncRNA-CTB89H12.4) (SEQ ID NO:19).

FIG. 16 is a representation of the comparative analysis for the expression levels of hsa-miRNA-106b (miR-106b) and hsa-miR-137 (miR-137) between: A): healthy controls and patients with coronary artery disease (CAD) defined in this study as patients with early and late angina time and patients with acute myocardial infarction (AMI); B): angina and AMI patients; C): patients with early and late angina time, in which the early angina time of sample collection is 1 to 10 hours after onset of chest pain, while late angina time of sample collection is 24 to 72 hours after onset of chest pain; and D): outpatients suspected of angina with history of chest pain confirmed (positive) or dismissed (negative) by stress ECHO/Treadmill test. Chi-square value of non-parametric Kruskal Wallis test, p value <0.01 is considered a high statistical significance, p value ≤0.05 is considered a significant difference between both groups.

FIG. 17A to FIG. 17H is a representation of the Boxplots graph illustrating the significantly high serum expression levels of hsa-miR-106b (miR-106b) (A) and hsa-miR-137 (miR-137) (B) in coronary artery disease patients compared to healthy control group; the expression levels of hsa-miR-106b (C) and hsa-miR-137 (D) were also significantly higher in AMI patients compared to angina patients (p<0.01); additionally, higher expression levels were detected in late angina patients (24 to 72 hours after onset of chest pain) for hsa-miR-106b (E) and hsa-miR-137 (F) compared to early angina patients (1 to 10 hours after onset of chest pain); Finally, the expression levels of hsa-miR-106b (G) and hsa-miR-137 (H) were significantly higher in outpatient suspected angina patients whom they were positive by ECHO/ECG Treadmill stress test compared to negative stress test group.

FIG. 18 is a representation of the Diagnostic and Prognostic efficacy of hsa-miR-106b (miR-106b) and hsa-miR-137 (miR-137) in patients with myocardial injury [ROC curve analysis]. AUC: area under the curve, ROC: receiving operating characteristics.

FIG. 19A to FIG. 19D is a representation of the Receiving Operating Characteristics Curves (ROC) illustrating: (A): a 100% sensitivity for both hsa-miR-106b (miR-106b) and hsa-miR-137 (miR-137), while, 94% specificity for hsa-miR-106b, and 95% specificity for hsa-miR-137 to diagnose and discriminate between patients with coronary artery disease and healthy controls; (B): a sensitivity of 87% and specificity of 79% were demonstrated for hsa-miR-106b compared to 75% sensitivity and 72% specificity for hsa-miR-137 to discriminate between early and late angina patients; (C): a high prognostic potentials were demonstrated for both hsa-miR-106b and hsa-miR-137 to discriminate angina from AMI patients; and (D): both Nourin related hsa-miR-106b and hsa-miR-137 showed a 100% sensitivity and 85% specificity in discriminating ECHO/ECG Treadmill positive stress test of outpatient angina patients with history of chest pain from patients with non-angina and negative test.

FIG. 20 is a representation of the comparative analysis for the expression levels of mRNA-ANAPC11 (ANAPC11) and mRNA-FTHL-17 (FTHL-17) between: (A): healthy controls and patients with coronary artery disease (CAD) composed of patients with early and late angina time and acute myocardial infarction (AMI); (B): angina and AMI patients; (C): patients with early and late angina time, in which the early angina time of sample collection is 1 to 10 hours after onset of chest pain, while late angina time of sample collection is 24 to 72 hours after onset of chest pain; and (D): outpatients suspected of angina with history of chest pain confirmed (positive) or dismissed (negative) by ECHO/ECG Treadmill stress test. Chi-square value of non-parametric Kruskal Wallis test, p value <0.01 is considered a high statistical significance, p value ≤0.05 is considered a significant difference between both groups.

FIG. 21 is a representation of the comparative analysis for the expression levels of lncRNA-CTB89H12.4 between: (A): healthy controls and patients with coronary artery disease (CAD) composed of patients with early and late angina time and acute myocardial infarction (AMI); (B): angina and AMI patients; (C): patients with early and late angina time, in which the early angina time of sample collection is 1 to 10 hours after onset of chest pain, while late angina time of sample collection is 24 to 72 hours after onset of chest pain; and (D): outpatients suspected of angina with history of chest pain confirmed (positive) or dismissed (negative) by ECHO/ECG Treadmill stress test. Chi-square value of non-parametric Kruskal Wallis test, p value <0.01 is considered a high statistical significance, p value ≤0.05 is considered a significant difference between both groups.

FIG. 22A to FIG. 22L is a representation of the Boxplots graph illustrating a significant high serum expression levels of mRNA-FTHL-17 in: (A): coronary artery disease compared to healthy control group, (B): in AMI compared to angina patients, and in (D): patients with chest pain that were positive to ECHO/ECG Treadmill stress test compared to negative stress test patients (p<0.01). Similar results were observed for the expression of mRNA-ANAPC11 in the same compared groups (E, F and H). In addition, patients with late stage angina (24 to 72 hours) showed a significant downregulation of serum mRNA-FTHL-17 (C) and mRNA-ANAPC11 (G) compared to early angina (1 to 10 hours) group (p<0.01). On the other hand, a significant decrease in serum levels of lncR-CTB89H12.4 was detected in: (I): Coronary artery disease compared to healthy control group, in (J): AMI compared to angina patients, and in (L): patients with chest pain that were positive to ECHO/ECG Treadmill stress test compared to negative stress test patients (p<0.01). In contrary, a significant high expression levels of lncR-CTB89H12.4 was detected in angina patients at early stage of disease compared to late stages.

FIG. 23 is a representation of the Diagnostic and Prognostic efficacy of mRNA-FTHL-17, mRNA-ANAPC11 and lncR-CTB89H12.4 in patients with coronary artery disease (CAD) [ROC curve analysis].

FIG. 24A to FIG. 24D is a representation of the Receiving Operating Characteristics Curves (ROC) illustrating: (A): the sensitivity and specificity for both mRNA-FTHL-17, mRNA-ANAPC11 and lncR-CTB89H12.4, to diagnose and discriminate between patients with coronary artery disease and healthy controls; (B): discriminates between early and late angina patients; (C): to discriminate AMI from angina patients; and (D): in discriminating ECHO/Treadmill positive stress test from patients with negative test.

FIG. 25A to FIG. 25D indicate the expression pattern and level of the Nourin-based molecular biomarker hsa-miR-137 (miR-137) in relation to currently used standard procedures to determine the presence or absence of angina in patients with history of chest pain. Currently, stress test is used to measure the health of heart by determining how it responds to exertion (e.g., exercise) and that electrocardiogram (ECG) is used with the exercise stress test to record the electrical activity of the heart and can diagnose heart rhythm problems and damage. Additionally, echocardiogram (ECHO) uses sound waves to produce a video image of the heart with any abnormalities. Similarly, the invasive Nuclear Thallium is currently used to identify myocardial ischemia. FIG. 25 indicates (A): serum samples collected before conducting the ECHO/ECG Treadmill stress test (refer to as Pre) from healthy control, as well as from suspected angina patients whom they were positive and negative 30 minutes after ECHO/ECG Treadmill stress. The graph shows significantly higher levels of hsa-miR-137 were detected in samples taken Pre-stress test of angina positive patients compared to the very low expression detected in Pre-stress test from angina negative patients. The low level of hsa-miR-137 in non-angina patients was comparable to baseline values in healthy controls; (B): serum samples taken 30 minutes after conducting the ECHO/ECG Treadmill stress test (Post) suspected angina patients whom they were positive and negative ECHO/ECG Treadmill stress test. Significantly higher levels of hsa-miR-137 were detected the Post samples of positive stress test patients compared to the very low expression detected in the Post samples of negative stress test patients; (C): This graph shows the combined expression pattern of the level of hsa-miR-137 taken before (Pre) and after (Post) the stress test demonstrating that high expression levels were detected Pre and Post stress test in patients with positive test, while, low expression levels were detected Pre and Post stress test in patients with negative stress test; and (D): Boxplots graph illustrating significantly ($p<0.001$) higher serum expression levels of hsa-miR-137 in positive patients before and after the stress test compared to the low expression levels detected in the negative stress test group. There was no statistical difference in the hsa-miR-137 gene expression before and after the stress test in positive and negative patients.

FIG. 26A to FIG. 26D indicate the expression pattern and level of the Nourin-based molecular biomarker hsa-miR-106b (miR-106b) in: (A): serum samples taken before conducting the ECHO/ECG Treadmill stress test (refer to as Pre) from negative healthy control, as well as suspected angina patients whom they were positive and negative 30 minutes after ECHO/ECG Treadmill stress. The graph shows significantly higher levels of hsa-miR-106b were detected in samples taken Pre stress test of positive angina patients compared to the very low expression detected in the Pre stress test of the negative patients, which was comparable to baseline values in healthy controls; (B): serum samples taken 30 minutes after conducting the ECHO/ECG Treadmill stress test (Post) suspected angina patients whom they were positive and negative by ECHO/ECG Treadmill stress test. Significantly higher levels of hsa-miR-106b were detected the Post samples of positive stress test patients compared to the very low expression detected in the Post samples of negative stress test patients; (C): This graph shows the combined expression pattern of the level of hsa-miR-106b taken before (Pre) and after (Post) the stress test demonstrating that high expression levels were detected Pre and Post stress test in patients with positive test, while, low expression levels were detected Pre and Post stress test in patients with negative stress test; and (D): Boxplots graph illustrating significantly ($p<0.01$) higher serum expression levels of hsa-miR-106b in positive patients before and after the stress test compared to the low expression levels detected in the negative stress test group. Interestingly, there was statistical ($p=0.02$) difference in the hsa-miR-106b gene expression before and after the stress test in positive, but not in the negative patients.

FIG. 27A to FIG. 27D indicate significantly higher levels of hsa-miR-137 (miR-137) (A) and miR-106b (C) were detected in Post samples of positive stress test patients compared to the very low expression detected in Post samples of negative stress test patients. Both Nourin-related hsa-miR-137 (B) and hsa-miR-106b (miR-106b) (D) showed a 100% sensitivity and 85% specificity in discriminating ECHO/ECG Treadmill stress test of outpatient angina patients with history of chest pain from patients with non-angina and negative test (a cut-off of 8 for hsa-miR-137 and a cut-off of 172 for hsa-miR-106b). They also possess a discriminating cut-off value of 3.5 for both miRNAs to diagnose coronary artery disease patients from healthy controls.

FIG. 28A to FIG. 28D indicate the serum gene expression pattern and level of the Nourin-based molecular biomarker hsa-miR-137 (miR-137) in serum samples obtained at presentation, from UA patients (n=30), whom their diagnosis was confirmed by invasive coronary angiography and negative Troponin, STEMI patients (n=16), and healthy controls (n=16). Coronary angiogram test was conducted at Cath labs and it determined arteries blood supply, helping physicians spot blockages and diagnose angina patients. FIG. 25 indicates (A): significantly higher expression pattern of hsa-miR-137 was detected in UA compared to healthy ($p<0.001$), STEMI compared to UA ($p<0.001$), as well as STEMI compared to healthy ($p<0.001$). There is none to a minimal gene expression of miR-137 in normal non-stressed tissues; (B): Boxplots graph illustrating gene expression of hsa-miR-137 was up-regulated by 1,185-fold in UA (median=1,244.41) compared to healthy (1.05), and by 2.5-fold in STEMI (3,162.72) compared to UA; (C): Boxplots graph illustrating that there is no significant difference in gene expression of hsa-miR-137 detected in serum and plasma samples obtained from UA, STEMI and healthy control, supporting the use of either serum or plasma samples; and (D): Boxplots graph illustrating a statistical significance ($p<0.05$) of hsa-miR-137 gene expression level between male and female in UA patients, but not in STEMI patients ($p>0.05$).

FIG. 29A to FIG. 29D is a representation of the comparative analysis for hsa-miR-137 (miR-137) expression levels between: (A): healthy and acute coronary syndromes (ACS) patients composed of UA and STEMI (n=46) ($p<0.01$). These results support our previous findings that the Nourin "protein" measured by leukocyte chemotaxis assay and antibody/ELISA, is elevated in ACS patients and not in healthy subjects; (B): hsa-miR-137 gene expression in healthy, UA, and STEMI as described in FIG. 28B; (C): mRNA-FTHL-17 gene expression in healthy, UA, and STEMI, where there was upregulation in STEMI and UA with a statistical difference of $p<0.01$ between UA and STEMI, as well as between healthy and STEMI, but there was no statistical difference between healthy and UA; and (D): lncR-CTB89H12.4 gene expression in healthy, UA, and STEMI, where a significant downregulation was indicated in STEMI patients and there is a statistical difference between STEMI, UA and healthy ($p<0.0001$). Healthy controls showed upregulation of lncR-CTB89H12.4.

Figure 30A:
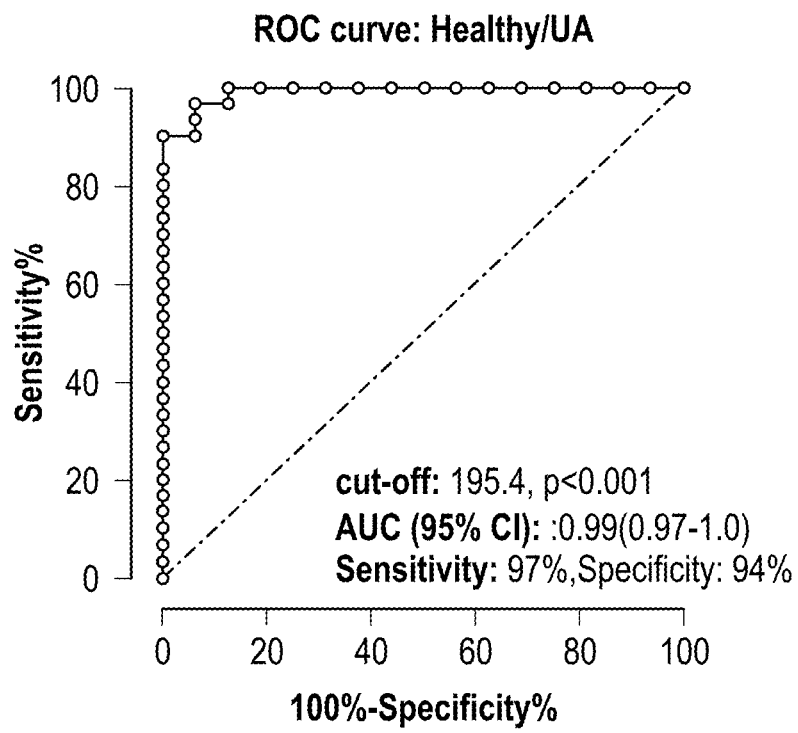
Figure 30B:
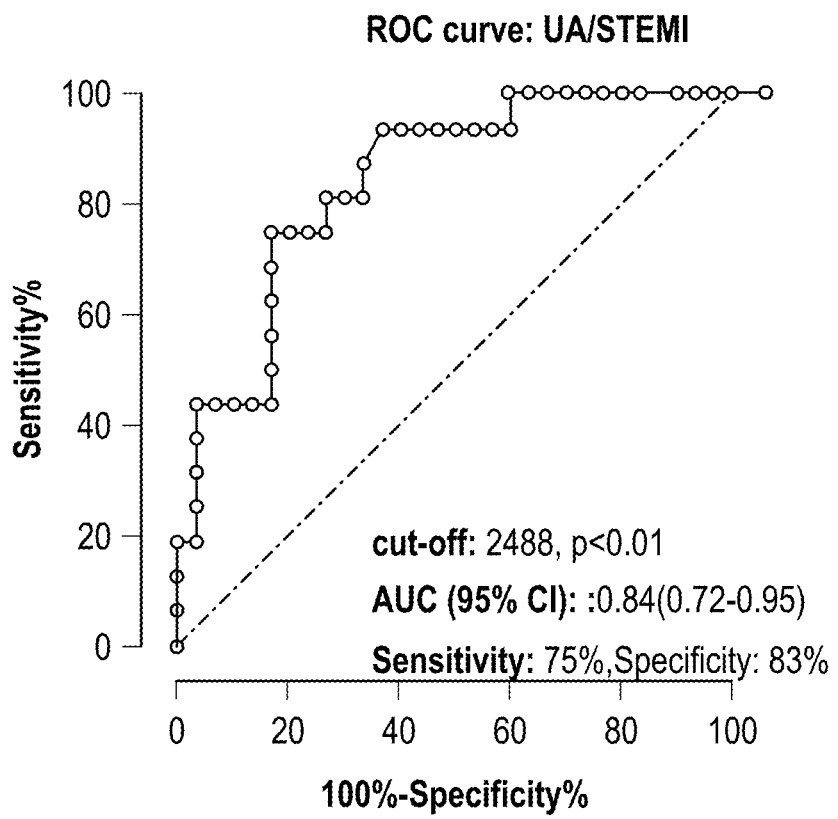
Figure 31A:
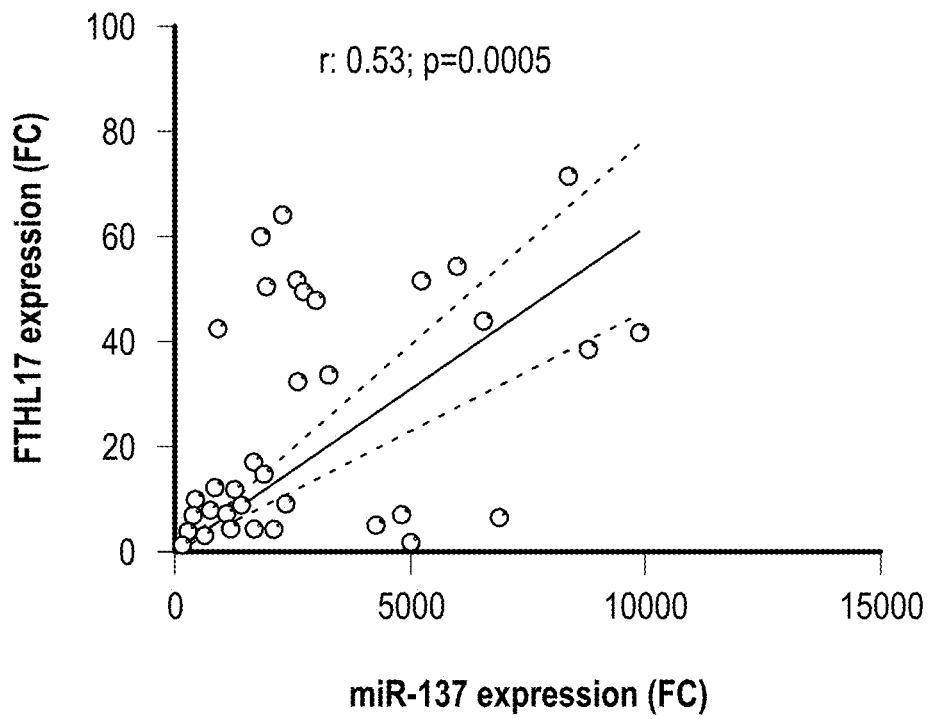
Figure 31B:
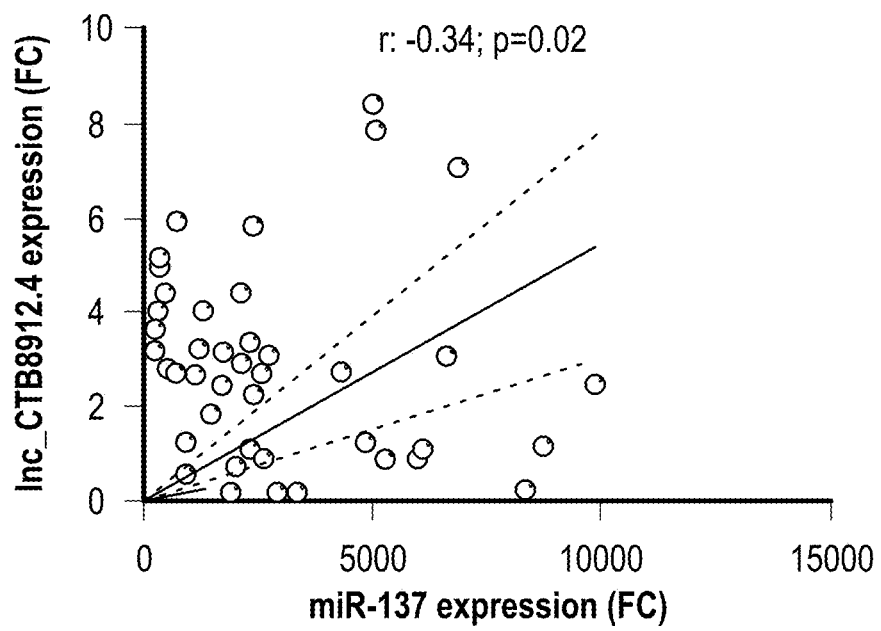
Figures 31C, 31D:
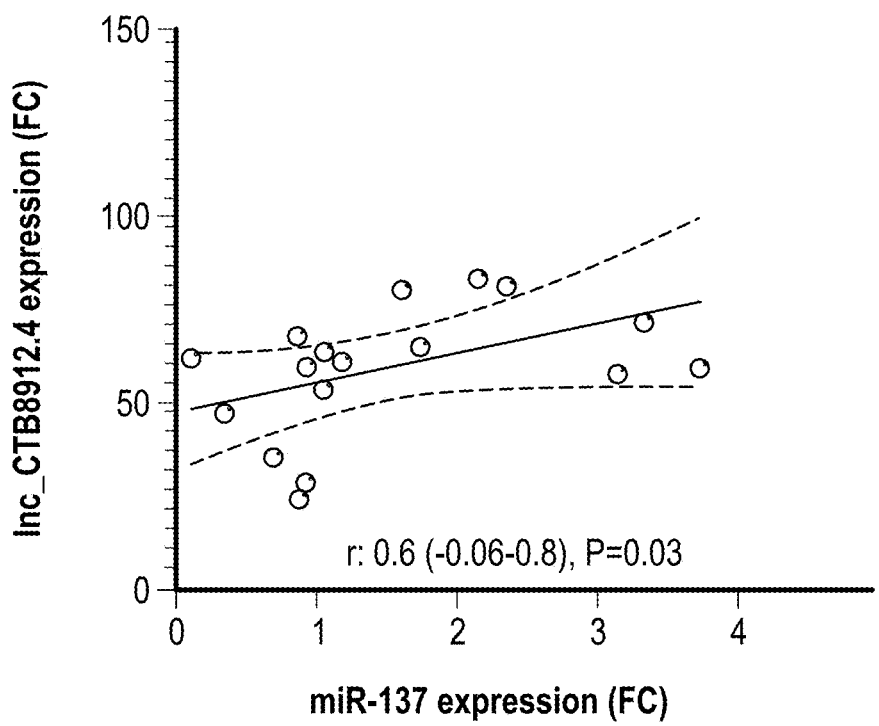

FIG. 30A to FIG. 30B is a representation of the Receiving Operator Characteristics (ROC) analysis revealed: (A): a statistically significant difference ($p<0.001$) at a cutoff: 195.4 for hsa-miR-137 (miR-137) to discriminate UA from healthy with a test sensitivity and specificity of 97% and 94%, respectively; and (B): a statistically significant difference ($p<0.01$) at a cutoff: 2,488 for hsa-miR-137 to discriminate UA from STEMI with a diagnostic test sensitivity of 75% and specificity of 83%.

FIG. 31A to FIG. 31D is a Spearman's correlation analysis revealed correlation between hsa-miR-137 (miR-137)/mRNA-FTHL-17/lncR-CTB89H12.4 in ACS patients (UA+STEMI) (n=46) with a significant association of hsa-miR-137 with mRNA-FTHL-17 ($p=0.0005$), and hsa-miR-137 with lncR-CTB89H12.4 ($p=0.02$).

FIG. 32A to FIG. 32D indicate the serum gene expression pattern and level of the Nourin-based molecular biomarker hsa-miR-106b (miR-106b) in serum samples obtained at presentation, from UA patients (n=30), whom their diagnosis was confirmed by invasive coronary angiography and negative Troponin, STEMI patients (n=16), and healthy controls (n=16). (A): significantly higher expression pattern of hsa-miR-106b were detected in UA compared to healthy ($p<0.001$), STEMI compared to UA ($p<0.001$) and STEMI compared to healthy ($p<0.001$). There is none to a minimal gene expression of miR-106b in normal non-stressed tissues; (B): Boxplots graph illustrating gene expression of hsa-miR-106b was up-regulated by 150-fold in UA compared to healthy, and by 4.6-fold in STEMI compared to UA; (C): Boxplots graph illustrating that there is no significant difference in gene expression of hsa-miR-106b detected in serum and plasma samples obtained from UA, STEMI and healthy control, supporting the use of either serum or plasma samples; and (D): Boxplots graph illustrating no statistical significance ($p>0.05$) of hsa-miR-106b gene expression level between male and female in UA and STEMI patients.

FIG. 33A to FIG. 33D is a representation of the comparative analysis for hsa-miR-106b (miR-106b) expression levels between: (A): healthy and ACS patients composed of UA and STEMI (n=46) ($p<0.01$), supporting our previous findings that the Nourin "protein" measured by leukocyte chemotaxis assay and antibody/ELISA, is elevated in ACS patients, but not in healthy subjects; (B): hsa-miR-106b gene expression in healthy, UA, and STEMI as described in FIG. 32B; (C): mRNA-ANAPC11 gene expression in healthy, UA, and STEMI, where there was upregulation in STEMI and UA with statistical difference ($p<0.0001$) between UA and healthy, as well as STEMI and healthy, but there was no statistical difference between UA and STEMI; and (D): lncR-CTB89H12.4 gene expression in healthy, UA, and STEMI, where a significant downregulation was indicated in STEMI patients and there is a statistical difference between STEMI, UA and healthy ($p<0.0001$). Healthy controls showed upregulation of lncR-CTB89H12.4.

Figure 34A:
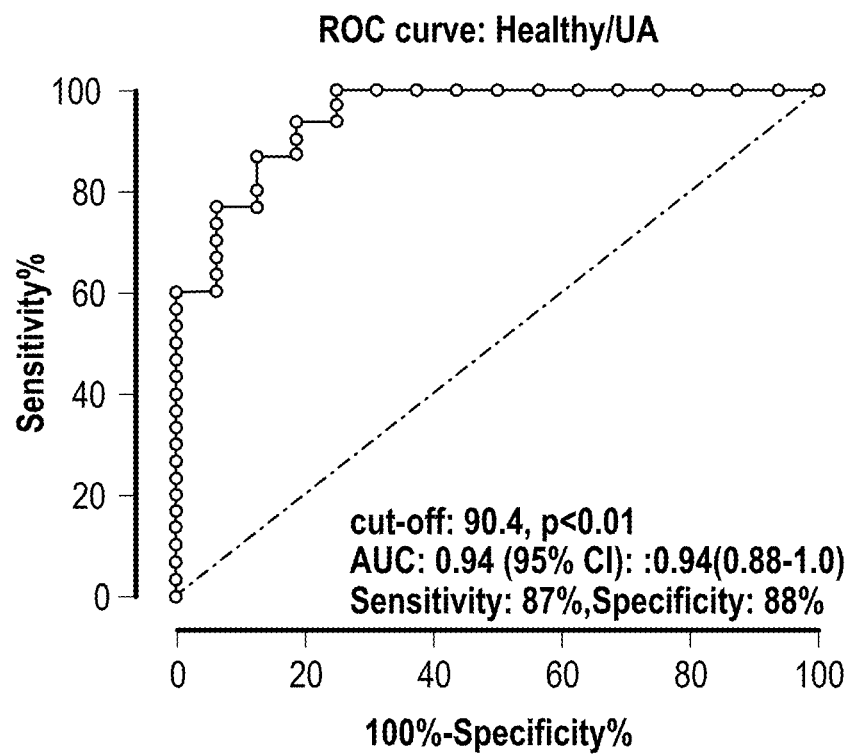
Figure 34B:
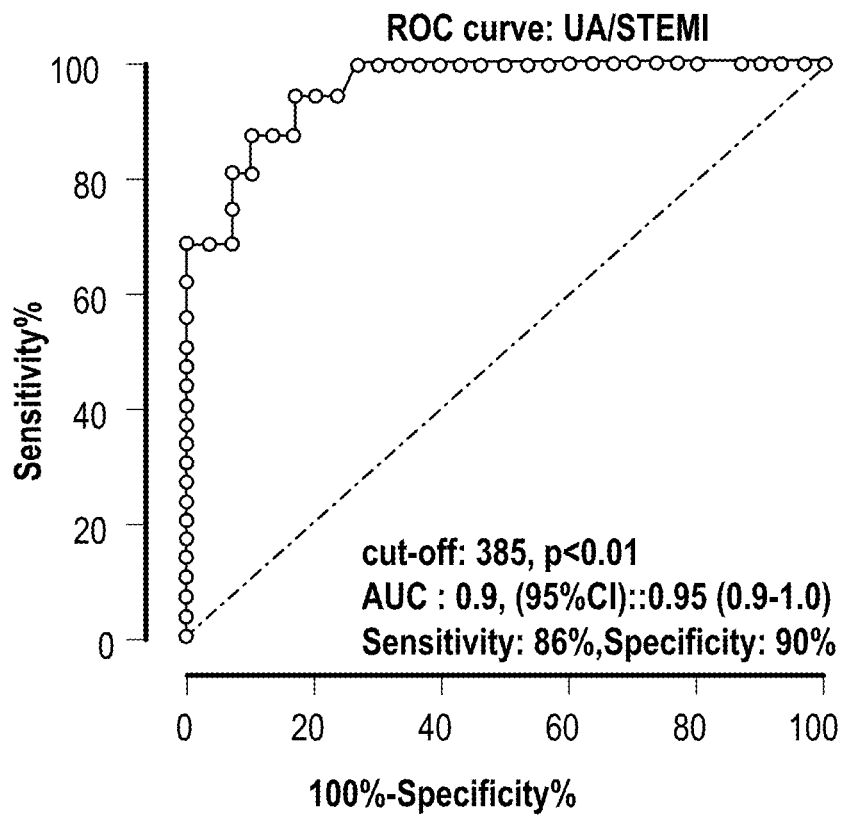
Figure 35A:
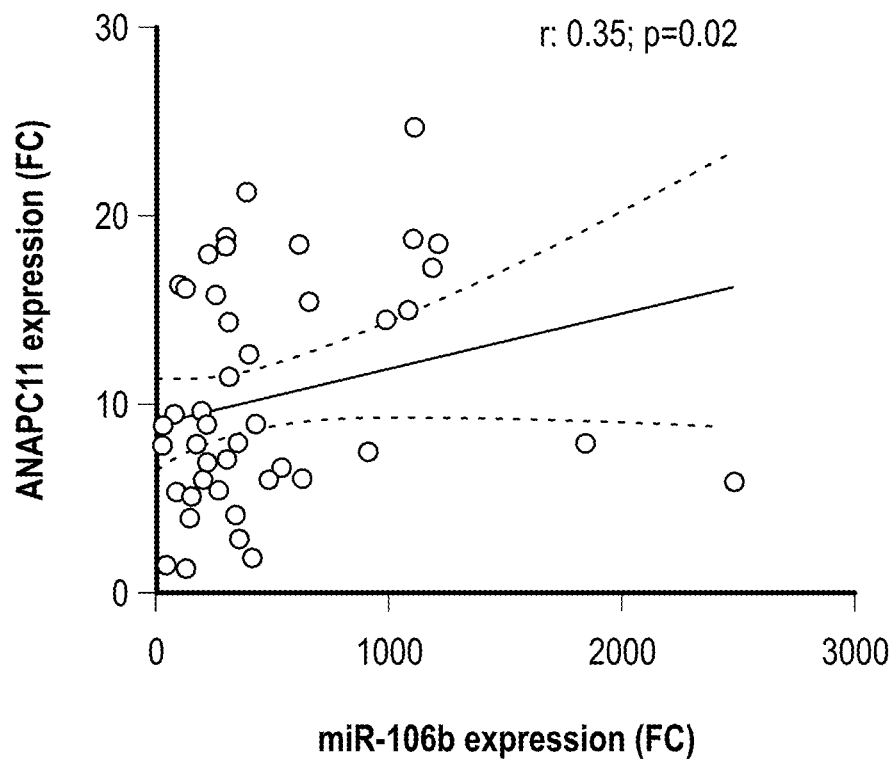
Figure 35B:
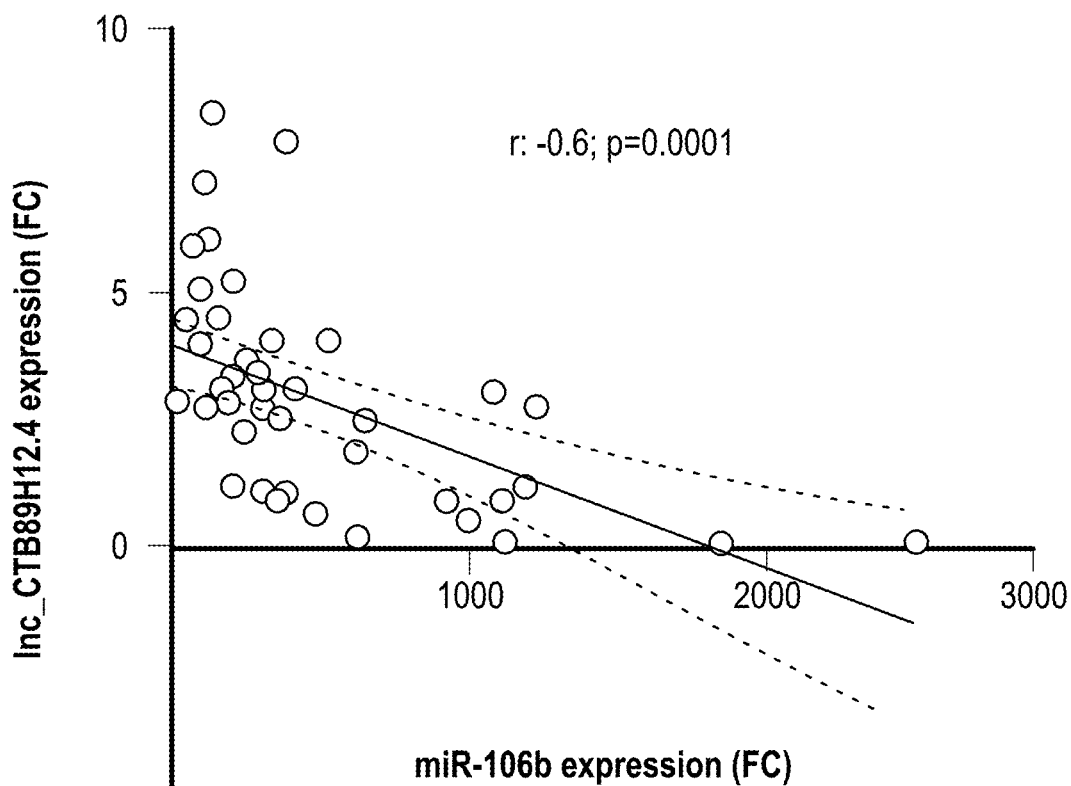
Figures 35C, 35D:
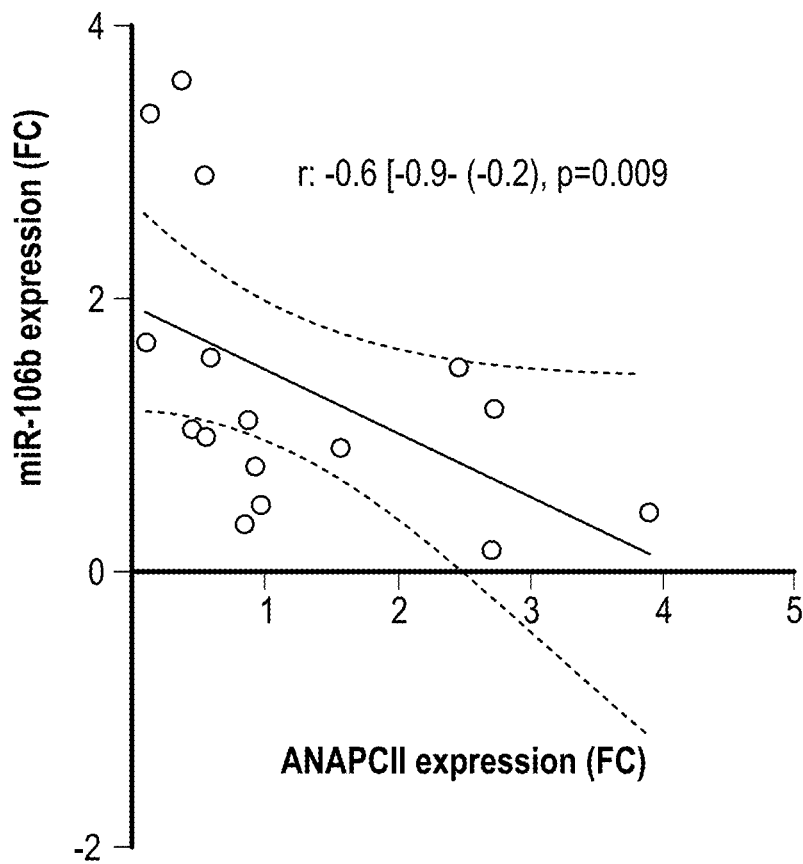

FIG. 34A to FIG. 34B is a representation of the Receiving Operator Characteristics (ROC) analysis revealed: (A): a statistically significant difference ($p<0.01$) at a cutoff: 90.4 for hsa-miR-106b (miR-106b) to discriminate UA from healthy with a test sensitivity and specificity of 87% and 88%, respectively; (B): a statistically significant difference ($p<0.01$) at a cutoff: 385 for hsa-miR-106b to discriminate UA from STEMI with a diagnostic test sensitivity of 86% and specificity of 90%.

FIG. 35A to FIG. 35D is a representation of the Spearman's correlation analysis revealed correlation between hsa-miR-106b (miR-106b)/mRNA-ANAPC11/lncR-CTB89H12.4 in ACS patients (UA+STEMI) (n=46) with a significant association of hsa-miR-106b with mRNA-ANAPC11 ($p=0.02$), and hsa-miR-106b with lncR-CTB89H12.4 ($p=0.0001$).

Figure 36A:
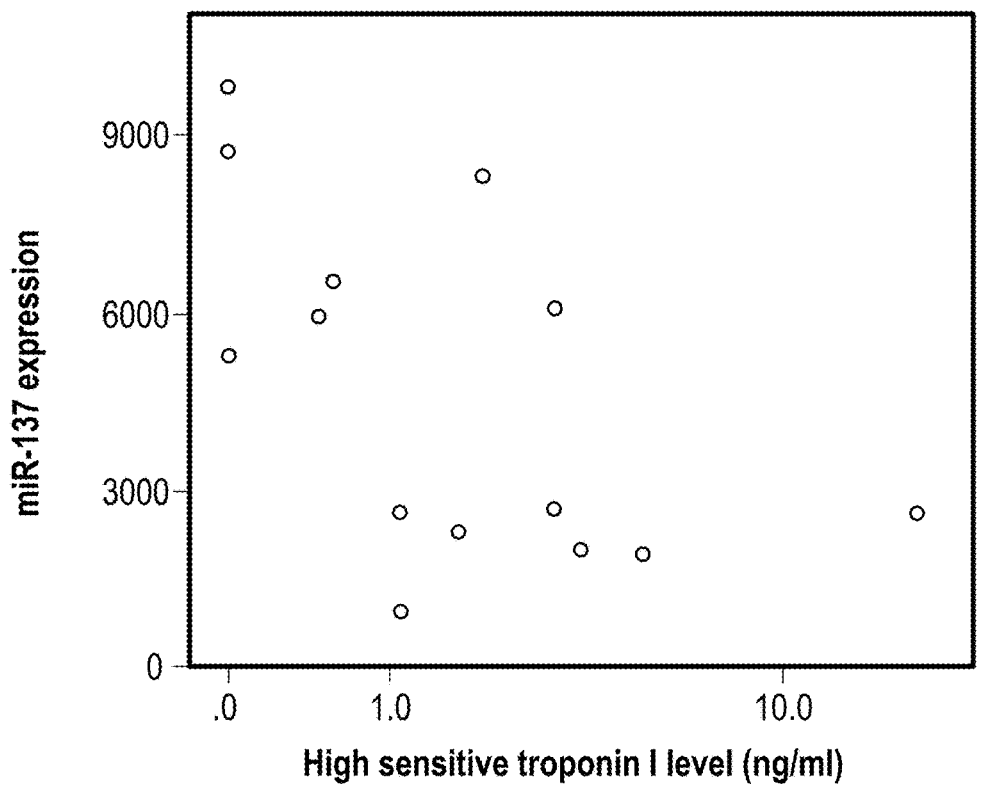
Figure 36B:
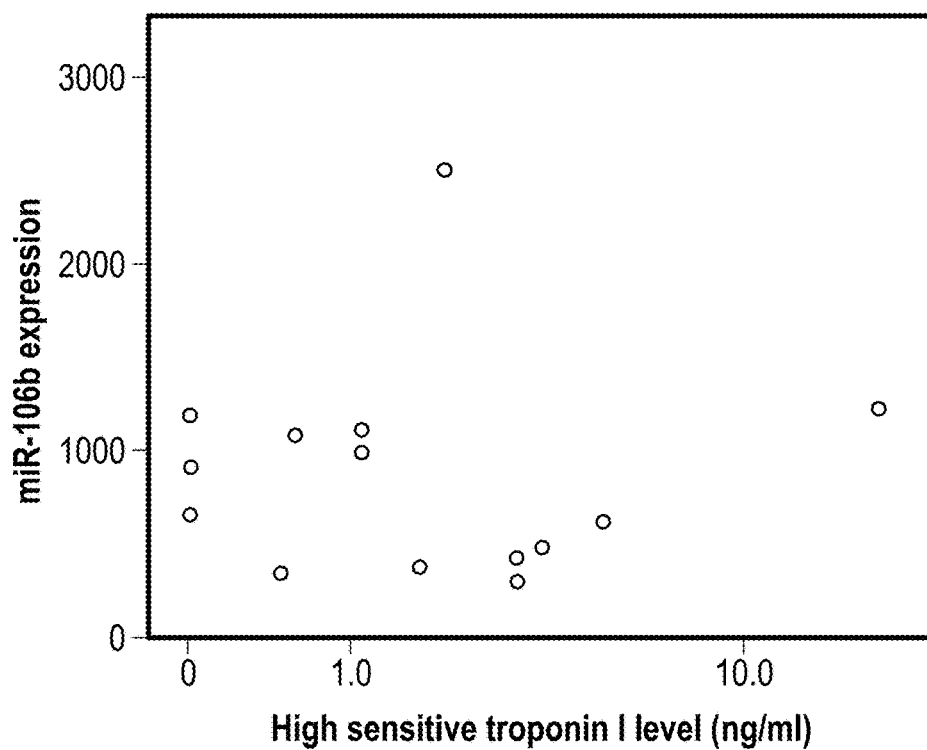

FIG. 36A to FIG. 36B indicate high gene expression levels of Nourin-dependent hsa-miR-137 (miR-137) (A) and hsa-miR-106b (miR-106b) (B) in serum samples collected from STEMI patients at presentation to hospital ED in comparison to Troponin levels in same patients. Graphs also indicate that in 3 patients out of the 16 STEMI patients, the standard cardiac-biomarker hs-Troponin I was "undetectable" and still below the clinical decision level (below the 99th of URL), while all 16 STEMI patients showed high expressions of both hsa-miR-137 and hsa-miR-106b at presentation to ED. This finding further confirms that the Nourin biomarkers are detected "earlier" than Troponin in STEMI patients, and that Nourin gene expression and protein were detected at presentation without the need for additional waiting as in the case of Troponin for some patients. Roche Elecsys Cobas was used to measure Troponin I.

Figure 37A:
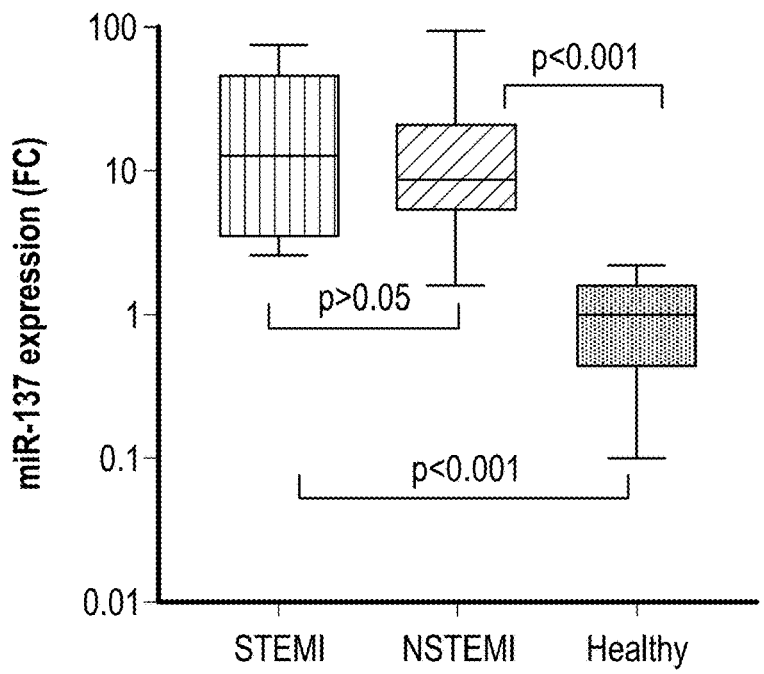
Figure 37B:
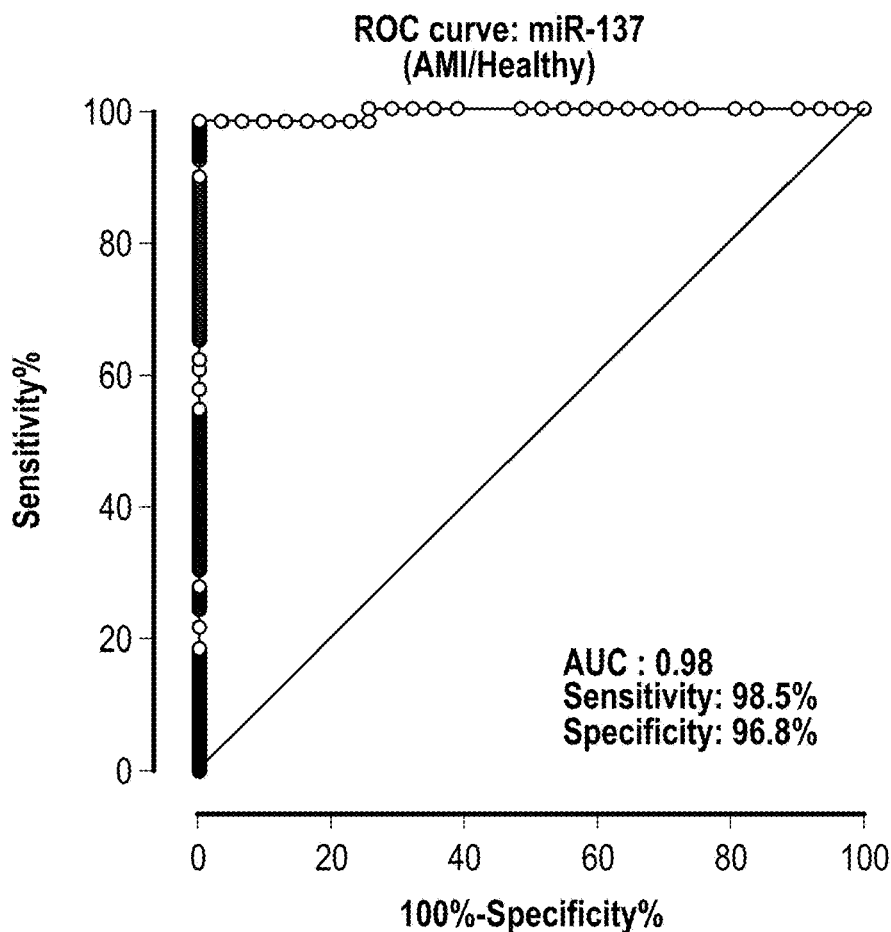

FIG. 37A to FIG. 37B indicate high gene expression levels of Nourin gene-based RNA molecular network biomarker, hsa-miR-137 (miR-137) in: (A): serum samples of STEMI (n=55) and NSTEMI (n=14) patients at presentation to hospital ED with chest pain within first 8 hours and Troponin levels above the decision limit. Low level of gene expression was detected in healthy subjects (n=31), where there was none to a minimal gene expression of miR-137 in normal non-stressed tissues. There was a statistically significant difference of $p<0.001$ between AMI (STEMI+NSTEMI) patients and healthy, but not between STEMI and NSTEMI patients ($p>0.05$); and (B): Receiving Operator Characteristics (ROC) analysis also revealed a statistically significant difference in hsa-miR-137 that discriminated AMI patients from healthy controls with a test sensitivity and specificity of 98.5% and 96.8%, respectively.

Figure 38:
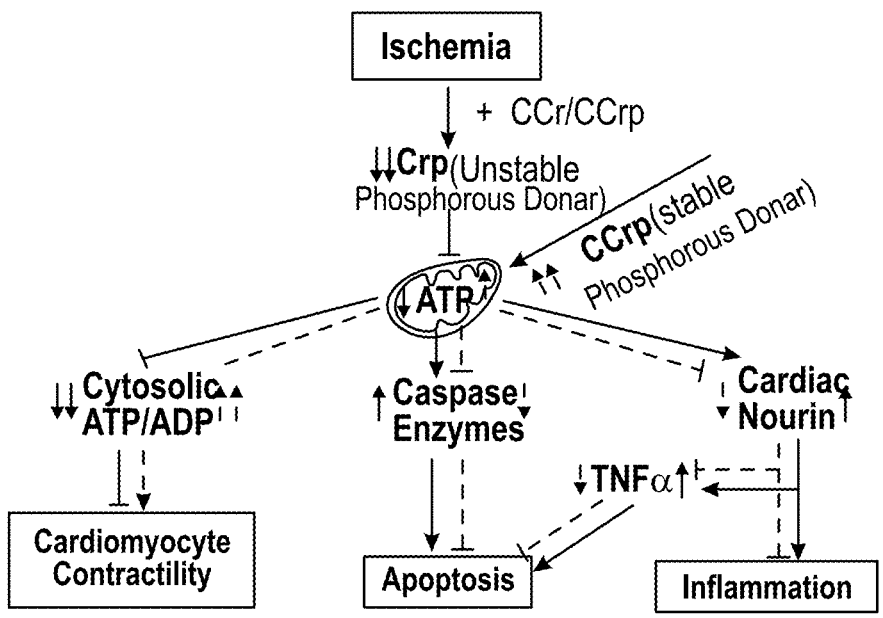

FIG. 38 is a representation of the proposed mechanism of action of the cardioprotective benefits of Cyclocreatine (CCr) and Cyclocreatine Phosphate (CCrP).

Figure 39A:
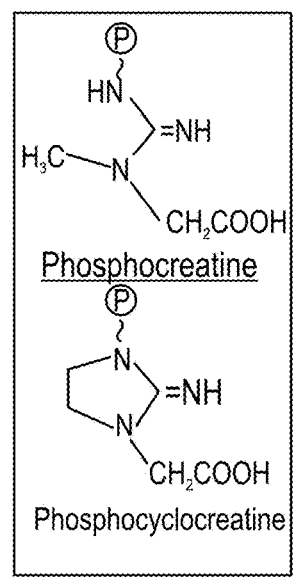
Figure 39B:
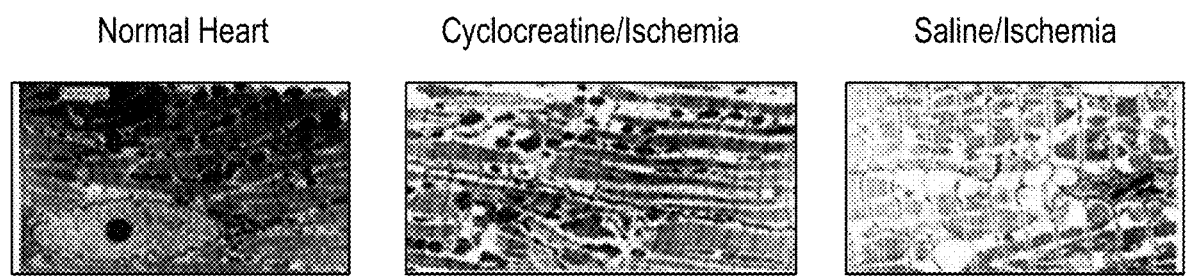

FIG. 39A to FIG. 39B indicate: (A): the chemical structure of Phosphocreatine (CrP) and Cyclocreatine Phosphate (CCrP); and (B): how Cyclocreatine significantly reduced myocardial cell injury in the intact AMI dog model of LAD occlusion for 1 hour followed by reperfusion for 2 hours.

Figure 40A:
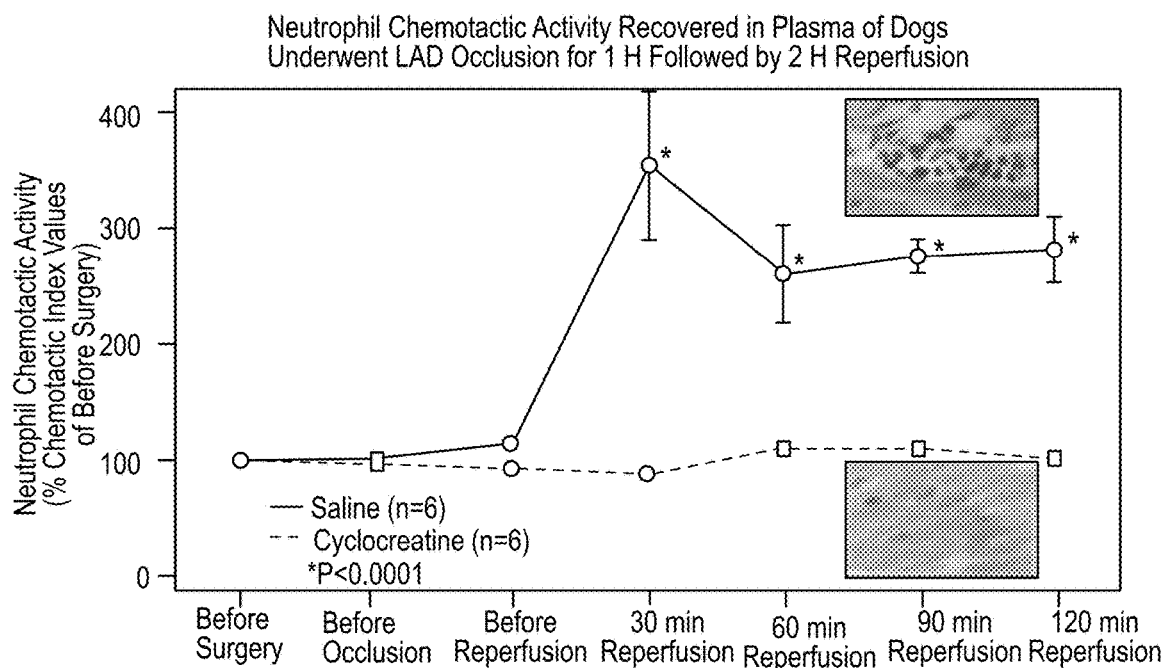
Figure 40B:
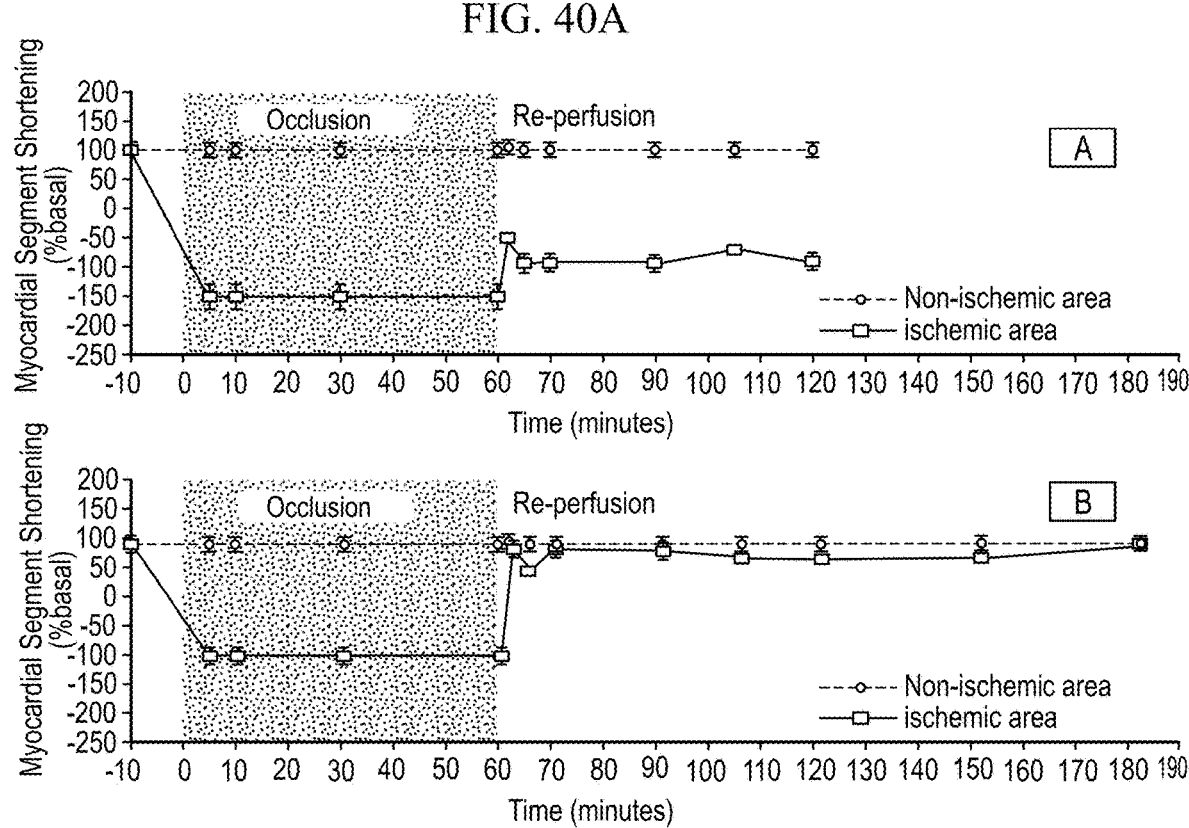

FIG. 40A to FIG. 40B indicate: (A): Cyclocreatine inhibits levels of Nourin protein in plasma samples in the intact AMI dog model of LAD occlusion for 1 hour followed by reperfusion for 2 hours, as well as reduces neutrophil accumulation into the myocardium after reperfusion for 2 hours; and (B): Cyclocreatine B immediately restores heart contractile function during reperfusion compared to control saline hearts A which never recovered in the intact AMI dog model of LAD occlusion for 1 hour followed by reperfusion for 2 hours.

Figure 41A:
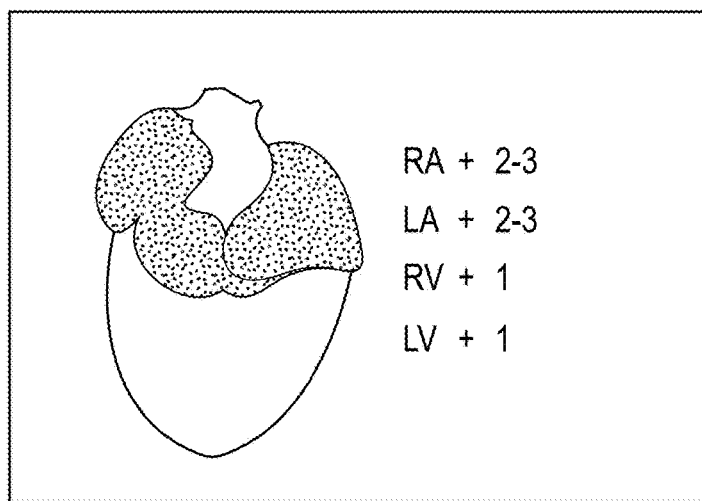
Figure 41B:
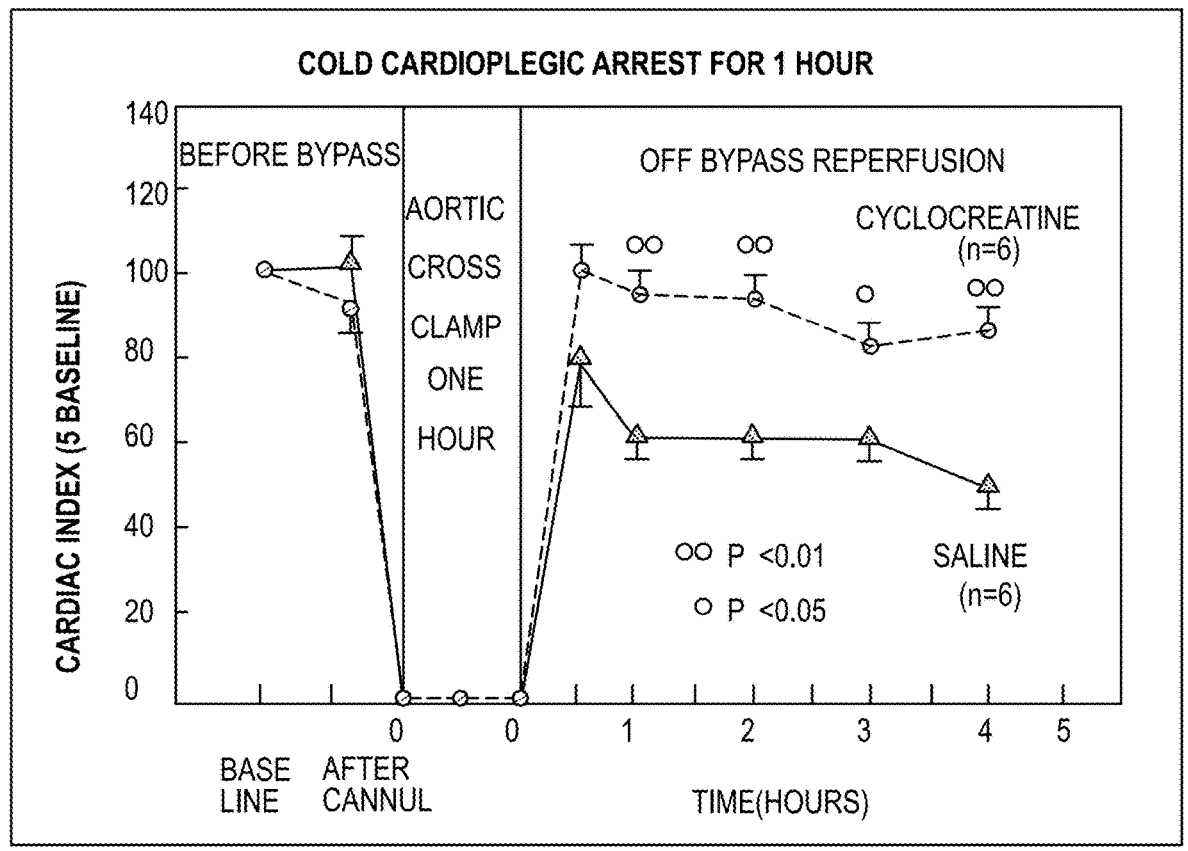

FIG. 41A to FIG. 41B indicate: (A): much higher neutrophil accumulation after reperfusion in the right and left atria (+2-3) compared to the right and left ventriculars (+1) in the intact canine model of cold cardioplegic arrest and aortic cross-clamping for 1 hour followed by reperfusion on bypass for 45 min and then off bypass for 4 hours; and (B): post-bypass cardiac output was significantly better in CCr-treated hearts compared to that of controls, where the CCr-treated hearts achieved over 90% of the baseline function throughout the 4 hours of reperfusion, while control hearts achieved only 60% of the baseline function. Dogs were injected intravenously with saline or CCr (500 mg/kg) for 1 hour before initiating the experiment. Although all control saline-treated dogs required defibrillation to resume cardiac contractility, CCr-treated dogs resumed immediate contractility during reperfusion without the need for defibrillation.

Figure 42A:
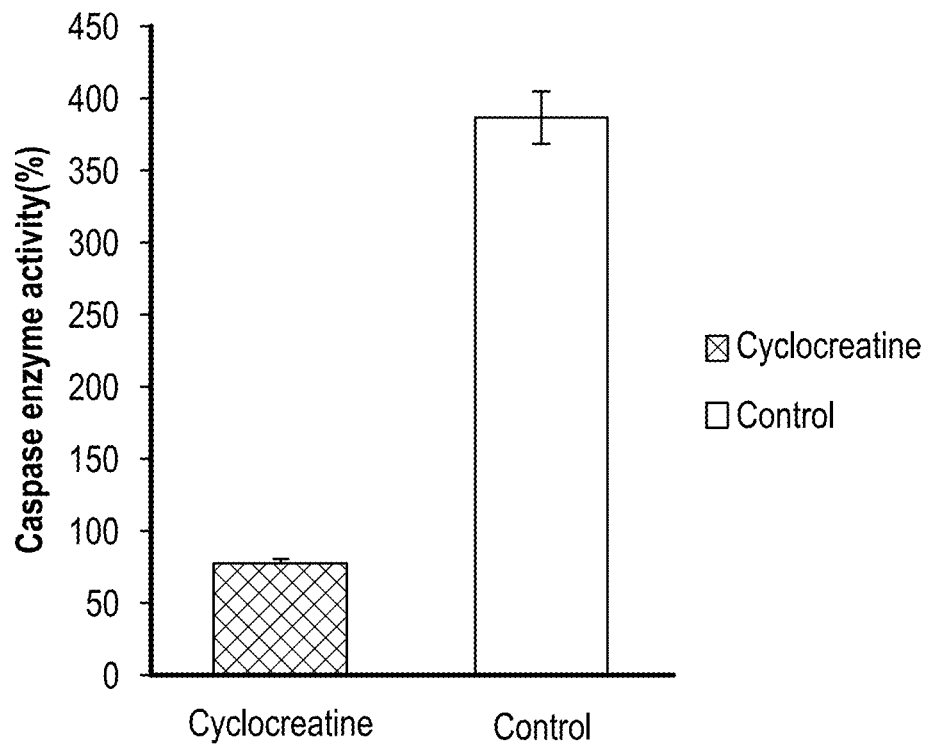
Figure 42B:
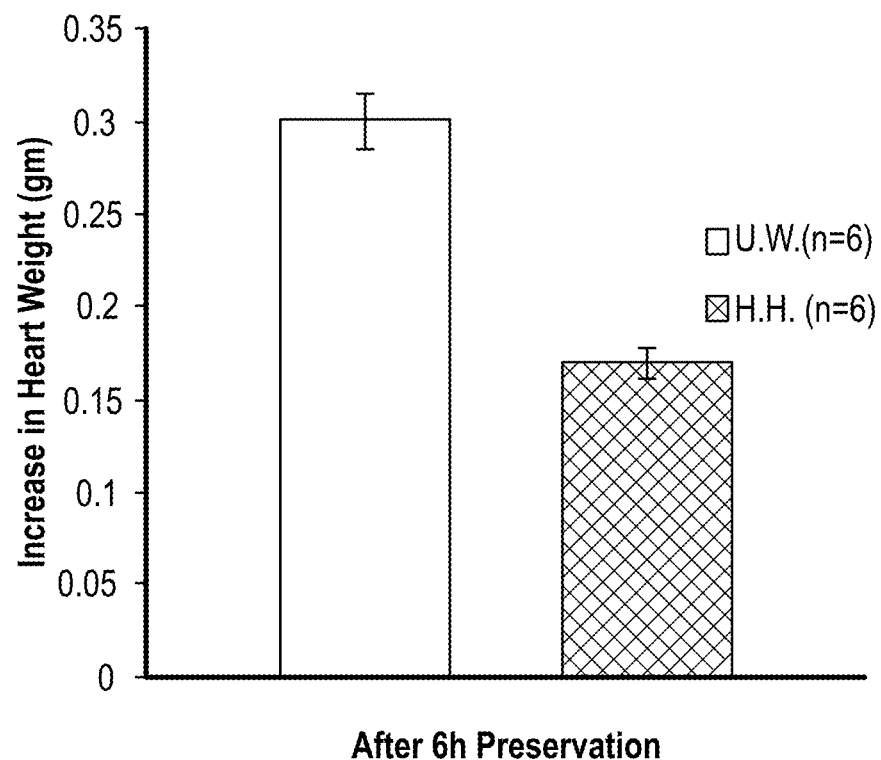

FIG. 42A to FIG. 42B indicate: (A): Cyclocreatine reduces apoptotic enzyme activity in the non-heartbeating dog model of heart transplantation. Dog hearts underwent 1 hour of global warm ischemic arrest then hearts were explanted and perfused Ex vivo for an Additional 4 hours with a cold lactated ringers solution containing Cyclocreatine, while control hearts received cold lactated ringers' solution alone, and (B): Cyclocreatine Phosphate (CCrP) reduces heart weight after 6 hours of cold storage in HH solution (UW+CCrP) compared to control (UW).

FIG. 43 provides that Cyclocreatine Phosphate protects rat donor hearts against ischemic injury during harvesting and prolonged cold storage for 22 Hours and 24 Hours, as well as after grafting the hearts for 3 days (Saline=5 and CCrP=6). CCrP protection was evident in CCrP grafted hearts at day 3 where the myocardial color and the consistency of the degree of contractility were almost the same as day zero after transplantation. Additionally, the day 3 ECHO showed the continued preservation of the myocardial wall thickness and mass which are the main criteria that determine the degree of myocardial ischemia over a period of time. Most the control grafted hearts, on the other hand, continued to show evidence of ischemia, as well as loss of the wall thickness and the cardiac mass by day 0 and day 3.

FIG. 44A to FIG. 44D present the gene expression level of Nourin RNA network composed of miR-137/mRNA-FTHL-17/lncR-CTB89H12.4 in the standard isoproterenol (ISO) model of HF and demonstrate how the administration of Cyclocreatine Phosphate (CCrP) inhibited gene expression of Nourin RNA network. (A) and (B): indicate the significantly high gene expression level of miR-137 in serum samples collected at day 14 from ISO/saline rats compared to normal rats. The ISO/saline rats had upregulation of miR-137 by 8.91-fold (Mean=10.25) compared to healthy rats received saline (1.15) (p<0.0001), where there was none to a minimal gene expression of miR-137 in normal non-stressed rats. CCrP treatment significantly (p<0.0001) reduced miR-137 gene expression at doses of 0.4 g/kg, 0.8 g/kg and 1.2 g/kg by 33%, 75% and 68%, respectively. Additionally, CCrP administration to healthy rats at 0.8 g/kg did not increase miR-137 gene expression (Mean=1.60) and it was comparable to the level expressed in saline-treated healthy rats (1.15); (C): The ISO/saline rats had upregulation of mRNA-FTHL-17 by 8.17-fold (Mean=8.26) compared to healthy rats received saline (1.01) (p=0.0002). CCrP treatment significantly (p=0.04) reduced mRNA-FTHL-17 gene expression at doses of 0.4 g/kg, 0.8 g/kg and 1.2 g/kg by 16%, 30% and 75%, respectively. Additionally, CCrP administration to healthy rats at 0.8 g/kg did not increase mRNA-FTHL-17 gene expression (Mean=0.67) and it was comparable to the level expressed in saline-treated healthy rats (1.01); and (D): The ISO/saline rats had downregulation of lncR-CTB89H12.4 (Mean=0.3) compared to healthy rats received saline (1.1) (p=0.002). CCrP treatment significantly (p=0.002) increased lncR-CTB89H12.4 gene expression at doses of 0.4 g/kg, 0.8 g/kg and 1.2 g/kg by 1.33-fold, 7.66-fold and 14.33-fold, respectively. Additionally, CCrP administration to healthy rats at 0.8 g/kg had a comparable lncR-CTB89H12.4 gene expression level (Mean=1.3) as the saline-treated healthy rats (1.1). Results suggest lack of cardiac toxicity by CCrP.

Figure 45:
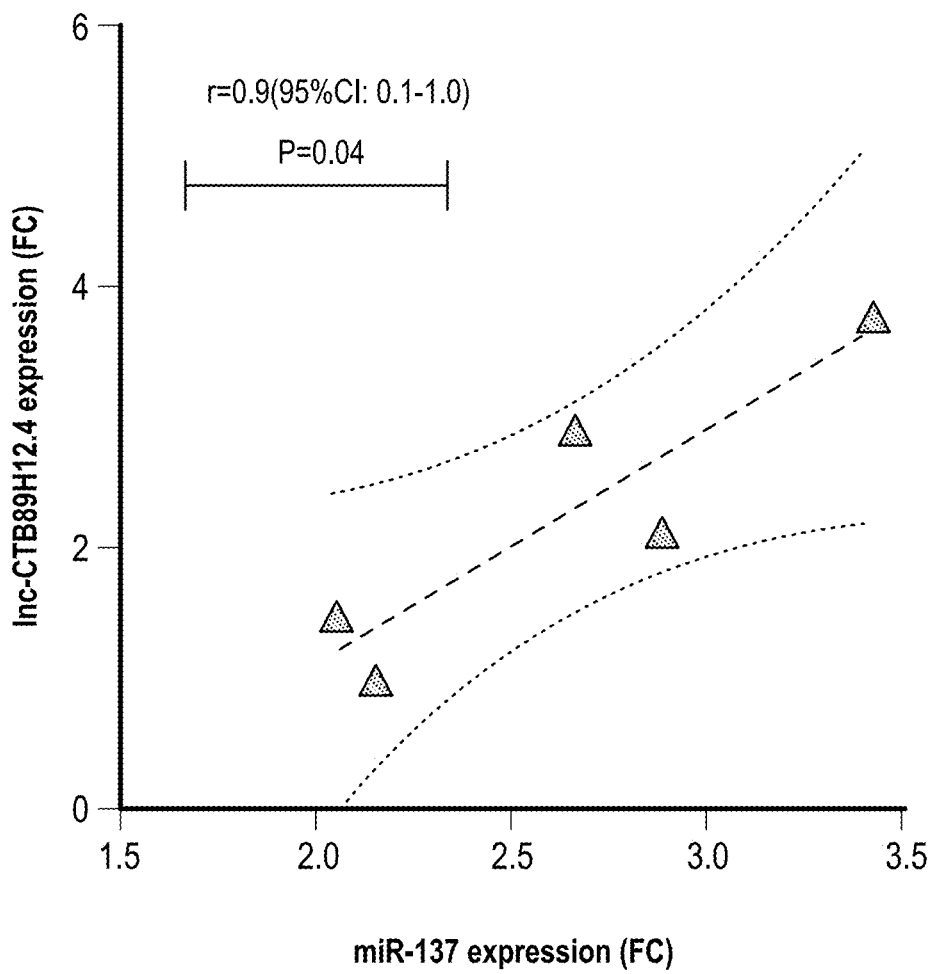

FIG. 45 is a representation of the correlation analysis was conducted between miR-137/mRNA-FTHL-17/lncRNA-CTB89H12.4 in the ISO/saline rats treated with ISO/CCrP at 0.8 g/kg. The only significant correlation was found between miR-137 and lncR-CTB89H12.4 (p=0.04) in ISO/CCrP group. No significant correlation was detected between miR-137/mRNA-FTHL-17/lncR-CTB89H12.4 in the ISO group (p>0.05).

FIG. 46A to FIG. 46D present the gene expression level of Nourin RNA network composed of miR-106b/mRNA-ANAPC11/lncR-CTB89H12.4 in the standard isoproterenol (ISO) rat model of HF and how the administration of Cyclocreatine Phosphate (CCrP) inhibited gene expression of Nourin RNA network. (A) and (B): indicate the significantly high gene expression level of miR-106b in serum samples collected at day 14 from ISO/saline rats compared to normal rats. The ISO/saline rats had upregulation by 8.74-fold (Mean=40.38) compared to healthy rats received saline (4.62) (p<0.0001). CCrP treatment significantly (p<0.001) reduced miR-106b gene expression at doses of 0.4 g/kg, 0.8 g/kg and 1.2 g/kg by 18%, 44% and 72%, respectively. Additionally, CCrP administration to healthy rats at 0.8 g/kg did not increase miR-106b gene expression (Mean=5.62) and it was comparable to the level expressed in saline-treated healthy rats (4.62); (C): ISO/saline rats had upregulation of mRNA-ANAPC11 by 101.4-fold (Mean=101.4) compared to healthy rats received saline (1.0) (p=0.0002). CCrP treatment significantly (p=0.04) reduced mRNA-ANAPC11 gene expression at doses of 0.4 g/kg, 0.8 g/kg and 1.2 g/kg by 18%, 31% and 70%, respectively. Additionally, CCrP administration to healthy rats at 0.8 g/kg did not increase mRNA-ANAPC11 gene expression (Mean=0.9) and it was comparable to the level expressed in saline-treated healthy rats (1.0); and (D): The ISO/saline rats had downregulation of lncR-CTB89H12.4 (Mean=0.3) compared to healthy rats received saline (1.1) (p=0.002). CCrP treatment significantly (p=0.002) increased lncR-CTB89H12.4 gene expression at doses of 0.4 g/kg, 0.8 g/kg and 1.2 g/kg by 1.33-fold, 7.66-fold and 14.33-fold, respectively. Additionally, CCrP administration to healthy rats at 0.8 g/kg had lncR-CTB89H12.4 gene expression (Mean=1.3) had a comparable level of expression as the saline-treated healthy rats (1.1). No significant correlation was detected between miR-106b/mRNA-ANAPC11/lncR-CTB89H12.4 in the ISO/saline group (p>0.05). Similarly, no significant correlation was detected between miR-106b/mRNA-ANAPC11/lncR-CTB89H12.4 in the ISO/CCrP group (0.8 g/kg) (p>0.05).

FIG. 47A to FIG. 47D present the cardioprotective benefits of CCrP administration in the standard isoproterenol (ISO) rat model of HF by preventing the development of HF and restoring normal cardiac function of ejection fraction (EF %) measured by ECHO analysis. EF is an important measurement of how well the heart is pumping, and it is used to help classify heart failure and guide treatment. FIG. 47 indicates: (A): ejection fraction; (B): cardiac biomarker CK-MB; (C): collagen deposition; and (D): heart weight.

Figure 48:
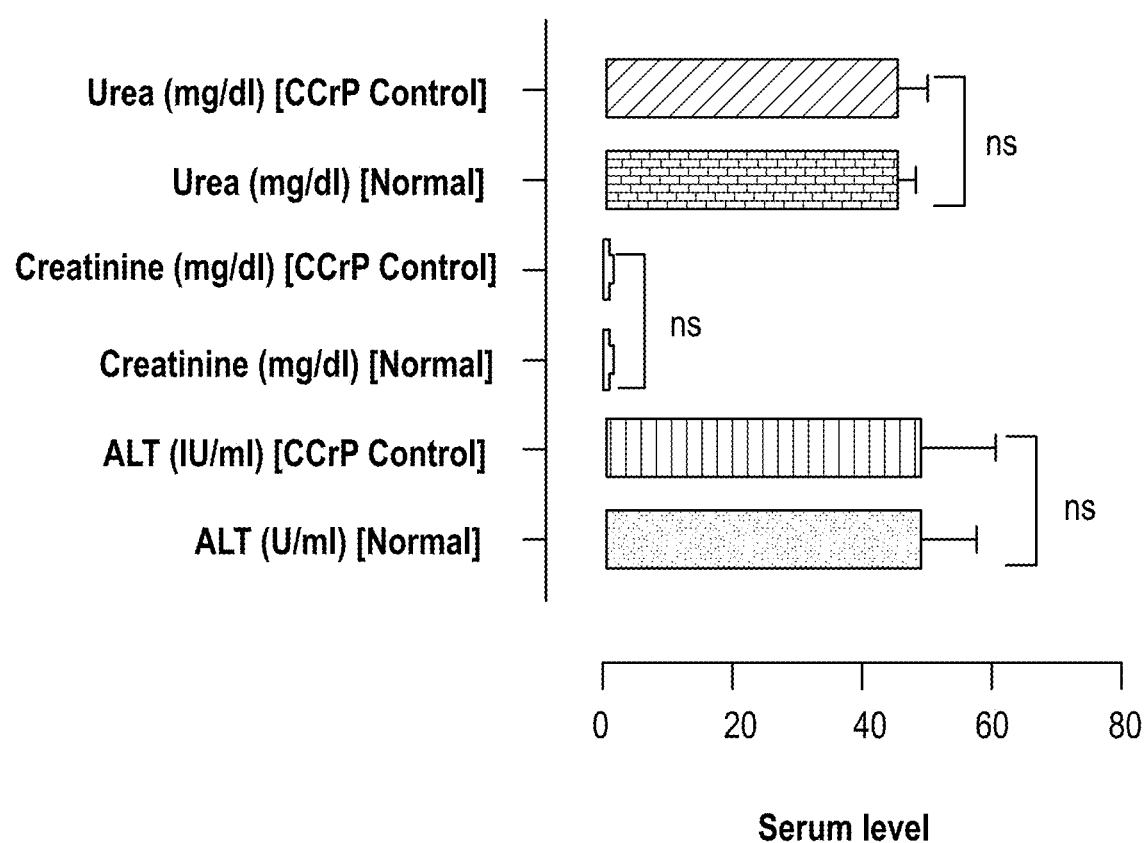

FIG. 48 indicates the safety of CCrP at a dose of 0.8 g/kg, injected IP daily to healthy rats for 14 days and showed no toxicity in liver and renal function. There was no significant difference between normal rats treated with saline or CCrP for the levels of liver enzyme ALT, kidney Creatinine and Urea. Similarly, the expression level of Nourin RNA network (miR-137, miRNA-106b, mRNA-FTHL-17, mRNA-ANAPC11, and lncR-CTB89H12.4) was comparable in healthy rats treated with saline or CCrP (FIG. 44A-FIG. 44D and FIG. 46A-FIG. 46B). These results suggest lack of toxicity by CCrP.

Figure 49B:
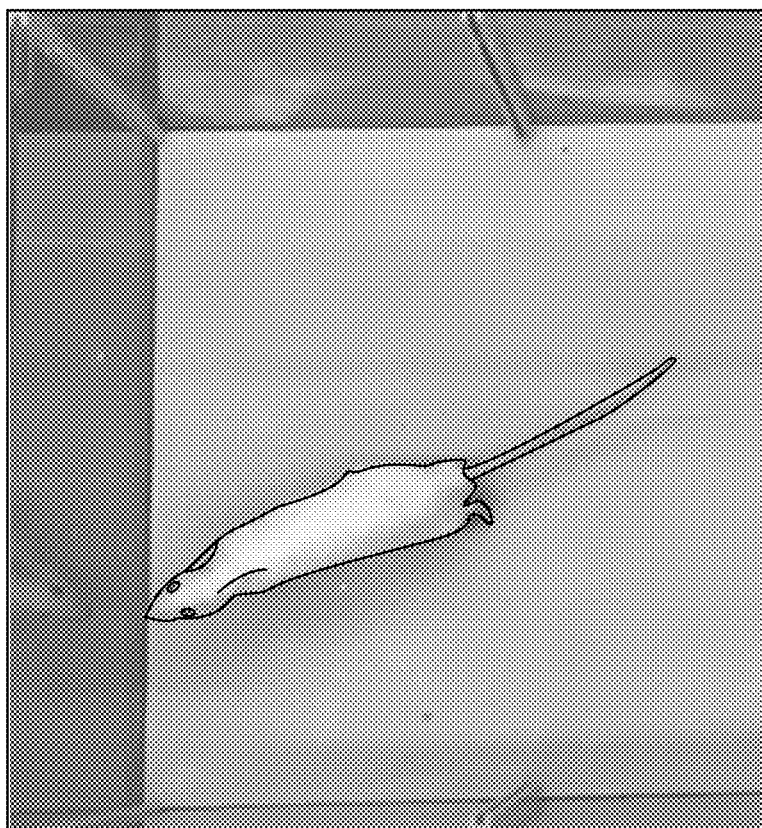
Figure 49A:
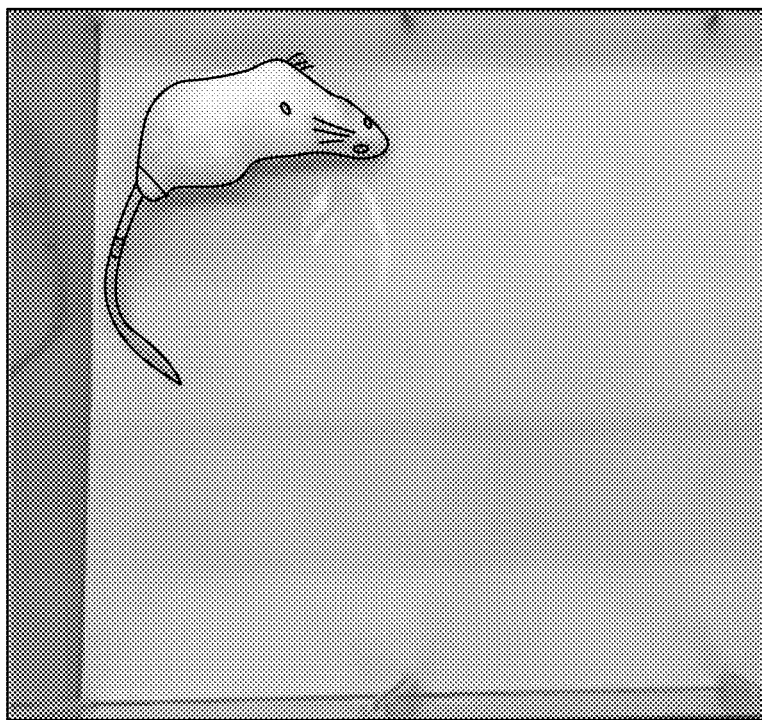

FIG. 49A and FIG. 49B are photos of a representative rat from: (A) ISO/saline group (n=6) with a "low physical activity" at day 14 before sacrifice where rats primarily stayed in place (FIG. 49A); and (B): ISO/CCrP group (n=5) showed "high physical activity" at day 14 before sacrifice, which is comparable to normal healthy control "saline" rats (FIG. 49B). These results indicate that treating ISO rats with CCrP prevented the development of heart failure and restored normal heart function and physical activity.

Figure 50:
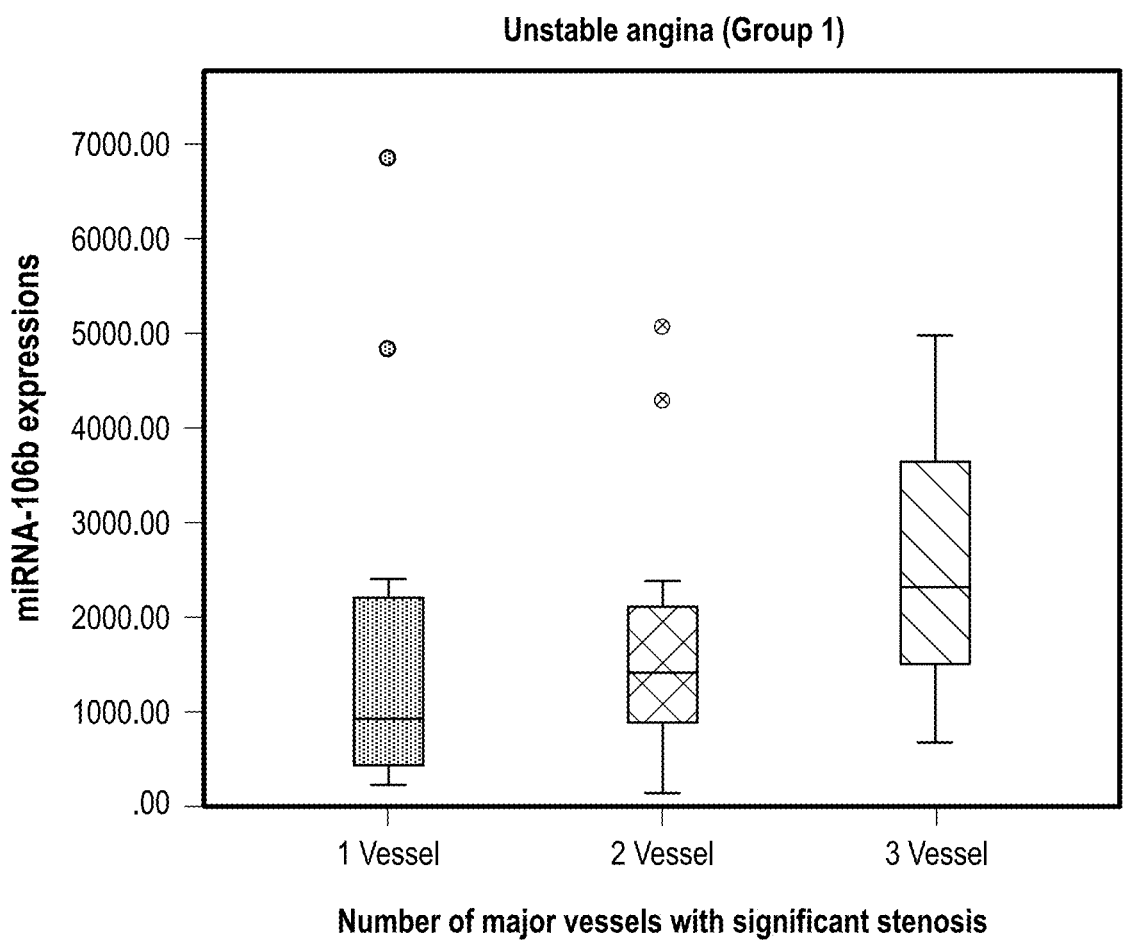

FIG. 50 indicates that different levels of hsa-miR-137 (miR-137) gene expression in UA patients with various vessels of stenosis. The gene expression of hsa-miR-137 (a marker of cell damage), was higher in UA patients with three vessels (n=2) of stenosis compared to patients with one (n=14) or two vessels (n=14). Although there was no statistical difference between the 3 groups, results suggest an association between hsa-miR-137 gene expression and myocardial ischemia. The higher gene expression of hsa-miR-137 level, suggestive of higher myocardial ischemia.

Figure 51:
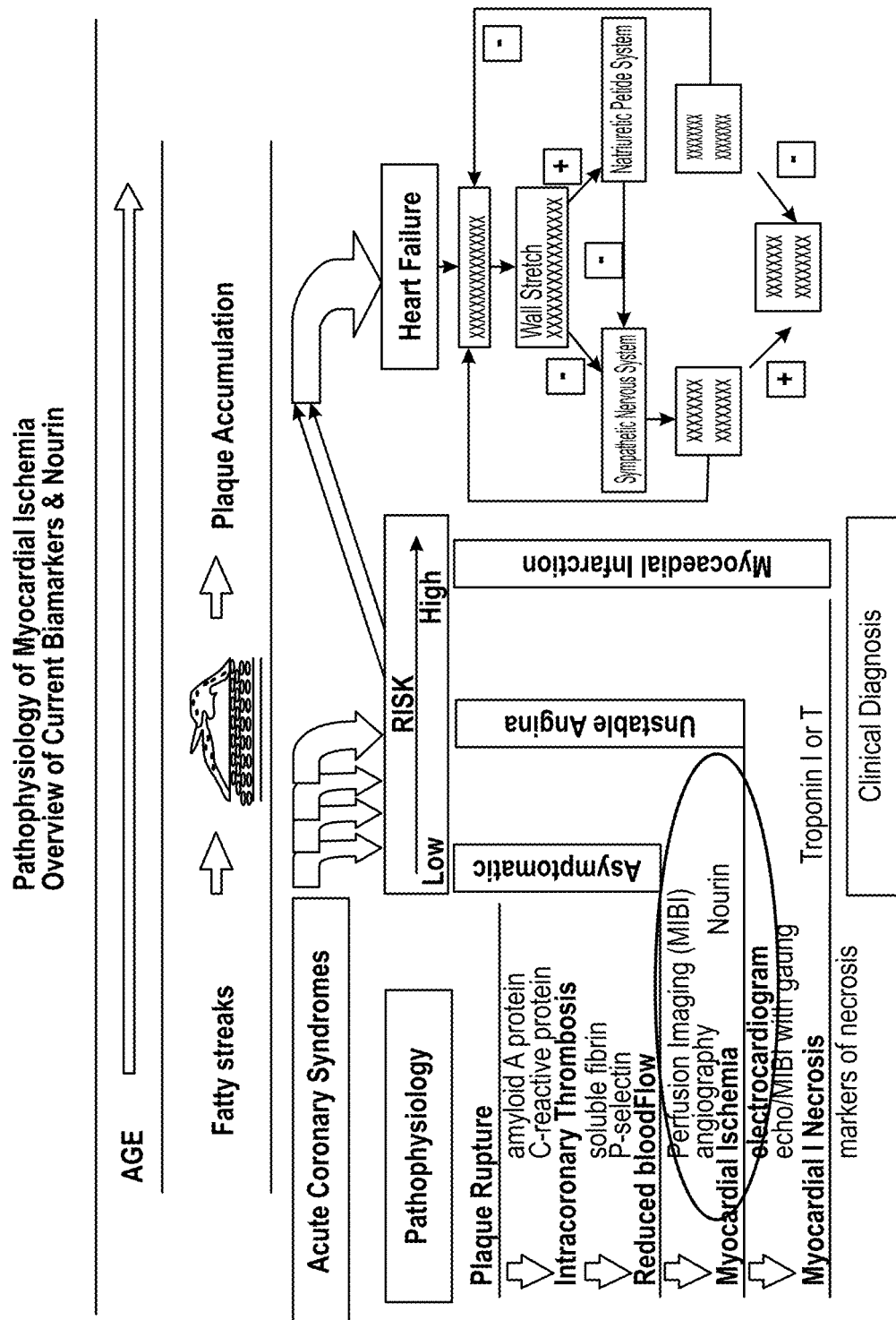
Figures 53A, 53B, 53C, 53D:
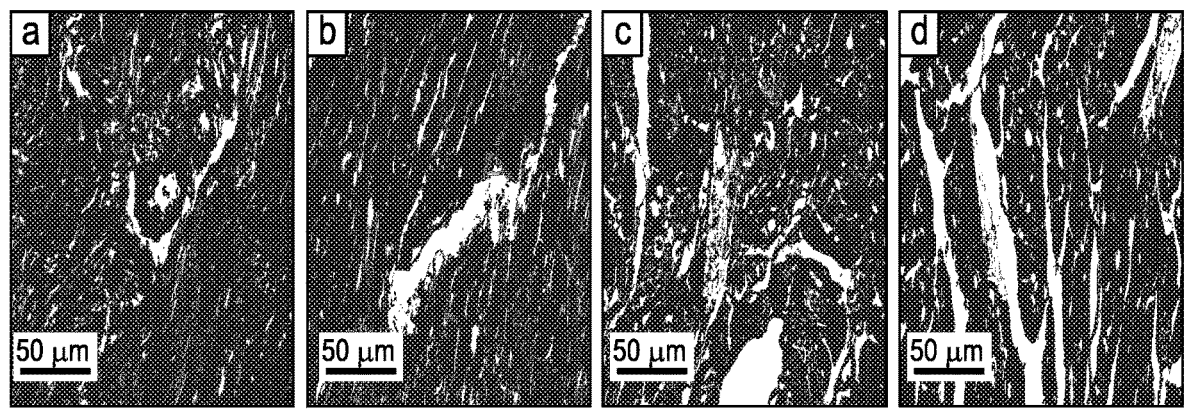

FIG. 51 indicates a pathophysiology of myocardial ischemia and an overview of current biomarkers comparing to Nourin.

FIG. 52 indicates synthetic f-Met-Leu-Phe (fMLP) (SEQ ID NO:23).

FIG. 53A to FIG. 53D indicate histopathological changes of hearts of ISO/saline rats and the effect of the administration of CCrP. Specimens (a-d) are collected at day 14 after saline or CCrP treatment, stained with Masson's trichrome for estimation of myocardial fibrosis (blue color) as follows; (a) no fibrosis was observed in control healthy rats treated with saline, (b) no fibrosis was observed in control healthy rats treated with CCrP at a dose of 0.8 g/kg/day, (c) high fibrosis was observed in ISO/saline rats, and (d) very low fibrosis with histology close to normal in ISO/CCrP at a dose of 0.8 g/kg/day.

DETAILED DESCRIPTION OF THE INVENTION

The present invention may be understood more readily by reference to the following detailed description of the invention taken in connection with the accompanying drawing figures, which forms a part of this disclosure. It is to be understood that this invention is not limited to the specific devices, medicines, systems, conditions or parameters described and/or shown herein and that the terminology used herein is for the example only, and is not intended to be limiting of the claimed invention. Also, as used in the specification including the appended claims, the singular forms 'a', 'an', and 'the' include the plural, and references to a particular numerical value includes at least that particular value unless the content clearly directs otherwise. Ranges may be expressed herein as from 'about' or 'approximately' another particular value. When such a range is expressed it is another embodiment. Also, it will be understood that unless otherwise indicated, dimensions and material characteristics stated herein are by way of example rather than limitation, and are for better understanding of sample embodiment of suitable utility, and variations outside of the stated values may also be within the scope of the invention depending upon the particular application.

Embodiments will now be described in details with reference to the accompanying drawings. To avoid unnecessarily obscuring in the present disclosure, well-known features may not be described, or substantially the same elements may not be redundantly described, for example. This is for ease of understanding. The drawings and the following description are provided to enable those skilled in the art to fully understand the present disclosure and are in no way intended to limit the scope of the present disclosure as set forth in the appended claims.

In accordance with one embodiment of the present invention, it discloses a method for prevention and treatment of ischemic diseases and aging-related disorders involving ischemia-induced injury, the method comprising administrating a therapeutically effective amount of a bioenergetic agent to a subject in need thereof, wherein the bioenergetic agent is a synthetic analogue that maintains and restores mitochondrial bioenergetics associated with ATP generation disrupted in ischemic events, defective ion homeostasis and mitochondrial redox shifts, and for preventing and treating ischemia-induced injury.

In one embodiment of the present invention, it discloses a novel ischemia-associated Nourin RNA-based integrated competing endogenous molecular network as additional biomarkers for cardiac ischemia patients. Using the amino acid sequence of Nourin purified from human hearts during reversible ischemia. The disclosed novel Nourin gene-based RNA network was previously identified through in silico data analysis after BLAST alignment with the Nourin sequence formyl substituted-MIINHNLAAINSHRSPGAD-GNGGEAMPGGGR (SEQ ID NO:15). The present disclosure according to the present invention also investigated the serum Nourin gene-based RNA network expression level and pattern in CAD, UA, AMI patients and healthy subjects in comparison to Troponin I level. The serum Nourin gene-based RNA network expression level was also investigated in a rat model of HF and compared to rats treated with the bioenergetic drug, Cyclocreatine Phosphate.

Nourin-based RNA Network is an essential part of central dogma; RNA delivers genetic and regulatory information and reflects cellular states. Based on high-through put sequencing technologies, cumulating data show that various RNA molecules are able to serve as biomarkers for the diagnosis and prognosis of various diseases, for instance, cancer and cardiac ischemia. In particular, detectable in various bio-fluids, such as serum, saliva and urine, extracellular RNAs (exRNAs) are emerging as non-invasive biomarkers for earlier diagnosis, disease progression, monitor, and prediction of drug therapy response in clinical trials. Although RNAs are unstable in alkaline conditions, they are easy to be detected and quantified at very low abundance. Compared to protein biomarkers, RNA biomarkers have more sensitivity and specificity. Standard qPCR technique enables traces of RNA sequences to be amplified and thus captured specifically with high sensitivity. Moreover, the cost of RNA biomarker is much lower than protein biomarker because detecting each protein requires a specific antibody. Compared with DNA biomarkers, RNA biomarkers have the advantage of providing dynamic insights into cellular states and regulatory processes than DNA biomarkers. Besides, RNA has multiple copies in a cell, which delivers more information than DNA. Moreover, some RNAs with specific structures, such as circular RNA, have the potential to exist stably in plasma and/or serum.

Competing endogenous RNAs (ceRNAs) have been reported to regulate the distribution of miRNA molecules on their targets and thereby impose an additional level of post-transcriptional regulation. In particular, a muscle-specific lncRNA, linc-MD1, sponges miRNA-133 to regulate the expression of MAML1 and MEF2C, transcription factors that activate muscle-specific gene expression.

Furthermore, it was recently reported that the overexpression pattern of miR-106b-5p (SEQ ID NO:21) in plasma of patients with atherosclerosis is more significantly changed than that of individuals without atherosclerotic disease. MiR-106b-5p targets multiple signal pathways in vascular endothelial cells, and might play an important role in the regulatory network of atherosclerotic gene expression and related to the process of formation and rupture of atherosclerotic plaque, along with tumor necrosis factor (TNF), toll like receptor (TLR) and hypoxia-inducible factor 1α (HIF-1α) and other signal pathways.

Studies by Elgebaly, S A et al. demonstrated that Nourin is rapidly released within 5 minutes by cardiovascular tissues in response to hypoxia and ischemia and that Nourin is a 3-KDa formyl peptide acts through formyl peptide receptors (FPR) on leukocytes and vascular endothelial tissues. As a potent inflammatory mediator, Nourin stimulates leukocyte chemotaxis, adhesion and activation. Specifically, Nourin stimulates the release of high levels of tumor necrosis factor-α, interleukin 8 and interleukin 10 by human monocytes leading to tissue inflammation post ischemic injury.

It was found that the levels of the muscle-specific lncRNA, linc-MD1 is strongly reduced in muscle cells of patients with Duchenne Muscular Dystrophy. In another study, it was reported that cardiac apoptosis-related lncRNA (CARL) could act as an endogenous miRNA-539 sponge to regulate PHB2 expression, mitochondrial fission and apoptosis. Modulation of their levels may provide a new approach for tackling apoptosis and myocardial infarction. Clearly, understanding this novel RNA crosstalk will lead to significant insight into gene regulatory networks and have implications in human development and disease.

Using both the functional leukocyte chemotaxis assay and immunoassay ELISA, our studies demonstrated that the cardiac-derived Nourin peptide is rapidly released by ischemic heart tissue while it is still "viable" before cells are dead, as well as by necrotic hearts. Consistence results showing the "early" release of Nourin by ischemic hearts were demonstrated using various species (human, dog, rat and cow), as well as several models of ischemic injury to include AMI (necrosis), global cardiac arrest (necrosis), cardiopulmonary bypass surgery (reversible ischemia) and heart transplantation (reversible ischemia). The early release of Nourin by ischemic injury (FIG. 14) is clinically significant to abort infarction, save heart muscles and reduce myocardial injury. Unlike Troponin, Nourin was detected in "fresh" blood samples collected from ACS patients, as well as "frozen" samples stored at −70° C. for 3 years. The Nourin gene-based RNA network is an essential part of central dogma where RNA delivers genetic and regulatory information and reflects cellular states. RNA molecules are able to serve as non-invasive biomarkers for earlier disease diagnosis and level of risk, as well as monitor disease progression and prediction of drug therapy response on heart tissue. Compared to protein-based biomarkers, RNA biomarkers have more sensitivity and specificity as it can be tissue and disease specific.

It is known in the art that autophagy is a process involved in the clearance of damaged proteins and organelles and facilitates cellular health under various stress conditions including hypoxia, ischemia or oxidative stress. Reports indicate that cardiomyocyte autophagy develops in the heart during AMI and it is rapidly activated within 30 minutes after coronary ligation.

In one embodiment of the present invention, the Nourin gene-based RNA molecular network of biomarkers related to the Nourin peptide sequence which comprise integrated competing endogenous molecular networks is composed of lncR-CTB89H12.4 (SEQ ID NO:19), hsa-miRNA-106b (SEQ ID NO:21), hsa-miRNA-137 (SEQ ID NO:22), mRNA-ANAPC11 (SEQ ID NO:20) and mRNA-FTHL-17 (SEQ ID NO:03), as well as the Nourin amino acid sequence of formyl substituted-MIINHNLAAINSHR (SEQ ID NO:16) as an autophagy-related RNA panel linked to cardiovascular ischemia to specifically identify ischemic cardiac events in patients with CAD, UA, AMI (STEMI and NSTEMI), as well as HF and compared with healthy subjects and symptomatic non-cardiac patients. It is disclosed that autophagy-related Nourin gene-based RNA molecular network may be utilized as an early biomarker for cardiac ischemia. Specifically, there was a downregulation of Nourin gene-based RNA network biomarker, lncR-CTB89H12.4 after an ischemic event in cardiac patients compared to healthy, non-ischemic, non-cardiac patients and control subjects. The downregulation of lncR-CTB89H12.4 was significantly associated with upregulation of hsa-miR-106b and hsa-miR-137 and their activation resulted in overexpression of mRNA-ANAPC11 and mRNA-FTHL-17 as well as mRNA-Nourin leading to an increased translation and production of high levels of Nourin protein as a formyl substituted-MIINHNLAAINSHR (SEQ ID NO:16).

In another embodiment of the present invention, Nourin gene-based RNA molecular network is disclosed as additional biomarkers for coronary artery disease patients. Using the amino acid sequence of Nourin purified from human reversible ischemic hearts during cardiac arrest of patients undergoing cardiopulmonary bypass surgery, the Applicant has identified the Nourin gene-based RNA network through in silico data analysis after BLAST alignment with formyl substituted-MIINHNLAAINSHRSPGAD-GNGGEAMPGGGR (SEQ ID NO:15).

In one embodiment of the present invention, the Nourin gene-based RNA molecular network of biomarkers related to the Nourin peptide sequence expression level and pattern were analyzed in serum samples of patients with CAD, UA, AMI (STEMI and NSTEMI), as well as HF and compared with healthy subjects and symptomatic non-cardiac patients. The novel Nourin gene-based RNA molecular network of biomarkers integrated competing endogenous network, which comprises: (1) ferritin heavy chain like polypeptide mRNA-17 (mRNA-FTHL-17) gene (SEQ ID NO:03); (2) anaphase promoting complex subunit mRNA-11 (mRNA-ANAPC11) gene (SEQ ID NO:20); (3) *Homo sapiens* micro RNA-106b (hsa-miRNA-106b) (SEQ ID NO:21), which is a marker of cell damage, regulates the expression of Nourin gene and is linked to myocardial ischemia and ischemic cardiac events, gets upregulated after ischemic cardiac events in myocardial ischemia and is linked to overexpression of mRNA-FTHL-17 and mRNA-ANAPC11; (4) *Homo sapiens* micro RNA-137 (hsa-miRNA-137) (SEQ ID NO:22), which is a marker of inflammation and regulates the expression of Nourin gene and is linked to myocardial ischemia and ischemic cardiac events, gets upregulated after ischemic cardiac events in myocardial ischemia and is linked to overexpression of mRNA-FTHL-17 and mRNA-ANAPC11; (5) long non-coding intergenic RNA-(lncRNA-CTB89H12.4) (SEQ ID NO:19) an autophagy-related gene for cardiac ischemia and upstream regulates hsa-miR-106b and hsa-miRNA-137 (refer, FIG. 15A to FIG. 15I) and it is downregulated after ischemic cardiac events in myocardial ischemia resulting in higher levels of hsa-miRNA-137 and hsa-miRNA-106b, and to overexpression of mRNA-FTHL-17 and mRNA-ANAPC11 and consequently Nourin gene, and Nourin protein and thus, provides the competing and opposing endogenous RNA network that is downregulated after ischemic cardiac events in myocardial ischemia and is linked to increased translation and production of high levels of Nourin protein via the increase in hsa-miRNA-137, hsa-miRNA-106b, mRNA-FTHL-17, mRNA-ANAPC11, Nourin gene, and Nourin protein levels; and (6) formyl substituted-MIINHNLAAINSHR (SEQ ID NO:16) gene for Nourin mRNA.

In one embodiment of the present invention, the utilization of Nourin integrated genetic epigenetic approach, lncR-CTB89H12.4 may be involved in epigenetic activation of hsa-miR-106b and hsa-miR-137 with subsequent modulation of mRNA-ANAPC11 and mRNA-FTHL-17, respectively with translation of Nourin formyl substituted-MIINHNLAAINSHR (SEQ ID NO:16), and with potential role in CAD, UA, AMI (STEMI and NSTEMI), as well as HF pathogenesis. Standard qPCR-based validation of the network was done in serum from CAD, UA, AMI (STEMI and NSTEMI), as well as HF and symptomatic non-cardiac patients and healthy subjects.

Compared with messenger RNAs presenting an average of 2,000 nucleotides long, mature miRNAs have a length of only ~21 to 23 nucleotides. Their subsequent targeting mechanisms show a great deal of complexity because each miRNA can target thousands of transcripts, and one mRNA can contain several target sites for different miRNAs. Currently there are over 2,000 known miRNAs in humans and more are constantly being discovered and added to the miRNA database, "miRBase". Several microRNAs have been shown to play major roles in myocardial ischemia. A previous study showed that microRNA-137 was downregulated as the cardiomyocyte differentiates and proliferates, suggesting that miR-137 may play a critical role in cardiomyocyte regeneration. However, there has been no report yet on whether miRNA-137 gguccucuga cucucuucgg ugacggguau ucuugggugg auaauacgga uuacguuguu auugcuuaag aauacgcgua gucgaggaga guaccagcgg ca (SEQ ID NO:04) is differentially expressed in pathological cardiomyocytes such as AMI. miRNA-137 gguccucuga cucucuucgg ugacggguau ucuugggugg auaauacgga uuacguuguu auugcuuaag aauacgcgua gucgaggaga guaccagcgg ca (SEQ ID NO:04) has an important role in controlling embryonic neural stem cell fate. The down-regulated expression of miR-137 was observed in glioma stem cells and it regulates neuronal maturation. Additionally, miRNA-137 is decreased in Alzheimer disease patients. The lncR-CTB89H12.4 [AC021078.1-201 (ENST00000499521.2)] is located on chromosome 5 and has 2 exons. lncR-CTB89H12.4 is also related to cardiomyocyte regeneration and angiogenesis.

In another embodiment of the present invention, the method for screening and diagnosis of ischemic diseases and aging-related disorders involving ischemia-induced injury according to the present invention, wherein it is preferred that the biomarker of the present invention for cardiovascular diseases including: CAD, UA, AMI (STEMI and NSTEMI), as well as HF fulfill a number of the following criteria, including:
(1) it should be tissue-specific and abundantly expressed in heart tissues;
(2) its expression level in circulation under normal conditions should be extremely low or undetectable;
(3) in coronary artery disease patients, it should be quickly released into the circulation from the damaged heart and stably expressed for some time with a long half-life within the sample;
(4) accessible using noninvasive methods;
(5) the capability of rapid and accurate detection with a high degree of sensitivity and specificity to the disease; and
(6) allows early detection with sensitivity to relevant changes in the disease.

Circulating miRNAs fulfill a number of these criteria. They are stable in blood circulation, they are often regulated in a tissue- and pathology-specific manner, and they can be detected with high sensitivity and specificity using sequence-specific amplification.

It has been hypothesized that necrosis of cardiac cells after AMI results in the leakage of miRNAs into the circulation and that miRNAs highly, and preferably, specifically expressed in the heart might be used to diagnose acute coronary events. The identification of stable circulating miRNAs launches a new generation of potential biomarkers, for which assays can be developed with relative ease, at a relatively low expense, but with potentially better specificity and sensitivity. These assays could easily be designed to combine a large number of circulating miRNAs, which could drastically change the use and interpretation of circulating biomarkers as known in the art. At the moment, most studies are investigating the usefulness of individual miRNAs as biomarker for disease, but none of the prior art document has reported that a combination of multiple miRNAs like the Nourin RNA network, which are related to each other and cardiovascular ischemia, would provide greater accuracy with high sensitivity and specificity.

In another embodiment of the present invention, the method for prevention and treatment of ischemic diseases and aging-related disorders involving ischemia-induced injury according to the present invention, wherein the therapeutically effective amount of a bioenergetic agent comprises an amount in a range between 0.3 g and 1.2 g per kg of mammalian body weight, administered daily as required.

In another embodiment of the present invention, the method for prevention and treatment of ischemic diseases and aging-related disorders involving ischemia-induced injury according to the present invention, wherein the ischemia-induced injury comprises mammalian tissue subject to injury, hypoxia or ischemia.

In another embodiment of the present invention, the method for prevention and treatment of ischemic diseases and aging-related disorders involving ischemia-induced injury according to the present invention, wherein the administration of the bioenergetic agent is carried out prophylactically daily, 10, 30 to 60 minutes, or by injection immediately prior to injury to protect against ischemic damage, and to prevent, inhibit or reduce tissue deterioration and disease progression.

In another embodiment of the present invention, the method for prevention and treatment of ischemic diseases and aging-related disorders involving ischemia-induced injury according to the present invention, wherein the bioenergetic agent is administered therapeutically during injury or immediately post-injury for few hours, then daily for 1, 7 to 14 days, weeks, months and years to treat disease, to prevent and slowdown tissue deterioration, to inhibit or reduce disease progression, and to stop or reverse the pathologic process.

In another embodiment of the present invention, the method for prevention and treatment of ischemic diseases and aging-related disorders involving ischemia-induced injury according to the present invention, wherein the bioenergetic agent preserves mitochondrial biogenesis, prevents cell injury, prevents disease development, rejuvenates organ function, and restores normal physical activity.

In another embodiment of the present invention, the method for prevention and treatment of ischemic diseases and aging-related disorders involving ischemia-induced injury according to the present invention, wherein the bioenergetic agent is administered intravenously, intraperitoneally, orally, intranasally, subcutaneously, intrathecally, intraventricularly, or intramuscularly.

In another embodiment of the present invention, the method for prevention and treatment of ischemic diseases and aging-related disorders involving ischemia-induced injury according to the present invention, wherein the bioenergetic agent can cross the blood-brain barrier.

In another embodiment of the present invention, the method for prevention and treatment of ischemic diseases and aging-related disorders involving ischemia-induced injury according to the present invention, wherein the bioenergetic agent is administered to subjects comprising a group selected from stable coronary artery disease patients, unstable angina patients, acute myocardial infarction patients, hypoxia/ischemia-induced and aging-related heart failure patients, and hypoxia/ischemia-induced and aging-related atrial fibrillation patients.

In another embodiment of the present invention, the method for prevention and treatment of ischemic diseases and aging-related disorders involving ischemia-induced injury according to the present invention, wherein the bioenergetic agent is administered before and after as required to subjects undergoing cardiovascular surgical procedures, wherein the surgical procedures comprising cardiopulmonary bypass surgery, valve replacement, percutaneous coronary intervention and heart transplantation, wherein the bioenergetic agent is carried out by injection immediately prior to harvesting donor hearts and then placed in preservation solutions during transportation, wherein heart recipient patients do not receive the bioenergetic agent.

In another embodiment of the present invention, the method for prevention and treatment of ischemic diseases and aging-related disorders involving ischemia-induced injury according to the present invention, wherein the bioenergetic agent is administered to subjects comprising a group selected from hypoxia/ischemia-induced, comprising of coronary artery disease, unstable angina, acute myocardial infarction, atrial fibrillation, Takotsubo cardiomyopathy, transient ischemic attack, and aging-related Alzheimer patients, and hypoxia/ischemia-induced and aging-related heart failure and stroke patients.

In another embodiment of the present invention, the method for prevention and treatment of ischemic diseases and aging-related disorders involving ischemia-induced injury according to the present invention, wherein the bioenergetic agent is administered to subjects undergoing neurologic surgical procedures, the surgical procedures comprising intracerebral hemorrhage surgery, arterial repair, non-nerve-related surgery that is capable of causing ischemia of the nervous system and other brain surgery to protect against ischemic damage, and to prevent, inhibit or reduce tissue deterioration and disease progression.

In another embodiment of the present invention, the method for prevention and treatment of ischemic diseases and aging-related disorders involving ischemia-induced injury according to the present invention, wherein the bioenergetic agent is selected from the group consisting of Cyclocreatine and Cyclocreatine phosphate.

In one embodiment of the present invention, a method for screening, diagnosing, and predicting therapy response with an agent in ischemic diseases and aging-related disorders, the method comprising the steps of:
a) administering Isoproterenol with or without an agent to be screened for therapy for ischemic diseases and aging-related disorders to cause myocardial injury for inducing ischemia-induced heart failure, wherein myocardial injury is evident within the first 24 hours after administration;
b) assaying a sample obtained after 14 days of the administration in step (a) for gene expression level of a Nourin gene-based RNA molecular network biomarkers related to the Nourin peptide sequence, the biomarkers comprising a group of genes selected from anaphase promoting complex subunit mRNA-11 (mRNA-ANAPC11) gene, ferritin heavy chain like polypeptide mRNA-17 (mRNA-FTHL-17) gene, *Homo sapiens* micro RNA-106b (hsa-miRNA-106b), *Homo sapiens* micro RNA-137 (hsa-miRNA-137), Nourin gene mRNA;
c) assaying the sample for gene expression level of lncR-CTB89H12.4, a Nourin gene-based RNA molecular network of biomarkers related to the Nourin peptide sequence;
d) assaying the sample for gene expression level of the cardiac marker CK-MB;
e) assessing the subject for amount of collagen deposition;
f) assessing the subject for amount of fibrosis;
g) assessing the subject for heart weight;
h) assessing the subject for amount of ejection fraction;
i) assessing the subject for physical activity level;
j) assessing normal subject for heart function;
k) correlating the gene expression level of step (b) with the gene expression level of the lncR-CTB89H12.4 of step (c);
l) correlating the gene expression level of step (b) with the level of the cardiac marker CK-MB of step (d);
m) correlating the gene expression level of step (b) with the amount of collagen deposition of step (e);
n) correlating the gene expression level of step (b) with the amount of fibrosis of step (f);
o) correlating the gene expression level of step (b) with the heart weight of step (g);
p) correlating the gene expression level of step (b) with the amount of ejection fraction of step (h);
q) correlating the gene expression level of step (b) with the physical activity level of step (i);
r) correlating the gene expression level of step (b) with the heart function of step (j);
s) analyzing the gene expression level of step (b) 14 days after the administration of step (a); and
t) identifying subjects responding to medical treatment with the agent as responders, wherein the subjects having a drop in gene expression level in step (s) are responders, whereas the subjects having an increase in gene expression level in step (s) are non-responders for the agent,
and wherein, a high gene expression level after just Isoproterenol administration is a marker of Isoproterenol induced cardiotoxicity and myocardial injury,
an increase in gene expression level after combined administration of Isoproterenol and the agent is a marker of Isoproterenol induced cardiotoxicity and myocardial injury with no effect of the agent,
a drop in gene expression level to normal non-ischemic level after combined administration of Isoproterenol and the agent is a marker of prevention of ischemic injury by the agent, when CK-MB level is not elevated,
a drop in gene expression level to normal non-ischemic level after combined administration of Isoproterenol and the agent is a marker of prevention of development of heart failure by the agent,
a drop in gene expression level to normal non-ischemic level after combined administration of Isoproterenol and the agent is a marker of prevention of development of heart failure by the agent, when there is no increase in fibrosis, collagen deposition and heart weight,
a drop in gene expression level to normal non-ischemic level after combined administration of Isoproterenol and the agent is a marker of prevention of development of heart failure by the agent, when there is an increase in ejection fraction and physical activity,
a drop in gene expression level to normal non-ischemic level after combined administration of Isoproterenol and the agent is a marker of prevention of development of heart failure by the agent, wherein there is an up-regulation of lncR-CTB89H12.4 and a downregulation of hsa-miRNA-137 and hsa-miRNA-106b with no change in mRNA-FTHL-17 and mRNA-ANAPC11 gene expression level,
a drop in gene expression level to normal non-ischemic level after combined administration of Isoproterenol and the agent is a marker of prevention of development of heart failure by the agent which is indicative of improvements of heart health, a drop of gene expression level to normal non-ischemic level after combined administration of Isoproterenol and the agent is a marker of prevention of development of heart failure by the agent, when there is no change in heart function which is indicative of absence of toxicity, a drop in gene expression level to normal non-ischemic level after combined administration of Isoproterenol and the agent is a marker of prevention of development of heart failure by the agent in a dose response manner, wherein the amount of the agent is in the range of 0.4 g/kg/day, 0.8 g/kg/day, and 1.2 g/kg/day, an up-regulation of hsa-miRNA-137, hsa-miRNA-106b, mRNA-FTHL-17 and mRNA-ANAPC11, and a downregulation of lncR-CTB89H12.4 are new biomarkers for left ventricular remodeling, wherein their levels are indicator of the degree of remodeling, and predictive of heart failure diseases, and a downregulation of hsa-miRNA-137, hsa-miRNA-106b, mRNA-FTHL-17 and mRNA-ANAPC11, and an up-regulation of lncR-CTB89H12.4 after medical treatment and drug-testing is indicative of successful therapy and lack of cardiac toxicity.

In another embodiment of the present invention, the method for screening and predicting therapy response with an agent in ischemic diseases and aging-related disorders, according to the present invention, wherein the Isoproterenol is administered subcutaneously.

In another embodiment of the present invention, the method for screening and predicting therapy response with an agent in ischemic diseases and aging-related disorders, according to the present invention, wherein the Isoproterenol is administered at an amount of 85 mg/kg/day and 170 mg/kg/day, respectively for 2 consecutive days.

In another embodiment of the present invention, the method for screening and predicting therapy response with an agent in ischemic diseases and aging-related disorders, according to the present invention, wherein the agent is Cyclocreatine phosphate. In an alternate embodiment the agent is Cyclocreatine.

In another embodiment of the present invention, the method for screening and predicting therapy response with an agent in ischemic diseases and aging-related disorders, according to the present invention, wherein the agent is administered intraperitoneally.

In another embodiment of the present invention, the method for screening and predicting therapy response with an agent in ischemic diseases and aging-related disorders, according to the present invention, wherein the agent is administered daily for 14 days at an amount of 0.4 g/kg/day, 0.8 g/kg/day, and 1.2 g/kg/day, wherein there is no change by 0.8 g/kg/day in heart, liver and kidney function which is indicative of absence of organ toxicity by Cyclocreatine phosphate.

In one embodiment of the present invention, the preclinical study of the invention confirmed the following:
(1) the rapid release of Nourin by reversible ischemic hearts (cells are sick, but still alive) before necrosis;
(2) the rapid release of Nourin by necrotic tissues when ischemic injury persists;
(3) identification of the biological activity and mode of action of Nourin as a potent inflammatory mediator associated with cardiac inflammation;
(4) purification of Nourin released by reversible ischemic human hearts (patients undergoing bypass surgery);
(5) identification of amino acid sequence of Nourin released by human reversible ischemic hearts; and
(6) development of an antibody-based ELISA assay against the amino acid sequence of the Nourin epitope N-f-MII.

In one embodiment of the present invention, the clinical application of the Nourin functional assay (leukocyte Chemotaxis) and Nourin ELISA immunoassay (Nourin epitope f-MII) successfully established that:
(1) Nourin released by reversible ischemic hearts was detected in cardioplegic samples collected from patients undergoing open heart surgery within 10 minutes of cardiac arrest and in serum and plasma samples collected from patients experiencing unstable angina while the heart muscles are "sick, but still alive". A very important finding to permit early crucial therapy and save heart muscles from progressing to necrotic injury;
(2) Nourin is much earlier than the current gold standard Troponin in diagnosing unstable angina and AMI patients at presentation with the need for additional serial testing;
(3) Nourin can diagnose NSTEMI patients immediately upon arrival to hospital ED without the required 2 to 6 hours wait for Troponin to be released by necrotic hearts at measurable levels in blood samples;
(4) Nourin can differentiate patients presenting to hospital ED with chest pain due to cardiac AMI from symptomatic non-cardiac patients; and
(5) in comparison to the lack of stability of Troponin, Nourin is stable in ACS patients' samples kept frozen for three years.

The rapid and accurate diagnosis of symptomatic unstable angina and heart attack patients at presentation to hospital ED and outpatient clinics play a significant role in saving patients' lives. Therefore, there is a crucial need for biomarkers that can quickly diagnose ACS patients while the myocardial tissue is still viable to permit early crucial therapy to save heart muscles and reduce myocardial necrosis and heart failure. Approximately 50% of AMI patients progress to heart failure. Therefore, the present disclosure established that the autophagy-related Nourin gene-based RNA network as an early new biomarker for cardiac ischemia to save heart tissue.

In one embodiment of the present invention, an assay for the detection of one or more small molecules that are released as a result of certain heart disorders, including angina and AMI are disclosed. Unlike the Troponin assay currently in use as a marker of necrosis, the Nourin assay according to the invention uses a biomarker for reversible ischemia before death. The Nourin assay can be used to diagnose angina patients presenting with chest pain to hospital ED and in outpatient clinics, and also can be used to distinguish between cardiac patients (angina and heart attack) and non-heart related patients with symptoms of chest pain, as well as healthy individuals.

Therefore, in view of the above the Nourin assay, it can:
(1) identify and "rule in or out" unstable angina patients with high confidence;
(2) differentiate with high sensitivity and specificity between unstable angina patients and healthy individuals;
(3) identify and "rule in or out" heart attack patients with high confidence;
(4) differentiate with high sensitivity and specificity between unstable angina patients and heart attack patients;
(5) complement and enhance the usefulness of Troponin assay to "rule in or out" heart attack patients;
(6) unlike Troponin, it can immediately identify unstable angina and heart attack patients at presentation to hospital ED and eliminates the current required two to six hours of waiting; thus, allows crucial therapy to save heart muscles from dying;
(7) reduce health care expenses by eliminating unnecessary hospital admissions of non-cardiac chest pain patients; and
(8) also reduce potential medical lawsuits due to missed diagnosis of unstable angina patients.

In another embodiment of the present invention, the aforementioned assay involves the use of at least one, and preferably five Nourin RNAs that are released as a result of cardiac ischemia including CAD, UA, AMI, and HF. More specifically, the invention provides for the use of the qPCR assay to detect a Nourin molecular network composed of lncR-CTB89H12.4 (SEQ ID NO: 19), has-miRNA-106b, hsa-miRNA-137 gguccucuga cucucuucgg ugacggguau ucuugggugg auaauacgga uuacguuguu auugcuuaag aauacgcgua gucgaggaga guaccagcgg ca (SEQ ID NO: 04), mRNA-ANAPC11 and mRNA-FTHL-17 as an autophagy-related RNA panel linked to each other and to cardiovascular ischemia to specifically identify ischemic cardiac events.

In another embodiment of the present invention, the use of one or the three qPCR assays to detect Nourin RNAs that are released from cardiac tissue cells upon an episode of CAD, UA, AMI and HF. The aforementioned RNAs, used alone or in combination, can thus be used to detect stable angina, UA, AMI (STEMI and NSTEMI) and HF, and to diagnose the cause of chest pain in patients as cardiac or con-cardiac. It is pertinent to note that, the RNAs can differentiate between patients experiencing or having recently experienced UA and AMI from those having chest pain, but not experiencing of having ACS related to heart ischemia.

In addition, at least one, and preferably up to six of the aforementioned RNAs can be used to:
(1) detect subclinical or silent myocardial ischemia without infarction, as well as low grade myocardial ischemia without cell death;
(2) detect microvascular ischemia missed by current invasive angiography;
(3) identify disease risk and monitor progression; and
(4) predict drug therapy response on heart tissues in clinical trials.

In another embodiment of the present invention, it is evidenced that serum Nourin gene-based RNA network of has-miRNA-106b, hsa-miRNA-137, mRNA-ANAPC11 and mRNA-FTHL-17, as well as the Nourin protein measured by antibody to the Nourin polypeptide comprising of the epitope sequence N-f-MII are elevated in CAD, UA, AMI and HF, while the level of lncR-CTB89H12.4 dropped in AMI patients' samples. Based on these results, it is likely that miRNA-137-5p acggguauuc uugggugggau aau (SEQ ID NO:05) and miR-137-3p uuauugcuua agaauacgcg uag (SEQ ID NO:06) are also elevated in AMI patients' serum samples. Accordingly, combining the integrated genetic epigenetic approach of Nourin RNAs and the Nourin peptide could be a powerful panel of biomarkers for the early diagnosis of CAD, UA, AMI and HF patients. For polygenic diseases such as AMI and a complex human serum, it is expected that a single gene biomarker approach may not suffice for the high-performance requirement of AMI diagnosis. Therefore, by enlisting multiple Nourin gene network and the Nourin peptide that are functionally linked to each other and to AMI functional networks, it will increase the chance of success than the simpler conventional single-marker approach (e.g., Troponin) as a useful standing alone diagnostic and disease monitoring biomarkers, as well as to complement protein-based biomarkers and classical risk factors for CAD, UA, AMI and HF diagnosis and prognosis.

In another embodiment of the present invention, using standard chemotaxis functional assay and ELISA immunoassay, clinical studies demonstrated that the level of Nourin protein was 3-fold higher in plasmas of ACS (UA and AMI) patients who presented to the ED within 1.5 to 3.5 hours after the onset of symptoms, while the standard cardiac biomarkers Troponin T and CK-MB were not detected. After clinical confirmation of ACS patients, Troponin was detected in AMI patients' samples and lasted for 36 hours. Nourin was also detected in same samples after 32 hours of onset of chest pain. Nourin level was not tested beyond the 32 hours. Additionally, an ELISA assay using antibodies developed specifically against Nourin's epitope N-f-MII moiety (hereinafter referred as "Nour001-A") demonstrated clinically:
(1) the detection of high levels of cardiac Nourin in frozen plasma samples (−70° C. for 3 years) collected from ACS patients within the first 8 hours of chest pain when Troponin I level was below the clinical-decision level (below 0.07 ng/ml) but were later confirmed the diagnosis of ACS; thus, Nourin ELISA distinguished ACS patients from non-cardiac patients with chest pain.
(2) the detection of high levels of cardiac Nourin in AMI patients' fresh plasma samples collected within the first 8 hours of chest pain when Troponin I levels were below the clinical-decision level (below 0.07 ng/ml) but were later confirmed the diagnosis of AMI; thus, Nourin ELISA distinguished AMI patients from non-cardiac patients with chest pain; and
(3) Nourin was not detected in plasma samples collected from non-cardiac patients also presenting to the ED within the first 8 hours of chest pain with negative Troponin I.

It is pertinent to note that a number of studies have indicated that the post transcriptional regulatory RNAs such as circulating non-coding micro RNAs (miRNAs) and long non-coding RNAs (lncRNAs) are potential biomarkers for cardiovascular diseases such as AMI. Cardiac injury following AMI is known to increase the expression levels of circulating miRNAs such as miRNA-208a ugacgggcga gcuuuuggcc cggguuauac cugaugcuca cguauaagac gagcaaaaag cuuguuggug a (SEQ ID NO:07) miRNA-208a-5p gagcuuuugg cccggguuau ac (SEQ ID NO:08), miRNA-208a-3p auaagacgag caaaaagcuu gu (SEQ ID NO:09), miRNA-133 acaaugcuuu gcuagagcug guaaaaugga accaaaucgc cucuucaaug gauuuggucccuucaacca gcuguagcua ugcauuga (SEQ ID NO:01). miRNA-133a-5p agcugguaaa auggaaccaa au (SEQ ID NO:02), miRNA-133a-3p uuugguccccc uucaaccagc ug (SEQ ID NO:04), miRNA-1 ugggaaacau acuucuuuau augcccauau ggaccugcua agcuauggaa uguaagaag uauguaucuc a (SEQ ID NO:10), miRNA-1-5p acauacuucu uuauaugccc au (SEQ ID NO:11), miRNA-1-3p uggaauguaa agaaguaugu au (SEQ ID NO:12) and miRNA-499-5p uuaagacuug cagugauguu u (SEQ ID NO:13), miRNA-499a-3p aacaucacag caagucugug cu (SEQ ID NO:14). The concentration of miRNA-208a, miRNA-133a, and miRNA-499 is elevated after ACS suggesting that circulating miRNA as diagnostic biomarkers in cardiovascular diseases. The cardiac-specific miR-208a is the most promising STEMI biomarker reported. The first three miRNAs (miRNA-208a, miRNA-133, miRNA-1) peak at 3 hours after AMI and miRNA-499 at 12 hours. Experimentally, the levels of miRNAs in plasma were highly comparable with cardiac Troponin levels in their rat model of isoproterenol-induced myocardial injury. They found miRNA-208 to be undetectable at baseline, increased after 3 hours of isoproterenol treatment, and significantly elevated up to 12 hours. MiRNA-208 was also found to be rapidly induced in rodent models of AMI where it was undetectable in sham-operated animals, increased at 30 minutes, peaked at 3 hours, and disappeared from plasma at 24 hours. In a subgroup of 20 patients with AMI of which blood samples were collected within 4 hours after the onset of symptoms, miRNA-208 was detected in all patients, whereas Troponin I was only detected in 85% of the patients, confirming the superior sensitivity of miRNA-208 at early time points. In a clinical setting the differences in time courses of release between specific miRNAs and Troponin I might be valuable. Especially in the consideration of the fact that the Troponin I levels begin to rise only 3 to 8 hours after AMI, diagnosis via biomarkers with a faster cardiac release, such as miRNA-208, miRNA-1, and miRNA-133, might be beneficial.

The release of miRNAs can be: (a) actively secreted and these molecules are referred to as circulating miRNAs, (b) through a jab junction dependent mechanism and (c) as a consequence of cellular content release (macrovesicles, exosomes) following necrosis, for instances during an AMI. MicroRNAs play a pivotal role in a wide range of regulatory processes in the cells and in fact miRNAs deficiencies or excesses have been linked to a number of cardiovascular diseases. The apparent minimal effects of miRNAs under non-stress conditions as compared to their specific involvement during responses to AMI make miRNAs attractive diagnostic targets with little or no effects from normal non-stressed tissues. Similarly, the circulating lncRNA MIAT has been expressed in AMI patients and was able to distinguish STEMI from NSTEMI. However, the circulating lncRNA UCA1 decreased in AMI patients at two hours after the onset of symptoms. At this stage, certain miRNAs individually or in combination may possibly complement protein-based biomarkers and classical risk factors for AMI diagnosis and prognosis.

Circulating miRNAs are emerging as blood-based biomarkers for cardiovascular diseases since they offer many attractive features of biomarkers. They are stable in the circulation, their sequences are evolutionarily conserved, their expression is often tissue or pathology specific, and their detection is based on sequence-specific such as in the case of Nourin, features that are helpful in the development of sensitive and specific assays. In cardiovascular disease, "distinctive patterns" of circulating miRNAs have thus far been found for AMI, coronary artery disease (CAD), hypertension, heart failure (HF), and viral myocarditis (VM). Circulating miRNAs are found to be remarkably stable in plasma even under harsh conditions as boiling, low or high pH, long-term storage at room temperature, and in multiple freeze-thaw cycles. lncRNAs are also found to be present in circulation in a remarkably stable form, which can withdraw multiple freeze-thaw cycles and are resistant against RNase-mediated degradation.

Additional procedures to detect the circulating Nourin RNAs in cardiac patients' samples are by measuring exosomes and extracellular vesicles. In addition to the use of the standard qPCR, the Nourin-based RNA network can be detected in cardiac patients' samples using gold coated magnetic nanoparticles as a non-PCR based technique. For this Nanogold assay, the Nourin RNAs will be either extracted or measured directly in patients' samples without purification or pre-amplification. The Nanogold assay uses magnet beads coated with specific probe and gold nanoparticles to facilitate both RNA extraction and detection of expression using nanoparticles which seems to save time and cost. This assay will measure the Nourin RNA panel of markers in various sera samples. A citrate-capped gold nanoparticles (AuNPs) assay for the direct detection of unamplified Nourin-based RNA network in sera samples for the early diagnosis of AMI patients. The assay employs magnet nanoparticles (MNPs) functionalized with Nourin-based RNA-specific oligonucleotides for capturing and purifying the target RNA and AuNPs for detection. The method depends on colorimetric determination of unamplified RNA. In addition, Nourin-based RNA panel of markers can be detected in cardiac patients' samples using the technology provided commercially, for example by Multiplex miRNA assays measuring the Nourin-based RNA network via total circulating RNAs, Multiplex miRNA assays with FirePlex® particle technology enable simultaneous profiling of 65 miRNAs directly from small amounts of biofluid or FFPE, without RNA purification or pre-amplification. Assays can be customizable for the Nourin-based RNA panel of markers and suitable for both discovery and verification studies. Readout uses a standard flow cytometer. Additionally, sensor chip procedures can be used to detect the Nourin-based RNA network and the Nourin protein including and not limited to Nourin epitope f-MII.

Molecular miRNAs represent an important class of small regulatory RNAs that control gene expression post transcriptionally by targeting mRNAs for degradation or translation inhibition. In stable CAD patients, the expression level of miR-1, miR-208a and miR-423-5p did not show significant differences in comparison to control group. Also, there was no significant increase of number of the 3 miR copies at 6, 12 and 24 hours after PCI. However, there was a significantly higher number of miR-423-5p copies in patients with acute AMI before the PCI. After 6, 12, and 24 hours post-procedure the expression level was similar to the control group and significantly lower than the baseline level. Conversely, the expression level of miR-1 and miR-208a were not significantly different than in the control group before Percutaneous Coronary Intervention (PCI).

The early diagnosis and proper treatment of UA can reduce the chance of acute myocardial infarction, and reduce high mortality and morbidity rates. However, there is a lack of reliable and valid biomarkers in the diagnosis of UA. The usefulness of circulating miRNAs for differentiating UA from non-ischemic chest pain (NICP) in the ED has been reported. Using microarrays analysis, the expressions of circulating miRNAs in patients with UA were evaluated relative to individuals with NICP (control subjects). Circulating miR-21, miR-25, miR-92a, miR-106b, miR-126 and miR-451 levels were measured in 98 patients with UA and 95 control subjects in the ED. To investigate the underlying functions of miRNAs in UA, bioinformatic analysis of validated miRNAs was conducted. Circulating miRNAs were upregulated in UA compared with the control group. The circulating levels of miRNAs (miR-21, miR-25, miR-106b, miR-126) are significantly higher in UA patients compared with patients with NICP, and the addition of the medical history that combined ECG, age, risk factors and troponin is useful to detect or rule out UA. Similarly, although miR-106b profiling using microarrays analysis screening showed increased levels in UA patients, these studies did not determine the clinical significance of the elevation of miR-106b and its correlation to UA as a diagnostic marker.

Early studies have revealed a complex role for miRNAs in major biological processes such as development, differentiation, growth and metabolism. MiR-137 in particular, has been of great interest due to its critical role in brain function and putative involvement in the etiology of cardiovascular diseases, neuropsychiatric disorders and cancer. Restoration of miR-137 expression has also been shown to inhibit cell proliferation, migration and metastasis, and induce cell cycle arrest, differentiation and apoptosis. These properties of miR-137 propose its potential for prognosis, diagnosis and as a therapeutic target for treatment of several human neurological and neoplastic disorders. The regulatory function of miR-137 in oxidative stress-induced cardiomyocyte apoptosis was studied. Activated leukocytes release oxidative stress such as hydrogen peroxide (H2O2) which induces significant apoptosis and up-regulated miR-137. Studies demonstrated that miR-137 is a critical regulator in cardiomyocyte apoptosis. In retinal diseases, the apoptosis of retinal ganglion cells (RGCs) is a hallmark of several optic neuropathies. Studies demonstrated that miR-137 acts as a hypoxia-responsive gene in RGCs. It was observed that overexpression of miR-137 markedly aggravated hypoxia-induced cell apoptosis, whereas inhibition of miR-137 effectively protected RGCs against hypoxia-induced apoptosis. The study demonstrated that miR-137 targets Notch1 expression, revealing a novel link between miR-137 and Notch signaling, and suggesting that a miR-137/Notch1 axis may serve as a potential molecular target for the treatment of hypoxia-induced retinal diseases. Furthermore, reported studies suggest that overexpression of miR-137 in the whole brain induces several phenotypes that are relevant to aspects of psychiatric disorders, such as schizophrenia. Based on these findings, miR-137 Tg mice may have the potential to become a useful tool in researching the pathophysiology of psychiatric disorders.

Virtually all episodes of ACS, including UA, STEMI (ST elevation myocardial infarction), where ischemic changes are detected by ECG and NSTEMI (non-ST elevation myocardial infarction), where no ischemic changes are detected by ECG, are associated with the loss of myocardiocytes, inflammation, fibrosis, and cardiac remodeling, which all together represent the leading pathogenetic mechanisms of HF. The pathophysiological basis of HF in patients who have experienced an episode of AMI is complex and multifaceted, involving edema, apoptosis, and necrosis of myocardiocytes after prolonged acute coronary ischemia, which ultimately promotes maladaptive cardiac remodeling and culminates in ventricular dilatation and hypertrophy. The leading symptoms of HF are attributable to gradual impairment of LV myocardial function, and thus include dyspnea and limited exercise tolerance.

Heart failure-related left ventricular remodeling is a complex process involving cardiac myocyte death, fibrosis, inflammation, ventricular remodeling, and loss of contractile activity. CAD is a leading cause of HF and that LV remodeling is derived mainly from patients of myocardial infarction. In response to ischemic/reperfusion injury, cardiomyocyte loss is through cell death pathways such as necrosis, apoptosis, or possibly excessive autophagy.

Cardiac remodeling refers to a progressive series of changes in the size, shape, and function of the heart that are initiated by damage to the myocardium or increases in wall stress. Remodeling is a major factor in the development and progression of HF. It involves changes in both the cardiomyocytes and the makeup of the extracellular matrix (ECM). The latter consists of an intricate weave of (predominantly) collagen fibrils that play a vital role in maintaining the structural and functional integrity of the heart.

The immune system plays a significant role in ventricular remodeling, and its persistent activation may lead to long-term cardiac injury. In the next stage of infarct healing, ischemically injured and dying cardiac myocytes release intracellular proteins such as the cardiac-derived inflammatory mediator, Nourin into the circulation and trigger an inflammatory response. Inflammatory cells, including neutrophils, monocytes, macrophages, and lymphocytes infiltrate the tissue. These immune cells remove dead myocytes and pave the way for healing. After resolution of the inflammatory response, cardiac fibroblasts proliferate and secrete extracellular matrix proteins such as collagen I to form a fibrotic scar that replaces dead myocytes. The resulting tightly cross-linked, fibrotic scar with significant tensile strength serves to prevent rupture. This remodeling of the LV continues progressively in response to increases in wall stress, provoking cardiac myocyte hypertrophy in the infarct border zone, wall thinning, and chamber dilation. This global adverse remodeling response leads to increases in both LV end-diastolic and end-systolic volumes and reduced ejection fraction.

Ventricular remodeling is also a deposition of excessive extracellular matrix. This surplus extracellular matrix, which constitutes scar or fibrosis, promotes both contractile dysfunction and rhythm disturbances. As a result, cardiac fibrosis contributes to morbidity and mortality in many forms of heart disease. Indeed, the amount of fibrotic scar in the myocardium correlates strongly with the increased incidence of arrhythmias and sudden cardiac death. Extracellular matrix deposition and fibrosis formation occur through the action of cardiac fibroblasts. In the setting of pathological stress, fibroblasts proliferate and differentiate into myofibroblasts, thereby gaining the capacity to contract and secrete collagen I, collagen III, and fibronectine. Within the LV facilitate, both collagenous and myofibroblasts propagate the arrhythmic phenotype of the remodeled heart.

Cardiac fibrosis is an independent and predictive risk factor for heart failure. Some evidence suggests that the modulation of cardiac fibrosis alters the arrhythmic phenotype in patients with heart disease. To date, no therapeutic strategy has been developed to specifically target fibrosis in the heart. lncRNAs are involved in the pathogenesis of cardiac fibrosis. Fender (lncRNA) is involved in the pathogenesis of cardiac fibrosis via regulating miR-106b/SMAD3axis.

The immune system also plays a significant role in ventricular remodeling, and its persistent activation may lead to long-term cardiac injury. The upregulation of miR-106b promotes cardiomyocyte inflammation, which may be an early regulatory mechanism. MicroRNAs involve in the pathophysiological progress in heart failure and it is expected that microRNAs will be widely used in heart failure diagnosis and therapy. The posttranscriptional regulation of gene expression by microRNAs controls the highly complex multi-cell lineage process of cardiac tissue formation. In recent years, multiplex experimental models have provided evidence that changes in expression levels of miRs are associated with cardiovascular disease. AMI patients had significantly higher levels of plasma miR-21, compared to healthy controls. miR-21 was shown to be a novel biomarker that was predictive of LV remodeling after AMI. In addition, levels of miR-21 correlated with several traditional markers of AMI; creatine kinase-MB (CK-MB), creatine kinase (CK) and cardiac troponin I (cTnI), with comparable diagnostic accuracy. Levels of serum miR-1 were also positively associated with myocardial infarct size. In post-AMI patients, miR-1 was significantly correlated with (a) the absolute change in infarct volume, (b) showed a trend for positive correlation with LV ejection fraction and (c) was associated with AMI mortality.

Additional studies indicated that lncRNA Fendrr was up-regulated in the heart tissues of transverse aortic constriction (TAC) induced cardiac fibrosis mouse models, determined by RT-QPCR. Loss-function of Fendrr significantly alleviated the cardiac fibrosis phenotypes induced by TAC, indicating that Fendrr is required for the pathogenesis of cardiac fibrosis. Experimentally Fendrr directly targets miR-106b, by which the lncRNA promotes cardiac fibrosis (indicated by the elevation of Col1a1, Col3a1, CTGF and ACTA2 expression) in a miR-106b mediated manner. Collectively, these findings highlight the axis of Fendrr/miR-106b/Samd3 in the pathogenesis of cardiac fibrosis, which may be a promising target for clinical intervention target of cardiac fibrosis. Experimentally, circulating levels of miR-423-5p and miR-106 were markedly increased in hypertension-induced HF, which was confirmed via RT-qPCR analysis of plasma RNA from hypertensive rats. The expression of miR-137 was also detected by RT-qPCR and western blot analysis in spontaneously hypertensive rat hearts. miR-137 may promote cardiac remodeling in these rats by upregulation of Ang II and the TGF-B1/Smad3 signaling pathway; in addition, captopril intervention can inhibit miR-137 expression. Therefore, miR-137 not only indicates the presence of high blood pressure, it may also reflect its severity. These results indicate that several miRs can reflect disease progression to a certain extent, and may be used as biomarkers of hypertensive HF.

Ischemic stroke is related to a variety of physiological and pathological processes including autophagy and apoptosis. Growth arrest-specific 5 (GAS5), a long non-coding RNA (lncRNA), is known to negatively regulate cell survival and plays a key role in the pathogenesis of numerous diseases. Studies indicated that GAS5 may promote the progression of ischemic stroke through acting as a competing endogenous RNA (ceRNA) for miR-137 to mediate the Notch1 signaling pathway, which contributes to an extensive understanding of ischemic stroke and may provide novel therapeutic options for this disease. Thus, LncRNA GAS5 regulates ischemic stroke as a ceRNA for miR-137 to regulate the Notch1 signaling pathway.

There is a role of biomarkers in HF in conjunction with the clinical and physical assessment. Biomarkers can provide greater diagnostic accuracy than the physical assessment alone. The diagnostic strength of natriuretic peptides is their high sensitivity for "ruling out" HF; however, as the value increases, HF becomes more likely. Defining "rule-in" cutoffs for HF is complicated because multiple factors influence natriuretic peptide levels. The natriuretic peptides are released by the heart in response to myocardial tension and increased intravascular volume and provide accurate tests for the diagnosis of heart failure compared with echocardiography. Brain natriuretic peptides (BNP) and Troponins are the benchmark biomarkers used for the stratification of risk of cardiac dysfunction in patients with AMI. In addition to Troponins as markers of myocardial cell death and BNPs as markers of hemodynamic cardiac stress, other biomarkers of different pathogenetic pathways have been reported. These include: cardiac fibrosis (especially galectin-3), inflammation (C-reactive protein (CRP), growth differentiation factor-15 (GDF-15), osteoprotegerin and extra-cardiac involvement (red blood cell distribution width (RDW)). However, studies indicated that during the early phase of myocardial ischemia, the prognostic value of emergent biomarkers for new-onset HF or deterioration of cardiac function in patients with AMI, suggesting that, in most cases, the use of these diagnostic biomarkers of cardiac dysfunction does not translate into efficient risk prediction of HF.

The natriuretic peptides are the best-established and best-evaluated markers to help in the proper diagnosis and exclusion of HF. Natriuretic peptides have led the way as a diagnostic and prognostic tool for the diagnosis and management of HF. They can provide important information about disease severity and help in the detection, diagnosis, prognosis, and management of HF. Monitoring their concentrations in blood not only can provide the clinician information about the diagnosis and severity of HF but also can improve prognostication and treatment strategies. However, there is still a critical need for novel diagnostic biomarkers and new therapeutic interventions to decrease the incidence of HF. Recently, there is increasing evidence that circulating miRNAs (miRNAs), i.e. endogenous, stable, single-stranded, short, non-coding RNAs, can be used as diagnostic biomarkers for CVD. Furthermore, miRNAs represent potential novel therapeutic targets for several cardiovascular disorders. MicroRNAs regulate gene expression at the posttranscriptional level by targeting the 3'-untranslated region of mRNA sequences. They are stable in the circulation and have been explored as potential biomarkers in coronary artery disease, myocardial infarction, hypertension, diabetes mellitus, viral myocarditis, and HF. Inflammatory markers have, also, been evaluated for predicting new-onset HF. In the ABC study (Health, Aging, and Body Composition), IL-6, tumor necrosis factor-α, and CRP were associated with new-onset HF, but when all 3 markers were added to the model, IL-6 emerged as the strongest marker.

Current circulating biomarkers for cardiovascular disease are based on specific proteins, such as troponins and natriuretic peptides. The development of new protein-based biomarkers is often rather cumbersome because of the complexity of protein composition in blood, the diversity of post-translation modifications, the low abundance of many proteins, and the difficulties in developing assays for high-sensitivity detection. Detection of blood-based biomarkers is usually based on antibodies, which may exhibit cross-reactivity with other proteins. Therefore, circulating miR-NAs offer many features to make them an attractive class of biomarkers. They are stable; their sequences are evolutionarily conserved; microRNA expression is often tissue or pathology specific; and because they are detected by real-time PCR, assays can be highly sensitive and specific. Circulating miRNAs have been identified as potential biomarkers of HF. Recent evidence suggests that miRNAs are involved in the development and progression of HF. Several miRNAs have been identified as potential candidates that could be used as diagnostic biomarkers for HF to provide valuable clinical information. Additionally, they may be important tools in monitoring the progress of therapeutic interventions. Medical interventions are also associated with changes in miRNA levels. Compared to stable HF patients, individuals with advanced HF with left ventricular (LV) assist device implantation express higher cardiac myomirs; muscle-specific miRNAs; miR-208b, miR-208a and miR-499; and myomirs miR-1 and miR-133b. Furthermore, miR-208b and miR-499 are released in the coronary sinus after cardioplegia and reperfusion to markedly higher levels than that present prior to surgery.

Changes in the levels of circulating miRNAs have been reported in AMI patients with ischemia-related HF, including increases in miR-1, miR-133, miR-21, miR-29b, miR-192, miR-194, miR-34a, miR-208, miR-499, miR-423, miR-126, miR-134, miR-328 and miR-486, and decreases in miR-106, miR-197 and miR-223. In animal models of AMI, serum levels of miR-1, a regulator of cardiac muscle development and differentiation, peaked 6 h post AMI and returned to basal levels after 3 days. Levels of serum miR-1 were also positively associated with myocardial infarct size. In post-AMI patients, miR-1 was significantly correlated with (a) the absolute change in infarct volume, (b) showed a trend for positive correlation with LV ejection fraction and (c) was associated with AMI mortality. AMI patients had significantly higher levels of plasma miR-21, compared to healthy controls. miR-21 was shown to be a novel biomarker that was predictive of LV remodeling after AMI. In addition, levels of miR-21 correlated with several traditional markers of AMI; creatine kinase-MB (CK-MB), creatine kinase (CK) and cardiac Troponin I (cTnI), with comparable diagnostic accuracy.

A higher level of circulating miR-208a was observed in patients with AMI that peaked 3 h after reperfusion, compared with unstable angina patients. Elevated miR-208a was significantly associated with increased risk of mortality or HF within 6 months after the AMI. Although miR-208b was not independently associated with the AMI clinical outcome after adjustment for cTnT, circulating miR-208a levels strongly correlated with cTnI and CK-MB released from the infarcted area.

Level of plasma cardiac myocyte-associated miR-499 was highly elevated and correlated with cTnI in AMI patients, which suggests its release from injured cardiomyocytes. Compared to miR-1 or miR-208, miR-499 had a more accurate predictive value that was significantly greater than the most reliable biomarkers of AMI; cTnI and CK-MB. Changes in the levels of circulating miR-499 were associated with unstable angina and non-ST elevation myocardial infarction in patients presenting within 3 h of symptom onset. This supports a role for serum miR-499 as a potentially novel biomarker to accelerate the diagnosis of acute coronary syndrome patients. The sensitivity and specificity of miR-499 were greater than cTnI, suggesting that miR-499 could be an independent risk factor for perioperative MI. These findings also suggest that circulating miR-499 could be an early biomarker for the identification of perioperative MI in cardiac surgery. It has been reported that there is a significant elevation of miR-423 at 1, 3, and 12 months after AMI, compared to baseline levels. However, there are no significant correlations between miR-423 expression and indices of LV function and remodeling; echocardiographic parameters, levels of cTn I or BNP. Circulating miR-133a and miR-423-5p failed as biomarkers for left ventricular remodeling after myocardial infarction. Thus, it was concluded that circulating levels of miR-133a and miR-423-5p are not useful biomarkers of LV remodeling after AMI.

Although current therapies for heart failure patients include, angiotensin converting enzyme (ACE) inhibitors, angiotensin receptor blockers (ARBs), aldosterone antagonists, and β-adrenergic receptor blockers (β-blockers), which manifest significant efficacy in reducing morbidity and mortality in patients with chronic systolic heart failure. However, in many instances, disease progression continues unabated. Additionally, novel disease targets are continually being discovered, however, most therapeutics do not demonstrate consistent efficacy in patients; many prove to be ineffective, even deleterious, before reaching Phase III clinical trials.

Cardiac fibrosis is an independent and predictive risk factor for heart failure. Some evidence suggests that the modulation of cardiac fibrosis alters the arrhythmic phenotype in patients with heart disease. To date, no therapeutic strategy has been developed to specifically target fibrosis in the heart. Cardiac remodeling refers to a progressive series of changes in the size, shape, and function of the heart that are initiated by damage to the myocardium or increases in wall stress. Remodeling is a major factor in the development and progression of HF. It involves changes in both the cardiomyocytes and the makeup of the extracellular matrix (ECM). The latter consists of an intricate weave of (predominantly) collagen fibrils that play a vital role in maintaining the structural and functional integrity of the heart. Thus, targeting the reduction of fibrosis and collagen synthesis by the bioenergetic CCrP (FIG. 53 and Example 17), is a new therapeutic approach for the prevention and treatment of HF.

It was shown that suppression of myocardial contractility plays an important role in the development of heart failure; therefore, there is a need for cardiotonic agents to improve the contractile function of the failing heart. Additionally, studies indicated that the development and progression to HF are associated with a decline in energy reserve capacity that ultimately reaches a threshold after which compensatory mechanisms can no longer support the decreasing energy supply. Growing evidence indicates that derangements in myocardial fuel metabolism and bioenergetics contribute to the development of heart failure. Stored myocardial high-energy phosphate (phosphocreatine) are reduced in humans with pathological ventricular hypertrophy, with further decline during the transition to heart failure. Notably, the [phosphocreatine]/[ATP] ratio correlates with heart failure severity and is a strong predictor of cardiovascular mortality. Thus, targeting energy metabolic disturbances and corresponding upstream regulatory events occurring during the early stages of HF is an important first step toward the identification of new therapeutic targets to improve the outcomes of current therapies. Mitochondrial energy source could, therefore, be a promising therapeutic target to improve mitochondrial biogenesis. Currently, there are no drugs that specifically target mitochondrial biogenesis in HF patients.

Mitochondrial abnormalities and reduced capacity to generate ATP can have a profound impact in heart failure. Abnormal mitochondria are also linked to myocyte injury because they are a major source of reactive oxygen species (ROS) production that can induce cellular damage. Abnormal mitochondria promote programmed cell death through the release of cytochrome c into the cytosolic compartment and activation of caspases. Bendavia was reported to improve cellular ATP levels and prevent pathological ROS formation. However, in the EMBRACE STEMI (Evaluation of Myocardial Effects of Bendavia for Reducing Reperfusion Injury in Patients with Acute Coronary Events—ST-Segment Elevation Myocardial Infarction) trial, Elamipretide did not improve the primary or secondary outcomes. In the randomized placebo-controlled trial of Elamipretide in HF, the drug was shown to reduce left ventricular volumes; however, the confidence intervals were wide in this small study, and there were no changes in biomarker data. Elamipretide is currently being investigated in larger HF studies to determine its effect on cardiac remodeling and clinical outcomes.

After an ischemic event, approximately 15% to 20% of the hypoperfused myocardial zone, previously perfused by the culprit coronary artery, undergoes necrosis within minutes, but it takes up to 6 hours for the remaining 80% to 85% to progress from ischemic damage to permanent necrosis. Timely reperfusion produces a greater amount of salvaged myocardium; but it is also a major component of reperfusion injury. The greater clinical emphasis on rapid reperfusion of ischemic myocardium opens a window of opportunity for new cardioprotective therapies to address the associated pathophysiology. Although many well-controlled experimental studies were reported, to date, there are no available pharmacologic therapies that effectively reduce reperfusion injury. Lethal myocardial reperfusion injury may account for up to 50% of the final myocardial infarct size and up to 50% of AMI patients will advance to heart failure.

The degree of impaired contractile function after AMI is determined by the scar size: large scars result in progressive chronic heart failure. Furthermore, the influx of large number of neutrophils and inflammatory mediators after an AMI have been proposed as major contributors for microvascular obstruction and post-AMI adverse LV remodeling leading to heart failure. Although inflammation is an important contributor to the pathogenesis of early and late myocardial reperfusion injury. Inflammation also plays a key role in the healing process essential for cardiac repair and scar formation. Therefore, it is critical to achieve the "right balance" between limiting the early 'harmful' inflammation in the first few minutes to hours after reperfusion and allowing the 'beneficial' inflammation required for tissue repair. In 1970s, investigators tested the gold standard anti-inflammatory agents, corticosteroids for their role in treating AMI to control inflammation. Although some studies have shown increase in patients' survival in the first three days of hospitalization, concern was reflected in other studies regarding the potential for corticosteroids to impair and retard wound healing after 3 days resulting in wall thinning and rupture.

Therefore, there is an urgent need for effective new therapeutic drugs which provide protection of heart muscle for CAD, ACS and HF patients experiencing myocardial ischemia and, thus, save ischemic muscles from progressing to necrosis and heart failure. Saving heart muscles from progressing to permanent damage will particularly be crucial for the outcome of AMI patients who are undergoing angioplasty/percutaneous coronary intervention (PCI) to reduce their progression to heart failure (HF). Depending on the infarct size, up to 50% of AMI patients will proceed to suffer from HF, which is known for its devastating disability. Cyclocreatine Phosphate is a novel mechanism that has the ability to save the reversible ischemic cardiac muscles from progressing to permanent necrosis and, thus, improve AMI patients' outcome (reducing disability associated with HF), quality of life and patients' financial burden.

Preservation of mitochondrial energy metabolism by Cyclocreatine Phosphate (CCrP) is a novel therapeutic target potential which can also be applied in a number of additional "ischemic" conditions including: atrial fibrillation (AF), Takotsubo cardiomyopathy, cardiac surgeries, stroke, and Alzheimer. Currently, there are no drugs specifically target mitochondrial biogenesis in these ischemia-related diseases. Preservation of the energy source ATP, will present a promising therapeutic approach to prevent the development, as well as, treat HF patients. This invention demonstrated that healthy rats treated with CCrP (0.8 gm/kg) for 14 days, showed no toxicity in heart, liver and renal function. Since CCrP showed strong cardioprotective activities against ischemic heart diseases (AMI, bypass, heart transplantation and HF), CCrP can also be useful to prevent and treat other cardiac ischemic diseases (e.g., atrial fibrillation, Takotsubo cardiomyopathy and cardiac surgeries including valve replacement), as well as aging-related neurodegenerative diseases (e.g., cerebral ischemic stroke and Alzheimer).

Atrial fibrillation (AF)—is the most frequently observed arrhythmia in the United States and is associated with increased mortality and morbidity. Its incidence is age-related and expected to rise due to the aging population. Consequently, AF will contribute significantly to the socio-economic burden. Symptoms due to AF are highly variable. The rapid and irregular ventricular rate seen in AF may cause severe palpitations, dizziness, angina, dyspnea, or heart failure. Life-threatening complications of the arrhythmia, such as severe ischemia, hypotension, loss of consciousness, and heart failure, are the most common clinical indications for emergency cardioversion. The goal of current therapy including Beta-blockers, Calcium-channel blockers, is to reduce "resting heart rate" to less than 80 to 90 beats per minute and prevent inappropriately high ventricular rates during activity. Anticoagulated medicines are also used to reduce thromboembolism formation. Therapy of (longstanding) persistent AF has high failure rates, with 20-60% of patients showing recurrence of AF within three months after ablation or electrical cardioversion. Therapy failure in AF is related to the presence of structural remodeling of the myocardium, which, in turn, impairs electrical activation of the atria ("electropathology"). Atrial inflammation, reduction of ATP and ischemia are also pathways underlying AF-induced cardiac structural remodeling. The influx of large number of neutrophils and inflammatory mediators have been proposed as major contributors in AF. Accordingly, there is a need to develop more mechanism-directed AF therapies. Since it has been previously demonstrated that the administration of CCrP preserved mitochondrial ATP energy metabolism, reduced myocardial ischemic injury and inflammation resulting in immediate restoration of contractile function during early reperfusion without arrhythmia, CCrP can present a novel therapeutic approach in AF. Therefore, CCrP can improve and prevent the development of AF by preventing ischemic injury and inflammation, as well as AF-induced cardiac structural remodeling. CCrP presents a new mechanism and therapy for AF patients by preventing ischemic injury and protecting against inflammation-induced arrythemia.

Additionally, functioning as an anti-inflammatory, CCrP inhibits leukocyte recruitment and activation to release a number of toxic mediators of cytokine storms, digestive enzymes and free radicals. In the AMI canine model, the administration of Cyclocreatine reduced myocardial cell injury, circulating Nourin and cardiac inflammation, resulting in immediate restoration of contractile function during reperfusion. Similarly, in the bypass canine model, the administration of Cyclocreatine resulted in immediately restoration of strong contractile function "without arrythemia", while all control dogs required defibrillation. Bypass dogs showed stronger inflammatory response in the atria than ventricles. Therefore, CCrP can present a novel anti-arrhythmic therapeutic approach in AF, by preventing ischemic injury, inflammation-induced arrhythmia, AF-induced cardiac structural remodeling.

Takotsubo cardiomyopathy (broken-heart syndrome)—is a reversible acute heart failure frequently precipitated by an emotional or physical stress. It presents clinically as an acute myocardial infarction triggered by an emotionally or physically stressful event. The administration of CCrP can, therefore, prevent stress-induced ischemic injury and the development of acute HF.

Surgical Procedures—CCrP can also function as a cardioprotective against ischemic injury in scheduled surgical procedures including, and not limited to PCI, valve replacement, cardiopulmonary bypass surgery, and heart transplantation.

Cerebral Ischemia (Stroke)—ischemia and subsequent reperfusion is known to induce irreversible tissue damage with the consequence of more or less pronounced impairments. The prevalence rate of stroke in U.S. was estimated to be approximately 1 in 59 or 1.69% or 4.6 million people. Cerebral ischemia with the resulting strokes is considered as one of the three major causes of death in all countries. In addition, the increase in the number of individuals with physical or mental handicaps after stroke presents considerable problems in terms of quality of life and socioeconomic costs. Despite recent medical and surgical advances, the general approach to prevent acute ischemic brain damage remains inadequate. Up till now, there are no clinical effective protocol for amelioration of brain damage caused by ischemia and reperfusion. Although over the last decades, significant progresses have been made in the development of thrombolytic therapies for acute ischemic stroke, these thrombolytic therapies have restrictive time window. In addition, these therapies have increased risk of cerebral hemorrhage which limits their application for certain patients. Clearly, there is a crucial need to develop neuroprotective new therapies to prevent and treat acute ischemic brain which could be implemented alone or in combination with thrombolytic approaches to improve clinical outcome of more patients with acute ischemic stroke. CCrP can be administrated prophylactically to high risk patients including aging population to protect against brain ischemic injury. CCrP can also be administered immediately after an ischemic event to protect against deterioration of areas adjacent to ischemic tissues, thus minimize cell injury, loss of function and disability.

Heart and brain are among parts of the body requiring the greatest amounts of energy and they are the most affected during failures of the mitochondria to generate ATP in aging due to diminished vascularization that leads to hypoxia and ischemia. Thus, preservation of the energy source ATP by CCrP, will also present a promising therapeutic approach as a new "age-modifier therapy" to prevent the development and to treat Alzheimer's disease (AD) similar to HF (described in this invention).

Alzheimer's disease (AD)—is one of the most common neurodegenerative diseases in the elderly, affecting 40 million people worldwide. The prevalence of AD is strongly correlated with age, imposing a greater socioeconomic burden as life expectancy continues to increase. Recent estimates predict that in the next four decades, the world's proportion of people aged 65 years and older will account for nearly 22% of the total population—from the present 800 million to 2 billion people. Although this increase in life expectancy is reflective of the healthcare achievements, the socioeconomic costs associated with a higher chronic disease burden have necessitated the development of robust prevention and management strategies that are both safe and immediately executable.

Due to the high energy demands of neurons and glia, a considerable amount of ATP is consumed in the brain. Also, because no energy storage (such as fat or glucose) is available in the central nervous system (CNS), brain cells must continually produce ATP to maintain activity and energy homeostasis. With aging, oxygen delivery to cells and tissues is impaired due to diminished vascularization, thereby increasing the susceptibility of neurons to damage. Thus, hypoxic (neuronal) adaptation is significantly compromised during aging. Many neurological diseases, such as stroke and Alzheimer's disease (AD) are characterized by hypoxia, a state that is believed to only exacerbate disease progression. AD is a pressing public health problem with no effective treatment. Existing therapies only provide symptomatic relief without being able to prevent, stop or reverse the pathologic process. While the molecular basis underlying this multifactorial neurodegenerative disorder remains a significant challenge, mitochondrial dysfunction appears to be a critical factor in the pathogenesis of this disease. It is therefore important to target mitochondrial dysfunction in the prodromal phase of AD to slow or prevent the neurodegenerative process and restore neuronal function. The relationship between hypoxia and AD could open the avenue for effective preservation and pharmacological treatments of this neurodegenerative disease by using the novel bioenergetic drug, CCrP. It has been previously demonstrated that CCrP crosses blood brain barrier and functions as a potent neuroprotective agent by preventing ischemic injury and restoring organ function. Additionally, similar to heart tissue, Nourin protein was quickly released within 2 minutes by brain and spinal cord tissues in response to ischemia. Because of the great similarities between heart and brain and that both require high demand of ATP, the administration of CCrP will be as effective in preventing ischemic injury and restoring neurologic function in stroke and AD, similar to what has been previously demonstrated in aging-related HF.

Clinically, AD is associated with the progressive loss of essential cognitive functions and progressive hippocampal and cortical brain atrophy. Death occurs, on average, 9 years after diagnosis. AD is pathologically defined by the widespread brain distribution of amyloid-beta peptide (Aβ) plaques, neurofibrillary tangle (NFT) formation, as well as synaptic and neuronal loss. Despite growing understanding of the disease, it remains unclear how these pathological features relate to the specific disease processes. The amyloid cascade hypothesis continues to serve as the predominant model of AD pathology. This hypothesis suggests the overproduction of AP as the causal trigger in the disease process. AP is derived from the amyloidogenic cleavage of the amyloid precursor protein (APP), protein cleaved by two endoproteases. The disease progression is associated by the accumulation of Aβ peptides and other misfolded proteins such as tau protein (microtubule-associated protein). The accumulation of these peptides eventually leads to cell death and its associated manifestations such as dementia and behavioral changes. These manifestations are brought about due to the triggering of oxidative stress and inflammation. Increasing evidence suggests that hypoxia facilitates the pathogenesis of AD through accelerating the accumulation of Afl, increasing the hyperphosphoration of tau, impairing the normal functions of blood-brain barrier, and promoting the degeneration of neurons. Additionally, similar to the aging-related HF disease, hypoxia in AD results in reduction of ATP production, impaired mitochondrial function, increased ROS production, neuronal injury and inflammation. Mitochondrial function may be improved by enhancing mitochondrial biogenesis through caloric restriction and exercise, as well as the administration of CCrP crosses the blood brain barrier. Resveratrol is a natural product known for its anti-ageing properties due to calorie restriction like effects. It prevents oxidative damage and decreases apoptosis and cell injury. Resveratrol's take on other neurological disorders is due to its anti-oxidative, anti-apoptotic, anti-inflammatory and cognitive and motor enhancement properties. It decreases oxidative stress and inflammation as noted by the decrease in inflammatory cytokines such as TNF-α, IL-6 and IL-1β.

AD is a pressing public health problem with no effective treatment. Existing therapies only provide symptomatic relief without being able to prevent, stop or reverse the pathologic process. While the molecular basis underlying this multifactorial neurodegenerative disorder remains a significant challenge, mitochondrial dysfunction appears to be a critical factor in the pathogenesis of this disease. It is therefore important to target mitochondrial dysfunction in the prodromal phase of AD to slow or prevent the neurodegenerative process and restore neuronal function. Studies reported mechanisms of action and translational potential of current mitochondrial and bioenergetic therapeutics for AD including: mitochondrial enhancers to potentiate energy production; antioxidants to scavenge reactive oxygen species and reduce oxidative damage; glucose metabolism and substrate supply; and candidates that target apoptotic and mitophagy pathways to remove damaged mitochondria. While mitochondrial therapeutic strategies have shown promise at the preclinical stage, there has been little progress in clinical trials thus far. Current FDA-approved drugs for AD treatment include: N-methyl-D-aspartic acid (NMDA) receptor antagonist memantine and cholinesterase inhibitors donepezil, galantamine, and rivastigmine. These drugs augment cholinergic neurotransmission or attenuate excitotoxic neuronal injury. However, they only provide palliative benefits at best, with limited impact on the underlying disease mechanisms. Therefore, there is an urgent need for interventions that not only impact the aging process in favor of sustained brain health, but also promote successful brain aging in the context of neurodegenerative diseases.

Since heart and brain require the greatest amounts of energy, they are the most affected during failures of the mitochondria to generate ATP due to hypoperfusion, mitochondrial dysfunction is a key to aging and aging-related disease such as cardiovascular and Alzheimer's diseases. There is a link between the energy status of the cell and impaired organ function. Reduction of ATP production and the increase of oxidative stress are major triggers of neurons, and cardiac myocytes dysfunction, thereby contributing to not only "disease development," but also progression of age-related disorders. The progression of HF is associated with diminished energy metabolism and a decrease in ATP synthesis capacity and a decrease in overall ATP levels. Age-related changes in mitochondria are associated with decline in mitochondrial function and ATP production. Aging is characterized by a general decrease in O2 supply to tissues and a reduction in tissue pO2. A diminished vascularization (lack of blood flow) in aging alters the diffusion of O2 at the capillary tissue level, and at an advanced stage, this can lead to tissue hypoxia.

Autophagy is an intracellular self-digesting pathway to remove abnormal organelles, malformed proteins, and surplus or unnecessary cytoplasmic contents through lysosomal digestion. It is the main lysosomal degradative machinery, plays a major role in maintaining cellular homeostasis and, thus, a healthy state in an organism. This process recycles unnecessary or damaged substances, therefore, not only providing nutrients to maintain vital cellular functions in times of starvation but also eliminating potentially harmful cellular materials. Importantly, the autophagic rate declines with increasing age, suggesting a functional correlation between aging and autophagy. Indeed, the deregulation of autophagy is involved in the onset of various age-related diseases such as cancer, cardiomyopathy, type II diabetes, and neurodegeneration. Early studies on rat hepatocytes suggested that the execution of autophagy depends on energy availability since inhibition of ATP production stalls autophagic flux. Until recently, aging was regarded as an unregulated and inescapable consequence of the accumulation of incidental damage in macromolecules and/or organelles. However, the discovery of multiple ways to extend the lifespan in a variety of different model organisms, e.g., by genetic and pharmacological means, developed the formulation of alternative aging theories that consider aging as a molecular program. Therefore, there is a need to develop future therapeutic interventions to improve energy supply with the goal of improving the quality of life in the elderly and reduce the development and progression of age-related diseases such as HF and Alzheimer.

In the present invention, CCrP is a mitochondria-targeted protective compound which prevents mitochondrial dysfunction and constitutes a potential new therapeutic strategy in the prevention and treatment of ischemic and aging-related cardiovascular and central nervous system diseases including but not limited, to CAD, UA, AMI, AF, HF, Takotsubo cardiomyopathy, cardiac surgeries, Alzheimer and stroke.

In the present invention, CCrP can also function as anti-aging drug during the aging process due to its ability to preserve mitochondrial function and increase ATP production, thus, decreases apoptosis and inflammation, resulting in restoration of cognitive and motor function. As an age-modifier therapy, CCrP can rejuvenation tissue by not only providing cellular energy (ATP), but also by maintaining healthy autophagy by inhibiting gene expression of Nourin-dependent m-R-137 (marker of ischemic injury) and miR-106b (marker of inflammation) with a potential of reducing and slow down aging.

CCrP is a novel mechanism for preventing development of heart failure. The bioenergetic CCrP is a promising first-in-class cardioprotective drug that prevents the development of heart failure due to ischemia. Thus, preservation of ATP by CCrP treatment prevents ischemic injury, reduces disease progression and restores organ function. In addition to HF, CCrP will slow down the aging process resulting in organ rejuvenation in of the aging-related diseases including, Alzheimer and stroke.

The present invention demonstrated that healthy rats treated with CCrP at an effective dose of 0.8 gm/kg for 14 days, showed no toxicity in heart, liver and renal function.

Although most reported studies have focused on investigating the functional role of single RNA entities, there is a need to determine the complex interaction between the different RNA molecules. The use of the RNA network approaches is crucial to understand the interaction of different noncoding RNA species to mediate a particular phenotype is required to fully comprehend the function of noncoding RNAs in mediating disease phenotypes.

In the present invention, it is reported that the Nourin protein and its regulatory signaling pathways comprising of: miR-137, miR-106b, mRNA-FTHL-17 and mRNA-ANAPC11, and lncR-CTB89H12.4. It has been previously demonstrated that the Nourin protein and its RNA network consistently diagnose myocardial ischemia in stable CAD, ACS, UA, AMI (STEMI and NSTEMI) and HF. Additionally, using clinical patient samples and animal models of cardiopulmonary bypass surgery, AMI and HF, the elevation of Nourin protein and its regulatory signaling pathways comprising of: miR-137, miRNA-106b, mRNA-FTHL-17 and mRNA-ANAPC11, and lncR-CTB89H12.4 responded positively to CCrP treatment. CCrP treatment prevented ischemic injury and significantly reduce both Nourin protein and gene expression to normal baseline level.

The present invention provides important multiple signal pathways for Nourin gene-related to the pathogenesis of cardiovascular disease (atherogenesis and inflammation) (hsa-miRNA-106b) and myocardial tissue Ischemic damage (has-miRNA-137). The association of hsa-miRNA-106b with CAD, UA, AMI and HF pathology and inflammatory pathway, as well as the association of has-miRNA-137 with myocardial ischemic injury, serve as the basis for the present diagnostic, prognostic and therapeutic applications.

Further, the disclosure according to the present invention provides important multiple signal pathways for Nourin gene-based RNA molecular network to the pathogenesis of cardiovascular disease including atherogenesis and cardiac inflammation where there is high gene expression of Nourin-dependent miRNA-106b as a marker of inflammation and myocardial tissue Ischemic damage where there is high gene expression of Nourin-dependent miRNA-137 as a marker of cell damage. The association of hsa-miRNA-106b with CAD, UA, AMI and HF pathology and inflammatory pathway, as well as the association of has-miRNA-137 with myocardial ischemic injury, serve as the basis for the present diagnostic and prognostic applications to differentiate cardiac patients from non-cardiac patients and healthy subjects.

Advantages of the Nourin protein and its regulatory RNA network according to the present invention as new emerging biomarkers of various cardiovascular ischemia-induced diseases, including: CAD, UA, AMI (STEMI and NSTEMI), and particularly HF, include:

1) The pathogenetic mechanisms underlying the relationship between Nourin release and development of ischemia-induced diseases including HF after myocardial injury, is well studied.
2) They are biomarkers of myocardial cell injury and the post-ischemic cardiac inflammatory response, and not the hemodynamic changes like BNP, thus, provide an opportunity to diagnose HF patients and predict which patients are at risk of HF or further cardiovascular events.
3) Can function as "diagnostic" biomarkers of HF patients.
4) Have a "prognostic" value by identifying deterioration of cardiac function immediately after AMI, thus, identifying new-onset of HF.
5) Can have a "predictive" value during the early phase of myocardial ischemia with efficient risk prediction of progression of a patient to HF.
6) Can be biomarkers for aspects related to patients' care after medical and surgical treatments to determine improvement or deterioration compared to before treatments or other approaches.
7) Can be biomarkers for management of HF patients by monitoring the progression of disease (or its improvement).
8) Can be biomarkers for aspects related to patients' clinical trials to determine improvement or deterioration in response to drug-tested therap.
9) Can be predictive biomarkers to select patients who are most likely to respond positively to a specific treatment.
10) Can be predictive biomarkers to give information about the effect of a therapeutic intervention by determining the benefits of medical and surgical treatments.
(11) Overexpression of Nourin gene-base RNA network was detected in rat serum samples in response to cardiac injury induced by the administration of Isoproterenol, indicating the capability of Nourin RNA network to function as cardiac biomarkers for drug-induced myocardial toxicity.
(12) Low baseline expression of Nourin gene-base RNA network was detected in rat serum samples in response to treating Isoproterenol rats with the cardioprotective Cyclo-creatine Phosphate, indicating the capability of Nourin RNA network to function as cardiac biomarkers for successful therapy.
13) Nourin-dependent miRNAs have specific roles in myocardial ischemia, where miR-137 is a marker of cell injury and miR-106b is a marker of inflammation. Thus, using both markers with different "modes of actions" gives more diagnostic accuracy.

The invention will be further explained by the following Examples, which are intended to purely exemplary of the invention, and should not be considered as limiting the invention in any way.

EXAMPLES

Example 1—Identify the Nourin Gene-Based RNA Molecular Network of Biomarkers for Cardiac Patients A combined approach of: (1) bioinformatic analysis (software analysis) using previous microarray studies was conducted and the results were related to our known Nourin peptide sequence to retrieve the Nourin-based RNAs; and (2) biomarker verification was conducted by determining the expression levels and pattern of Nourin RNAs in AMI patients' serum samples and compare them to healthy volunteers using standard qPCR.

To retrieve lncRNA-associated competing endogenous RNAs based on Nourin (Nourin ceRNAs) and to establish their clinical relevance in AMI patients based on previous microarray studies, the following three steps were conducted: (1) biomarker retrieval step to analyze ncRNA gene placement relative to AMI associated genes through public databases and to analyze lncRNA-miRNA interaction databases to lncRNA specific for AMI; (2) bioinformatic validation of the chosen lncRNA-associated competing endogenous RNAs related to AMI; and (3) using the standard quantitative real time PCR (qPCR) molecular assay to validate the chosen biomarker as a diagnostic marker for early detection of AMI in sera samples in comparison to the gold standard cardiac marker Troponin I.

Nourin RNA analysis was performed on serum samples collected from 69 AMI patients who were diagnosed with documented acute myocardial infarction and ongoing chest pain for 8 hours at the Emergency Department and 31 healthy normal volunteers with matching age and sex to the AMI patients' groups. AMI was diagnosed within the first 8 hours of chest pain on the basis of the presence of a blood clot in the coronary artery confirmed by angiography procedures and elevated serum Troponin I levels, in addition to clinical symptoms and history consistent with cardiac ischemia. The criteria for diagnosing AMI was in accordance with the American College of Cardiology/American Heart Association guidelines and reflected the clinical judgment of two experienced independent cardiologists. Patients were excluded from the study if they have a history of hepatitis, hepatic failure, end-stage renal failure, cardiomyopathy, congenital heart disease, bleeding disorders, previous thoracic irradiation therapy, autoimmune diseases, inflammatory diseases such as inflammatory bowel disease (IBD) and arthritis or malignant disease. Blood samples were obtained once within the first 8 hours of chest pain and were centrifuged and the serum was separated, aliquoted and stored immediately at −80° C. for further processing.

Blood samples were collected from 69 AMI patients and 31 healthy controls in primary blood collection tubes without clot activator and without anticoagulants such as EDTA or citrate (red-topped tubes). These blood samples were left at room temperature for a minimum of 30 min (and a maximum of 60 min) to allow complete blood clotting in the red-topped tubes. The clotted blood samples were then centrifuged at 1300×g at 4° C. for 20 min. The upper yellow serum was carefully removed, transferred to a polypropylene capped tube in 1 ml aliquots and stored at −80° C. until they are assayed by qPCR. All serum samples were labeled with a unique identifier to protect the confidentiality of the patients. None of the serum samples were allowed to thaw before analysis to minimize protein degradation and precipitation.

Biomarker validation using qPCR involved (1) extraction of the total RNA from serum samples (AMI and healthy); (2) generation of cDNA through reverse transcription; (3) measurement of cDNA using qPCR; and (4) evaluation of results by the plot curve analysis software of Rotor Gene to confirm specificities then amplification plot and data analysis. For the extraction of total RNA, including lncRNA, miRNA and mRNA from sera samples, miRNEasy RNA isolation kit (Qiagen, Hilden, Germany) was used according to manufacturer's instructions. The RNA samples were dissolved in 30 µl of nuclease-free water. The concentration of RNA was determined using a NanoDrop spectrophotometer (Thermo Scientific, USA). Total cDNA including cDNA for miRNA, mRNAs and lncRNA was prepared from sera samples and were loaded to Rotor Gene Thermal cycler (Thermo Electron Waltham, Mass.) using miScript II RT Kit (Qiagen, Germany) by adding 2 ul 10× miScript Nucleics Mix, 4 ul 5× miScript HiFlex Buffer, 1 ul miScript Reverse Transcriptase Mix and RNase free water to 2 ug RNA and the mixture was incubated for 60 minutes at 37° C. then for 5 minutes at 95° C.

Quantification of the expression pattern and levels of Nourin gene-based RNA network panel by qPCR included: lncR-CTB89H12.4 and FTHL-17 mRNA expression in sera samples were quantified by adding 10 ul 2×RT$^2$SYBR Green ROX qPCR Mastermix and QuantiTect SYBR Green PCR Kit, respectively, RT$^2$lncRNAq PCR Assay for RT$^2$ lncRNA qPCR Assay for Human CSNK1A1 (ENST00000499521) and Hs-FTHL17-1=SG QuantiTect Primer Assay (NM_031894), 2 ul template cDNA and RNase free water to a final volume of 20 ul Hs_ACTB_1_SG QuantiTect Primer Assay (NM_001101) was used as housekeeping gene to normalize our raw data as the invariant control for the samples, and compared with a reference sample. The PCR program for relative lncRNA-CTB89H12.4 quantification was conducted as follow: firstly, denaturation at 95° C. for 10 min; followed by 45 cycles of denaturation for 15 seconds at 95° C.; then annealing for 30 seconds at 55° C. and extension for 30 seconds at 70° C.

To quantify the expression of hsa-miR-137 in the different sera samples, the present example used miScript SYBR Green PCR Kit (Qiagen/SA Biosciences Corporation, Frederick, Md.) by adding 10 ul 2× miScript SYBR Green PCR Master Mix, 2 ul 10× miScript Universal Primer, 2 ul 10× miScript Primer Assay for either Hs_miR-137_1 miScript Primer Assay targets mature miRNA: hsa-miR-137 (MI-MAT0000429: 5'UUAUUGCUUAAGAAUACGCGUAG) or RNU6B, 2 ul template cDNA and RNase free water to a final volume of 20 ul. All the PCR primers were purchased from (Qiagen, Germany M D). The real-time cycler was programmed for relative quantification of FTHL-17 mRNA and Hsa-miRNA-137 as follows: initial activation step for 15 min at 95° C. to activate HotStarTaq DNA Polymerase. 40 cycle of PCR were performed under the following conditions; 15 seconds at 94° C., 30 seconds at 55° C. and 30 seconds at 72° C. for denaturation, annealing and extension respectively. Each reaction was carried out in triplicate. Relative quantification of RNA-based biomarker panel expression was calculated using Leviak method RQ=2−ΔΔCt method. The threshold cycle (Ct) value of each sample was calculated using the Rotor Gene real time PCR detection system (Qiagen, Hilden, Germany). Any Ct value more than 36 was considered negative. The results were analyzed by the plot curve analysis software of Rotor Gene. Amplification plots and Tm values were analyzed to confirm the specificities of the amplicons for SybrGreen-base amplification.

For Nourin RNA's stability in the collected blood samples, previously stored sera samples at −70 for about (4 to 6 months) was used in this example. Sera samples were processed within half an hour after collection and aliquoted to minimize freeze thaw cycle. Spin columns with small pore sizes were used in an attempt to concentrate serum RNA before the precipitation step and have checked the concentration and purity of RNA using UN spectrophotometer. Real time PCR was done after RNA extraction at the same day. Mean delta CT for housekeeping genes were 24 indicating average RNA expression. In general, RNAs are stable in serum for 2 years. miRNA and long non-coding RNA which are already most stable forms of RNA were assayed. In general, miRNAs are detected in serum or plasma in a remarkable stable form and can withstand repetitive freezing and thawing cycles. In addition, circulating miRNAs are resistant against RNase-mediated degradation.

Measurement of cardiac Troponin I was conducted in serum samples collected from AMI patients and healthy control samples. The manufacturer of cardiac Troponin I is Siemens (adiva contour). The cardiac Troponin I assay is a 3-site sandwich immunoassay using direct chemillumenscence. The units for the measurements are ng/ml and the 99th percentile upper reference limit (UPR) of a range 0.04 ng/ml.

All statistical data were executed using SPSS 22 Mann Whitney, independent t test, and chi-square test were used as appropriate to complete comparisons. To characterize the predictive value of the selected RNA-based biomarker panel for AMI, the Receiver Operating Characteristic (ROC) curve was carried out. The Spearman correlation was performed to detect the associations between RNA-based biomarker network expression and clinicopathological parameters. Two-tailed P value of 0.05 or less was supposed to be statistically significant.

Additional procedures to detect the circulating Nourin RNAs in cardiac patients' samples are by measuring exosomes and extracellular vesicles. Furthermore, in addition to the use of the standard qPCR, the Nourin-based RNA network can be detected in cardiac patients' samples using the gold coated magnetic nanoparticles as a non-PCR based technique. For this Nanogold assay, the Nourin RNAs will be either extracted or measured directly in patients' samples without purification or pre-amplification. This assay will measure the Nourin RNA panel of markers in various sera samples. In addition, Nourin-based RNA panel of markers can be detected in cardiac patients' samples using the technology provided commercially, for example by Multiplex miRNA assays measuring the Nourin-based RNA network via total circulating RNAs, Multiplex miRNA assays with FirePlex® particle technology enable simultaneous profiling of 65 miRNAs directly from small amounts of biofluid or FFPE, without RNA purification or pre-amplification. Assays can be customizable for the Nourin-based RNA panel of markers and suitable for both discovery and verification studies. Readout uses a standard flow cytometer. Additionally, sensor chip procedures can be used to detect the Nourin-based RNA network and the Nourin protein including and not limited to Nourin epitope N-f-MII.

Furthermore, the Point-of-Care (POC) procedures can be used to rapidly within 15 minutes detect in cardiac patients' samples the circulating Nourin RNAs including miR-137, miR-106b, FTHL-17 mRNA, ANAPC11 mRNA and lncR-CTB89H12.4 as well as the Nourin epitope N-f-MII. The POC diagnostics has been emerged as a promising real-world application. The POC ecosystem is evolving faster than ever and new technology has to fit into a broader landscape. Some of the main advantages of POC diagnostic device include the use of smaller sample volume, lower test costs and faster turn-around-times i.e., 15 minutes vs, 4 hours to 24 hours for PCR. Beside its rapid and precise response, its portability, low cost and non-requirement of specialized equipment are important advantages. The challenge is that the POC devices use smaller sample volumes to achieve the same detection limit as standardized laboratory equipment. It requires the integration of assay chemistry, fluidics, hardware and software.

A POC device can use a chip-based technology to examine different analytes in various samples including blood, urine and tissue biopsies. Microfluidics and biosensor can use numerous materials such as glass, silicon, polymer, and paper for the fabrication of microfluidics-based POC devices along with their wide range of biosensor applications. Recent development in nanomaterials, device design, and microfabrication technologies have made it possible to obtain POC devices with enhanced sensing characteristics. Breakthroughs such as the recently published method of 3D printing microfluidics lab-on-a-chip devices could help lead to cheaper mass-production of diagnostic devices. The use of smartphones paired to microfluidics could enable an increased range and ability of POC testing, with the development of devices such as the TRI analyzer on the horizon, it is possible to achieve limits of detection that are comparable to those obtained for the same assay measured with a conventional laboratory microplate reader, demonstrating the flexibility of the system to serve as a platform for rapid, simple translation of existing commercially available bio sensing assays to a POC setting. POC portable devices identification method can be based on microarray platform require extensive testing and validation comparing the outcome with more traditional methods of detection. Thus, the high-performance RNA-detection methods for all types of clinically relevant RNAs (mRNAs, miRNAs and lncRNAs) are based on molecular-biology techniques including and not limited to qPCR, microarrays, nanoparticles, microfluidics and biosensor.

Example 2—Retrieve Molecular Biomarkers Relevant to AMI and Related to the Nourin Peptide Sequence Bioinformatic analysis was done to retrieve biomarkers relevant to AMI and related to the Nourin peptide sequence based on previous microarray studies. The bioinformatic analysis included a number of blast programs to retrieve relevant genes to the Nourin peptide sequence. Ferritin heavy polypeptide 17 (FTLH-17) gene was retrieved after BLAST alignment 100% with the Nourin-1 peptide sequence (U.S. Pat. No. 7,659,091 B2) formyl substituted-MIINHNLAAINSHRSPGADGNGGEAMPGGGR (SEQ ID NO:15). Ferritin is the major intracellular iron storage protein in prokaryotes and eukaryotes. It is composed of 24 subunits of the heavy and light ferritin chains. Variation in ferritin subunit composition may affect the rates of iron uptake and release in different tissues. A major function of ferritin is the storage of iron in a soluble and nontoxic state. Then the Nourin gene-based RNA network was identified through in silico data analysis. For clinical validation of the chosen Nourin gene-based RNA network as diagnostic biomarkers for early diagnosis of AMI, the serum gene network expression of Nourin FTHL-17 mRNA, hsa-miR-137 and long non-coding lncR-CTB89H12.4 in AMI patients' serum samples collected within the first 8 hours of chest pain as well as in healthy control samples was investigated.

To retrieve the lncRNA-associated competing endogenous RNAs based on Nourin sequence and its relevant to AMI based on previous microarray studies, and then the following four BLAST programs were conducted to retrieve the relevant gene to the Nourin peptide sequence: (1) using Atlas database retrieving target gene involved that is relevant to the Nourin peptide. FTHL-17 gene was selected after BLAST alignment with the Nourin sequence formyl substituted-MIINHNLAAINSHRSPGAD-GNGGEAMPGGGR (SEQ ID NO:15) corresponding to Nourin-1 (U.S. Pat. No. 7,659,091 B2) with sequence identity 100% and confirmed by gene ontology which revealed that FTHL-17 gene is related to autophagy and cardiac ischemia (reversible and irreversible cardiac ischemia as seen in UA and AMI patients) as illustrated in FIG. 1, FIG. 2 and FIG. 3; (2) it was then confirmed that there was low expression of mRNA-FTHL-17 in normal tissues (FIG. 4 and FIG. 5). This low expression of mRNA-FTHL-17 mRNA in normal heart was reported in by two techniques out of three. For normal kidney, one technique proved low expression and other 2 techniques negative. Together, mRNA-FTHL-17 is expressed at low level in normal heart, but more than other tissues (FIG. 4 and FIG. 5); (3) next, by using Diana database miR-137 was retrieved that acts as epigenetic regulator of mRNA-FTHL-17 and by performing pathway enrichment analysis, it was confirmed that miRNA-137 is related to autophagy and cardiac ischemia (FIG. 6); and finally, (4) lncR-CTB89H12.4 that acts as miR-137 sponge was selected through Starbase database (FIG. 7).

Example 3—Differentiation of AMI Patients with Chest Pain from Healthy Controls Using the Nourin FTHL-17 mRNA Gene, Long Non-Coding Intergenic RNA-(lncRNA-CTB89H12.4) and *Homo sapiens* microRNA-137 (hsa-miRNA-137)

After identification of the Nourin gene-based RNA network retrieved through in silico data analysis, it was determined that the Nourin RNA expression pattern and level in 69 AMI patients presenting to hospital ED with chest pain within 8 hours after onset of symptoms and 31 healthy volunteers as an important first step to determine the biomarker signatures of Nourin that will be effective in AMI detection. Specifically, it was investigated that the Nourin gene-based RNA network expression as a novel AMI-specific RNA-based integrated competing endogenous network composed of ferritin heavy polypeptide 17 (FTHL-17 mRNA) gene, long non-coding intergenic RNA-(lncRNA-CTB89H12.4) and *Homo sapiens* microRNA-137 (hsa-miRNA-137) selected by in silico data analysis. Standard RT-qPCR-based validation of the network was used and the relation between the expression of Nourin RNA-based biomarker network and different clinicopathological factors was explored. The correlation between Nourin RNAs and the level of cardiac Troponin I was assessed by Spearman correlation.

Results revealed that the expression pattern and level of the Nourin-gene RNA network composed of long non-coding intergenic RNA-(lncRNA-CTB89H12.4), *Homo sapiens* microRNA-37 (hsa-miRNA-137), and FTHL-17 mRNA had high sensitivity and specificity for discriminating AMI patients from healthy controls (FIG. 8). The recorded average of onset of chest pain is 6.52 hours. There was no significant difference detected between the expression of serum Nourin RNAs and the distribution of sex, smoking, diabetes mellitus, cholesterol, hypertension and the type of treatment in the AMI group. Furthermore, the RNA-based network and Troponin I were detected in clinically documented AMI patients with anterior STEMI, inferior STEMI, as well as Non-TEMI (NSTEMI). There was a significant correlation, however, between Nourin FTHL-17 mRNA (FIG. 9) and microRNA-37 (hsa-miRNA-137) (FIG. 10) and the level of the standard cardiac marker, Troponin I with concomitant negative correlation between lncR-CTB89H12.4 (FIG. 11) and cardiac Troponin I level in AMI and healthy serum samples. Since there was a correlation between Nourin RNA molecular biomarker panel and cardiac Troponin I level in both AMI serum samples, a combined assay that uses the Nourin protein (e.g., epitope N-f-MII) and the Nourin multiple genes that are functionally linked to each other and to AMI molecular networks, increases the chance of a higher success to accurately diagnose AMI patients than the simpler conventional single-marker approach for Troponin I. The circulating transcriptome of the Nourin gene-based RNA network expression has been revealed as a potential class of non-invasive biomarker with high specificity and sensitivity for early detection of AMI. An integrative approach between differential FTHL-17 mRNA gene expression with the selected epigenetic regulators and this approach has generated an interesting new Nourin-based molecular biomarker panel (lncR-CTB89H12.4, hsa-miRNA-137, and FTHL-17 mRNA) for the early diagnosis of AMI patients presenting with chest pain to hospital ED and outpatient clinics. Since the Nourin RNAs are stable, specific and abundantly expressed in ischemic hearts, they will be an added value to the Nourin protein assays. In general, RNA biomarkers have more sensitivity and specificity with much less interference in serum samples and that the qPCR assay enables traces of RNA sequences to be amplified and thus captured specifically with high sensitivity. Moreover, the cost of RNA biomarker is much lower than protein biomarker because detecting each protein requires a specific antibody. The ROC curves analysis and the area under the curve (AUC) values were used to estimate the diagnostic value of our selected RNAs to differentiate AMI from healthy controls. The results implied that hsa-miRNA-137 and lncR-CTB89H12.4 are the most effective biomarkers for differentiating AMI patients from healthy people. The best discriminating cutoff values of hsa-miR-137, lncR-CTB89H12.4 and FTHL-17 mRNA were 2.29, 3.36 and 3.83, respectively with sensitivities of 98.6%, 97.1% and 82.6%, respectively. Collectively, it was deduced that the diagnostic accuracy for AMI detection would be improved by a concurrent measurement of serum lncR-CTB89H12.4, miR-137, and FTHL-17 mRNA to approximately 100% sensitivity and 98% accuracy in the present study. This result indicates that these thresholds could be used to discriminate AMI patients from healthy subjects.

Example 4—Confirmation of Prior Results Using the Cardiac-Derived Nourin Protein Previous studies by the Applicant had shown that the 3 KDa Nourin-1, is released shortly after an ischemic cardiac event, e.g., UA and AMI. Those studies relied on either a leukocyte functional chemotaxis assay or an immunoassay using (a) monoclonal sera raised against the native full-length Nourin-1 protein; and (b) polyclonal sera raised against a short peptide sequence derived from the N-terminus of Nourin-1 (Nour001-A) generated in mice.

The amino acid sequence formyl substituted-MIINHDDERKC (SEQ ID NO:17) was chemically synthesized and purified using HPLC. This peptide was conjugated to KLH using a proprietary method of Precision Antibody (Columbia, Md.), and mice were immunized. Tail bleeds were collected for determination of antibody titer at three weeks, and final cardiac bleeds were performed at four weeks to collect final sera. The collected sera were tested for specificity of binding to the immunogen as follows. Diluted sera were combined with a control peptide (MIINHDDERKC; SEQ ID NO:18) in excess to bind and remove antibodies in the sera that bind to any portion of the immunogen other than a portion that includes the formyl-methionine. The "cleared" sera were tested against a screening antigen having the sequence
formyl substituted-MIINHDDERKC (SEQ ID NO:17). From a comparison of the sequences, the screening antigen shows identity to the immunogen only at the N-terminal five residues. Results of an ELISA with the "cleared" sera contained antibodies that specifically bound to the formylated N-terminal sequence.

Using the functional leukocyte chemotaxis assay and the ELISA immunoassay (Nour001-A), clinical studies demonstrated that (1) the level of Nourin was 3-fold higher compared to healthy volunteers in plasmas of ACS (UA and AMI) patients who presented to hospital ED within 1.5 to 3.5 hours after the onset of symptoms, while the standard cardiac biomarkers Troponin T and CK-MB were not detected. After clinical confirmation of ACS patients, Troponin T was detected and it was persistent for 36 hours. Nourin which was also detected in samples after 32 hours; (2) the detection of high levels of cardiac Nourin in frozen plasma samples (−70° C. for 3 years) collected from ACS patients (UA and AMI) within the first 8 hours of chest pain when Troponin I levels were below the clinical-decision level (below the heart attack cut off of 0.07 ng/ml) but were later confirmed the diagnosis. The Nour001-A antibody assay showed a statistical significance difference (P=0.012) between samples from ACS patients and other non-cardiac patients with chest pain; (3) the detection of high levels of cardiac Nourin in AMI patients' fresh plasma samples collected within the first 8 hours of chest pain when Troponin I levels are below the clinical-decision level (below the heart attack cut off of 0.07 ng/ml) but were later confirmed AMI diagnosis demonstrating that Nourin is an earlier marker than Troponin I (FIG. 12). When the same samples were stored for one month at −20° C. then thawed and subjected to the same ELISA test procedure, the data obtained was similar to the results obtained using fresh samples, showing; (4) Nourin was not detected in plasma samples collected fresh from non-cardiac patients also presented to hospital ED within the first 8 hours of chest pain with negative Troponin I (FIG. 12). Thus, the Nour001-A antibody is useful in diagnosing patients suffering cardiac ischemic event and could differentiate between ACS (AMI and UA) samples taken from patients experiencing chest pain from chest pain patients but not suffering AMI or UA. Furthermore, the Nour001-A antibody assay distinguished AMI patients from non-cardiac patients using fresh and frozen samples.

Example 5—Up-Regulation of Nourin Gene-Based RNA Molecular Network and Protein in AMI The present invention of the Nourin gene-based molecular biomarker panel composed of FTHL-17 mRNA, hsa-miRNA-137 and lncR-CTB89H12.4 further confirmed the use of the cardiac-derived Nourin protein as a biomarker of AMI patients. The down-regulation of lncRNA-CTB89H12.4 after an AMI event resulted in up-regulation of hsa-miRNA-137 and activation of FTHL-17 mRNA with an increased translation and production of high levels of the cardiac-derived Nourin protein (FIG. 13). There is a minimal gene expression of FTHL-17 mRNA in normal non-stressed tissues. The Nourin RNA panel can be used individually or in combination with the protein-based biomarker Nourin for better and faster diagnosis of AMI patients presenting with chest pain to hospital ED and outpatient clinics. The Nourin molecular and protein-based assays are significantly earlier than current myoglobin, CK-MB and Troponin assays in detecting UA and AMI in patients presenting to the ED with chest pain (FIG. 14). Earlier identification of heart patients allows for early intervention to avoid permanent damage and heart attack that can lead to heart failure and death. In general, about 50% of heart attack patients suffer heart failure.

Although the currently identified circulating miRNA-208a, miRNA-133 and miRNA-1 peak in the blood at 3 hours after AMI, they are still markers of necrosis similar to Troponin. Nourin, on the other hand, is much earlier biomarker released by 'viable' ischemic tissue and, thus, provides fast diagnosis for crucial therapy (FIG. 14). Additionally, the low level of Nourin in blood samples collected from healthy individuals, makes Nourin an attractive diagnostic marker with little or no effect from normal non-stressed tissues. Furthermore, the Nourin RNA network will diagnose AMI with anterior STEMI, inferior STEMI as well as Non-STEMI (NSTEMI). Finally, Nourin panel of RNAs may be used to complement the protein-based Nourin and Troponin biomarkers as well as other classical risk factors for AMI diagnosis and prognosis. However, compared to protein-based biomarkers, RNA biomarkers have more sensitivity and specificity as it can be tissue and disease specific.

The Nourin assay using for example and not limited to Nourin including the Nourin panel of RNAs (qPCR, Nanogold, Multiplex, microfluidics and sensor ship) or Nourin epitope N-f-MII (leukocyte Chemotaxis, ELISA, sensor ship and MALDI-TOF [Matrix Assisted Laser Description Ionization-Time of Flight]) is expected to be used clinically in combination with Troponin for some better sensitive and specific diagnostic tests for acute coronary syndromes. The Nourin assays can identify unstable angina patients and complement and enhance the usefulness of Troponin tests to rule in or out unstable angina and AMI. If the Nourin assay does not detect elevated levels of Nourin RNA network and/or Nourin peptide, then ACS patients can be ruled out and the patients can be released from the hospital ED or a workup can begin to elucidate the true cause of the patients' chest pain syndromes. On the other hand, if the Nourin assay detect elevated levels of Nourin RNA network and/or Nourin peptide, the ACS patients can receive therapies in an earlier timeframe than is presently possible with current Troponin and thus eliminating the required long wait of 2 to 6 hours.

Example 6—Validation of the Nourin Gene-Based RNA Molecular Network as Biomarkers for Angina Patients with Negative Troponin The standard quantitative real time PCR (qPCR) molecular assay was used to validate the Nourin RNA Network, lncR-CTB89H-12.4, has-miRNA-06b, hsa-miRNA-137, mRNA ANAPC11 and mRNA FTHL-17 as diagnostic biomarkers for early diagnosis of angina patients in sera samples who showed negativity of the gold standard cardiac marker Troponin. Specifically, whether the Nourin RNA Network can: (1) be used to diagnose angina patients in hospital ED and outpatient clinics; (2) determine the severity of myocardial ischemia in angina patients and, thus, to be used as prognostic molecular biomarkers; (3) quantitively distinguish between angina and AMI patients; and (4) function with high confidence as non-invasive good negative test to exclude non-angina patients.

To determine whether the novel lncR-CTB89H-12.4, has-miRNA-106b, hsa-miRNA-137, mRNA ANAPC11 and mRNA FTHL-17 that genetically regulate the expression of Nourin gene could be used as an early diagnostic and prognostic molecular biomarkers in coronary artery disease, serum samples were collected from angina and AMI patients, as well from healthy subjects and non-angina patients with history of chest pain. The study was approved by the Institutional Review Board (IRB) and that the patients' gender is equally distributed among cardiac cases. The three groups are:

Angina Patients:

ngina was diagnosed on the basis of negative serum Troponin I and T levels, as well as clinical symptoms and history consistent with cardiac ischemia. Patients were recruited from:

(1) Hospital ED—serum samples were collected at arrival to hospital ED from typical and atypical angina patients (n=29) experiencing chest pain and have negative Troponin. Angina was confirmed in these 29 patients after the performance of Coronary Angiography or Angioplasty procedure. These patients experienced chest pain for 1 to 10 hours prior to arrival to hospital ED and they are referred to as "early" stage angina patients.

(2) Cath Lab—serum samples were collected from angina patients (n=18) with chest pain and negative Troponin scheduled for Coronary Angiography or Angioplasty procedure at the Cath Lab. Samples were collected before performing the procedure. These patients experienced chest pain for 24 to 72 hours prior to arrival to the Cath Lab and they are referred to as "late" stage angina patients.

(3) Outpatient—serum samples were collected from inter-mediate-risk patients (n=14) seen in outpatient clinics with history of chest pain suspected of angina. All 14 atypical patients had negative Troponin and were scheduled to be evaluated on standard treadmill stress test or dobutamine stress echocardiography (ECHO). Serum samples were collected 30 minutes after the completion of the treadmill stress test or ECHO. Because of the high false positive in females using the treadmill stress test, all female patients were evaluated only by the ECHO test. Positive angina patients (n=7) had positive stress ECG changes in the treadmill stress test or dobutamine stress ECHO, suggestive of ischemia. Negative non-angina patients (n=7) showed lack of evidence of ischemia during stress ECG or dobutamine stress ECHO.

AMI Patients:

Serum samples were collected at arrival to hospital ED from AMI patients (n=16) experiencing chest pain, positive Troponin and confirmed by Coronary Angiography or Angioplasty at the Cath Lab. These patients experienced chest pain for 1 to 10 hours prior to arrival to hospital Emergency Department (ED).

Healthy Individuals/Subjects:

Serum samples were collected from healthy individuals (n=16) with negative Troponin and negative treadmill stress test. All 16 subjects exercised on Treadmill to confirm absence of ischemic coronary disease after inducing stress. Serum samples were collected 30 minutes after the completion of the stress test. Males subjects were enrolled in this study to avoid the high false positive associated with females using the Treadmill stress test.

Analysis of Nourin RNAs (lncR-CTB89H12.4, hsa-miR-106b, hsa-miR-137, mRNA ANAPC11 and mRNA FTHL-17) was performed on serum samples collected from 47 chest pain patients [hospital ED (n=29), Cath Lab (n=18). Angina was diagnosed on the basis of negative serum Troponin I and T levels, as well as clinical symptoms and history consistent with cardiac ischemia. The level of Nourin-dependent RNA network was also evaluated in angina patients with history of chest pain and positive stress test (n=7), as well as in 7 chest pain non-angina outpatient with negative stress test. All 14 patients who underwent stress test exercise, had negative Troponin I. Patients were excluded from the study if they have: (1) positive Troponin I or T, (2) cardiomyopathy, (3) heart failure, (4) congenital heart disease, (5) end stage renal failure, (6) bleeding disorders, (7) previous thoracic irradiation therapy, (8) autoimmune diseases and inflammatory diseases such as inflammatory bowel disease (IBD) and arthritis, (9) malignant diseases, and (10) a history of hepatitis or hepatic failure. Blood samples were obtained once and were centrifuged and the serum was separated, aliquoted and stored immediately at $-80°$ C. for further processing.

Analysis of Nourin RNAs (lncRNA-CTB89H12.4, hsa-miR-106b, hsa-miR-137, mRNA ANAPC11 and mRNA FTHL-17) was performed on serum samples collected from 16 AMI patients whom they were diagnosed with documented acute myocardial infarction and ongoing chest pain for 1 to 10 hours prior to the arrival to hospital ED. AMI was diagnosed on the basis of the presence of a blood clot in the coronary artery confirmed by invasive coronary angiography procedures and elevated serum Troponin I and Troponin T levels (>0.40 ng/ml), in addition to clinical symptoms and history consistent with cardiac ischemia. The criteria for diagnosing AMI was in accordance with the American College of Cardiology/American Heart Association guidelines and reflected the clinical judgment of two experienced independent cardiologists. Patients were excluded from the study if they have (1) positive Troponin I or T, (2) cardiomyopathy or heart failure, (3) congenital heart disease, (4) end stage renal failure, (5) bleeding disorders, (6) previous thoracic irradiation therapy, (7) autoimmune diseases and inflammatory diseases such as inflammatory bowel disease (IBD) and arthritis, (8) malignant diseases, and (9) a history of hepatitis or hepatic failure. Blood samples were obtained once and were centrifuged and the serum was separated, aliquoted and stored immediately at $-80°$ C. for further processing.

Analysis of Nourin RNAs (lncR-CTB89H12.4, hsa-miR-106b, has-miR-137, mRNA-ANAPC11 and mRNA-FTHL-17) was performed on serum samples collected from 16 Healthy male volunteers with negative Troponin and negative treadmill stress test. Volunteers exercised on treadmill to confirm absence of ischemic heart disease. Samples were collected 30 minutes after the completion of the stress test. Females were excluded from this study because of the high false positive with the treadmill stress test procedure. Blood samples were obtained once within the first 8 hours of chest pain and were centrifuged and the serum was separated, aliquoted and stored immediately at $-80°$ C. for further processing.

Blood samples were collected from 54 positive angina, 7 negative non-angina, 16 AMI patients and 16 healthy controls in primary blood collection tubes without clot activator and without anticoagulants such as EDTA or citrate (red-topped tubes). These blood samples were left at room temperature for a minimum of 30 min (and a maximum of 60 min) to allow complete blood clotting in the red-topped tubes. The clotted blood samples were then centrifuged at 1300×g at $4°$ C. for 20 min. The upper yellow serum was carefully removed, transferred to a polypropylene capped tube in 1 ml aliquots and stored at $-80°$ C. until they are assayed by qPCR. All serum samples were labeled with a unique identifier to protect the confidentiality of the patients. None of the serum samples were allowed to thaw before analysis to minimize protein degradation and precipitation.

Biomarker validation using qPCR involved (1) extraction of the total miRNAs and total RNAs from serum samples (AMI and healthy); (2) synthesis of cDNA through reverse transcription; (3) measurement of cDNA using qPCR; and (4) evaluation of results by the plot curve analysis software of Rotor Gene to confirm specificities then amplification plot and data analysis. For the extraction of total RNA, including lncRNA, miRNA and mRNA from sera samples, miRNEasy RNA isolation kit (Qiagen, Hilden, Germany) was used according to manufacturer's instructions. The RNA samples were dissolved in 14 μl of nuclease-free water. The concentration of RNA was determined using a NanoDrop spectrophotometer (Thermo Scientific, USA). Total cDNA including cDNA for miRNA, mRNAs and lncRNA was prepared from sera samples and were loaded to Thermal cycler instrument (Thermo Electron Waltham, Mass.) using miScript II RT Kit (Qiagen, Germany), and the reaction mix is composed of 2 ul 10× miScript Nucleics Mix, 4 ul 5× miScript HiFlex Buffer, 1 ul miScript Reverse Transcriptase Mix and RNase free water to 2 ug RNA and the mixture was incubated for 60 minutes at $37°$ C. then for 5 minutes at $95°$ C.

Quantification of the expression pattern and levels of Nourin gene-based RNA network panel by qPCR included: lncR-CTB89H12.4, mRNA FTHL-17 and mRNA ANAPC11. Expression in sera samples were quantified by adding 10 ul 2×RT²SYBR Green ROX qPCR Mastermix and QuantiTect SYBR Green PCR Kit, respectively, RT²lncRNAq PCR Assay for RT² lncRNA qPCR Assay for Human CSNKIAI (ENST00000499521) (assay ID: LPH41640A), Hs_FTHL17_1_SG QuantiTect Primer Assay (NM_031894) (assay ID: QT00217966), Hs_ANAPC11 primer assay (assay ID: QT00243964), 2 ul template cDNA and RNase free water to a final volume of 20 ul Hs_ACTB_1_SG QuantiTect Primer Assay (NM_001101) (assay ID: QT00095431), was used as housekeeping gene to normalize our raw data as the invariant control for the samples, and compared with a reference sample. The PCR cycling program for relative lncR-CTB89H12.4 quantification was conducted as follow: firstly, denaturation at $95°$ C. for 10 min; followed by 45 cycles of denaturation for 15 seconds at $95°$ C.; then annealing for 30 seconds at $55°$ C. and extension for 30 seconds at $70°$ C.

To quantify the expression of hsa-miR-106b and hsa-miR-137, a miScript primer assays which target the hsa-miR-106b and hsa-miR-137 were purchased from Qiagen, Hilden, Germany. The primer assays ID and sequences are: hsa-miR-106b: miRNA: has-miR-106b-5p, assay ID: MIMAT0000680 with provided sequence "5'UAAAGUGCUGACAGUGCAGAU" and for hsa-miR 137, assay ID: MIMAT0000429 and provided sequence "5'UUAUUGCUUAAGAAUACGCGUAG". The RUN6 primer assay was used as a housekeeper gene for gene normalization.

For miRNAs amplification by quantitative Real time PCR (qPCR), miScript SYBR Green PCR Kit (Qiagen/SA Biosciences Corporation, Frederick, Md.) was used. The 20 μl reaction mix is prepared by adding 10 ul 2× miScript SYBR Green PCR Master Mix, 2 ul 10× miScript Universal Primer, 2 ul 10× miScript Primer, 2 μl of template cDNA and 4 μl RNase free water, miR-106b and RUN6. The real-time cycler was programmed for relative quantification of hsa-miR-106b and Hsa-miR-137 as follows: initial activation step for 15 min at 95° C. to activate HotStarTaq DNA Polymerase. 40 cycle of PCR were performed in the following conditions; 15 seconds at 94° C., 30 seconds at 55° C. and 30 seconds at 72° C. for denaturation, annealing and extension respectively. Each reaction was carried out in triplicate. Relative quantification of RNA-based biomarker panel expression was calculated using Leviak method RQ=2−ΔΔCt method. The threshold cycle (Ct) value of each sample was calculated using the Rotor Gene real time PCR detection system (Qiagen, Hilden, Germany). Any Ct value more than 36 was considered negative. The results were analyzed by the plot curve analysis software of Rotor Gene. Amplification plots and Tm values were analyzed to confirm the specificities of the amplicons for SybrGreen-base amplification.

For Nourin RNA's stability in the collected blood samples, previously stored sera samples at −70 for about (3 to 4 months) were assayed. Sera samples were processed within half an hour after collection and aliquoted to minimize freeze thaw cycle. Spin columns with small pore sizes were used in an attempt to concentrate serum RNA before the precipitation step and have checked the concentration and purity of RNA using U/V spectrophotometer. Real time PCR was done after RNA extraction at the same day. Mean delta CT for housekeeping genes were 24 indicating average RNA expression. In general, RNAs are stable in serum for 2 years. miRNA and long non-coding RNA which are already most stable forms of RNA were assayed. In general, miRNAs are detected in serum or plasma in a remarkable stable form and can withstand repetitive freezing and thawing cycles. In addition, circulating miRNAs are resistant against RNase-mediated degradation.

Measurement of cardiac Troponin I was conducted in serum samples collected from angina and AMI patients, non-angina and healthy control samples. The manufacturer of cardiac Troponin I is Siemens (adiva contour). The cardiac Troponin I assay is a 3-site sandwich immunoassay using direct chemillumenscence. The units for the measurements are ng/ml and the 99th percentile upper reference limit of a range 0.04 ng/ml. In some cases, Troponin T was also used.

All statistical data were executed using SPSS 22. A Shapiro-Wilk test was conducted on numerical results to assess if the variables are normally distributed, A Kruskal-Wallis test was performed to compare skewed variables, the gene expression is expressed as median value as data are not normally distributed. Two-tailed P value of 0.05 or less was supposed to be statistically significant.

Additional procedures to detect the circulating Nourin RNAs in cardiac patients' samples are by measuring exosomes and extracellular vesicles. Furthermore, in addition to the use of the standard qPCR, the Nourin-based RNA network can be detected in cardiac patients' samples using the gold coated magnetic nanoparticles as a non-PCR based technique. For this Nanogold assay, the Nourin RNAs will be either extracted or measured directly in patients' samples without purification or pre-amplification. This assay will measure the Nourin RNA panel of markers in various sera samples. In addition, Nourin-based RNA panel of markers can be detected in cardiac patients' samples using the technology provided commercially, for example by Multiplex miRNA assays measuring the Nourin-based RNA network via total circulating RNAs, Multiplex miRNA assays with FirePlex® particle technology enable simultaneous profiling of 65 miRNAs directly from small amounts of biofluid or FFPE, without RNA purification or pre-amplification. Assays can be customizable for the Nourin-based RNA panel of markers and suitable for both discovery and verification studies. Readout uses a standard flow cytometer. Additionally, sensor chip procedures can be used to detect the Nourin-based RNA network and the Nourin protein including and not limited to Nourin epitope N-f-MII.

Furthermore, the Point-of-Care (POC) procedures can be used to rapidly within 15 minutes detect in cardiac patients' samples the circulating Nourin RNAs including lncR-CTB89H12.4, has-miRNA-106b, has-miRNA-137, mRNA ANAPC11 and mRNA FTLH-17, as well as the Nourin epitope N-f-MII. The POC diagnostics has been emerged as a promising real-world application. The POC ecosystem is evolving faster than ever and new technology has to fit into a broader landscape. Some of the main advantages of POC diagnostic device include the use of smaller sample volume, lower test costs and faster turn-around-times i.e., 15 minutes vs, 4 hours to 24 hours for PCR. Beside its rapid and precise response, its portability, low cost and non-requirement of specialized equipment are important advantages. The challenge is that the POC devices use smaller sample volumes to achieve the same detection limit as standardized laboratory equipment. It requires the integration of assay chemistry, fluidics, hardware and software.

A POC device can use a chip-based technology to examine different analytes in various samples including blood, urine and tissue biopsies. Microfluidics and biosensor can use numerous materials such as glass, silicon, polymer, and paper for the fabrication of microfluidics-based POC devices along with their wide range of biosensor applications. Recent development in nanomaterials, device design, and microfabrication technologies have made it possible to obtain POC devices with enhanced sensing characteristics. Breakthroughs such as the recently published method of 3D printing microfluidics lab-on-a-chip devices could help lead to cheaper mass-production of diagnostic devices. The use of smartphones paired to microfluidics could enable an increased range and ability of POC testing, with the development of devices such as the TRI analyzer on the horizon, it is possible to achieve limits of detection that are comparable to those obtained for the same assay measured with a conventional laboratory microplate reader, demonstrating the flexibility of the system to serve as a platform for rapid, simple translation of existing commercially available bio sensing assays to a POC setting. POC portable devices identification method can be based on microarray platform require extensive testing and validation comparing the outcome with more traditional methods of detection. Thus, the high-performance RNA-detection methods for all types of clinically relevant RNAs (mRNAs, miRNAs and lncRNAs) are based on molecular-biology techniques including and not limited to qPCR, microarrays, nanoparticles, microfluidics and biosensor.

Example 7—Using the Nourin Expression Levels of Micro RNAs, Hsa-miRNA-106b (miR-106b) and has-miRNA-137 (miR-137) to Differentiate: (1) Coronary Artery Disease (Angina and AMI) Patients from Healthy Controls; (2) Angina from AMI Patients; (3) Patients with Early Stage and Late Angina Time; and (4) Suspected Outpatient Angina Patients from Non-Angina by Stress ECHO/ECG Treadmill Test The novel Nourin miR-106b and miR-137 that genetically regulate the expression of Nourin gene could be used as an early diagnostic and prognostic molecular biomarkers in coronary artery disease defined here as stable and unstable angina, as well as AMI patients. FIG. 16 and FIG. 17A-FIG. 17H summarize the expression levels of Nourin miR-106b and miR-137 in serum samples of angina and AMI patients, as well as controls and revealed: (1) the detection of high levels of Nourin miR-106b and miR-137 in symptomatic angina patients with negative Troponin; (2) a high statistical significant difference ($p<0-01$) between the higher expression levels of miR-106b and miR-137 in CAD patients with an increase of 280-fold and 1900-fold; respectively compared to healthy control group; (3) significantly higher levels were detected in AMI patients compared to angina, reflecting the association between Nourin miRNAs and high extensive myocardium injury ($p<0-01$). AMI patients showed 4.67-fold increase for miR-106b and 2.44-fold increase for miR-137 compared to angina patients; (4) higher expression levels were positively correlated to disease severity in late angina patients compared to early angina; (5) the high expression levels of Nourin miRNAs detected in patients suspected of angina with history of chest pain, correlated with positive ECHO/ECG Treadmill stress test results, while low expression levels correlated with negative non-angina patients by stress test; and (6) the high statistical significant difference ($p<0-01$) between positive ECHO/ECG Treadmill stress test in angina patients and negative test in non-angina patients can be used as a non-invasive good negative test to exclude non-angina patients.

Specifically, as illustrated in FIG. 17A-FIG. 17H, there is a significantly high serum expression levels of miR-106b (FIG. 17A) and miR-137 (FIG. 17B) in coronary artery disease (stable and unstable angina and AMI) patients compared to healthy control group; the expression levels of miR-106b (FIG. 17C) and miR-137 (FIG. 17D) were also significantly higher in AMI patients compared to angina patients ($p<0.01$); additionally, higher expression levels were detected in late angina patients (24 to 72 hours after onset of chest pain) for miR-106b (FIG. 17E) and miR-137 (FIG. 17F) compared to early angina patients (1 to 10 hours after onset of chest pain); Finally, the expression levels of miR-106b (FIG. 17G) and miR-137 (FIG. 17H) were significantly higher in outpatient suspected angina patients whom they were positive by ECHO/ECG Treadmill stress test compared to negative stress test group ($p<0.01$). No interference in the Nourin RNA results was observed in patients and control serum samples when the non-specific inflammatory mediator CRP was elevated.

Statistically, FIG. 18 summarizes the diagnostic and prognostic efficacy of miR-106b and miR-137 in patients with coronary artery disease and controls using Receiving Operating Characteristics Curves (ROC) [ROC curve analysis]. FIG. 19A-FIG. 19D illustrate: (A): a 100% sensitivity for both miR-106b and miR-137, while, 94% specificity for miR-106b, and 95% specificity for miR-137 to diagnose and discriminate between patients with coronary artery disease and healthy controls; (B): a sensitivity of 87% and specificity of 79% were demonstrated for miR-106b compared to 75% sensitivity and 72% specificity for miR-137 to discriminate between early and late angina patients; (C): a high prognostic potentials were demonstrated for both miR-106b and miR-137 to discriminate angina from AMI patients; and (D): both Nourin related miR-106b and miR-137 showed a 100% sensitivity and 85% specificity in discriminating ECHO/ECG Treadmill positive stress test of outpatient angina patients with history of chest pain from patients with non-angina and negative test. Thus, the two selected miR-106b and miR-137 related to Nourin gene are good positive test to diagnose ACD patients and good negative test to exclude non-cardiac patients.

The sensitivities and specificities of miR-106b and miR-137 as an early diagnostic biomarkers in angina patients plotted by the Receiving Operating Characteristics curves demonstrated that miR-106b and miR-137 can discriminate between (1) angina and AMI patients; (2) early and late stage angina patients, (3) angina from non-angina, and (4) between coronary heart disease and healthy control. The high diagnostic and prognostic potential of the Nourin related miRNAs will open the era for early diagnosis of angina patients that have a chest pain with negative Troponin and, therefore, direct clinicians for the proper management and save patients' life.

The bioinformatics analysis revealed that both miR-106b and miR-137 related to Nourin gene regulates the expression of Nourin protein via sponging of Nourin gene. The molecular pathway by which miR-106b and miR-137 regulates the expression of Nourin gene are evident in coronary artery diseases and strongly linked to myocardial ischemia. Wherein the upregulation of miR-106b and miR-137, results in overexpression of mRNA ANAPC11 and mRNA FTHL-17; respectively. Moreover, both miRNAs were upstream regulated by lncR-CTB89H12.4. The downregulation of lncR-CTB89H12.4 has been detected in myocardial ischemia and is significantly associated with higher levels of miR-106b and miR-137, and it is linked to overexpression of mRNA-ANAPC11 and mRNA-FTHL-17.

Results indicate high significant difference in the expression of miR-106b and miR-137 between early cases of angina in which samples were collected within 1 to 10 hours from the onset of chest pain, and late angina in which samples were collected within 24 to 72 hours from onset of chest pain. The miR-106b expression level was 50% higher in late angina patients compared to early angina patients with high statistical significance ($p<0.01$). Similarly, miR-137 expression level showed 42% increase in late angina patients compared to early angina patients.

These results reflect that both miR-106b and miR-137 could be used as predictors for disease progression and tissue damage in cardiac patients. Additionally, because of the high sensitivity and specificity of the Nourin RNA network, it will likely diagnose microvascular angina patients that otherwise would be missed by current Angiography procedure and ECHO/ECG treadmill stress test. Furthermore, since Nourin gene is not expressed nor that it is released by normal non-ischemic heart, it can be used with high confidence to exclude non-cardiac patients presenting to hospital ED and in outpatient clinics with chest pain.

The treadmill stress test and the dobutamine stress ECHO are the current standard procedures used to diagnose angina patients after inducing ischemia by exercise. However, the treadmill stress test has low sensitivity and specificity and is associated with high false positive results, particularly in females. These facts are making the proper diagnosis of angina patients to be a problematic clinical issue. Therefore, a study was conducted to evaluate whether miR-106b and miR-137 can diagnose patients with history of chest pain suspect of angina. The expression levels of miR-106b and miR-137 have been analyzed in patients with history of chest pain and positive stress test, and then compared to those with also chest pain, but negative stress test. Results revealed that the expression levels of miR-106b and miR-137 were significantly increased in patients with positive stress test, while their expression was low in patients with negative stress test equivalent to healthy control.

The Nourin-related miR-106b and miR-137 are considered a good positive test for angina patients with chest pain, as well as a good negative test for non-angina patients. These results reflect the significance of the Nourin miRNA biomarkers to diagnose angina and to differentiate high risk from standard risk patients.

Since the Nourin RNAs are stable, specific and abundantly expressed in ischemic hearts, they will be an added value to the Nourin protein assays. In general, RNA biomarkers have more sensitivity and specificity with much less interference in serum samples and that the qPCR assay enables traces of RNA sequences to be amplified and thus captured specifically with high sensitivity. Moreover, the cost of RNA biomarker is much lower than protein biomarker because detecting each protein requires a specific antibody.

Figure 22A:
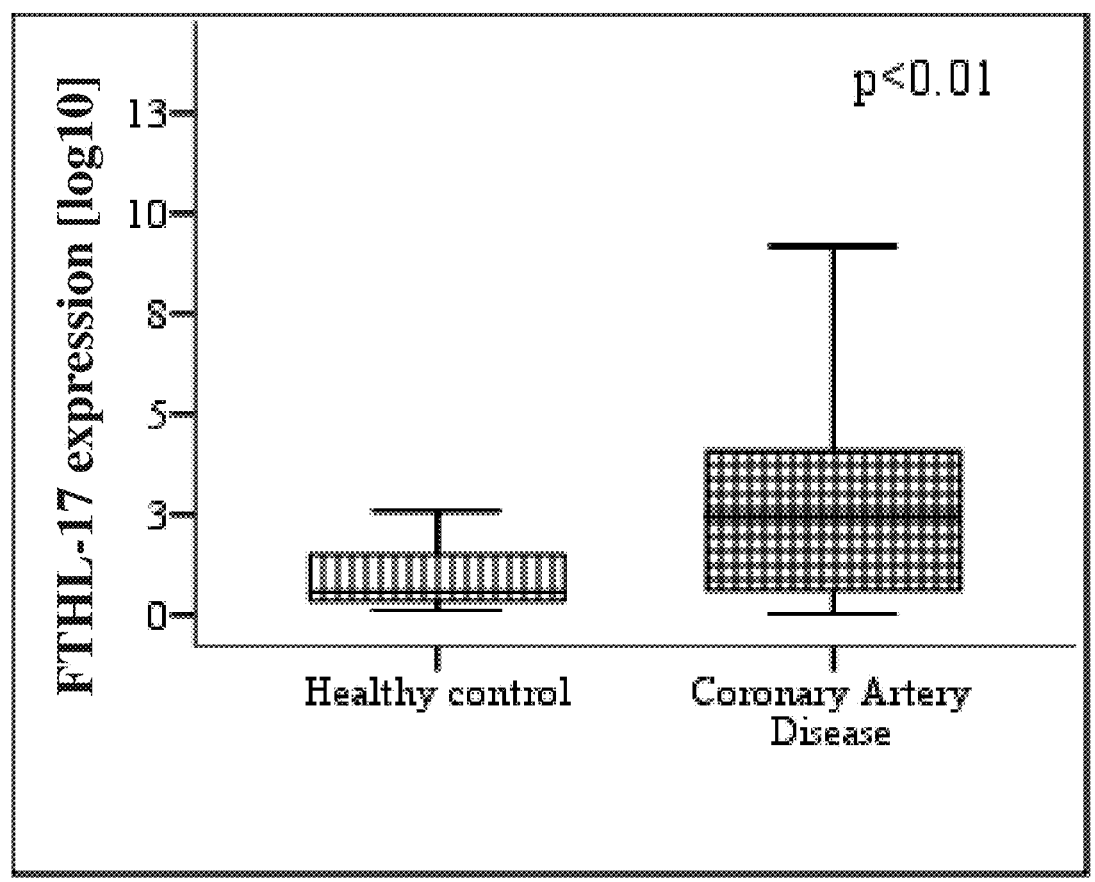
Figure 22B:
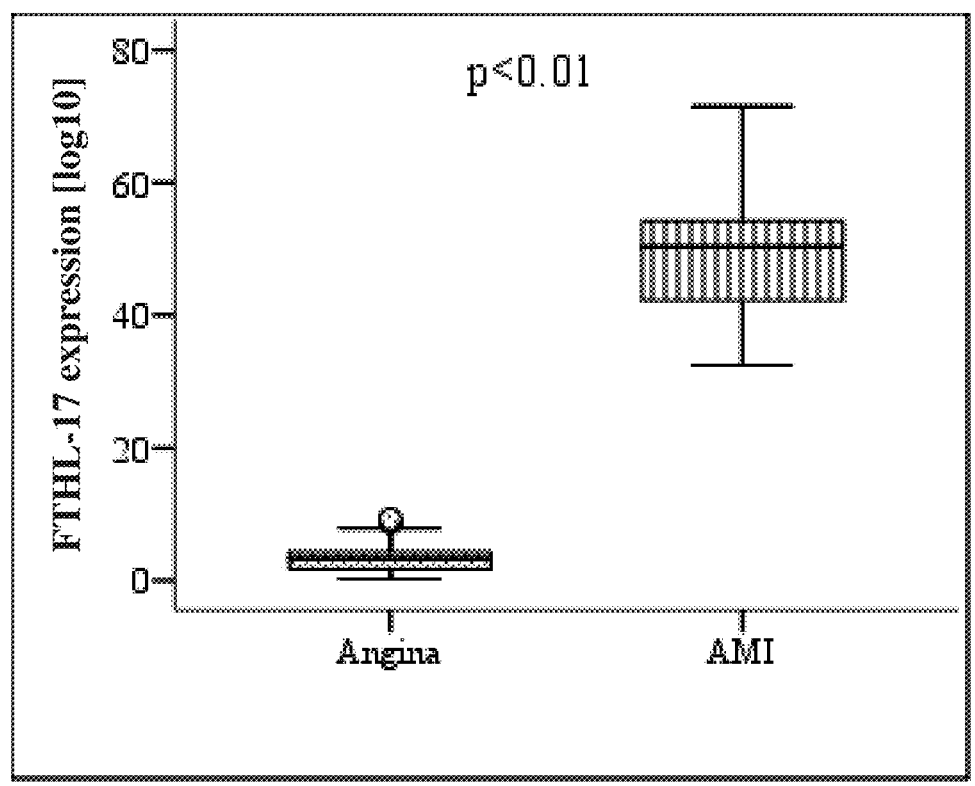
Figure 22C:
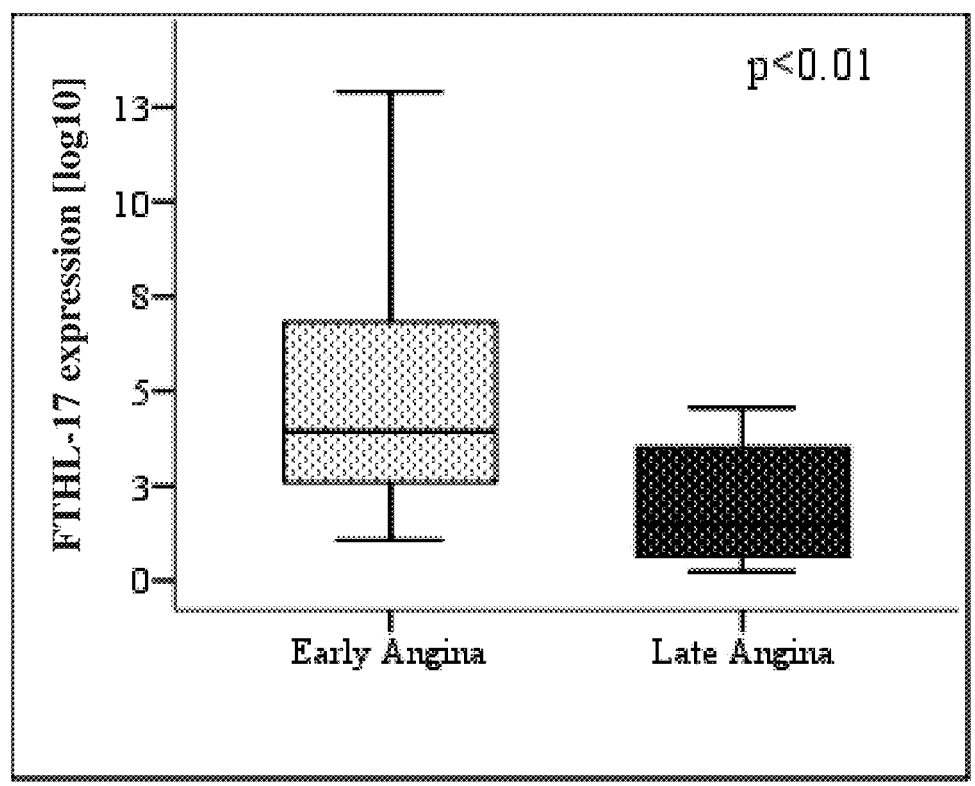
Figure 22D:
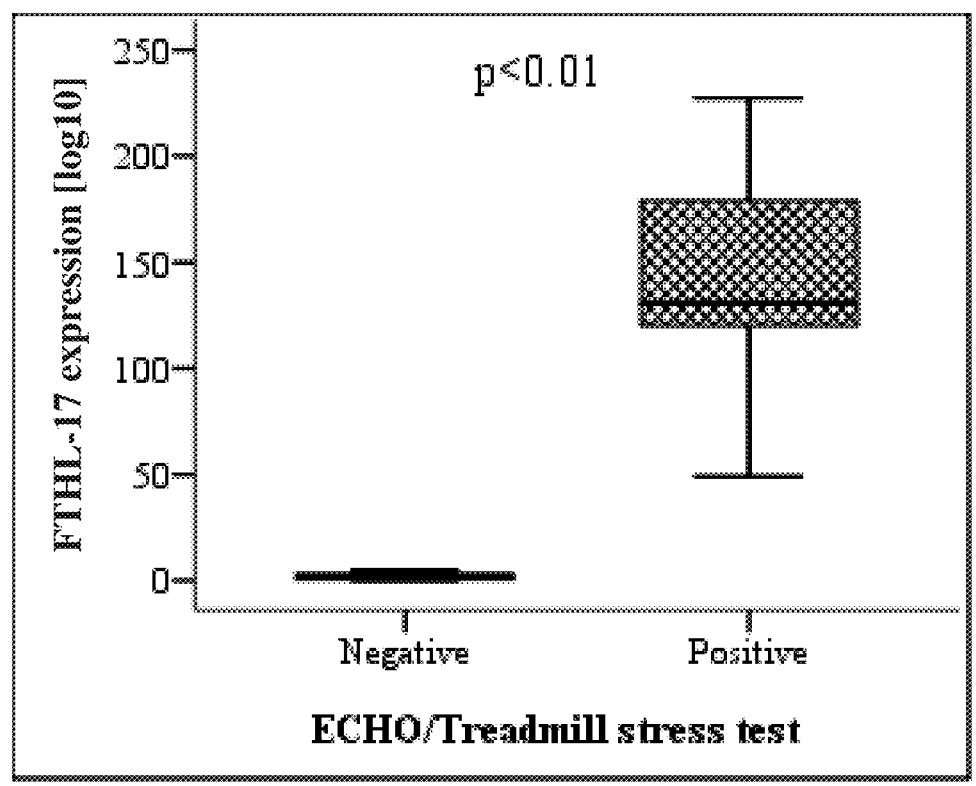
Figure 22E:
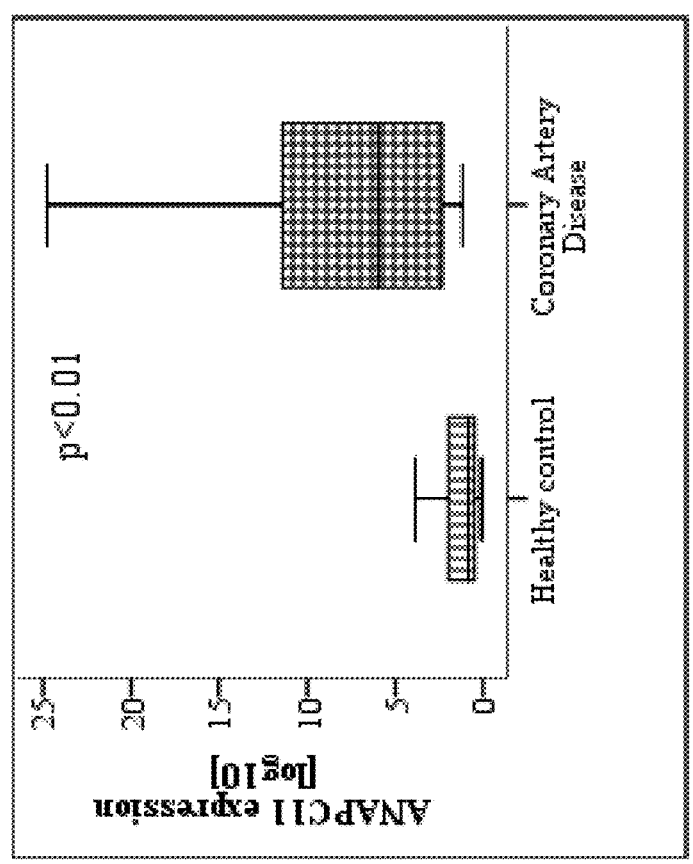
Figure 22F:
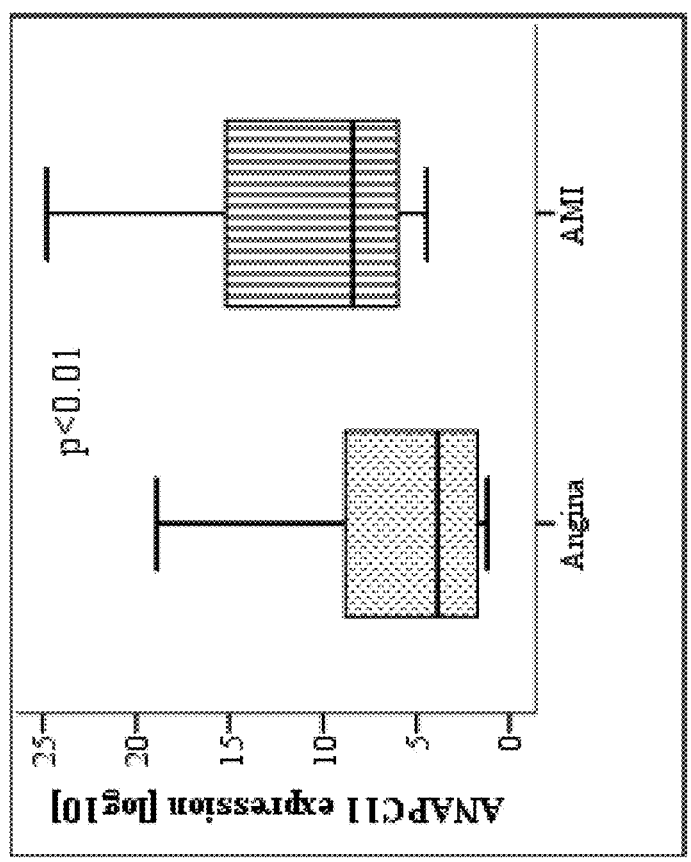
Figure 22G:
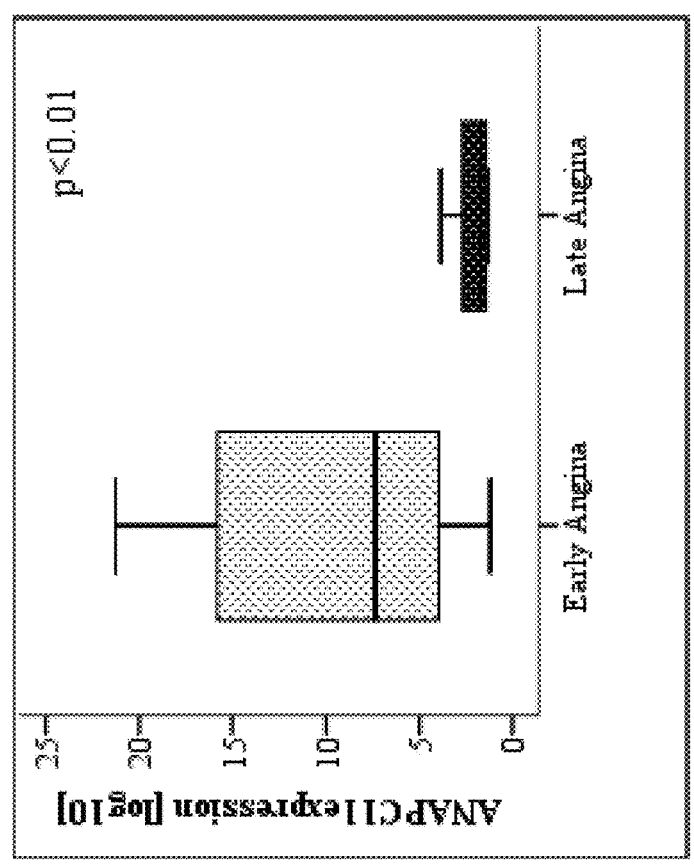
Figure 22H:
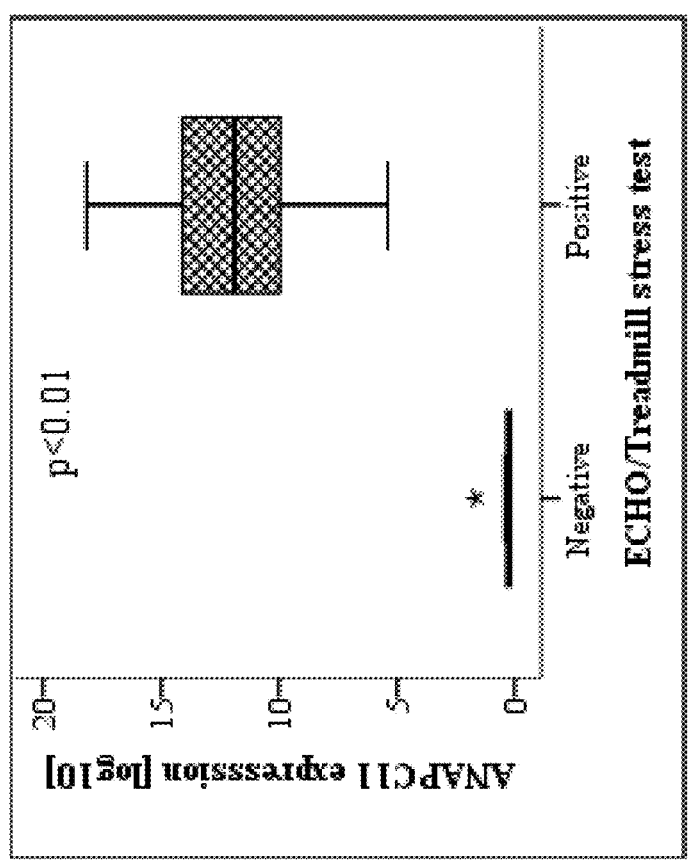
Figure 22I:
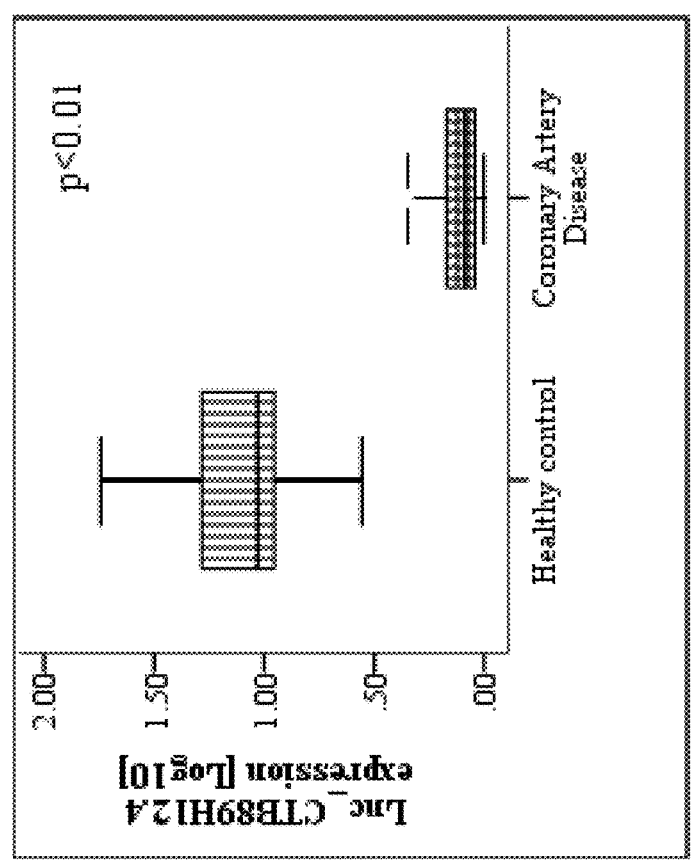
Figure 22J:
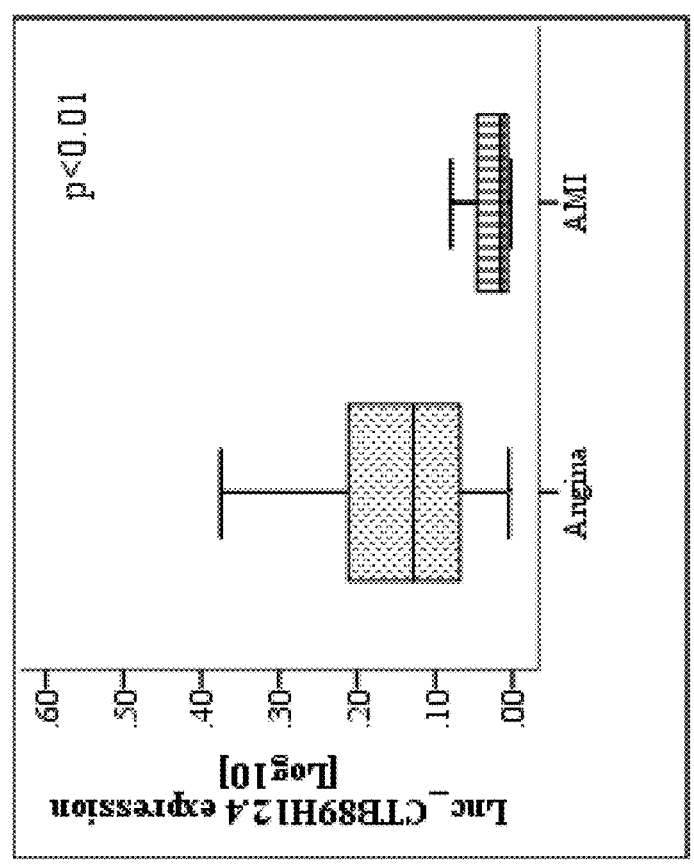
Figure 22K:
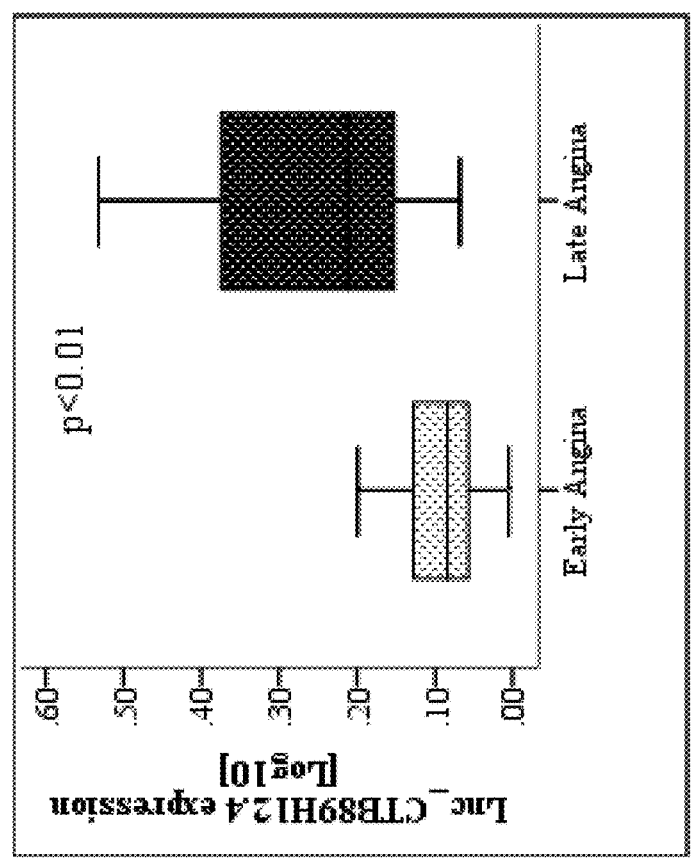

Example 8—the Expression Level of LncR-CTB89H12.4, FTHL-17 and ANAPC11 Genes Selected by Gene Ontology Bioinformatics Analysis, Showed a High Evidence to be Related to Nourin Protein Expression, and they Represent a Signaling Pathway in the Pathogenesis of Ischemic Heart Disease. The Three Genes Level Expression were Tested to Differentiate: (1) Coronary Artery Disease (Angina and AMI) Patients from Healthy Controls; (2) Angina from AMI Patients; (3) Patients with Early Stage and Late Stage Angina Time; and (4) Suspected Outpatient Angina Patients from Non-Angina by Stress ECHO/ECG Treadmill Test Results summarized in FIG. 20, FIG. 21 and FIG. 22A-FIG. 22L revealed a significant higher expression levels of FTHL-17 and ANAPC11 genes in CAD patients compared to healthy control group, in which FTHL-17 gene expression was increased by 12-folds and by 14-folds for ANAPC11 gene in CAD patients than the control healthy group (FIG. 22A and FIG. 22C). Conversely, the lncR-CTB89H-12.4 gene was significantly downregulated by 9-folds in CAD compared to control healthy group. Moreover, by assessing the difference in gene expression levels between angina and AMI patients, a significant higher expression levels (p<0.01) for FTHL-17 and ANAPC11 were observed in AMI patients compared to angina. Specifically, AMI showed 16.66-fold increase over angina for FTHL-17 and 2.1-fold increase for ANAPC11 in AMI over angina (FIG. 22B and FIG. 22F). On the other hand, the lncR-CTB89H12.4 was significantly downregulated in AMI patients versus the angina patients (p<0.01), data are presented in FIG. 22J. Furthermore, in order to investigate the association between the FTHL-17, ANAPC11 and lncR-CTB89H12.4 genes expression levels and the duration of chest pain, which directly reflects the degree of myocardium cell damage due to ischemia, the three genes expression were measured in patients with early stage angina and compared to those with late stage of angina. Results indicated significant decrease in FTHL-17 (FIG. 22C) and ANAPC11 (FIG. 22G) by approximately 2.3-folds; respectively in late angina than in early angina patients (p<0.01). Meanwhile, the lncR-CTB89H12.4 was significantly upregulated by 2.5-folds in late angina compared to early angina patients (FIG. 22K).

Figure 22L:
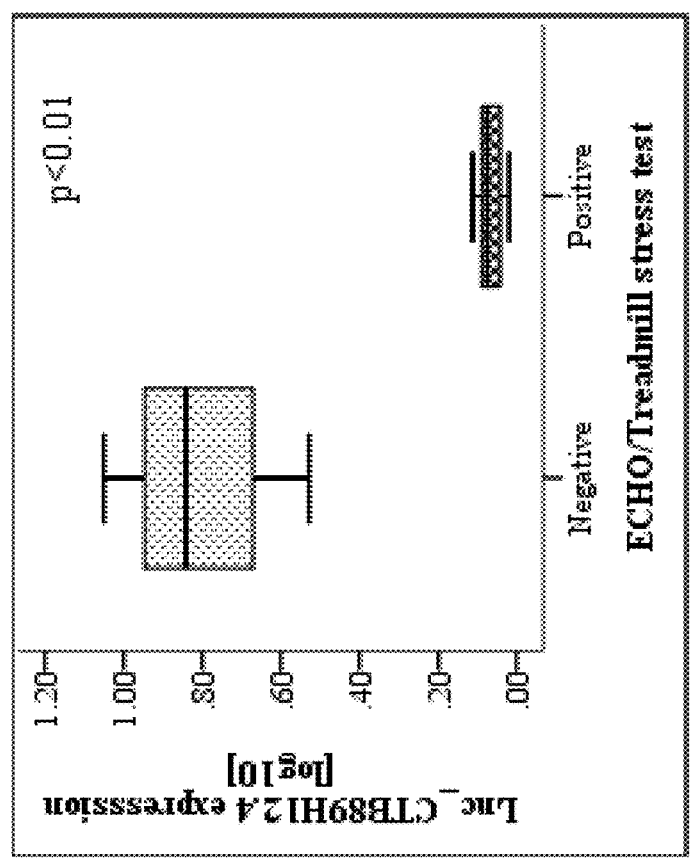

The Treadmill stress test and the dobutamine stress ECHO are used currently to diagnose angina patients after inducing ischemia by exercise. However, the test didn't achieve an acceptable percentage of sensitivity and specificity and is associated with high false positive results, particularly in females. These facts making the proper diagnosis of angina patients is a problematic clinical issue. Therefore, in the current study, the FTHL-17, ANAPC11 and lncR-CTB89H-12.4 genes expression was measured to evaluate whether these genes could diagnose patients with history of chest pain suspect of angina. The expression levels of FTHL-17, ANAPC11 and lncR-CTB89H-12.4 have been analyzed in patients with history of chest pain and positive stress test, and then compared to those with negative stress test. Results revealed that the expression levels of FTHL-17 (FIG. 22D) and ANAPC11 (FIG. 22H) were significantly increased in patients with positive stress test, while their expression values were lower in patients with negative stress test equivalent to healthy control. On the other hand, the lncR-CTB89H12.4 was significantly decrease by 8-folds in patients with positive ECHO/Treadmill stress test compared to those with negative stress test (FIG. 22L).

Figure 24A:
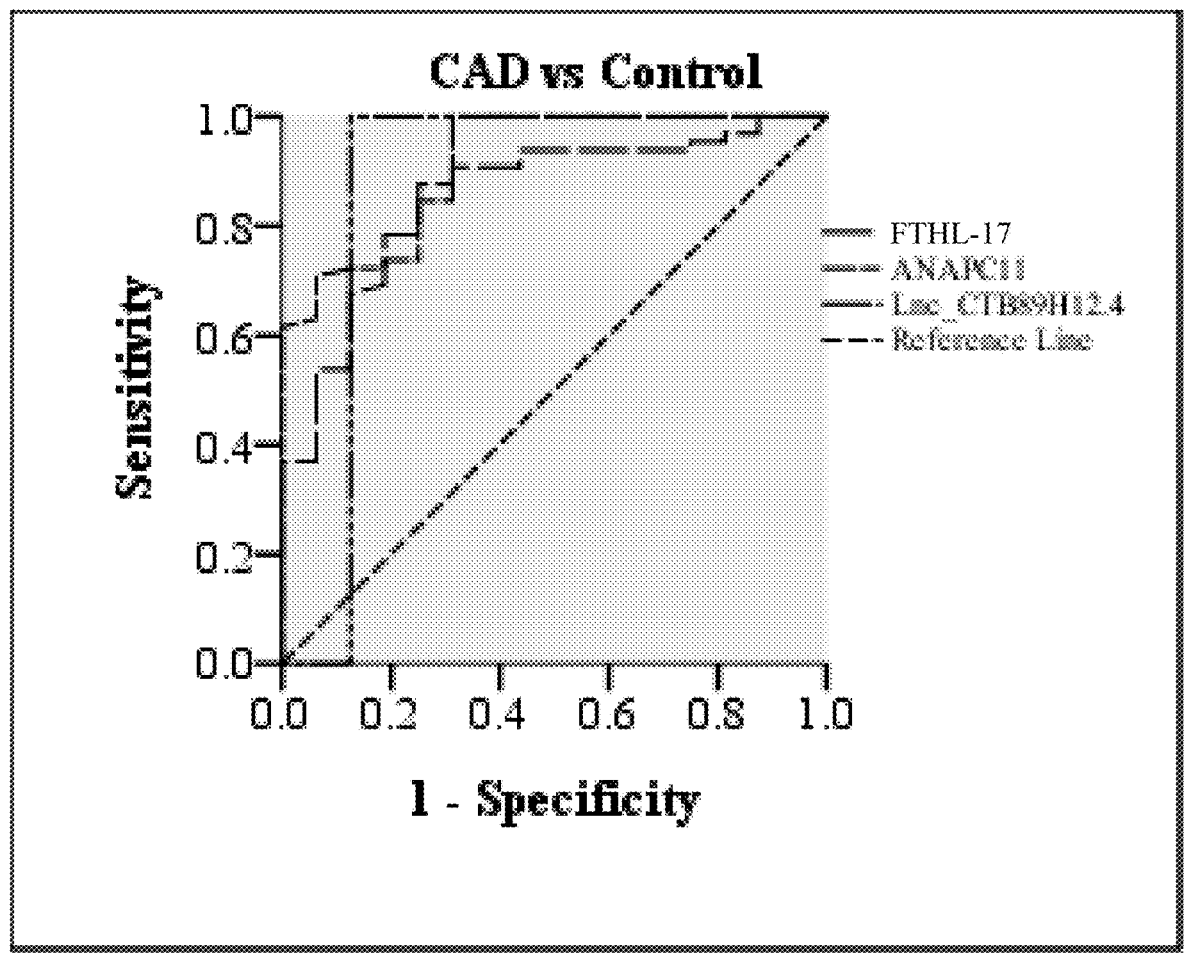
Figure 24B:
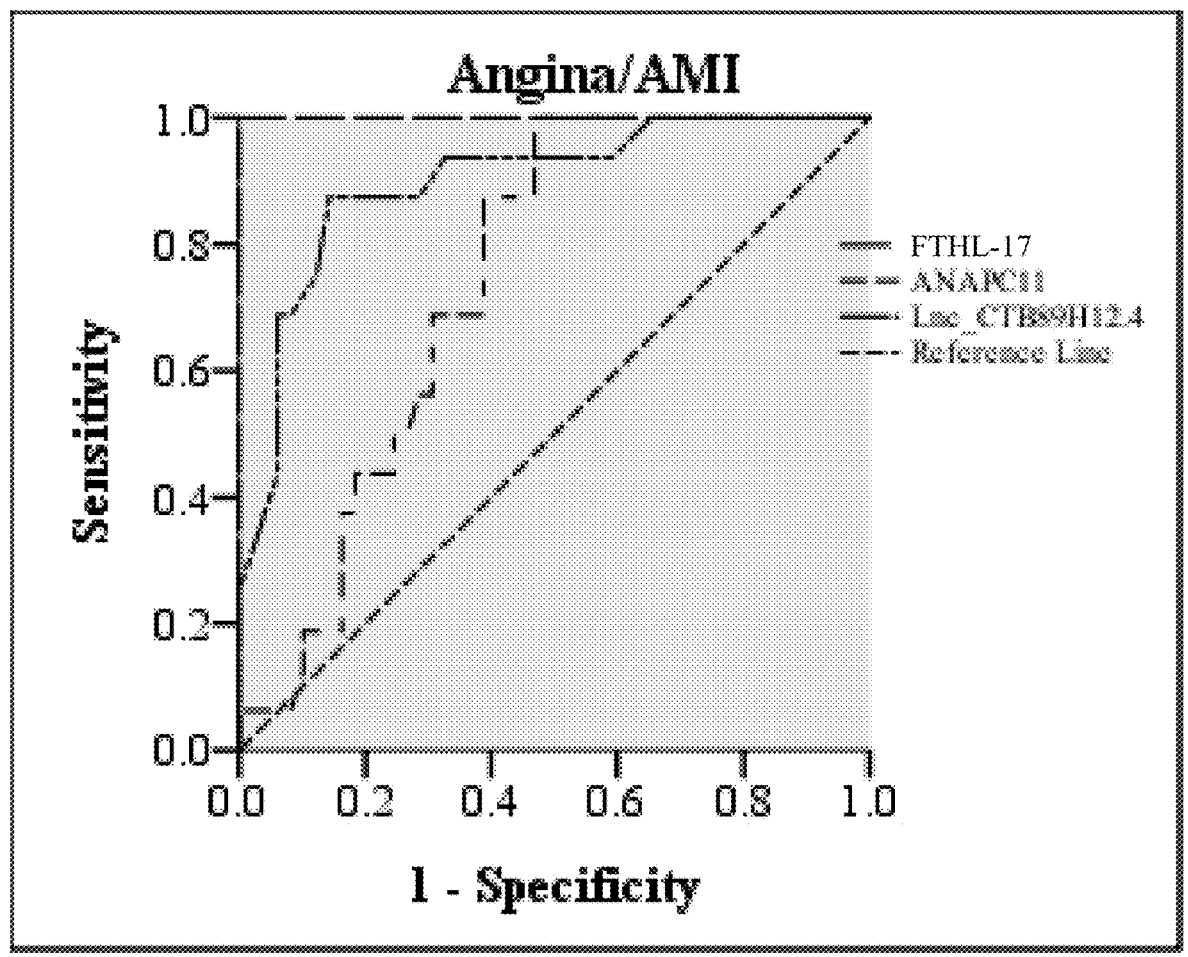
Figure 24C:
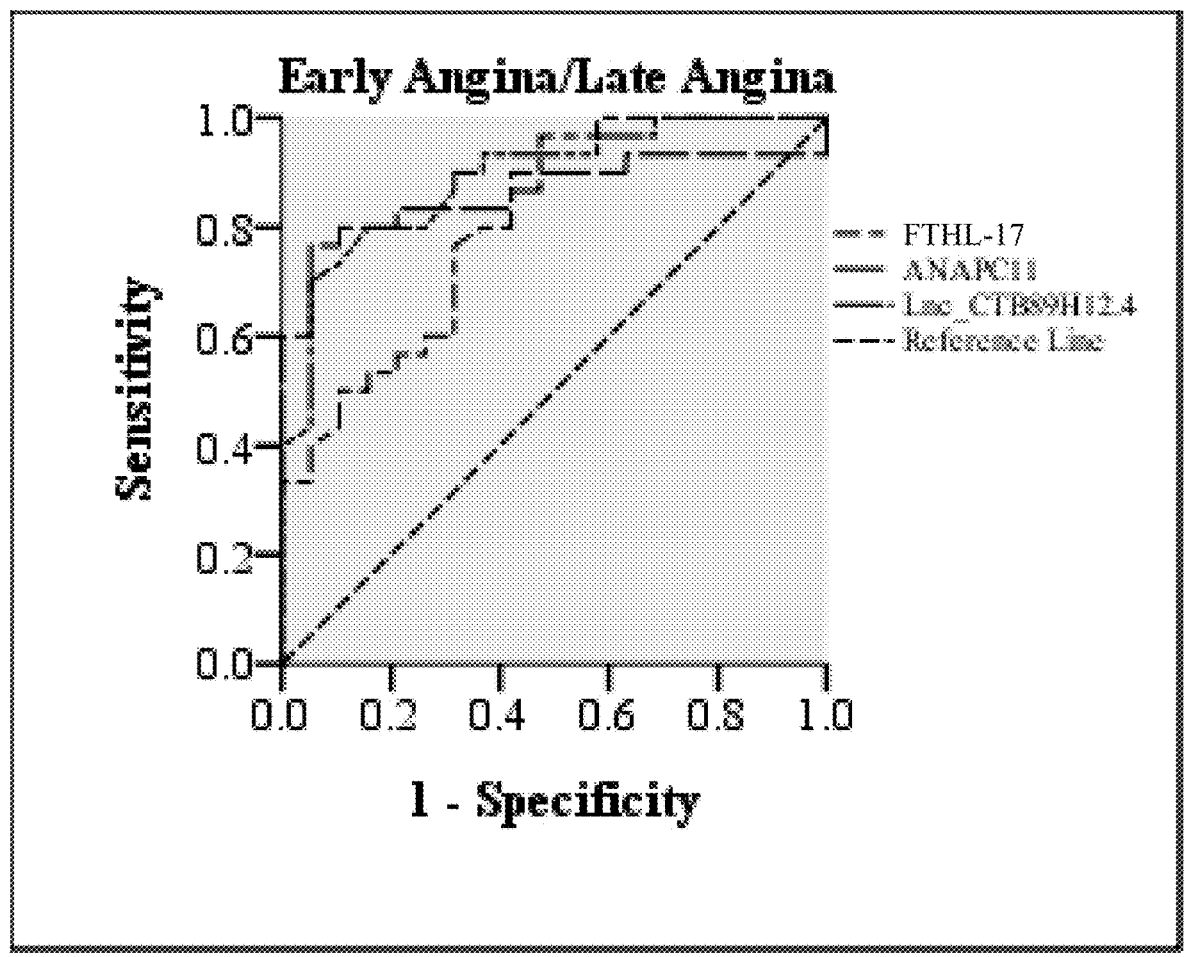
Figure 24D:
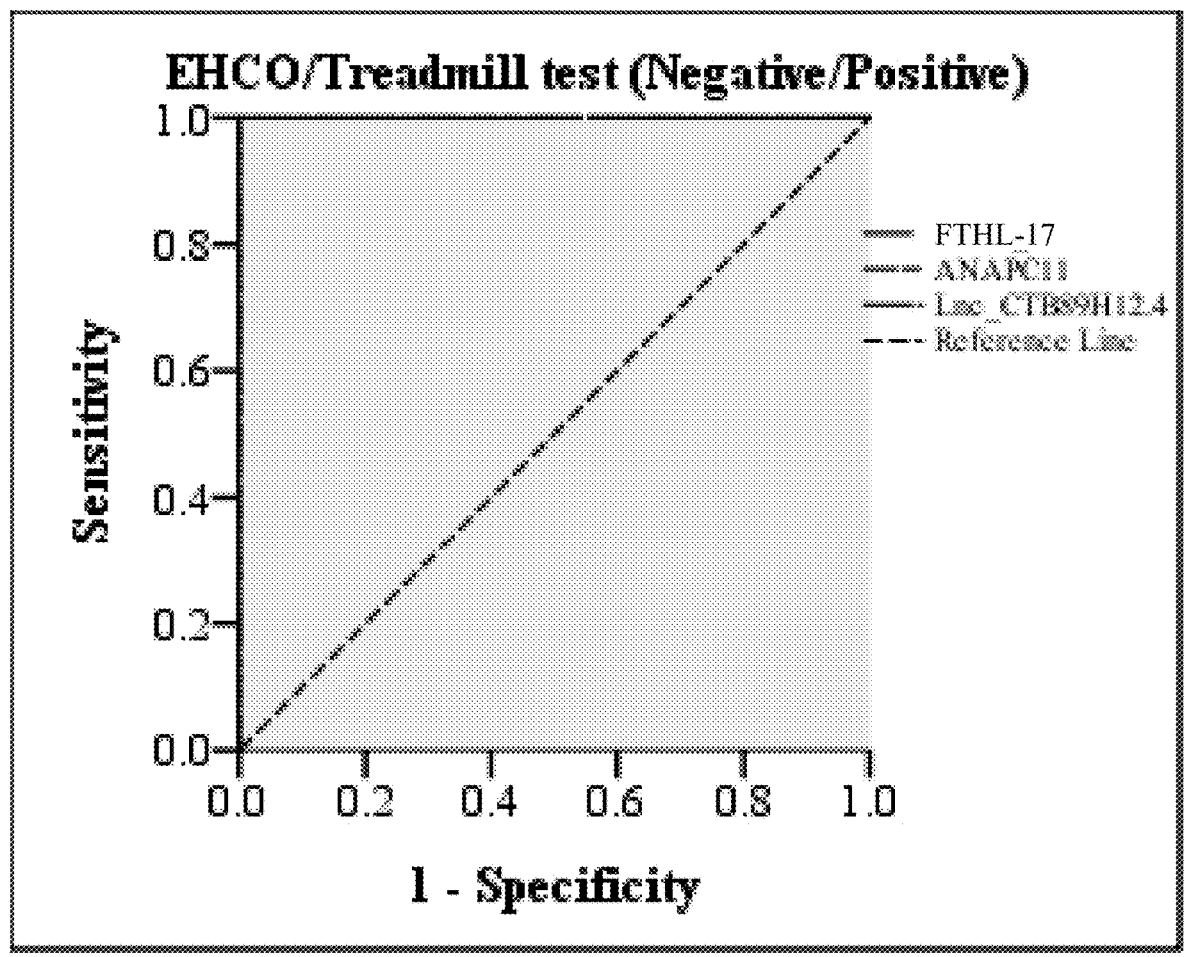

Studies were conducted to evaluate the diagnostic and prognostic potential of Nourin-related "mRNA FTHL-17, mRNA NAPC11 and lncR-CTB89H12.4" genes in (1) discriminating patients with CAD from healthy control; (2) differentiating AMI from angina patients; (3) assessing the degree of myocardial injury by differentiating early stage angina from late; and (4) finally, confirming query (suspected) angina in patients presented with acute chest pain in hospital ED and outpatient clinics. Accordingly, as indicated in FIG. 23 and FIG. 24A-FIG. 24D, a Receiving operating Characteristics curve (ROC) was conducted for the three tested genes. Results revealed that at a cut-off value of 3.2 for the FTHL-17 gene expression can differentiate CAD patients from healthy controls with 72% sensitivity and 81% specificity, and for ANAPC11, the biomarker sensitivity and specificity were 65% and 93% at discriminating cut-off value of 3.8. In contrast, the lncR-CTB89H12.4 possess 84% sensitivity and 88% specificity at a cut off value of 0.27 (FIG. 24A).

The prognostic potential of FTHL-17, ANAPC11 and lncR-CTB89H-12.4 was evaluated to investigate their potential to discriminate: (1): angina from AMI patients (FIG. 24B), the highest sensitivity (100%) was demonstrated for FTHL-17, followed by 75% for lncR-CTB89H-12.4 and the least sensitivity (68%) was detected for ANAPC11. However, specificity of 86% was observed for FTHL-17 and lncR-CTB89H-12.4, and only 70% specificity was reached for ANAPC11; (2): to discriminate early from late stage angina patients (FIG. 24C), the FTHL-17 biomarker possesses the highest sensitivity (100%) and specificity (96%) among other biomarkers in discriminating early from late angina, followed by the lncR-CTB89H12.4 which achieved 72% sensitivity and 87% specificity. While ANAPC11 showed a low sensitivity of 68% and specificity of 62% as discriminating biomarker between different stages of angina; and (3): to discriminate patients with positive ECHO/ECG Treadmill stress test from negative stress test patients (FIG. 24D), the more interesting findings that the ANAPC11 gene possess the highest specificity (90%) to discriminate patients with positive from negative stress test compared to 84% for lncR-CTB89H-12.4 and 65% FTHL-17. However, the three biomarkers reached similar sensitivity of 80%. Results further indicated that there was no interference in the Nourin RNA detection observed in patients and control serum samples when the non-specific inflammatory mediator CRP was elevated.

Overall summary indicates:

1. higher expression levels of miR-106b and miR-137 have been observed in patients with coronary heart disease by 280-folds for miR-106b and 1900-folds for miR-137 compared to healthy control group, with high statistical significance; reflecting the high specificity and sensitivity of Nourin miRNAs in the diagnosis of coronary heart disease with chest pain.

2. the miR-106b expression level was higher by 50% in late stage angina patients compared to early angina patients, with high statistical significance, and wherein, the miR-137 expression level was increased by 42% in late stage angina patients compared to early angina, with high statistical significance; reflecting disease progression and the extend of tissue damage in angina patients.

3. the expression of miR-106b was significantly increased by 137-folds in chest pain angina patients with positive ECHO/ECG Treadmill stress test, compared to non-angina patients with a negative stress test; reflecting the high specificity and sensitivity of miR-106b biomarker in the diagnosis of angina in patients with history of chest pain. Wherein, the expression of miR-137 was significantly increased by 331-folds in angina patients with positive ECHO/Treadmill stress test compared to non-angina patients with a negative stress test; reflecting the high specificity and sensitivity of miR-137 biomarker in the diagnosis of angina patients with history of chest pain.

4. miR-106b and miR-137 for example, possesses a discriminating cut-off value of 3.5 for both miRNAs to diagnose coronary artery disease patients from healthy controls. Wherein, the cut-off values of 372 for miR-106b, and 2488 for miR-137 discriminated angina patients from AMI cases. Wherein, the cut-off values of 283 for miR-106b, and 1,240 for miR-137 differentiated between early and late stage angina. Wherein, miR-106b and miR-137 discriminated chest pain angina patients with positive ECHO/ECG Treadmill stress test from non-angina patients with negative test at a cut-off of 172 for miR-106b and a cut-off of 8 for miR-137.

5. miR-106b and miR-137 for example, discriminated angina patients from healthy controls with an approximately 100% sensitivity and 95% specificity. Wherein both miRNAs attributed a significant prognostic potential to discriminate angina patients from AMI patients, as well as between early and late stage angina patients. Wherein, miR-106b possesses an 87% sensitivity and 79% specificity in discriminating AMI from angina patients, while miR-137 possesses 75% sensitivity and 72% specificity. Wherein, high specificity for miR-106b which reaches a 96% in contrast to only 70% for miR-137 in discriminating early from late stage angina. Wherein, the negative ECHO/Treadmill stress test patients with history of chest pain, differentiated from positive stress test patients using miR-106b and miR-137 biomarkers with an 85% specificity and a 100% sensitivity.

6. the Nourin-related miR-106b and miR-137 are a good positive test for angina patients with chest pain, as well as a good negative test for non-angina patients, reflecting the significance of the Nourin miRNAs biomarkers to diagnose angina and to differentiate high risk patients from standard risk individuals.

7. the Nourin RNAs were not detected in healthy subjects nor in clinically confirmed non-angina patients with history of acute chest pain and negative Troponin. Wherein, said the Nourin molecular network is tissue-specific and abundantly expressed in heart tissues. Wherein, the Nourin lncR-CTB89H12.4, miR-106b, miR-137, mRNA-ANAPC11 and mRNA-FTHL-17, can be measured individually, and in combination.

Example 9—Up-Regulation of Nourin Gene-Based RNA Molecular Network in Angina

The present invention of the Nourin gene-based molecular biomarker panel composed of Nourin lncR-CTB89H12.4, miR-106b, miR-137, mRNA ANAPC11 and mRNA FTHL-17 further confirmed the use of the cardiac-derived Nourin protein as a biomarker for coronary artery disease patients. The down-regulation of lncR-CTB89H-12.4 after an ischemic event resulted in up-regulation of miR-106b and miR-137 and activation of mRNA-ANAPC11 and mRNA-FTHL-17 with an increased translation and production of high levels of the cardiac-derived Nourin protein. There is a minimal gene expression of FTHL-17 mRNA in normal non-stressed tissues. The Nourin RNA panel can be used individually or in combination with the protein-based biomarker Nourin for better and faster diagnosis of coronary artery disease patients presenting with chest pain to hospital ED and outpatient clinics. The Nourin molecular and protein-based assays are significantly earlier than current myoglobin, CK-MB and Troponin assays in detecting UA and AMI in patients presenting to the ED with chest pain. FIG. 14 indicates that the absence of biomarkers for angina patients, while several biomarkers are available for AMI patients. The present Nourin RNA assay can diagnose angina prior to a heart attack, and it can be detected immediately after the initiation of an acute chest pain in angina patients which lasted for up to at least 72 hours after an event. Much higher expression levels of micro Nourin RNAs were detected in late angina than early stage. Furthermore, the micro Nourin RNAs were significantly higher in angina patients with positive ECHO/ECG Treadmill stress test than negative non-angina. Additionally, the test can differentiate between angina and AMI patients, where the Nourin gene is expressed much higher in AMI than angina.

There is a minimal Nourin RNA gene expression in normal non-ischemic tissues. Because of the high sensitivity and specificity of the Nourin gene RNAs, they can diagnose microvascular angina patients that otherwise they would be missed by current Angiography procedures and ECHO/ECG Treadmill stress test. Earlier identification of heart patients allows for early intervention to avoid permanent damage and heart attack that can lead to heart failure and death. In general, about 50% of heart attack patients suffer heart failure.

Although the currently identified circulating miRNA-208a, miRNA-133 and miRNA-1 peak in the blood at 3 hours after AMI, they are still markers of necrosis similar to Troponin. Nourin, on the other hand, is much earlier biomarker released by 'viable' ischemic tissue and, thus, provides fast diagnosis of angina and AMI patients for crucial therapy (FIG. 14). Additionally, the low level of Nourin in blood samples collected from healthy individuals and non-angina patients with history of chest pain, makes Nourin biomarker as an attractive diagnostic marker with little or no effect from normal non-stressed tissues. Also, no interference in the Nourin RNA results was observed in patients and control serum samples when the non-specific inflammatory mediator, CRP was elevated.

Furthermore, Nourin panel of RNAs may be used to for classical risk factors for coronary artery disease diagnosis and prognosis. However, compared to protein-based biomarkers, RNA biomarkers have more sensitivity and specificity as it can be tissue and disease specific.

The Nourin assay using for example and not limited to Nourin including the Nourin panel of RNAs (qPCR, Nanogold, Multiplex, microfluidics and sensor ship) or Nourin epitope N-f-MII (leukocyte Chemotaxis, ELISA, sensor ship and MALDI-TOF [Matrix Assisted Laser Description Ionization-Time of Flight]). The Nourin assays can identify unstable angina patients and AMI. If the Nourin assay does not detect elevated levels of Nourin RNA network and/or Nourin peptide, then angina patients and AMI can be ruled out and the patients can be released from hospital ED or a workup can begin to elucidate the true cause of the patients' chest pain syndromes.

The Nourin assay using for example and not limited to Nourin including the Nourin panel of RNAs (qPCR, Nanogold, Multiplex, microfluidics and sensor ship) or Nourin epitope N-f-MII (leukocyte Chemotaxis, ELISA, sensor ship and MALDI-TOF [Matrix Assisted Laser Description Ionization-Time of Flight]) is expected to be used clinically in combination with Troponin for some better sensitive and specific diagnostic tests for acute coronary syndromes]). The Nourin assays can identify unstable angina patients and complement and enhance the usefulness of Troponin tests to rule in or out unstable angina and AMI. If the Nourin assay does not detect elevated levels of Nourin RNA network and/or Nourin peptide, then angina patients and AMI can be ruled out and the patients can be released from hospital ED or a workup can begin to elucidate the true cause of the patients' chest pain syndromes. On the other hand, if the Nourin assay detect elevated levels of Nourin RNA network and/or Nourin peptide, the ACS patients can receive therapies in an earlier timeframe than is presently possible with current Troponin and thus eliminating the required long wait of 2 to 6 hours.

Early identification of heart patients allows for early intervention to avoid permanent damage that can lead to ischemic heart failure and death. Specifically, early diagnosis of ischemic heart patients will allow for crucial intervention to avoid permanent damage and, thus, abort infarction, save heart muscles, reduce myocardial injury and the progression of patients to heart failure. In general, 50% of heart attack patients will suffer heart failure.

The Nourin protein and its multiple genes that are functionally linked to each other and to AMI functional networks, increase the chance of a higher diagnostic success than the simpler conventional single-marker approach for Troponin. The Nourin assays will also be used to identify patients at risk for coronary artery disease (CDA) since circulating miRNAs were found to have a distinct pattern in cardiovascular disease including: CAD, AMI, hypertension, heart failure (HF) and viral myocarditis (VM). Thus, Nourin can be used not only for early diagnosis and monitoring of ACS patients presented to hospital ED and outpatient clinics with chest pain, but also as a risk predictive biomarker to (1) screen high-risk patients (diabetes, high blood pressure, obesity, aging, smokers, high cholesterol, stress, etc.) for the identification of CAD and allow for crucial intervention to avoid permanent damage, abort infarction, save heart muscles and reduce myocardial injury; (2) screen CAD patients for risk assessment to predict which patients are at risk for developing AMI; (3) predict drug therapy response on heart tissue in clinical trials; (4) monitor the heart health after therapy and disease progression; (5) differentiate cardiac from non-cardiac experiencing chest pain; (6) determine the risk level of heart patients experiencing chest pain; (7) provide risk stratification of AMI patients; and (8) diagnose heart failure patients after AMI and determine their risk assessment and prognosis.

Example 10—Nourin Gene-Based RNA Molecular Network were Significantly Elevated in Stress Test Positive Angina Patients Before and 30 Minutes after the Dobutamine Stress Echocardiography (ECHO/ECG) Treadmill Stress Test and Correlated with Results of the Stress Test in Diagnosing Myocardial Ischemia in Angina Patients with Negative Troponin The standard quantitative real time PCR (qPCR) molecular assay described in Example 6 was used to determine: (1) whether the observed elevated gene expression levels of miR-137 and miR-106b in serum samples collected from positive angina patients 30 minutes "after" the Dobutamine stress Echocardiography (ECHO/ECG) Treadmill stress test (Example 7), are also elevated before the stress test; (2) whether the observed low gene expression levels of miR-137 and miR-106b in serum samples collected from negative non-angina patients after stress test (Example 7), are also low "before" the test; and (3) is there a correlation between miR-137 and miR-106b gene expression with results of the stress test in diagnosing myocardial ischemia in angina patients with negative Troponin?

Serum samples were collected from intermediate-risk patients (total of n=12) seen in outpatient clinics with history of chest pain suspected of angina. All 12 atypical patients had negative Troponin and were scheduled to be evaluated on standard treadmill stress test or ECHO. Because of the high false positive in females using the treadmill stress test, all female patients were evaluated only by the ECHO test. For controls, serum samples were collected from healthy individuals (n=16) with negative Troponin. All 16 volunteers also exercised on Treadmill to confirm absence of ischemic heart disease after inducing stress. Serum samples were collected "before" the stress test and 30 minutes "after" the completion of the stress test. Using standard qPCR technology, gene expression levels of miR-137 and miR-106b were determined in serum samples of 12 suspected stable angina patients with history of chest pain and 16 healthy volunteers. Out of the 12 patients, 5 had positive stress ECG changes in the treadmill stress test or dobutamine stress ECHO, suggestive of myocardial ischemia (positive angina), while 7 patients showed negative ECHO/ECG Treadmill stress test indicating lack of evidence of ischemia (negative angina).

Figure 25A:
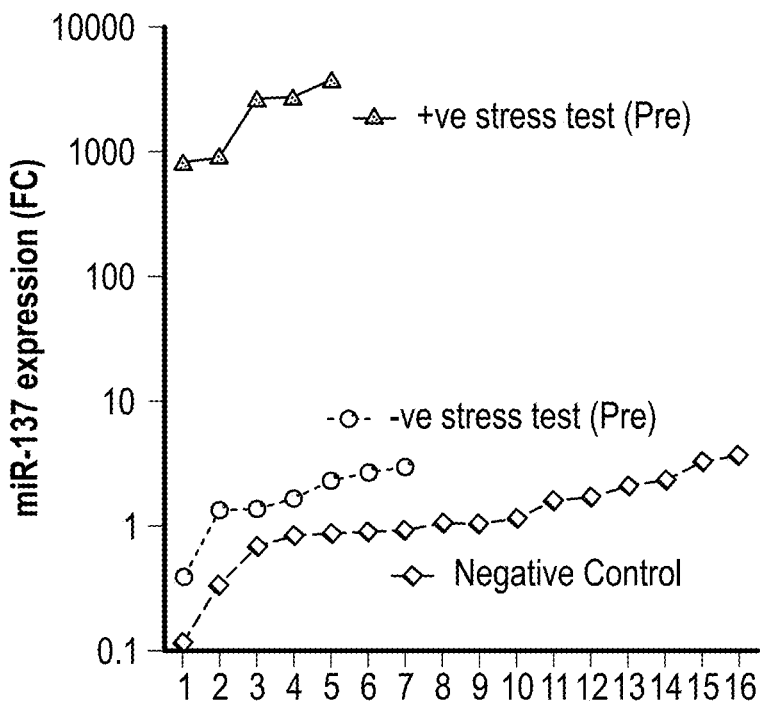
Figure 25B:
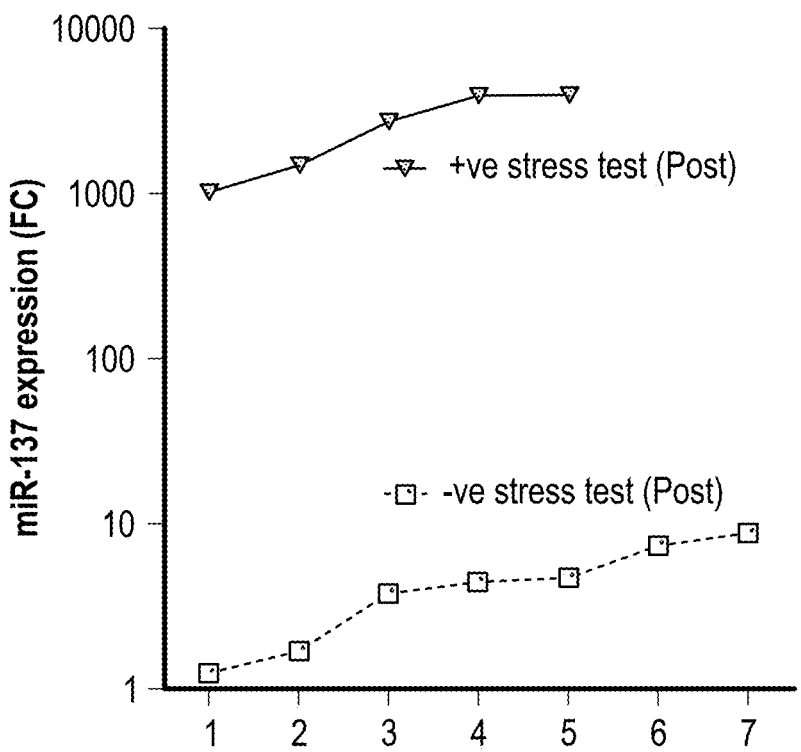
Figure 25C:
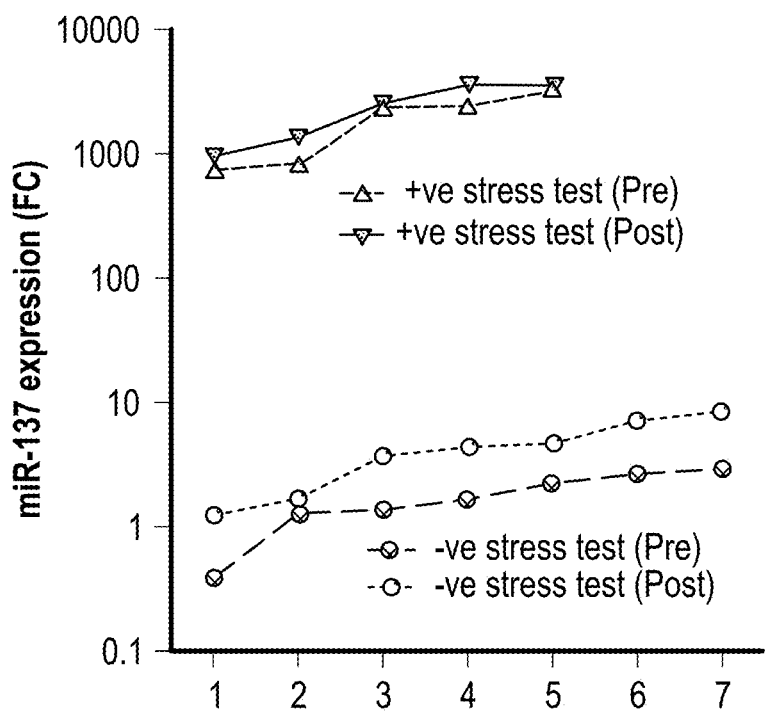
Figure 25D:
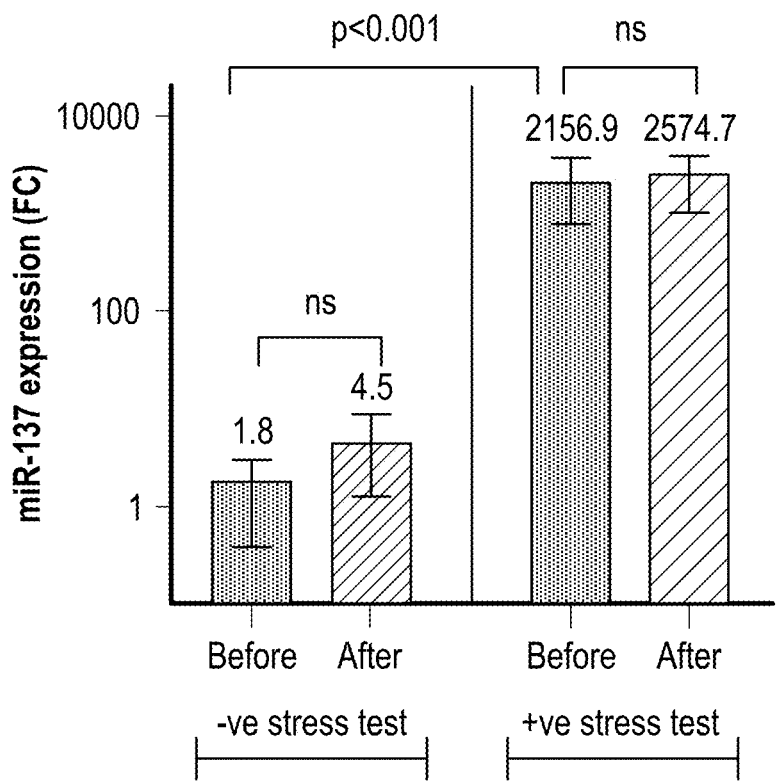

As indicated in FIG. 25A to FIG. 25D, and FIG. 26A to FIG. 26D we determined the gene expression levels of miR-137 and miR-106b in serum samples collected from the 12 intermediate-risk patients suspected angina subjects with negative Troponin and 16 healthy controls. FIG. 25A shows significantly higher levels of miR-137 were detected in samples taken Pre-stress test of positive patients (n=5) compared to the very low expression detected in the Pre-stress test of the negative patients (n=7). The low level was comparable to baseline values in healthy controls (n=16). FIG. 25B shows significantly higher levels of miR-137 were detected in Post-stress test of "positive" stress test patients compared to the very low expression detected in Post-stress test of "negative" stress test patients. The combined expression pattern and level of miR-137 taken before (Pre) and 30 minutes after (Post) the stress test is shown in FIG. 25C and demonstrates that high expression levels were detected Pre and Post stress test in patients with positive stress test, while, low expression levels were detected Pre and Post stress test in patients with negative stress test. FIG. 25D shows significantly ($p<0.001$) higher serum expression levels of miRNA-137 in positive patients before and after the stress test compared to the low expression levels detected in the negative stress test group. There was no statistical difference in the miRNA-137 gene expression level before the stress test compared to after the test in the positive and negative patients.

Figure 26A:
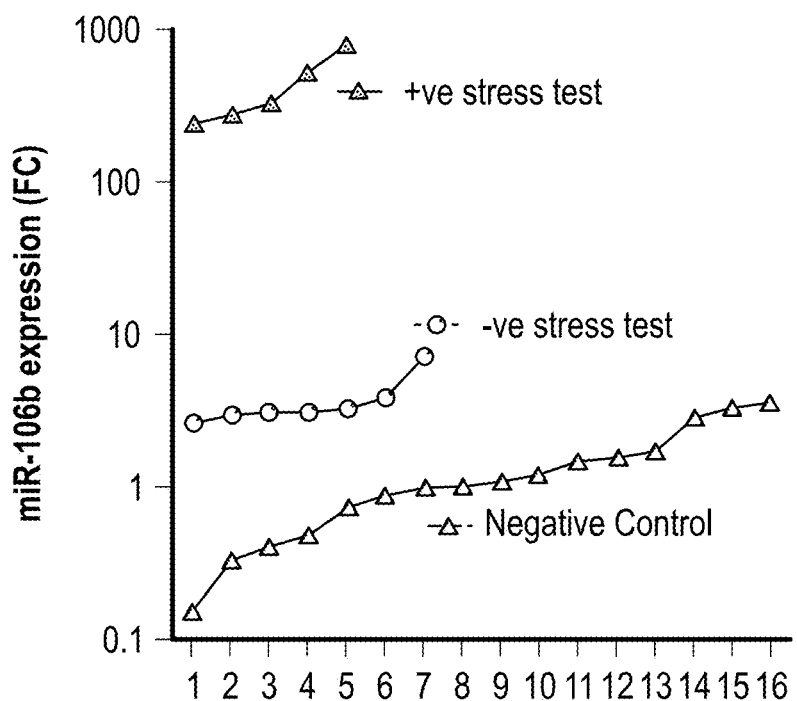
Figure 26B:
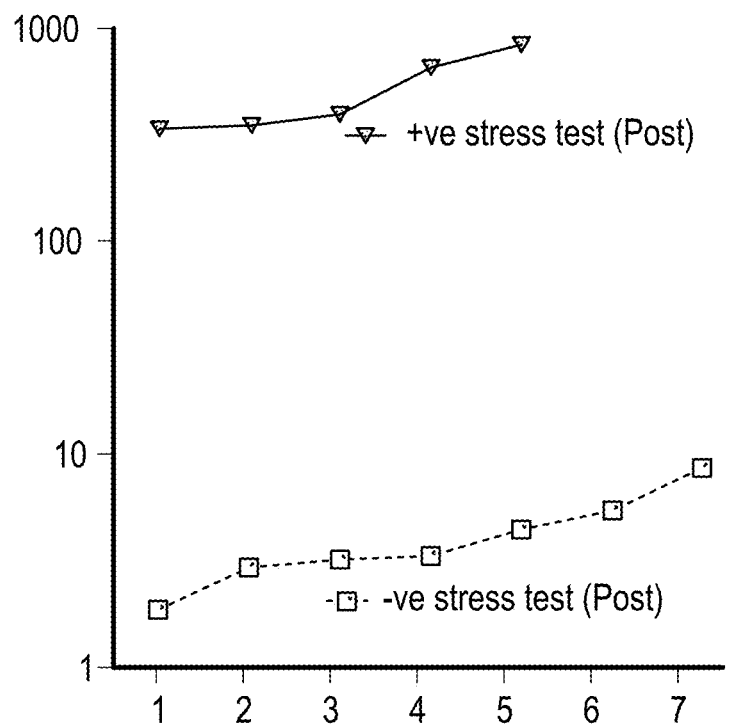
Figure 26C:
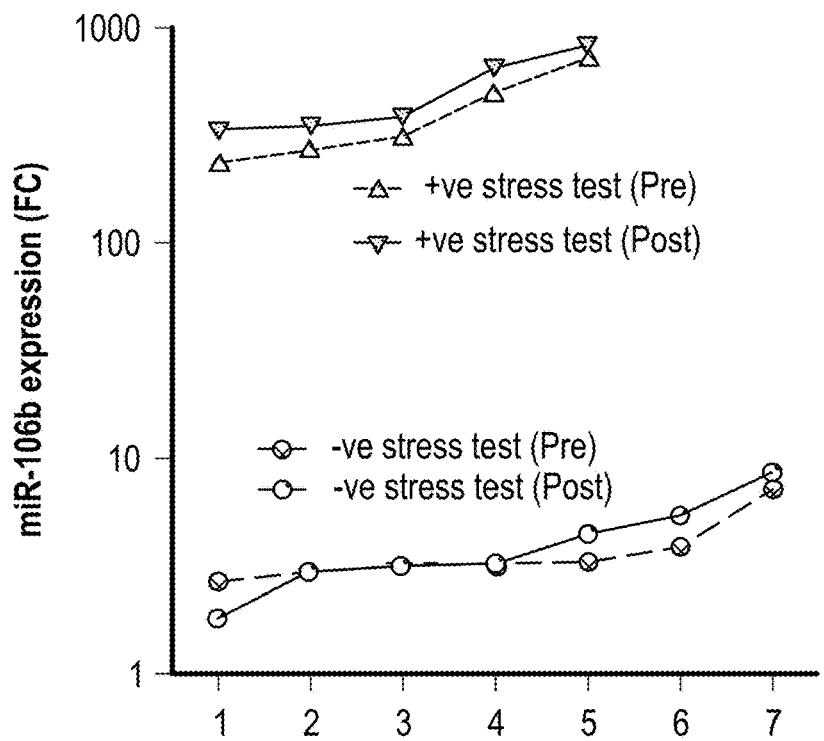
Figure 26D:
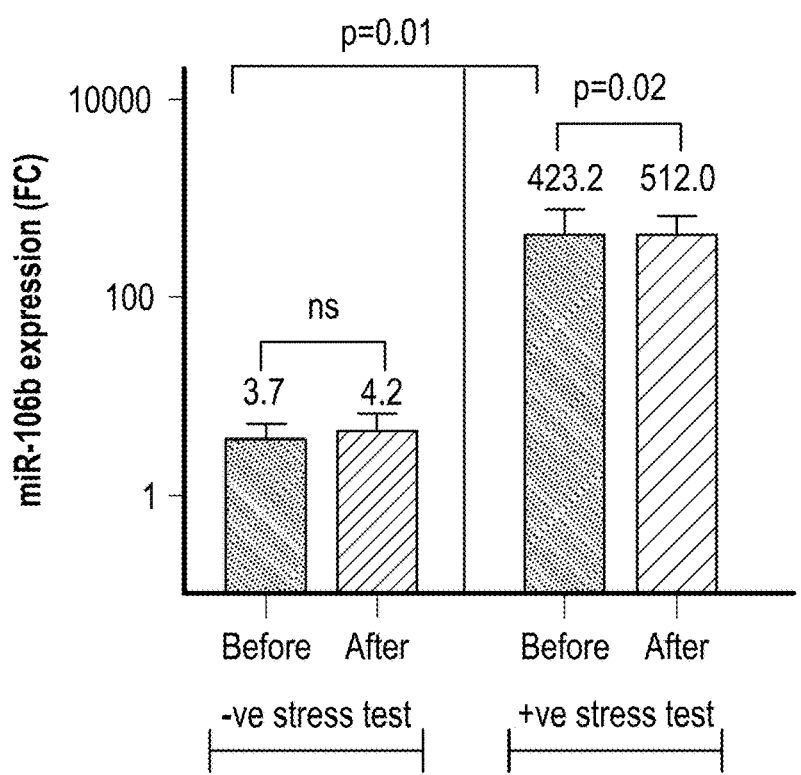

Similarly, FIG. 26A shows significantly higher levels of miRNA-106b were detected in samples taken Pre-stress test of positive patients (n=5) compared to the very low expression detected in the Pre-stress test of the negative patients (n=7), which was comparable to baseline values in healthy controls (n=16). FIG. 26B shows significantly higher levels of miR-106b were detected in Post-stress test of positive stress test patients compared to the very low expression detected in Post-stress test of negative stress test patients. The combined expression pattern and level of miR-106b collected before (Pre) and after (Post) the stress test is shown in FIG. 26C and demonstrates that high expression levels were detected Pre and Post stress test in patients with "positive" stress test, while, low expression levels were detected Pre and Post stress test in patients with "negative" stress test. FIG. 26D shows significantly ($p<0.01$) higher serum expression levels of miR-106b in positive patients before and after the stress test compared to the low expression levels detected in the negative stress test group. Interestingly, there was statistical ($p=0.02$) difference in the miRNA-106b gene expression before and after the stress test in positive patients, where higher gene expression was detected after the test. There was co statistical difference between before and after in the negative patients.

Figure 27A:
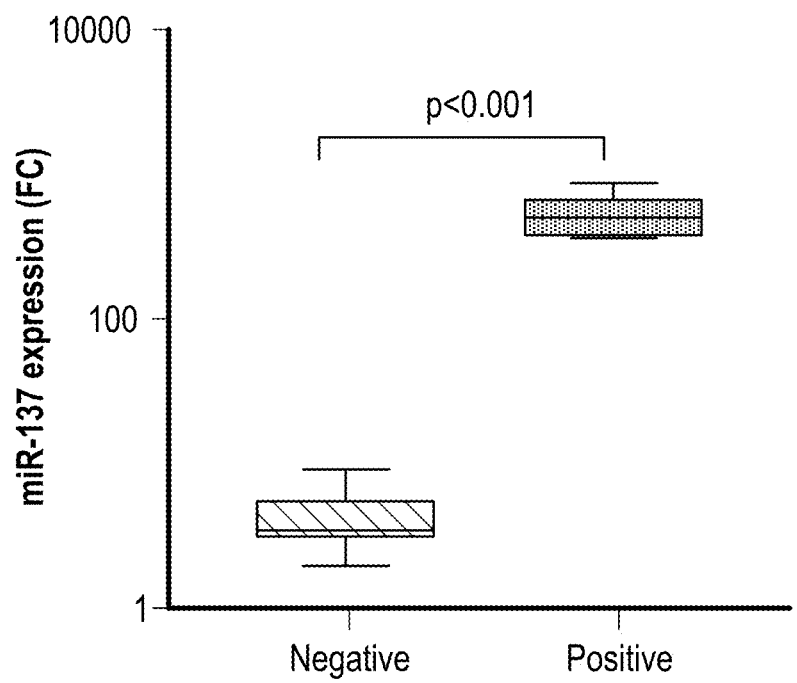
Figure 27B:
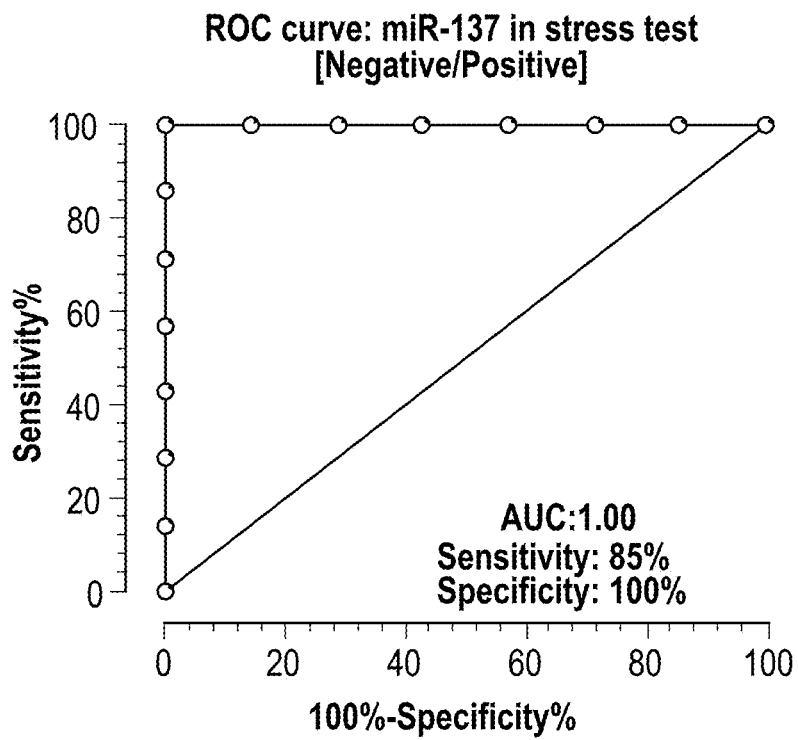
Figure 27C:
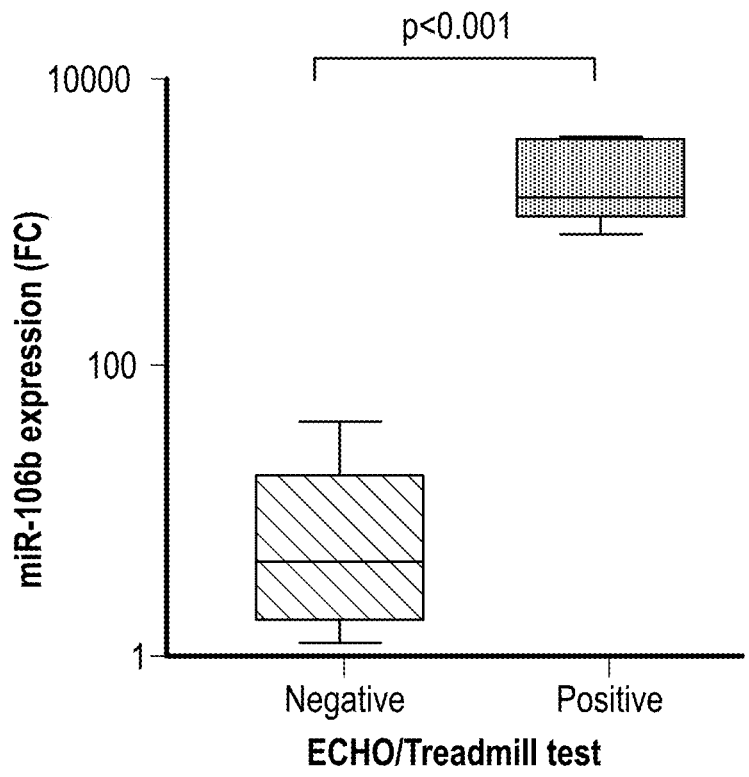
Figure 27D:
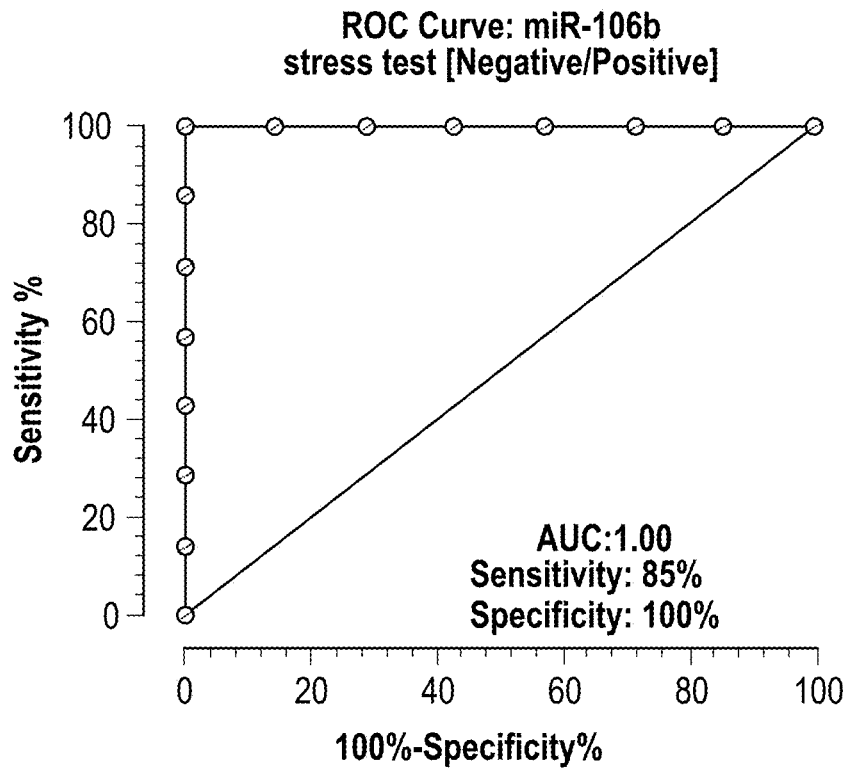

FIG. 27A and FIG. 27B show that miR-137 and miR-106b have 100% sensitivity and 85% specificity in discriminating ECHO/Treadmill angina positive stress test patients from patients with negative test (a cut-off of 8 for miR-137 and a cut-off of 172 for miR-106b). They also possess a discriminating cut-off value of 3.5 for both miRNAs to diagnose coronary artery disease patients from healthy controls.

In summary, patients whom exercise test was positive for myocardial ischemia had higher Nourin-dependent miR-137 and miR-106b expressions before and after the stress test. Also, patients whom exercise test was negative for myocardial ischemia had very low Nourin-dependent miR-137 and miR-106b expressions before and after the stress test. Results of this study further indicate that there is a significant elevated levels of Nourin molecular network of miR-137 and miR-106b in serum samples of symptomatic angina patients, but not in symptomatic non-cardiac patients and healthy individuals, and that the levels of miR-137 and miR-106b positively correlated with the ECHO/ECG Treadmill stress test results. These results, therefore, suggest the clinical use of the Nourin-dependent miR-137 and miR-106b as non-invasive fast diagnostic biomarkers in outpatient clinics to diagnose angina patients with chest pain and discriminate them from symptomatic non-cardiac patients and healthy individuals.

Previous studies have reported that in stable coronary artery disease (CAD) patients, the expression level of miR-1, miR-208a and miR-423-5p did not show significant differences in comparison to control group, and that there was no significant increase of number of the 3 miR copies at 6, 12 and 24 hours after Percutaneous Coronary Intervention (PCI) procedure. However, there was a significantly higher number of miR-423-5p copies, but not miR-1 and miR-208a, in patients with AMI before the PCI. After 6, 12, and 24 hours post-PCI procedure the expression level of miR-423-5p in these AMI patients was similar to the control group and significantly lower than the baseline level. Although PCI procedure is widely used to treat patients with CAD, the procedure is receiving a lot of criticism because of the limited morbidity and mortality benefits for some stable ACD patients. A major limitation is the lack of a simple blood test that can verify patients with large areas of severe ischemic myocardium in the stable subset of patients with coronary artery disease, whom they would likely benefit from the PCI procedure. Therefore, there is a need to develop a blood test to identify CAD patients whom they will benefit from the PCI procedure before conducting the procedure.

Since the Nourin RNA network diagnoses angina patients and determines the severity of myocardial ischemia in stable coronary patients, as well as it identifies angina patients before and after the ECHO/ECG Treadmill stress test, this invention provides a new simple non-invasive laboratory test to diagnose and quantitate the severity of myocardial ischemia in stable CAD patients with negative Troponin, and predict the patients' therapeutic benefits after PCI procedure. Specifically, the Nourin RNA network will be conducted at the Cath lab to identify the eligible stable CAD patients with moderate to severe ischemia who will benefit from the PCI procedure. Similarly, it can be used to determine in advance the therapeutic benefits for ischemic cardiac patients whom they are scheduled for surgical procedure including but not limited to: cardiopulmonary bypass, valve replacement, as well as heart transplantation.

Example 11—Nourin Gene-Based RNA Network (miR-137, miR-106b, mRNA-FTHL-17 and mRNA-ANAPC11, and lncR-CTB89H12.4) as Novel Early Diagnostic and Prognostic Molecular Biomarkers for Unstable Angina Patients at Presentation to Hospital ED No blood biomarker exits that can diagnose UA patients. Since Nourin is ischemia-dependent inflammatory mediator rapidly released by reversible ischemic myocardium "before" necrosis, and by necrotic cells, the Nourin amino acid sequence was used and Bioinformatics analysis was conducted to determine the regulated signaling pathway of the Nourin protein. As described in Example 6, the standard quantitative real time qPCR molecular assay was used to indicate that the underlying regulatory mechanism of Nourin involves lncRNA-CTB89H12.4, hsa-miR-137, has-miR-106b, mRNA FTHL-17 and mRNA ANAPC11 which are associated with ischemia. Specifically, miR-137 is a marker of cell damage and it is a hypoxia responsive autophagy-signaling pathway linked to myocardial ischemia and coronary artery disease, while, miRNA-106b is an inflammatory-signaling pathway linked also to myocardial ischemia.

For this study, serum samples were obtained once at presentation to ED from UA patients with acute chest pain within the first 10 hours. Invasive coronary angiography and negative Troponin (below the 99th of URL) were used to confirm all UA patients (n=30). Serum samples were also collected from STEMI patients (n=16) with significant ischemic ECG changes and elevation of Troponin at presentation and after 3 hours. As a control, serum samples were also collected from healthy subjects (n=16). All 30 symptomatic unstable angina patients diagnosed and confirmed on the basis of: (a) negative serum Troponin I or T levels at presentation to hospital ED; (b) clinical symptoms and history consistent with cardiac ischemia, and (c) confirmed by invasive coronary angiography and angioplasty procedure. Digital coronary angiograms were analyzed offline by experienced operator with an automated edge detection system (Philips Veenpluis 4-6, 5684 PC, Best, Netherland) by using dye-filled guiding catheter as a reference. Assessment was conducted by visual inspection to estimate the presence of coronary stenosis, atherosclerotic plaques, ruptured plaques, and intra coronary thrombi. Stenosis >50% in left main and >70% in other vessels were considered significant. The number of major vessels that were significantly affected was calculated as: 14 UA patients had one vessel occlusion, 14 UA patients had two vessels occluded, and 2 UA patients three vessels occluded.

The criteria for diagnosing unstable angina was in accordance with the American College of Cardiology/American Heart Association guidelines and reflected the clinical judgment of two experienced independent cardiologists. Patients were excluded from the unstable angina group if they have: (1) positive Troponin I or T; (2) cardiomyopathy; (3) heart failure, (4) congenital heart disease; (5) end stage renal failure; (6) bleeding disorders; (7) previous thoracic irradiation therapy; (8) autoimmune diseases and inflammatory diseases such as inflammatory bowel disease (IBD) and arthritis; (9) malignant diseases; (10) a history of hepatitis or hepatic failure; and (11) C-Reactive Protein (CRP) level greater than 10 mg/L. Similarly, STEMI patients were excluded from the study if they have the same above listed exclusion criteria except that they had to have positive Troponin I or T at presentation and 3 hours after admission. Samples of eligible subjects were centrifuged at 1300×g at 4° C. for 20 min and serum was carefully removed, transferred to a polypropylene capped tube in 1 ml aliquots and stored at −80° C. until they are assayed by qPCR.

Typical and atypical UA patients experiencing acute chest pain were included in the study where 19 are males (63.3%) and 11 are females (36.6%). Twenty one of the 30 UA patients (70%) had previous known CAD which progressed to experience UA. Mean age was 60.1±8.2 years (minimum 35 years, maximum 76 years). Majority of UA and STEMI patients experienced chest pain for 1 to 10 hours prior to arrival to hospital ED. For the UA patients (n=30), 12 had normal ECG (40%), 16 patients had non-significant ECG changes (53.3%) and only 2 cases had significant ischemic ECG changes (6.7%). All 16 STEMI patients had significant ischemic ECG changes and positive Troponin, there was 12 males (75%) and 4 females (25%). Mean age was 54.4±12.7 years (minimum 25 years and maximum 81 years). Among all subjects presented with STEMI; half of patients had Anterior STEMI, and only 6% had lateral STEMI. Mean duration from onset of chest pain till presentation was 5.8±1.9 hours (minimum 2 hours, maximum 10 hours). 15 subjects were treated with primary PCI strategy, and only 1 subject was referred for urgent CABG. High-sensitive cardiac Troponin (hs-cTn) was measured twice in allacute chest pain patients. First set was at presentation and the second was done after 3 hours from admission. Troponin was also measured once in healthy volunteers to confirm the absence of cardiac disease. All healthy control subjects (n=16) were young volunteers (mean age 32.9±9.9). The Nourin RNA network was measured only at serum and plasma samples collected at presentation. Serum gene expression profile of miR-137, miR-106b, mRNA-FTHL-17 and mRNA-ANAPC11, and lncR-CTB89H12.4 were measured in UA patients (n=30), as well as in STEMI patients (n=16) with positive Troponin and healthy volunteers (n=16). Serum samples were collected at presentation to hospital ED from symptomatic UA and STEMI patients.

Figure 28A:
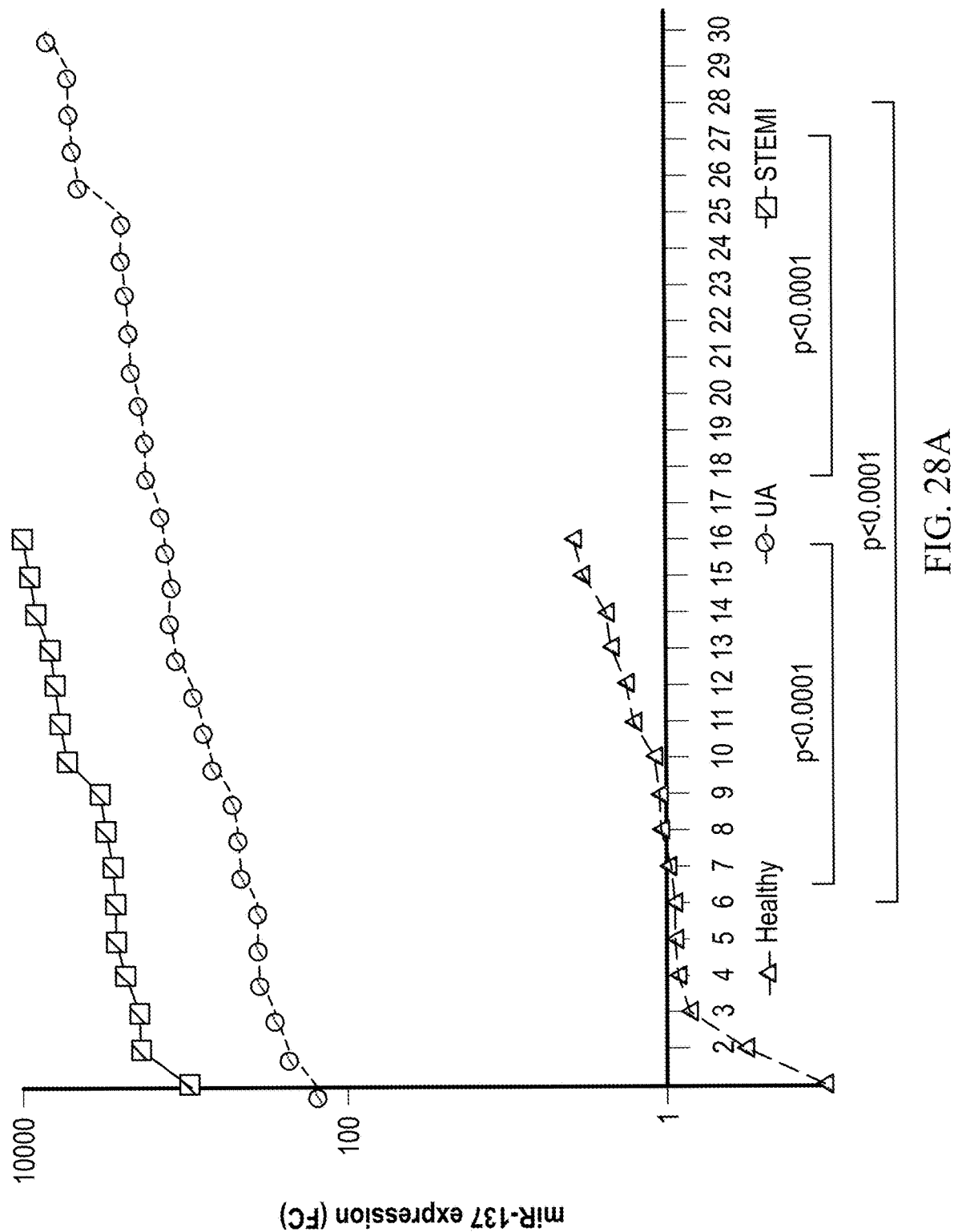
Figure 28B:
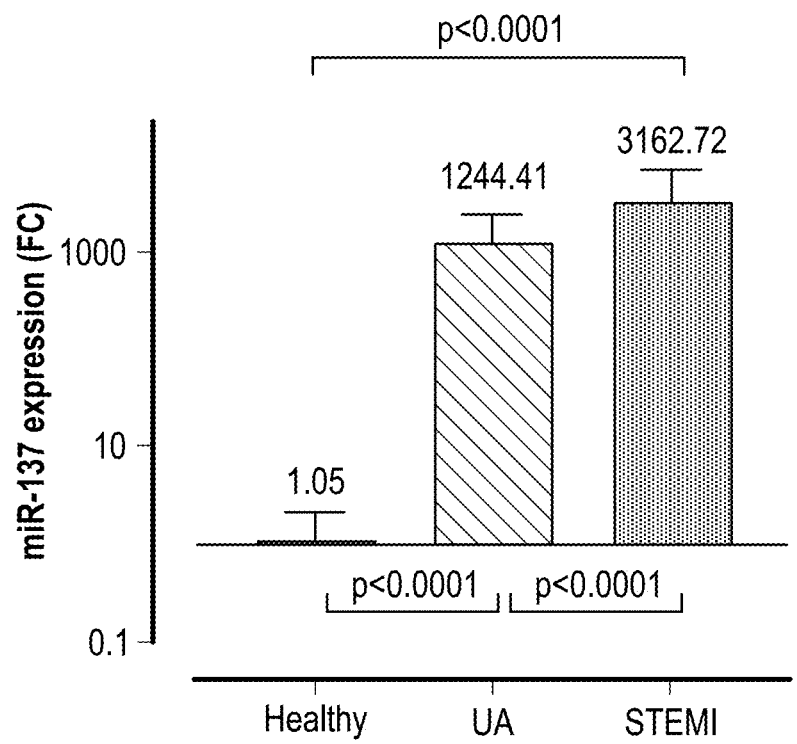
Figure 28C:
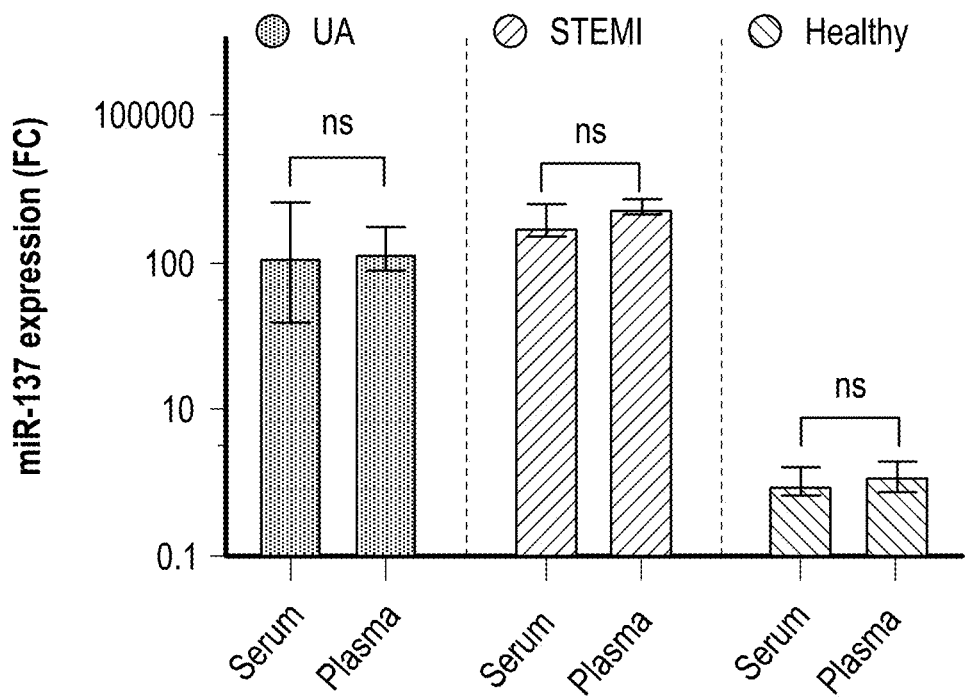
Figure 28D:
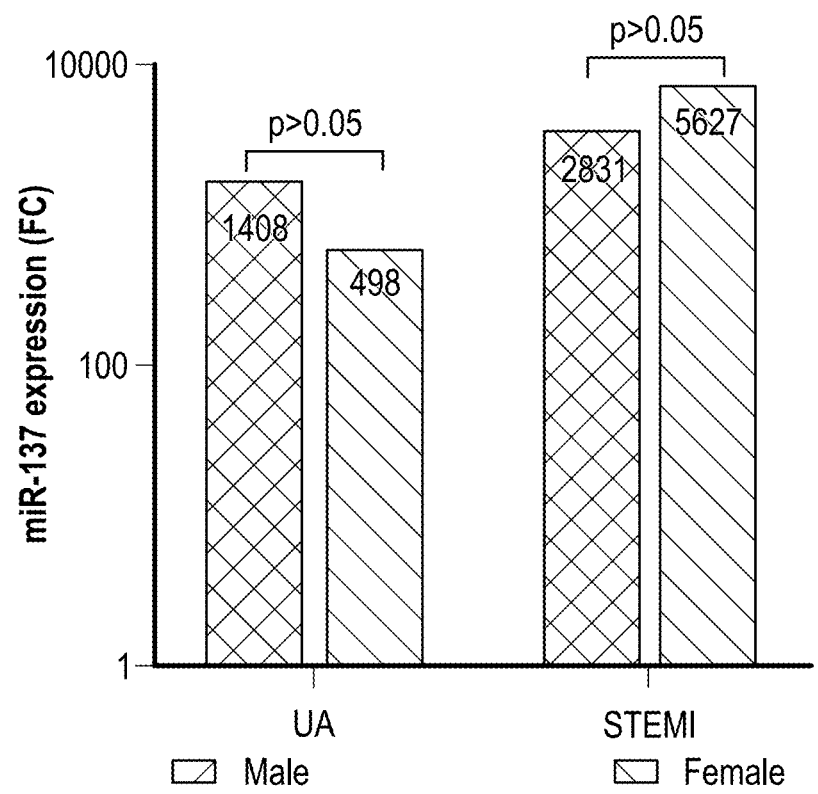

Significantly higher expression pattern of miR-137 was detected in UA compared to healthy (p<0.001), as well as in STEMI compared to UA (p<0.001) and in STEMI compared to healthy (p<0.001) (FIG. 28A). The gene expression of miR-137 was up-regulated by 1,185-fold in UA (median=1, 244.41) compared to healthy (1.05), and by 2.5-fold in STEMI (3,162.72) compared to UA (FIG. 28B). There was no significant difference in gene expression of miR-137 detected in serum and plasma samples obtained from UA, STEMI and healthy control, supporting the use of either serum or plasma samples to measure the Nourin RNA network (FIG. 28C). Although there was a statistical significance (p<0.05) of miR-137 gene expression level between male and female in UA patients, there was no gender difference in STEMI patients (p>0.05) (FIG. 28D).

Figure 29A:
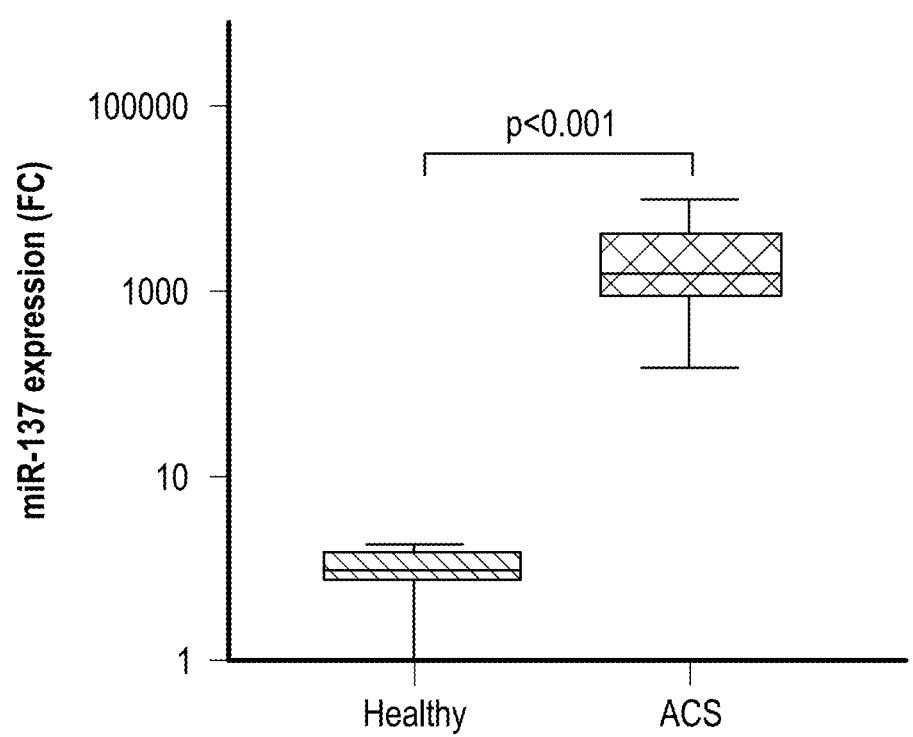
Figure 29B:
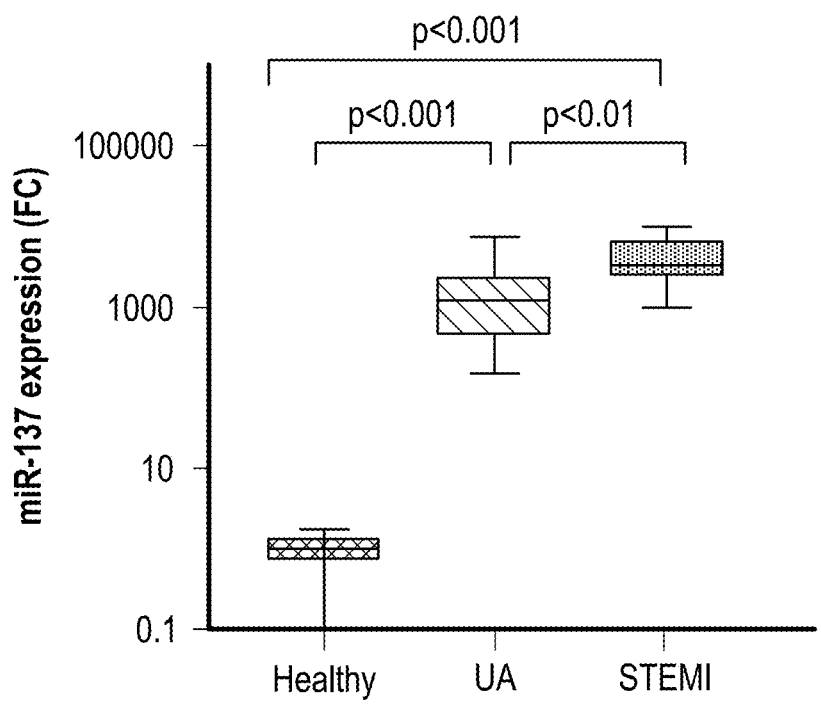
Figure 29C:
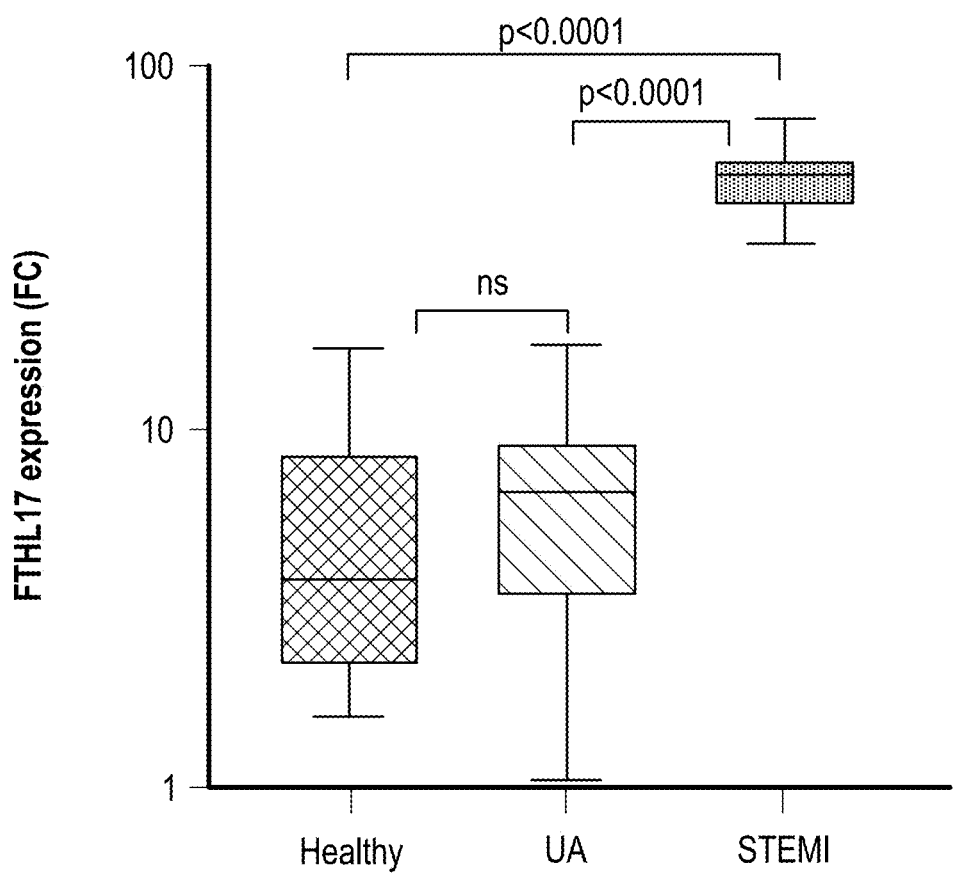
Figure 29D:
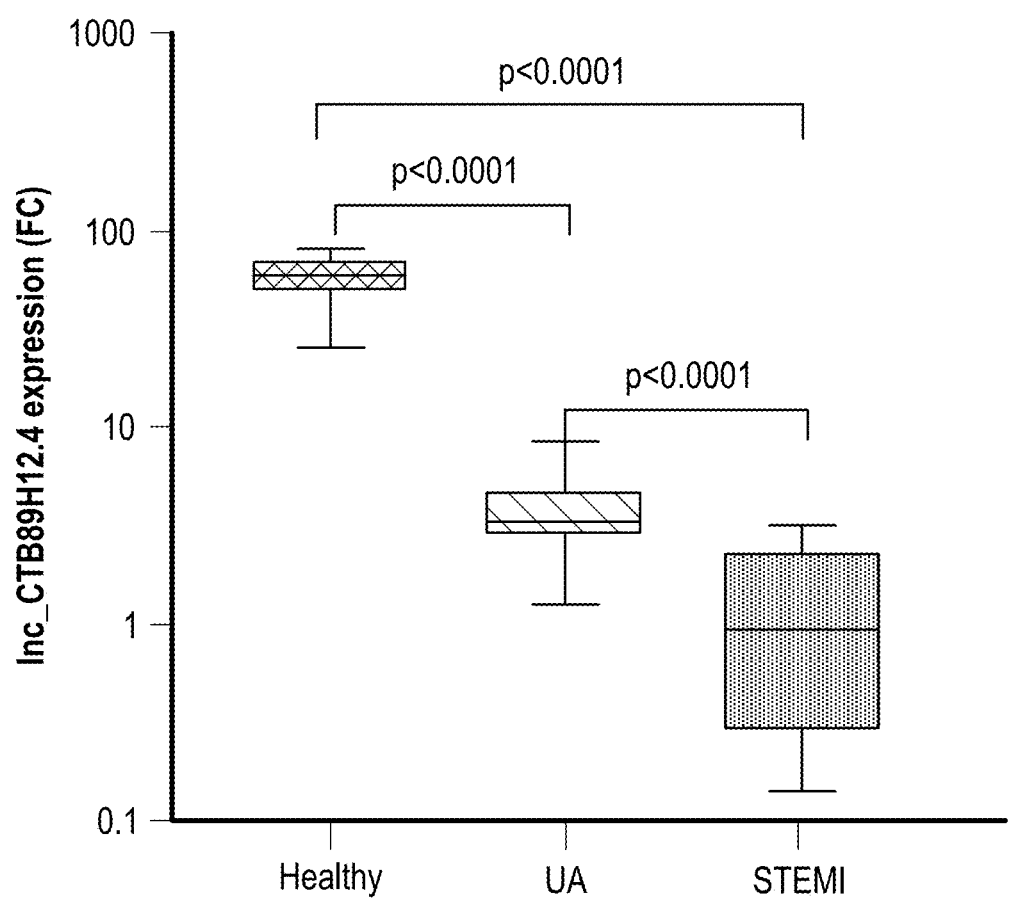

Additionally, FIG. 29A shows high miR-137 expression level between healthy and ACS patients (UA+STEMI) (n=46) (p<0.01), supporting our previous findings that the Nourin "protein" measured by both the leukocyte chemotaxis assay and antibody/ELISA, is significantly elevated in ACS patients compared to symptomatic non-cardiac patients and healthy subjects. FIG. 29B shows high miR-137 expression level of UA compared to healthy (p<0.001), STEMI patients compared to UA patients (p<0.001), as well as STEMI patients compared to healthy (p<0.001). There was upregulation of mRNA-FTHL-17 in STEMI and UA with a statistical difference of p<0.01, as well as between STEMI and healthy, but there was no statistical difference between UA and healthy (FIG. 29C). Additionally, there was a significant downregulation of lncR-CTB89H12.4 in STEMI patients with a statistical difference of p<0.0001 between STEMI, UA and healthy. Healthy controls showed upregulation of lncRNA-CTB89H12.4. A Receiving Operator Characteristics (ROC) analysis revealed a statistically significant difference (p<0.001) at a cutoff: 195.4 for miR-137 to discriminate UA from healthy with a test sensitivity and specificity of 97% and 94%, respectively, and a statistically significant difference (p<0.01) at a cutoff: 2,488 for miR-137 to discriminate UA from STEMI with a diagnostic test sensitivity of 75% and specificity of 83% (FIG. 30A-FIG. 30B). A Spearman's correlation analysis revealed correlation between miR-137/ANAPC11/lncR-CTB8912.4 in ACS patients (UA+STEMI) (n=46) with a significant association of miR-137 with mRNA FTHL-17 (p=0.0005), and miR-137 with lncR-CTB89H12.4 (p=0.02) (FIG. 31A-FIG. 31D). Thus, the down-regulation of lncR-CTB89H12.4 after ischemia resulted in the up-regulation of miR-137 and activation of mRNA-FTHL-17. As a marker of cell damage, the Nourin-dependent miR-137 is a promising early diagnostic biomarker indicating UA patients and discriminating between UA and STEMI. Regulations of Nourin-related miR-137 are by lncR-CTB89H12.4 and mRNA-FTHL-17.

Figure 32A:
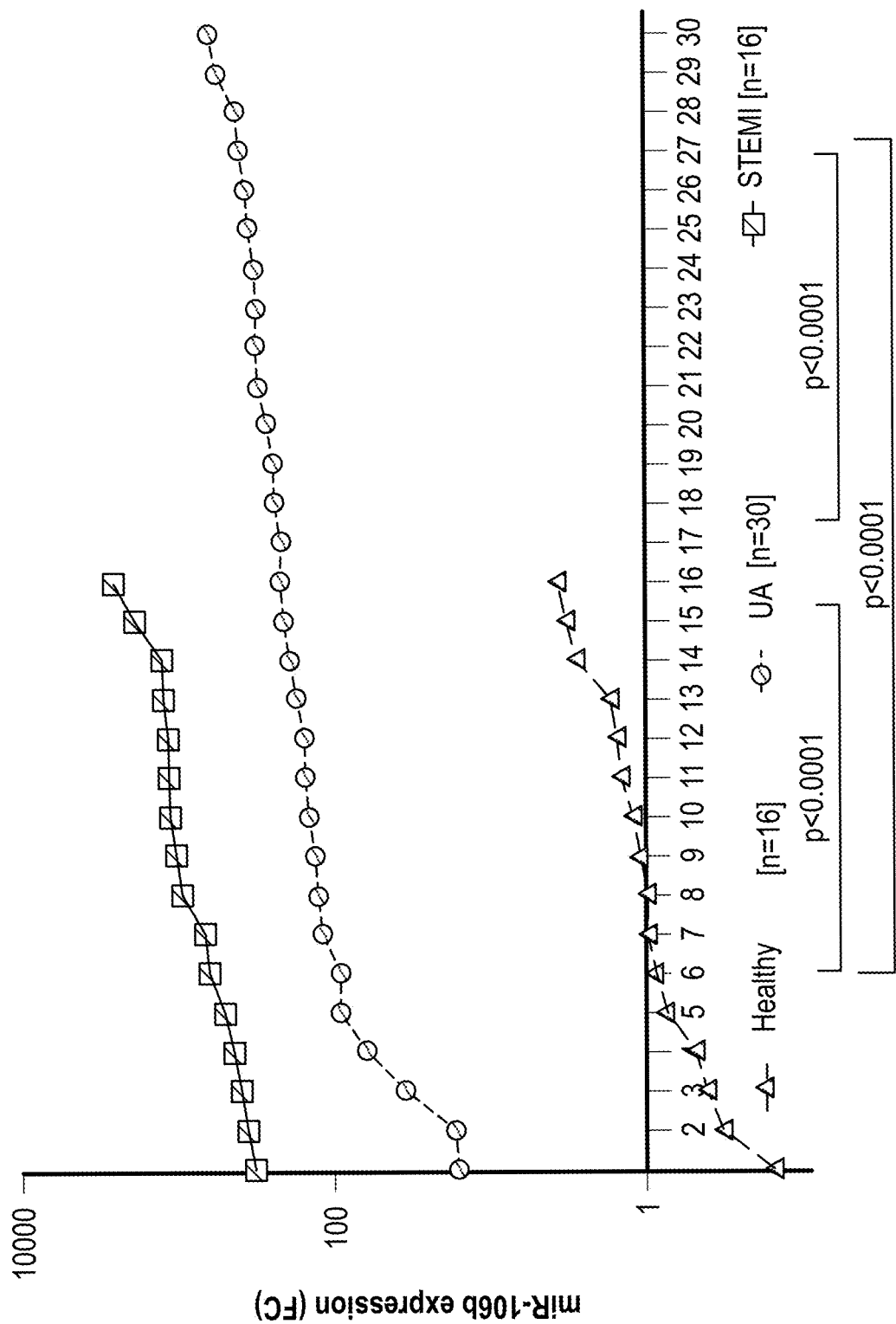
Figure 32B:
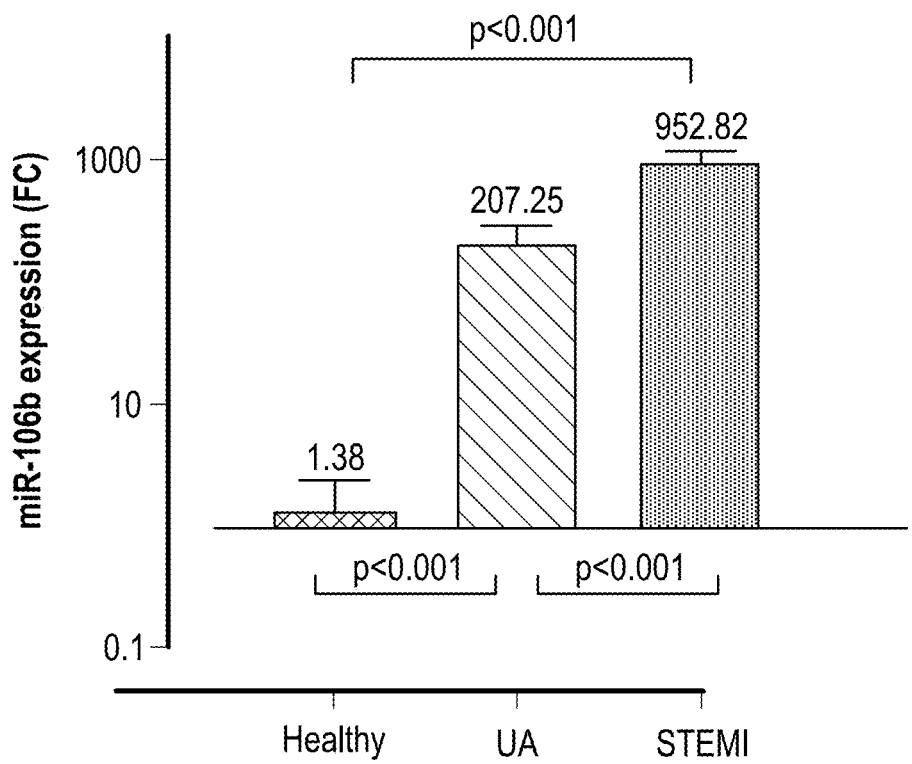
Figure 32C:
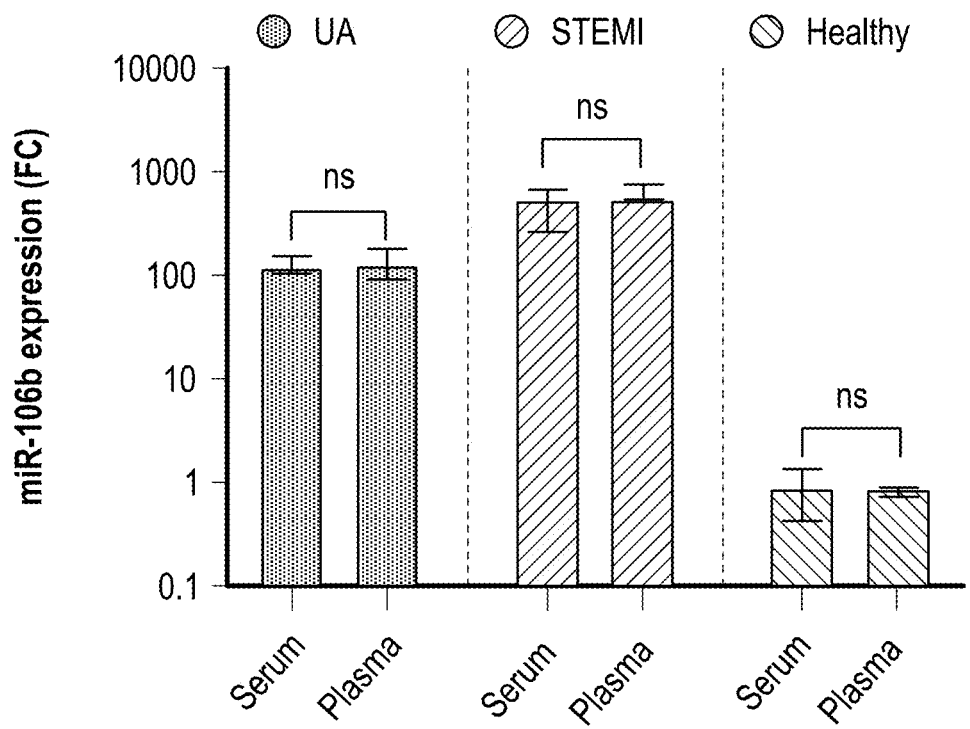
Figure 32D:
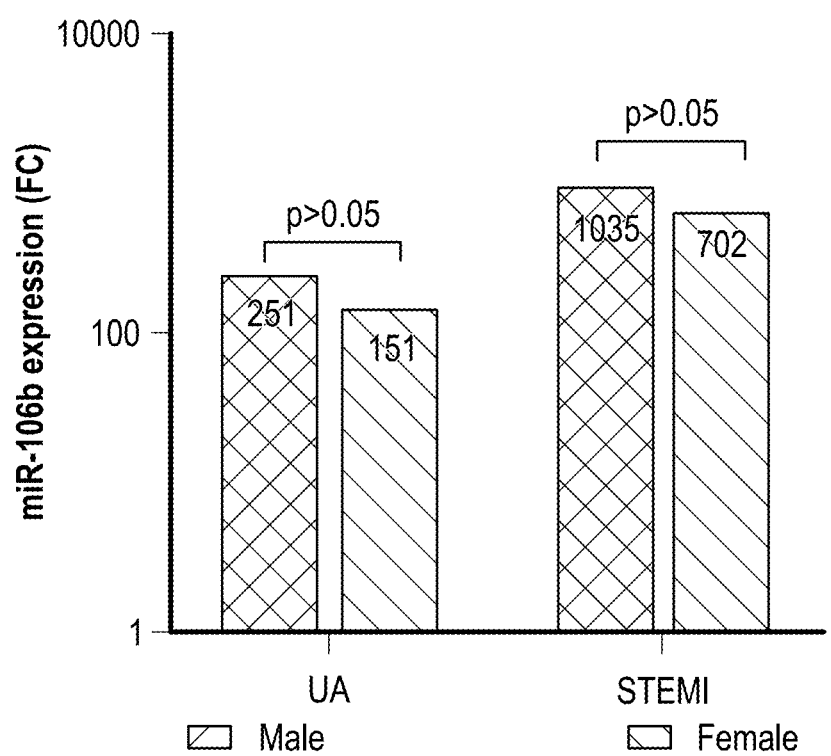
Figure 33A:
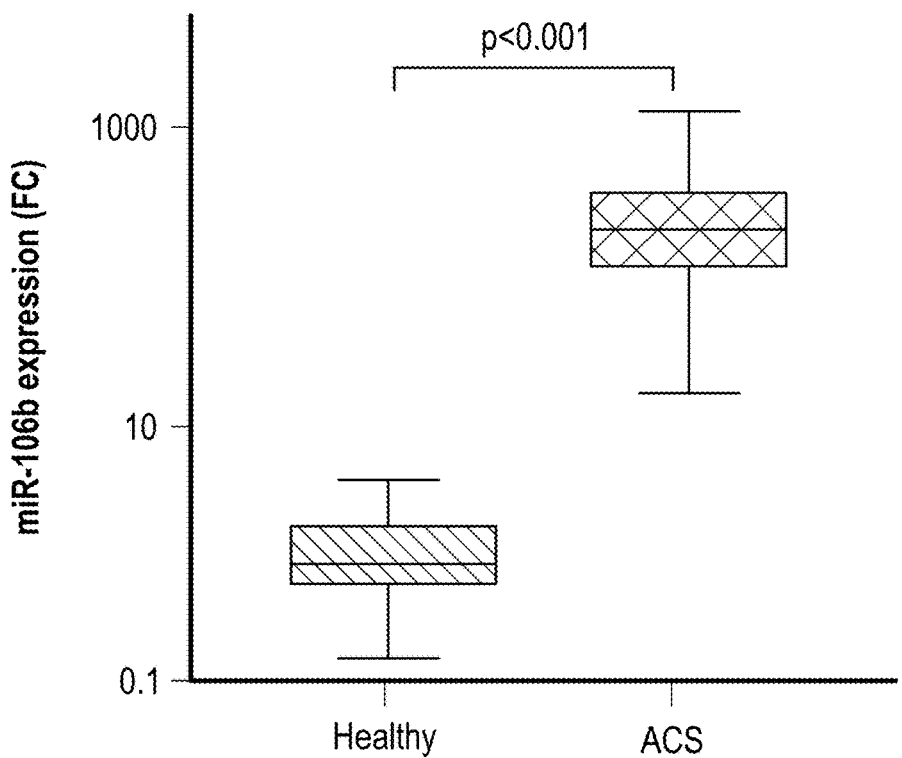
Figure 33B:
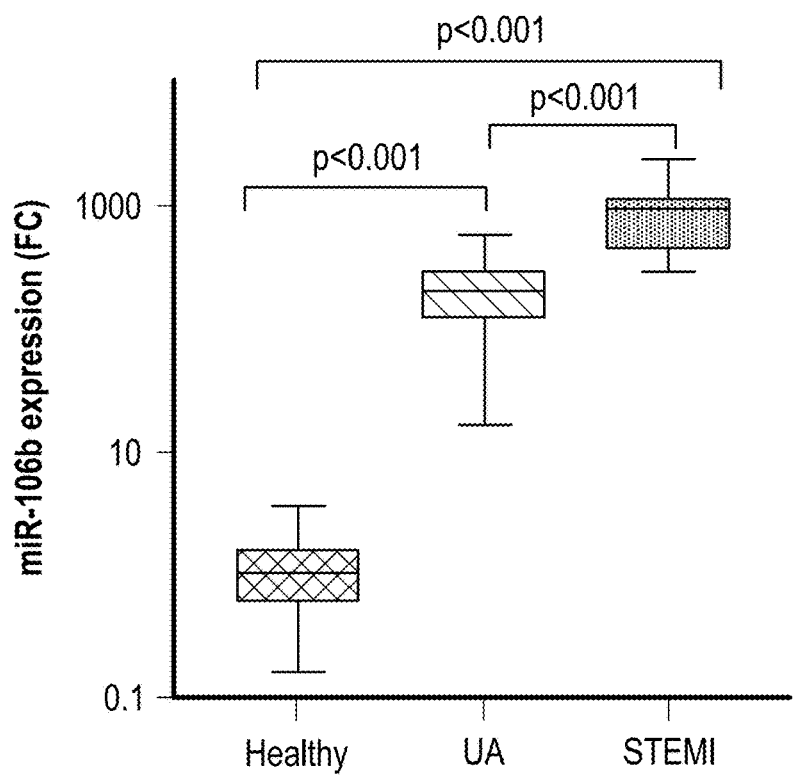
Figure 33C:
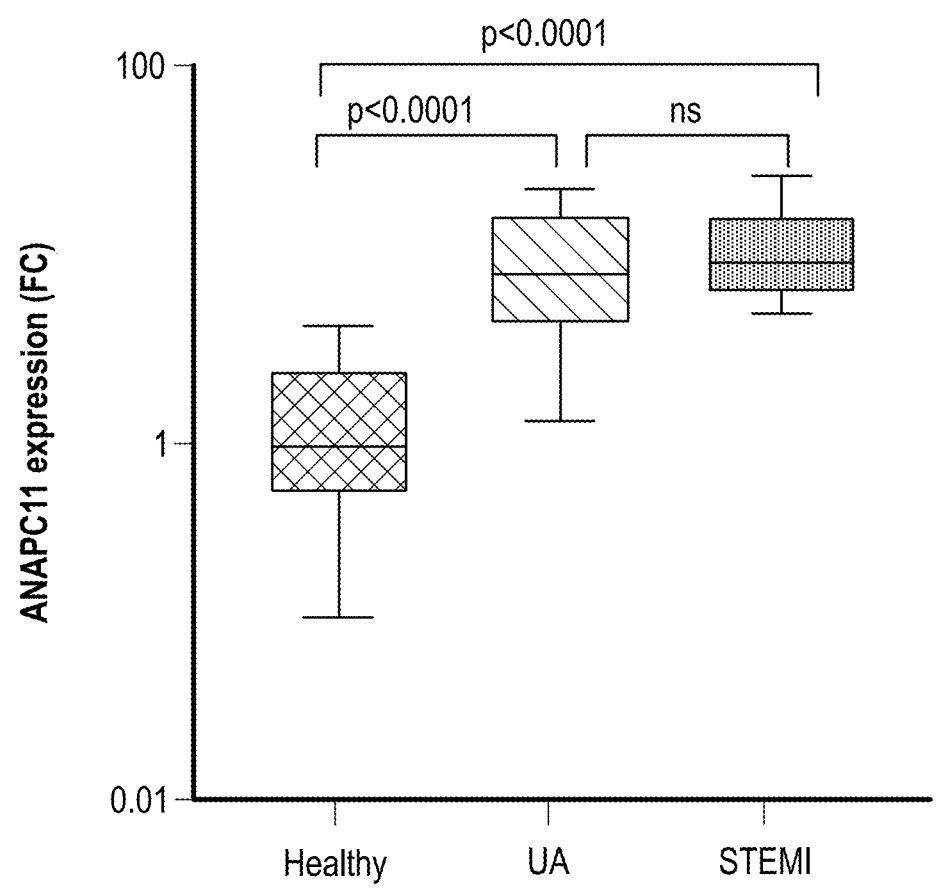
Figure 33D:
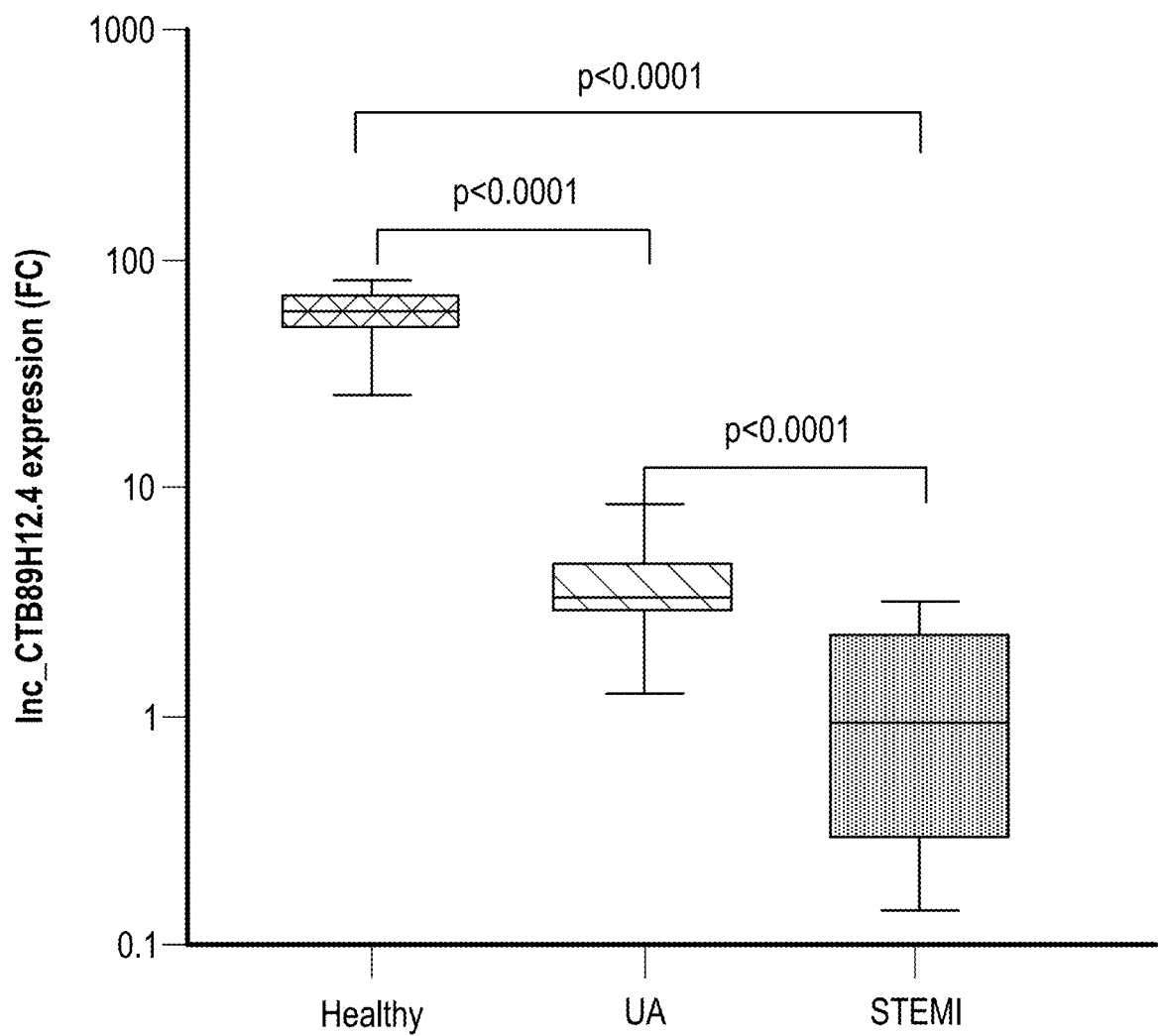

Similar to miR-137, significantly higher expression pattern of miR-106b was detected in UA compared to healthy subjects (p<0.001), STEMI patients compared to UA (p<0.001) and STEMI patients compared to healthy subjects (p<0.001) (FIG. 32A and FIG. 32B). The gene expression of miR-106b was up-regulated by was up-regulated by 150-folds in UA compared to healthy, and by 4.6-folds in STEMI compared to UA (FIG. 32B). There was no significant difference in gene expression of miR-137 detected in serum and plasma samples obtained from UA, STEMI and healthy control, supporting the use of either serum or plasma samples to measure Nourin-related RNA network (FIG. 32C). There was no statistical significance (p>0.05) of miRNA-106b gene expression level between male and female in UA and STEMI patients (FIG. 32D). Additionally, FIG. 33A shows high miR-106b expression level between healthy and ACS patients (UA+STEMI) (n=46) (p<0.01), supporting our previous findings that the Nourin "protein" measured by leukocyte chemotaxis assay and antibody/ELISA, is significantly elevated in ACS patients compared to symptomatic non-cardiac and healthy subjects. FIG. 33B shows high miR-106b expression level of UA compared to healthy (p<0.001), STEMI compared to UA (p<0.001) and STEMI compared to healthy (p<0.001). There was upregulation of mRNA-ANAPC11 in STEMI and UA with a statistical difference of (p<0.0001) between UA and healthy, as well as between healthy and STEMI, but there was no statistical difference between UA and STEMI (FIG. 33C). Additionally, there was a significant downregulation of lncR-CTB89H12.4 in STEMI patients with a statistical difference of p<0.0001 between STEMI, UA and healthy. Healthy controls showed upregulation of lncR-CTB89H12.4. A Receiving Operator Characteristics (ROC) analysis revealed a statistically significant difference (p<0.01) at a cutoff: 90.4 for miR-106b to discriminate UA from healthy with a test sensitivity and specificity of 87% and 88%, respectively; (B): a statistically significant difference (p<0.01) at a cutoff: 385 for miR-106b to discriminate UA from STEMI with a diagnostic test sensitivity of 86% and specificity of 90%. (FIG. 34A-FIG. 34B). A Spearman's correlation analysis revealed a correlation between miR-106b/mRNA ANAPC11/lnc-CTB8912.4 in ACS patients (UA+STEMI) (n=46) with a significant association of miR-106b with mRNA ANAPC11 (p=0.02), and miR-106b with lncR-CTB89H12.4 (p=0.0001) (FIG. 35A-FIG. 35D). Thus, the down-regulation of lncR-CTB89H12.4 after ischemia resulted in the up-regulation of miR-106b and activation of mRNA-ANAPC11. Nourin-dependent miR-106b is a promising early inflammatory biomarker indicating UA patients and discriminating between UA and STEMI. Regulations of Nourin-related miR-106b by lncR-CTB89H12.4 and mRNA-ANAPC11.

In summary, this UA+STEMI study indicates that:
1. the Nourin-dependent miR-137 and miR-106b, selected by Gene Ontology Bioinformatics Analysis, regulate the expression of Nourin protein.
2. the expression level of lncR-CTB89H12.4, mRNA FTHL-17 and mRNA ANAPC11, selected by Gene Ontology Bioinformatics Analysis, show a high evidence to be related to Nourin protein expression.
3. the high expression level of miR-137, miR-106b, mRNA-FTHL-17, mRNA-ANAPC11 and lncR-CTB89H12.4 genes represent a signaling pathway in the pathogenesis of ischemic heart disease including and not limited to UA and AMI.
4. there was a very strong association between miR-137 in UA and STEMI samples and the increase in gene expression level of mRNA-FTHL-17, which is responsible for the translation of the Nourin protein, as has been previously demonstrated that Nourin protein was significantly elevated in ACS patients.
5. there was a very strong association between miR-106b in UA and STEMI samples and the increase in gene expression level of mRNA-ANAPC11, which is responsible for the translation of the Nourin protein, as has been previously demonstrated that Nourin protein was significantly elevated in ACS patients.
6. the down-regulation of lncR-CTB89H12.4 after ischemia resulted in the up-regulation of miR-137 and miR-106b and activation of mRNA-FTHL-17 and mRNA-ANAPC11 with an increased translation and production of high levels of Nourin protein.
7. In normal healthy subjects, gene expression of miR-137 and mRNA FTHL-17 were very low and there was upregulation of lncR-CTB89H12.4 which correlated very well with the low level of Nourin protein in healthy serum samples. Ischemia upregulates gene expression of Nourin-related miR-137 which activates its mRNA-FTHL-17, resulting in Nourin synthesis and elevation in circulation; events which do not occur in normal non-ischemic subjects where gene expression of miR-137 and mRNA-FTHL-17 was extremely low.
8. In normal healthy individuals, gene expression of miR-106b and mRNA-ANAPC11 were very low and there was upregulation of lncR-CTB89H12.4 which correlated very well with the low level of Nourin protein in healthy serum samples. Ischemia upregulates gene expression of Nourin-dependent miR-106b which activates its mRNA-ANAPC11, resulting in Nourin synthesis and elevation in circulation; events which do not occur in normal non-ischemic subjects where gene expression of miR-106 and mRNA-ANAPC11 extremely low.
9. no significant difference in gene expression of miR-137 and miR-106b were detected in "serum" and "plasma" samples obtained from UA, STEMI and healthy control, supporting the use of either serum or plasma samples to measure the gene expression level of Nourin RNA-based network.
10. high expression levels of Nourin RNA molecular network were detected in UA and AMI patients, but not in healthy individuals.
11. in the absence of current laboratory tests to diagnose symptomatic UA patients, the Nourin RNA molecular network can be used as an early novel diagnostic and prognostic biomarkers for UA patients. Specifically, Nourin RNA molecular network can diagnose UA early at presentation at hospital ED to permit crucial therapy to save heart muscles. The Nourin molecular test can also identify UA patients before their progression to AMI.
12. the Nourin RNA molecular network can be used as an early novel diagnostic and prognostic biomarkers to identify AMI patients at presentation immediately after the initiation of an ischemic event without the need of any wait as seen in Troponin.
13. the novel Nourin RNA molecular network can differentiate with high confidence between UA patients and healthy subjects, between UA and STEMI, as well as between STEMI and healthy.
14. the novel Nourin RNA molecular network can quantitatively distinguish between UA patients and healthy, thus, function with high confidence as a non-invasive "Rule in" for UA patients and exclude normal individuals.
15. the novel Nourin RNA molecular network can quantitatively distinguish between UA and AMI patients, thus, function with high confidence as a non-invasive laboratory test to discriminate UA from STEMI patients in order to quickly select the appropriate treatments.

Example 12—Gene-Based RNA Molecular Network (miR-137, miR-106b, mRNA-FTHL-17 and mRNA-ANAPC11, and lncR-CTB89H12.4) are Early Diagnostic Biomarkers to Accelerate the Diagnosis of UA, STEMI and NSTEMI The standard quantitative real time PCR (qPCR) molecular assay described in Example 6 was used in this study. As indicated in Example 11, serum gene expression profile of miR-137 and miR-106b were measured in UA patients (n=30) confirmed by invasive coronary angiography and negative Troponin, as well as in STEMI patients (n=16) with significant ischemic ECG changes and elevation of Troponin, and healthy volunteers (n=16). Serum samples were collected at presentation to hospital ED from symptomatic UA and STEMI patients. Although high gene expression levels of Nourin-dependent miR-137 (FIG. 36A) and miR-106b (FIG. 36B) were detected "at arrival" to ED in all 16 STEMI patients, the standard cardiac-biomarker hs-Troponin I (Roche Elecsys Cobas) was undetectable in 3 patients out of the 16 STEMI patients and it was still below the clinical decision level (below the 99th of URL). This finding indicates that the Nourin RNA network is detected earlier than Troponin in STEMI patients and further confirms our previous findings that the Nourin "protein" measured by both leukocyte chemotaxis assay and antibody/ELISA, was elevated in ACS patients earlier than Troponin and CK-MB.

Additionally, we determined the miR-137 gene expression in patients presenting with acute chest pain with either ST elevation myocardial infarction (STEMI), where ischemic changes are detected by Electrocardiogram (ECG), or non-ST elevation myocardial infarction (NSTEMI) with no ischemic changes by ECG, where patients wait for up to 6 hours after arrival for the release and detection of Troponin. As indicated in FIG. 37A, high gene expression levels of the Nourin-dependent miR-137 was detected "at presentation" to hospital ED not only in STEMI patients (n=55), but also in NSTEMI (n=14) patients. Both STEMI and NSTEMI patients presented to ED within first 8 hours of chest pain. STEMI and NSTEMI patients had positive Troponin levels above the decision limit. Very low level of miR-137 gene expression was detected in healthy volunteers (n=31). There was a statistically significant difference of p<0.001 between AMI patients (STEMI+NSTEMI) and healthy subjects, but there was no significance difference between STEMI and NSTEMI patients (p>0.05) (FIG. 37A). Furthermore, Receiving Operator Characteristics (ROC) analysis revealed a statistically significant difference for miR-137 to discriminate AMI patients from healthy controls with a test sensitivity and specificity of 98.5% and 96.8%, respectively (FIG. 37B).

In summary, the present study further confirms that Nourin is "early" released by "sick" myocardial cells before necrosis and indicates that:
1. elevated level of Nourin miR-137 and miR-106b gene expression at presentation to ED is associated with the diagnosis of unstable angina patients.
2. elevated level of Nourin miR-137 gene expression at presentation to ED is associated with the diagnosis of NSTEMI patients,
3. elevated level of Nourin miR-137 and miR-106b gene expression at presentation to ED was detected in STEMI patients earlier than Troponin.
4. elevated level of Nourin protein at presentation to ED was detected in ACS patients earlier than Troponin and CK-MB.
5. the present Nourin biomarkers can be used as a novel test to accelerate the diagnosis of UA, STEMI and NSTEMI patients at presentation to ED.
6. the present Nourin biomarkers can be used as a novel test to diagnose NSTEMI patients at presentation without the need to wait as required by Troponin.
7. high sensitivity and specificity of miR-137 and miR-106b, thus, they could be early biomarkers and an independent risk factor for the identification of myocardial injury not only in stable CAD and ACS patients, but also in patients undergoing cardiac surgery.

Example 13—Gene Expression Level of Nourin Gene-Based RNA Molecular Network as Indicative of the Severity of Myocardial Ischemia The level of Nourin-gene based RNA molecular network is associated with severity of myocardial ischemia; the higher gene expression, the increased severity of myocardial ischemia. As described in the above Examples, Nourin can determine the severity estimation of myocardial ischemia as negative, low, moderate and severe:
a) Negative myocardial ischemia—healthy individuals have no gene expression, as baseline values with negative myocardial ischemia;
b) Negative myocardial ischemia—symptomatic non-ischemic patients with negative ECHO/Treadmill stress test have gene expression comparable to healthy with negative myocardial ischemia;
c) Negative myocardial ischemia—symptomatic non-ACS patients at presentation to hospital ED have gene expression comparable to healthy with negative myocardial ischemia;
e) Low to mild myocardial ischemia—CAD patients have gene expression with "low to mild" myocardial ischemia based on the fact that 70% of unstable angina patients had known CAD and progressed to experience unstable angina with moderate level of myocardial ischemia;
f) Moderate myocardial ischemia—unstable angina patients at presentation to hospital ED have gene expression with "moderate" myocardial ischemia;
g) Severe myocardial ischemia—STEMI and NSTEMI patients at presentation to hospital ED have gene expression with "severe" myocardial necrosis.

Additionally, results illustrated in FIG. 38 indicate that miR-137 gene expression, as a marker of cell damage, was higher in UA patients with three vessels of stenosis compared to patients with one or two vessels. Although there was no statistical difference between the 3 groups (1 vessel, 2 vessels and 3 vessels), results suggest an association between the level of miR-137 gene expression and myocardial ischemia. Higher gene expression of miR-137 level, is suggestive of higher myocardial ischemia.

Additionally, FIG. 51 indicates a pathophysiology of myocardial ischemia and an overview of current biomarkers comparing to Nourin. Aging is the dominant risk factor for clinically significant atherosclerotic lesion formation. Atherosclerosis is triggered by sometimes subtle physical or chemical insults to the endothelial cell layer of arteries including insults such as, physical injury or stress as a result of direct trauma or hypertension, hyperlipidemia, chronically elevated blood glucose levels, toxins and infection. Fatty streaks are the first signs of atherosclerosis which is a disease of chronic inflammation characterized by a dysfunctional interplay between the immune apparatus and lipids. Immune cells, as well as nonimmune cells, drive plaque inflammation through a complex crosstalk of inflammatory mediators. These lesions occur in the aorta and coronary arteries. Cytokines such as TNF-α, IL-10, IL-2, IL-8, IL-6 TGF-β2, and TGF-β3 are key players during acute and chronic inflammation in atherosclerosis.

It has been previously reported that the 3 KDa Nourin is released by "vascular endothelial cells" in response to: (a) ischemia in isolated coronary arteries, (b) ischemia and physical stress in extended vein grafts, and (c) endotoxin treatment to human aortic vascular endothelial cells (HAVEC). It was further demonstrated that Nourin induced acute and chronic inflammation and stimulated human monocytes, neutrophils and vascular endothelial cells to release several cytokine mediators including, TNF-α, IL-1β, IL-8, adhesion molecules LECAM-1, ICAM-1 and ELAM-1, as well as Collagenase type IV, N-acetyl-B-glucosaminidase, Gelatinases and superoxide anion. Therefore, vascular-derived Nourin released by injured vessels plays a role in cellular pathways of the disease acute inflammation stage and chronic inflammation that promote atherosclerosis.

Atherosclerosis usually remains silent until plaque ruptures and the breakdown of integrity at the arterial surface triggers the formation of a thrombus leading to myocardial ischemia and necrosis. A number of biomarkers and invasive procedures are currently used to diagnose the following cardiovascular events (a) amyloid A protein and C-reactive protein for plaque rupture, (b) soluble fibrin and P-selectin (adhesion molecule) for intracoronary thrombosis, (c) radiolabeled perfusion imaging (MIBI) and coronary angioplasty for reduced blood flow, (d) electrocardiogram (ECG), ECHO and radiolabeled perfusion imaging (MIBI) for myocardial ischemia, and (e) Troponin I and T as markers of necrosis for myocardial necrosis.

As described in the present invention, Nourin protein and its regulatory molecular network are key novel early non-invasive biomarkers since they can diagnose patients with cardiovascular disease, including:
(a) patients with atherosclerosis (stable CAD),
(b) differentiated CAD patients from non-CAD patients with chest pain and healthy individuals,
(c) patients with plaque rupture with unstable angina,
(d) patients with plaque rupture with AMI,
(e) patients with plaque rupture with AMI earlier than Troponin, differentiated unstable angina from AMI patients,
(g) differentiated unstable angina and AMI patients from symptomatic non-cardiac and healthy individuals,
(h) patients with myocardial ischemia using the Nourin-dependent miR-137 as a "specific marker of myocardial ischemia",
(i) patients with myocardial ischemia using Nourin-related miR-106b which is a "marker of atherogenesis and inflammation" is expressed along with miR-137 when myocardial ischemia is associated with an inflammatory response, patients with non-ischemic inflamed hearts using miR-106b which is expressed in response to myocardial injury due to causes other than ischemia, including medicines, toxins, and viral and bacterial infection, and
(k) patients with heart failure.

Example 14—Cyclocreatine (CCr) and Cyclocreatine Phosphate (CCrP) Preserve ATP Production During Ischemia Mitochondrial dysfunction and reduction of ATP production are known to play an important role in ischemic heart diseases. A critical mechanism of how hypoxia/ischemia causes irreversible myocardial injury is through the exhaustion of ATP. Depletion of ATP during ischemia is one of the major factors in tissue apoptosis and inflammation. Contractile performance decreases precipitously and ceases when only 20% of ATP is depleted. To date, there are no clinical options available that directly address preservation of ATP during ischemia and reperfusion. Thus, CCrP is a new pharmacologic agent—that has the ability to maintain and restore myocardial energetics in the setting of ischemia and reperfusion; thus would address a very important unmet need in the clinical care of patients with myocardial ischemia and necrosis.

Creatine (Cr) is the naturally occurring compound necessary for myocardial contractility. Cyclocreatine (CCr) is a synthetic analogue of Cr and it acts as a potent bioenergetic protective agent by preserving high levels of ATP in ischemic myocardium. In the heart, Cr and CCr are converted to CrP and CCrP, respectively by the mitochondrial Creatine Kinase enzyme. When CCr is administered to animals before ischemia, it gets stored in myocardial tissue as CCrP, while when CCrP is administered intravenously, it loses its phosphorous group in circulation and becomes CCr. In the heart, CCr is converted to CCrP and stored in the myocardium until an ischemic event, in which it will generate ATP by phosphorylating adenosine diphosphate (ADP). During ischemia, the generation of ATP is through the CrP system (i.e., mitochondrial Creatine Kinase enzyme) as well as, glycolysis where the heart alternatively shifts to anaerobic glycolysis for its requisite energy production. Unfortunately, glycolysis is quite inefficient because ischemic heart catabolizes glucose and produces lactic acid. The generated tissue acidity results in a quick reduction of CrP function. On the other hand, CCrP is much more stable and is a superior long-acting phosphagen than CrP as it sustains ATP synthesis longer during ischemia by continuing phosphorylating ADP at low acidity. Thus, CCrP has the ability to sustain high levels of ATP during ischemia.

Cyclocreatine crosses the blood-brain barrier. In the Cyclocreatine Phosphate (CCrP) preparation, CCr represents only 40% of CCrP (FIG. 39A). CCrP is a new class of therapy which preserves cellular energy and prevents ischemic Injury. It is a first-in-class therapy which works directly on myocardial cells to prevent ischemic injury and protects again tissue deterioration. It works by preserving cellular ATP during ischemia and thus interfere with and reverse the ischemic pathology. It has been demonstrated that the significant cardioprotection of Nourexal in animal models of myocardial infraction, cardiopulmonary bypass surgery, cardiac arrest, and heart transplantation. Specifically, the FDA has recently awarded Nour Heart the Orphan Drug Status for Nourexal with the unique designation for the "Prevention of Ischemic Injury to Enhance Cardiac Graft Recovery and Survival in Heart Transplantation" (DRU-2015-4951).

FIG. 38 is a proposed mechanism of action of the cardioprotective effect of Cyclocreatine (CCr) and Cyclocreatine Phosphate (CCrP). Myocardial ischemia is a major denominator of many cardiac diseases, including: CAD, UA, AMI and HF. Myocardial apoptosis and inflammation are the hallmarks of the tissue response to ischemia/reperfusion injury. Depletion of ATP during ischemia is one of the major factors that accelerates the apoptotic process of healthy myocardial tissue and triggers inflammation. Our proposed mechanism of action of the cardioprotective benefits of CCr and CCrP is through the preservation of high levels of myocardial ATP during ischemia and reduction of tissue injury and circulating Nourin. During reperfusion, CCr and CCrP will also reduce tissue inflammation, apoptosis, and edema resulting in immediate restoration of post-ischemic contractile function, without arrhythmias.

Example 15—Cyclocreatine and Cyclocreatine Phosphate Prevent Myocardial Ischemic Injury and Restore Contractile Function During ischemia, myocardial ATP levels decrease by 65% at 15 minutes and by 90% at 40 minutes, thus contractile performance in vivo decreases precipitously and ceases when only 20% of ATP and 75% of creatine phosphate (CrP) are depleted. It has been demonstrated that when CCr was administered to dogs 60 minutes before the induction of myocardial ischemia by occluding the Left Anterior Descending (LAD) coronary artery for 1 hour. ATP synthesis continued during ischemia and its depletion was delayed resulting in over 85% preservation of of pre-ischemic ATP level with a loss of only 15%, and 97% preservation of the CrP (loss of 3%) during ischemia. This significant preservation is crucial since ATP depletion of more than 20% ceases contractility. Control saline-treated hearts maintained only 66% of the ATP, with a loss of 34%, resulting in loss of reperfusion cardiac contractility. Histologically, the CCr-treated hearts showed markedly less myocardial cell injury when compared to the control (saline) group (FIG. 39B). As indicated in FIG. 40B, Cyclocreatine treatment restored over 80% of contractile function immediately at reperfusion and for an additional 2 hours. On the other hand, contractile function of control saline dogs was ceased completely after LAD occlusion and never recovered during reperfusion. Cyclocreatine also exhibited anti-inflammatory activity by inhibiting the levels of circulating Nourin protein in plasma samples collected during the 2 hour reperfusion, as well as reduces neutrophil accumulation into the myocardium at the end of 2 hours (FIG. 40A).

Clinically, Myocarditis is a condition where there is inflammation of the heart muscle. Inflammation of the heart muscle limits the heart's ability to pump and can cause heart failure due to cardiac arrest or dilated cardiomyopathy. Therefore, "early" diagnosis of cardiac inflammation is key to preventing long-term heart damage. Viral infection is the most common cause of Myocarditis. Other causes are side effects of medications, autoimmune disorders, toxins and bacterial infections. Currently, Myocarditis can be diagnosed with the help of: (a) an electrocardiogram, echocardiogram, magnetic resonance imaging (MM) to detect signs of inflammation of the heart muscle, heart enlargement and poor pumping function and abnormal rhythms the heart; (b) invasive cardiac catheterization and endomyocardial biopsy to check for cardiac inflammation in heart biopsies; and (c) blood tests to measure Troponin levels.

We believe that the Nourin protein and its regulatory molecular network can be used as a non-invasive laboratory test for early diagnosis of cardiac inflammation. As indicated in FIG. 40A and FIG. 41A, high level of the inflammatory mediator, Nourin was released in response to myocardial ischemic injury and was associated with large accumulation of inflammatory cells during early reperfusion. We have also previously reported that Nourin was released in response to viral infection induced by influenza flu infection both in-vitro and in-vivo. Nourin was detected in serum samples collected as early as 6 hours of mice inoculated with Swine Flu H1N1 virus and was associated with the development of severe lung inflammation. The administration of the Nourin competitive inhibitor, Cyclosporin H significantly reduced lung inflammation and inhibited Nourin activity in-vitro. Additionally, high level of Nourin was detected in plasma samples collected from patients with moderate to severe influenza flu infection compared to mild infection. Furthermore, we demonstrated that Nourin is released by human vascular endothelial cells treated with the bacterial product, endotoxin. These studies suggest that the release of Nourin in response to viral and bacterial infection is associated with tissue inflammation.

Interestingly, results described in FIG. 25A and FIG. 26A can help explain the Nourin miRNAs involved in ischemic and non-ischemic myocardial injury, as follows: (a) FIG. 25A indicates 1,560-fold increase in miR-137 in angina patients with positive ECHO/ECG Treadmill stress test compared to non-angina patients with negative stress test; (b) although there was a very low increase of miR-137 (1.5-fold) in non-angina patients with negative ECHO/ECG Treadmill stress test compared to healthy individuals, there was no statistical difference between the two groups, suggesting absence of ischemic damage in non-angina patients as confirmed by the negative ECG analysis; (c) FIG. 26A indicates 98-fold increase in miR-106b in angina patients with positive ECHO/ECG Treadmill stress test compared to non-angina patients with negative stress test; (d) although there was a low increase of 2.9-fold miR-106b in non-angina patients with negative ECHO/ECG Treadmill stress test compared to healthy individuals, there was a significant statistical difference between the two groups of $p=0.001$, suggesting the presence of cardiac inflammation in symptomatic non-angina patients induced by a non-ischemic cause, possibly Myocarditis; (e) these results indicate that the Nourin-dependent miR-137, which is a marker of "ischemic injury" is released only in positive angina patients and not in non-angina patients or healthy individuals; and (f) on the other hand, the Nourin-dependent miR-106b, which is a marker of "tissue inflammation" is released in positive angina patients where ischemic injury is associated with cardiac inflammation, and also in much lower level in chest pain non-angina patients where cardiac inflammation is likely induced by other non-ischemic causes including, viral and bacterial infections, side effects of medications, autoimmune disorders, and toxins.

In an intact canine model of cold cardioplegic arrest and aortic cross-clamping for 1 hour followed by reperfusion on bypass for 45 min and then off bypass for 4 hours, much higher neutrophil accumulation after reperfusion was observed in the right and left atria (+2-3) compared to the right and left ventriculars (+1) (FIG. 41A). As shown in FIG. 41B, post-bypass cardiac output was significantly better in CCr-treated hearts compared to that of controls, where the CCr-treated hearts achieved over 90% of the baseline function throughout the 4 hours of reperfusion, while control hearts achieved only 60% of the baseline function. All CCr-treated hearts restored contractile function immediately post-ischemic without arrhythmias, while, all control hearts required defibrillation. Atrial fibrillation (AF) induces cardiac structural remodeling and there is a need to develop more mechanism-directed AF therapies that use the mitochondria as a novel potential therapeutic target in AF. Our studies suggest the use of Cyclocreatine as a new anti-arrhythmic drug to preserve mitichondrial function and prevent inflammation-induced atrial fibrillation.

FIG. 42A indicates that Cyclocreatine is an anti-apoptotic agent by reducing apoptotic enzyme activity in the non-heartbeating dog model of heart transplantation. Dog hearts underwent 1 hour of global warm ischemic arrest then hearts were explanted and perfused ex vivo for an additional 4 hours with a cold lactated ringers solution containing Cyclocreatine, while control hearts received cold lactated ringers solution alone. Results indicated that exsanguination to induce global warm ischemia, the heart of the CCr-treated dog took 9 minutes to stop beating and develop asystole, while, control hearts completely stopped beating after an average of only 2 minutes. Similarly, the myocardium of the CCr dog maintained a tissue pH of 7.04±0.1 during the warm ischemia period of 1 hour and throughout the ex vivo perfusion interval, which was close to its baseline level of 7.11. On the other hand, tissue pH in control hearts fell to a nadir of 6.00±0.25 during the induction of warm ischemia and never returned back to baseline levels during the ex vivo preservation period. Furthermore, when compared to controls, CCr treatment demonstrated:
1) Three-fold increase of myocardial ATP content compared to controls,
2) Reduced intracellular edema compared to control as measured by diffusion weighted imaging on MRI,
3) Reduced myocardial tissue lactic acidosis compared to control as measured by spectroscopic imaging on MM,
4) Reduced level of the cell injury marker Malondialdehyde compared to controls,
5) Significant reduction in apoptosis in CCr heart compared to controls as measured by Caspase enzyme activity.

FIG. 42A describes the reduction of the Caspase enzyme activities in the CCr group (25% reduction of baseline) compared to the significant stimulation observed in control dogs (3.86-fold increase over baseline). Interestingly, the significant reduction of Caspase activities in the CCr group indicates that the enzymes are present more in the "inactive proenzyme" forms.

Cyclocreatine Phosphate (CCrP) also reduced heart weight after 6 hours of cold storage in HH Solution (UW+CCrP) Compared to Control (UW) (FIG. 42B). Results indicated that the recovery of contractile function was significantly better in the CCrP treated-group (HH) compared to saline control. Furthermore, there was a higher weight gain in control hearts (UW) after 6 hours of cold storage compared to the CCrP-treated hearts (HH). As indicated in FIG. 42B, CCrP-treated hearts (HH) weighted only 0.25 gm while control hearts (UW) weighed 0.31 gm. The observed reduction of heart edema in the CCrP hearts (HH) is crucial for the restoration of contractile function during reperfusion at the end of 6-hour storage. As indicated in FIG. 43, it was further demonstrated that Cyclocreatine Phosphate at 0.8 g/kg protected rat grafted hearts against ischemic injury during harvesting and prolonged cold storage for 22 Hours and 24 hours in the in vivo rat syngeneic abdominal heterotopic heart transplantation for 3 days. The CCrP treatment increased the survival of the grafted hearts in recipient rats for 3 days. Lewis rats were used for both the donors and recipients to avoid immunologic rejection. This approach allowed a focus at determining the in vivo cardioprotective benefits of CCrP treatment and to evaluate whether CCrP would restore cardiac contractility after prolonged cold storage and increase graft survival. Echocardiography (ECHO) analyses were conducted 2 hours after transplantation at day 0 and at day 3 before sacrifice.

CCrP treatment showed significant cardioprotection against early reperfusion injury after transplantation as illustrated by the absence of delayed heart function in the first 1 minute and the restoration of strong contractile function in all CCrP-treated hearts minutes after transplantation. In the contrary, saline-treated control donor grafts showed a slow start of heart beating with weaker contractile function. CCrP-treated hearts at doses of 0.8 gm/kg, 1.2 gm/kg and 1.5 gm/kg showed strong beating scores of 4+ and 3+ respectively at both day 0 and day 3 (score of +4 is the highest). However, the low dose of 0.5 gm/kg, showed strong heart beating scores of 4+ and 3+ right after transplantation at day 0 but partial myocardial protection by day 3 with beating scores ranged from 2+ to 3+. Saline-treated control donor rats were evidently dilated with an increase in the sizes of both ventricles and atria. Additionally, the color was mildly cyanotic and the contractility was poor and irregular in rhythm. In most control grafted hearts, their heart beating score ranged from 1+ to 2+ at day 0 and day 3. Protection was shown in most of CCrP grafted hearts at day 3 where the myocardial color and the consistency of the degree of contractility were almost the same as day zero. Additionally, the day 3 ECHO showed the continued preservation of the myocardial wall thickness and mass which are the main criteria that determine the degree of myocardial ischemia over a period of time. Most the control grafted hearts, on the other hand, continued to show evidence of ischemia as well as loss of wall thickness and cardiac mass by day 0 and day 3 (FIG. 43).

In general, CCrP grafted hearts after 22 hours and 24 hours of incubation had good preservation of myocardial color and perfusion as well as contractile function as indicated by preservation of the myocardial wall thickness and mass compared to control saline grafted hearts. The general overall survival of the cardiac tissue of "CCrP-grafted hearts" was very good to excellent, while the general overall survival of the cardiac tissue of "control-grafted hearts" was poor. Based on these preclinical efficacy studies, the U.S. FDA has awarded the Orphan Drug Designation (ODD) status for CCrP for the: "Prevention of Ischemic Injury to Enhance Cardiac Graft Recovery and Survival in Heart Transplantation".

Example 16—High Gene Expression of Nourin Gene-Based RNA Molecular Network (miR-137, miR-106b, mRNA-FTHL-17, mRNA-ANAPC11 and lncR-CTB89H12.4) as Biomarkers for Left Ventricular Remodeling after Myocardial Injury in Standard Isoproterenol (ISO) Rat Model of Heart Failure, and that Cyclocreatine Phosphate (CCrP) Treatment Prevented Ischemic Injury and Inhibited Gene Expression of the Nourin Gene-Based RNA Molecular Network in the Rat Heart Failure Model Mitochondrial abnormalities and reduced capacity to generate ATP can have a profound impact in HF. Abnormal mitochondria are also linked to myocyte injury because they are a major source of reactive oxygen species (ROS) production that can induce cellular damage. Isoproterenol (ISO) is a beta-adrenergic agonist which in high doses cause pathologic and molecular changes in rat heart that are similar to myocardial injury in humans. It causes coronary vasoconstriction, exaggerates myocardial Ca2+ influx and causes shunting of blood away from the subendocardial layer, producing subendocardial ischemia and cellular ATP depletion. ISO undergoes autoxidation, generating highly toxic ROS, which activate apoptotic pathways in the myocardium which in turn lead to contractile dysfunction and cardiomyocyte cell death. Therefore, high doses of ISO are used to induce experimental myocardial injury and to validate the effectiveness of test drug against ischemia-induced HF.

Cardiovascular disease is the leading cause of mortality in the United States and in westernized countries with ischemic heart disease accounting for the majority of these deaths. Myocardial infarction is the most common cause of heart failure. Virtually all episodes of ACS, including UA and both ST elevation myocardial infarction (STEMI—ischemic changes detected by Electrocardiogram (ECG) and non-ST elevation myocardial infarction (NSTEMI—no ischemic changes by ECG), are associated with the loss of myocardiocytes, edema, inflammation, fibrosis, and cardiac remodeling, which all together represent the leading pathophysiological mechanisms of HF. The immune system plays a significant role in ventricular remodeling, and its persistent activation may lead to long-term cardiac injury. As described in this invention, it was demonstrated that the high gene expression of Nourin molecular RNA Network in ACS patients, including UA, STEMI and NSTEMI, but not in healthy individuals.

The standard quantitative real time PCR (qPCR) molecular assay described in Example 6 was used to determine the levels of Nourin RNA network in the ISO rat model of ischemia-induced HF. It was tested if the hypothesis that the levels of gene expression of Nourin molecular RNA Network (miR-137, miRNA-106b, mRNA FTHL-17, mRNA ANAPC11 and lncR-CTB89H12.4) will be elevated in HF rats, and that CCrP treatment will reduce their gene expression of Nourin molecular RNA Network in a dose-response manner.

25 male Wistar rats (180-220 g) were used: ISO/saline (n=6), ISO/CCrP 0.4 gm/kg/day (n=3), ISO/CCrP 0.8 gm/kg/day (n=5), ISO/CCrP 1.2 gm/kg/day (n=2), control/saline (n=5), and control/CCrP 0.8 gm/kg/day (n=4). Rats were injected S.C. with ISO for two consecutive days at doses of 85 and 170 mg/kg/day, respectively, then left for an additional 2 weeks. CCrP and saline were injected IP (1 ml) 24 hours and 1 hour before ISO administration, then daily for 2 weeks. Serum creatine kinase-MB (CK-MB) (U/L) measured 24 hours after last ISO injection. After 14 days, gene expression of Nourin-dependent miR-137 and miR-106b and their signaling pathways mRNA-FTLH-17, mRNA-ANAPC11 and lncR-CTB89H12.4 were evaluated by qRT-PCR (Example 6).

Figure 47A:
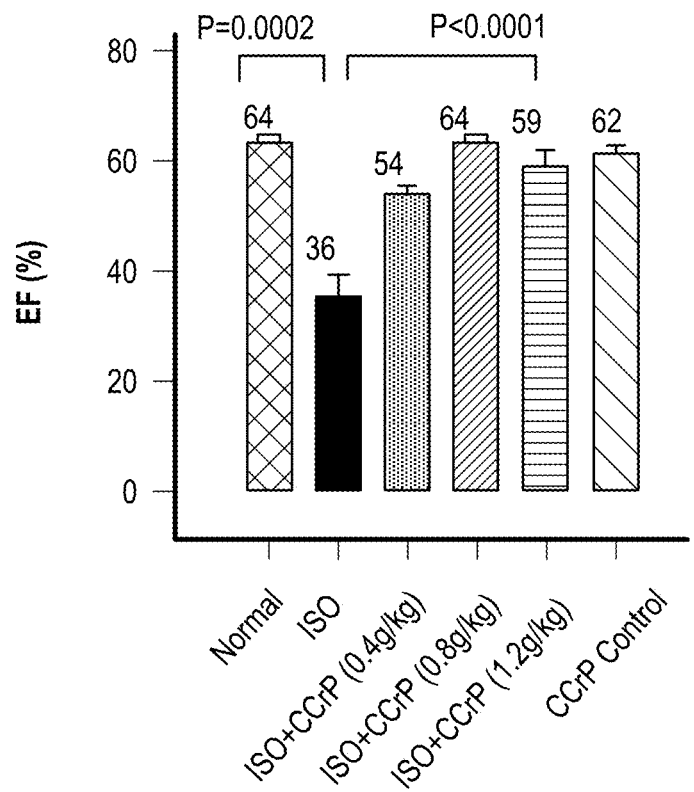
Figure 47B:
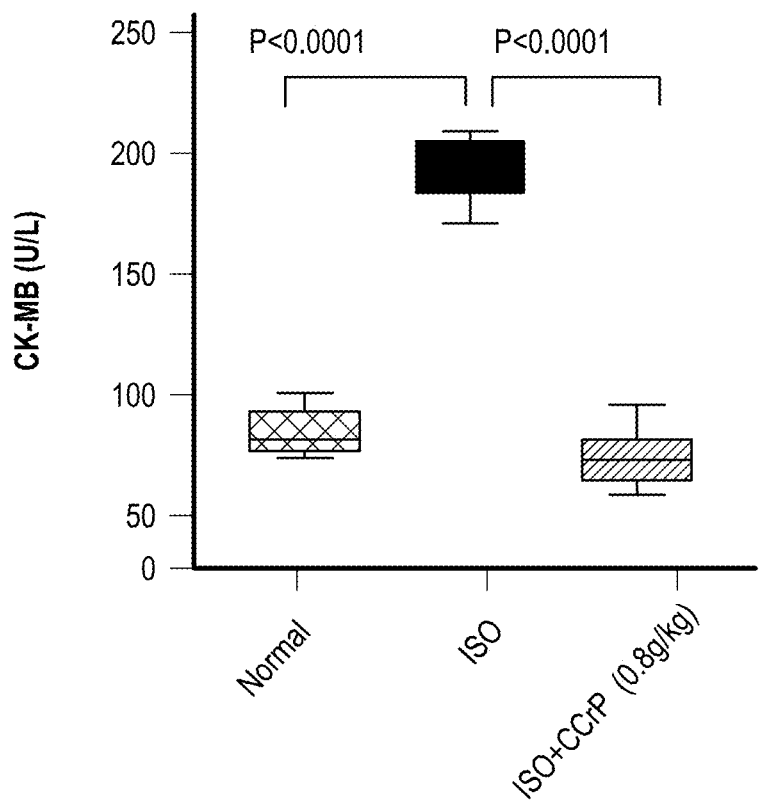

After 24 hours of the second and last ISO injection, it was confirmed that the development of myocardial injury by measuring the levels of necrotic biomarker, CK-MB (FIG. 47B). Although the saline-treated ISO rats (ISO/saline) had very high levels of CK-MB indicative of the presence of myocardial injury, CCrP-treated ISO (ISO/CCrP) rats showed low levels of CK-MB, which were comparable to the baseline healthy-saline rats (FIG. 47B). The absence of elevation of CK-MB in ISO/CCrP rats suggests that CCrP prevented ischemic injury and protected rats from the development of myocardial injury, thus, maintained healthy hearts.

After 14 days after the second and last ISO injection (end of study), Nourin-dependent miR-137 and miR-106b and their signaling pathways mRNA-FTLH-17, mRNA-ANAPC11 and lncR-CTB89H12.4 were measured in rat serum samples (n=25). As indicated in FIG. 44A-FIG. 44D, FIG. 45, and FIG. 46A-FIG. 46D, there was a significantly upregulation of gene expression of Nourin-related miR-137, miR-106b, mRNA-FTLH-17 and mRNA ANAPC11 in serum samples from ISO/saline rats, while normal "saline" rats showed very low gene expression. The ISO/saline rats had downregulation of lncR-CTB89H12.4 compared to healthy rats received "saline".

Figure 44A:
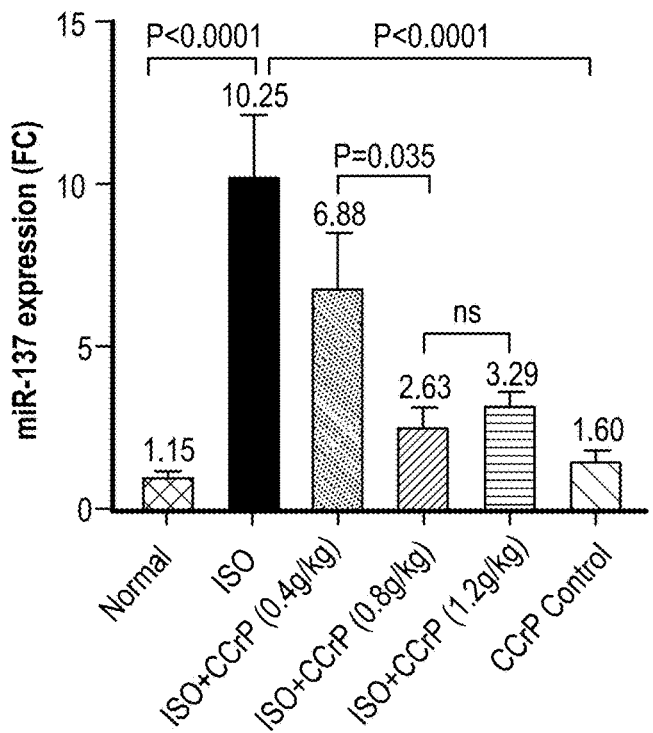
Figure 44B:
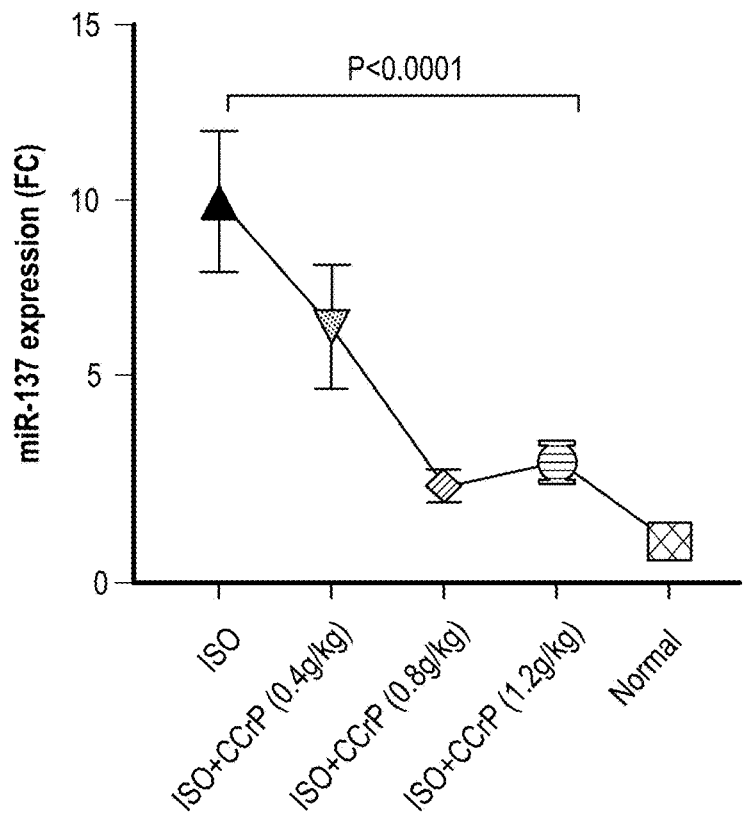
Figure 44C:
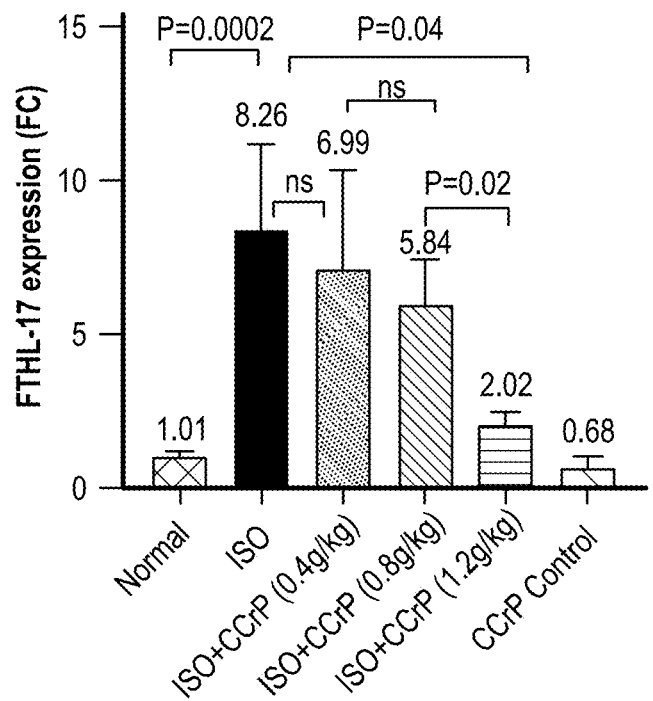
Figure 44D:
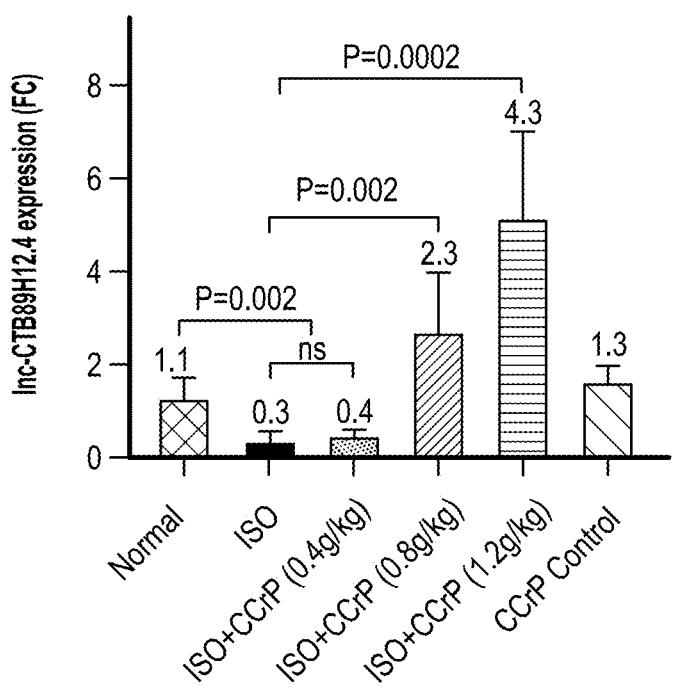

Specifically, as indicated in FIG. 44A-FIG. 44B, there is a significantly high gene expression level of miR-137 in serum samples collected at day 14 from ISO rats compared to normal rats. The ISO/saline rats had upregulation by 8.91-folds (Mean=10.25) compared to healthy rats received saline (1.15) ($p<0.0001$). CCrP treatment significantly ($p<0.0001$) reduced miR-137 gene expression at doses of 0.4 g/kg, 0.8 g/kg and 1.2 g/kg. CCrP at doses of 0.4 g/kg, 0.8 g/kg, and 1.2 g/kg by 33%, 75% and 68%, respectively. Additionally, CCrP administration to healthy rats at 0.8 g/kg did not increase miR-137 gene expression (Mean=1.60) and it was comparable to the level expressed in saline-treated healthy rats (1.15). The ISO/saline rats had upregulation of mRNA-FTHL-17 by 8.17-fold (Mean=8.26) compared to healthy rats received saline (1.01) ($p=0.0002$) (FIG. 44C). CCrP treatment significantly ($p=0.04$) reduced mRNA-FTHL-17 gene expression at doses of 0.4 g/kg, 0.8 g/kg and 1.2 g/kg by 16%, 30% and 75%, respectively. Additionally, CCrP administration to healthy rats at 0.8 g/kg did not increase mRNA-FTHL-17 gene expression (Mean=0.67) and it was comparable to the level expressed in saline-treated healthy rats (1.01). The ISO/saline rats had downregulation of lncRNA-CTB89H12.4 (Mean=0.3) compared to healthy rats received saline (1.1) ($p=0.002$) (FIG. 44D). CCrP treatment significantly ($p=0.002$) increased lncRNA-CTB89H12.4 gene expression at doses of 0.4 g/kg, 0.8 g/kg and 1.2 g/kg by 1.33-fold, 7.66-folds and 14.33-folds, respectively. Additionally, CCrP administration to healthy rats at 0.8 g/kg did not affect lncRNA-CTB89H12.4 gene expression (Mean=1.3), and its expression level is comparable to saline-treated healthy rats (1.1). FIG. 45 shows a correlation analysis which was conducted between miR-137/FTHL-17/lncR-CTB89H12.4 in the ISO (heart failure) rats treated with CCrP (0.8 g/kg). The only significant correlation was found between miR-137 and lncRNA-CTB89H12.4 ($p=0.04$) in the ISO/CCrP group where reduction of Nourin-related miR-137 is due to the "corrective" effect of CCrP on myocardial ischemia. No significant correlation was detected between miR-137/FTHL-17/lncR-CTB89H12.4 in the ISO/saline group ($p>0.05$).

Figure 46A:
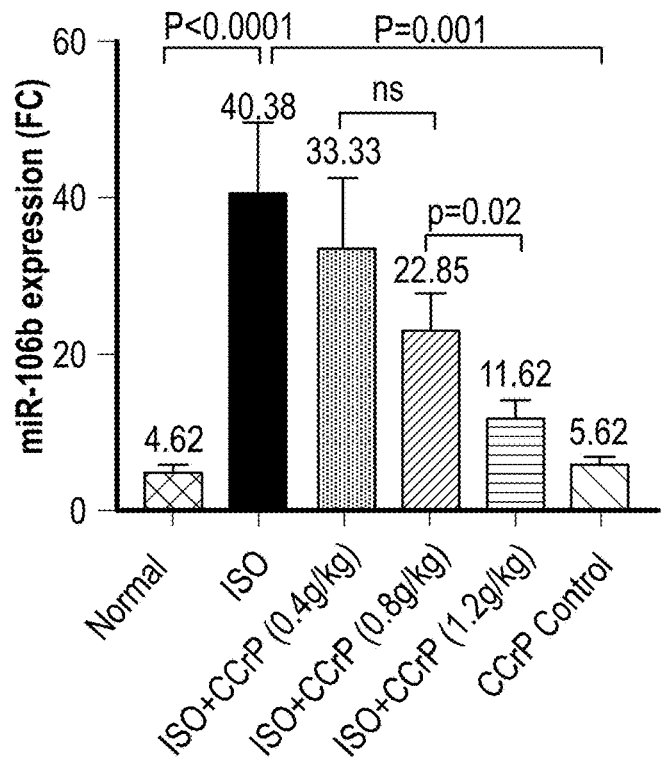
Figure 46B:
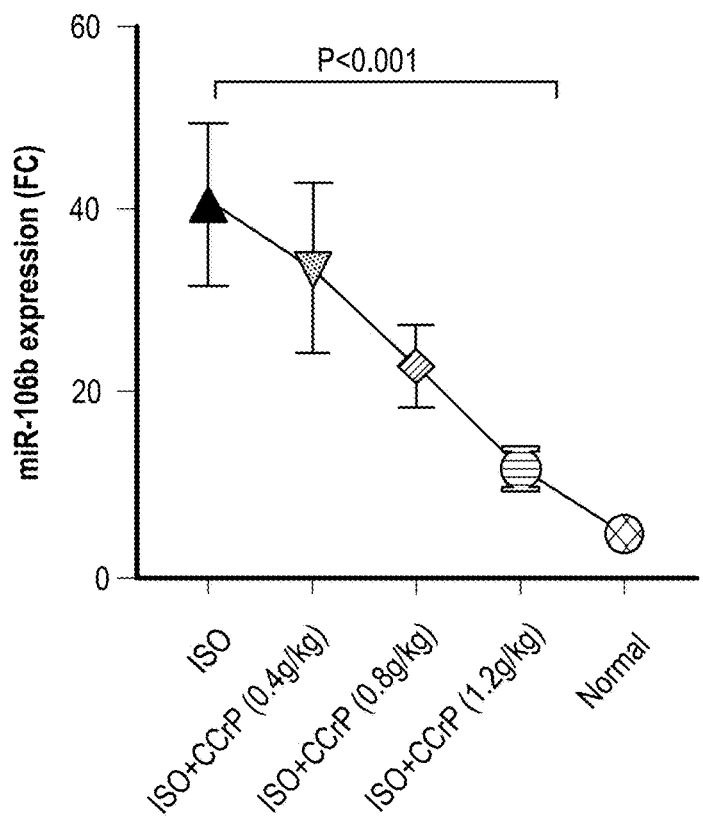
Figure 46C:
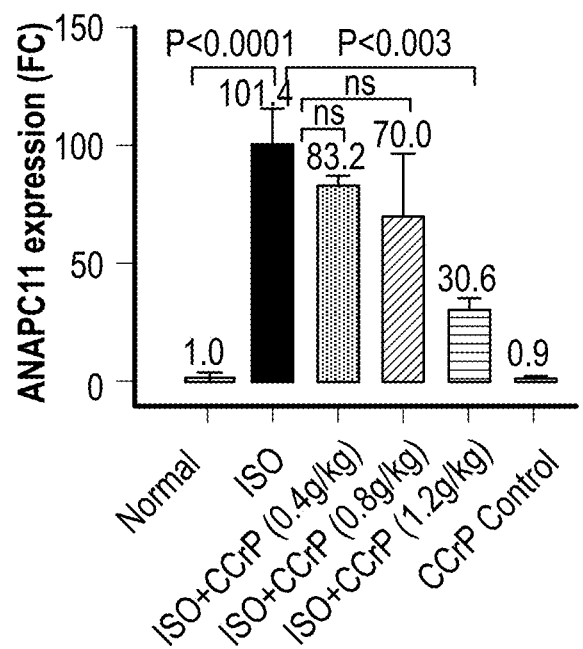
Figure 46D:
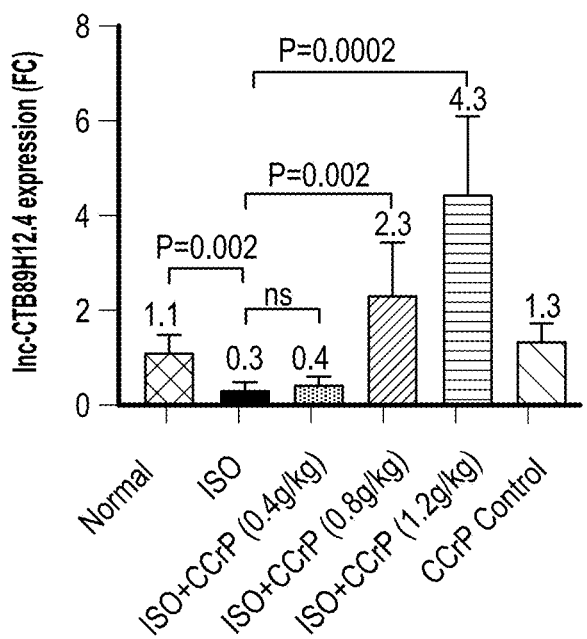

Similarly, FIG. 46A-FIG. 46D present gene expression level of Nourin RNA network composed of miR-106b/ANAPC11/lncR-CTB89H12.4 in the standard isoproterenol (ISO) rat model of HF (ISO/saline) and how the administration of Cyclocreatine Phosphate (CCrP) (ISO/CCrP) inhibited gene expression of Nourin RNA network. (FIG. 46A) and (FIG. 46B) indicate the significantly high gene expression level of miR-106b in serum samples collected at day 14 from ISO/saline rats compared to normal rats. The ISO/saline rats had upregulation by 8.74-folds (Mean=40.38) compared to healthy rats received saline (4.62) ($p<0.0001$). CCrP treatment significantly ($p<0.001$) reduced miR-106b gene expression at doses of 0.4 g/kg, 0.8 g/kg, and 1.2 g/kg by 18%, 44% and 72%, respectively. Additionally, CCrP administration to healthy rats at 0.8 g/kg did not increase miR-106b gene expression (Mean=5.62) and it was comparable to the level expressed in saline-treated healthy rats (4.62). The ISO/saline rats had upregulation of mRNA ANAPC11 by 101.4-fold (Mean=101.4) compared to healthy rats received saline (1.0) ($p=0.0002$) (FIG. 46C). CCrP treatment significantly ($p=0.04$) reduced mRNA ANAPC11 gene expression at doses of 0.4 g/kg, 0.8 g/kg and 1.2 g/kg by 18%, 31% and 70%, respectively. Additionally, CCrP administration to healthy rats at 0.8 g/kg did not increase mRNA FTLH-17 gene expression (Mean=0.9) and it was comparable to the level expressed in saline-treated healthy rats (1.0). The ISO/saline rats had downregulation of lncRNA-CTB89H12.4 (Mean=0.3) compared to healthy rats received saline (1.1) ($p=0.002$) (FIG. 46D). CCrP treatment significantly ($p=0.002$) increased lncRNA-CTB89H12.4 gene expression at doses of 0.4 g/kg, 0.8 g/kg and 1.2 g/kg by 1.33-folds, 7.66-folds and 14.33- folds, respectively. Additionally, CCrP administration to healthy rats at 0.8 g/kg had lncR-CTB89H12.4 gene expression (Mean=1.3) had a comparable level of expression as the saline-treated healthy rats (1.1). No significant correlation was detected between miR-106b/ANAPC11/lncR-CTB89H12.4 in the ISO/saline group (p>0.05). Similarly, no significant correlation was detected between miR-106b/ANAPC11/lncR-CTB89H12.4 the ISO/CCrP at dose of 0.8 g/kg (p>0.05).

Additionally, it was evaluated if the toxic effect of CCrP administration daily for 14 days to normal rats and whether CCrP would cause myocardial injury and stimulates expression of Nourin-dependent RNA network. As indicated in FIG. 44A-FIG. 44D and FIG. 46A-FIG. 46D, there was very low gene expression in CCrP control rats and there was no difference between CCrP control and normal saline control rats, suggesting lack of CCrP cardiac toxicity.

Recent evidence suggests that miRNAs are involved in the development and progression of HF. Several miRNAs have been identified as potential candidates that could be used as diagnostic biomarkers for HF to provide valuable clinical information. Additionally, they may be important tools in monitoring the progress of therapeutic treatments, since medical interventions are also associated with changes in miRNA levels. Experimentally, circulating levels of miR-423-5p and miR-106 were markedly increased in hypertension-induced HF, which was confirmed via RT-qPCR analysis of plasma RNA from hypertensive rats. Additionally, miR-106b is upregulated in cardiac tissue of patients with dilated cardiomyopathy and that miR-106b and miR-15b modulate apoptosis and angiogenesis in myocardial infarction. The expression of miR-137 was also detected by RT-qPCR and western blot analysis in spontaneously hypertensive rat hearts. miR-137 may promote cardiac remodeling in these rats by upregulation of Ang II and the TGF-B1/Smad3 signaling pathway; in addition, captopril intervention can inhibit miR-137 expression. Therefore, miR-137 not only indicates the presence of high blood pressure, it may also reflect its severity. These results indicate that several miRs can reflect disease progression to a certain extent, and may be used as biomarkers of hypertensive HF. Levels of serum miR-1 were also positively associated with myocardial infarct size. In post-AMI patients, miR-1 was significantly correlated with (a) the absolute change in infarct volume, (b) showed a trend for positive correlation with LV ejection fraction, and (c) was associated with AMI mortality. AMI patients, also, had significantly higher levels of plasma miR-21, compared to healthy controls. miR-21 was shown to be a novel biomarker that was predictive of LV remodeling after AMI, which correlated with several traditional markers of AMI; creatine kinase-MB (CK-MB), creatine kinase (CK) and cardiac troponin I (cTnI), with comparable diagnostic accuracy.

In summary, the disclosure according to the present invention indicates:
1) the higher expression level of Nourin-related miR-137 observed in HF rats compared to normal "saline" group with a highly significant difference (p<0.0001), could be explained by its over expression in response to ischemia;
2) similarly, Nourin-related miR-106b expression was markedly increased in the HF model compared to normal "saline" group with a highly significant difference (p<0.0001), which explains the effect of myocardial ischemia on the release of the inflammatory mediator Nourin protein as a consequence effect of overexpression of miR-106b;
3) after an ischemic event in the ISO/HF rat model, there was downregulation of lncR-CTB89H12.4 and upregulation of miR-137 and miR-106b which activated mRNA FTHL-17 and mRNA ANAPC11, respectively, resulting in an increase in translation of the Nourin protein;
4) Nourin-dependent RNA network expression level in ISO rats was compared to ISO/CCrP treated rats using 3 doses of CCrP (0.4 gm/kg/day, 0.8 gm/kg/day and 1.2 gm/kg/day);
5) significant reduction of the expression was detected in CCrP-treated HF model in a dose response manner with maximum efficiency with the effective dose of 0.8 g/kg/day;
6) reduction of Nourin-related gene expression observed after CCrP treatment, is due to the "corrective" effect of CCrP on myocardial ischemia;
7) the effect of CCrP on Nourin RNA network gene expression was comparable at the 3 doses:
   a) downregulation of miR-137 gene expression, by CCrP at doses of 0.4 g/kg, 0.8 g/kg, and 1.2 g/kg was 33%, 75% and 68%, respectively,
   b) downregulation of mRNA-FTHL-17 gene expression by CCrP at doses of 0.4 g/kg, 0.8 g/kg, and 1.2 g/kg was 16%, 30% and 75%, respectively,
   c) downregulation of miR-106b gene expression by CCrP at doses of 0.4 g/kg, 0.8 g/kg and 1.2 g/kg was 18%, 44% and 72%, respectively,
   d) downregulation of mRNA-ANAPC11 gene expression by CCrP at doses of 0.4 g/kg, 0.8 g/kg and 1.2 g/kg was 18%, 31% and 70%, respectively, and
   e) upregulation of lncRNA-CTB89H12.4 gene expression by CCrP at doses of 0.4 g/kg, 0.8 g/kg and 1.2 g/kg was 1.33-fold, 7.66-fold and 14.33-fold, respectively;
8) no observed toxic effect of CCrP when administered daily for 14 consecutive days to normal healthy rats. CCrP did not cause myocardial injury and did not stimulate expression of Nourin-dependent RNA network. There was a very low gene expression in CCrP-treated healthy rats which was not different than normal saline rats, indicating lack of CCrP cardiac toxicity;
9) the upregulation of Nourin RNA network can be used as early diagnostic and prognostic biomarkers for cardiomyocyte injury and inflammation in HF patients;
10) CCrP prevented ischemic injury and inhibited gene expression of the Nourin molecular RNA network in ISO/HF rats; and
11) Nourin RNA network can be used as molecular therapeutic targets to prevent cell injury and inflammation in patients with ischemic diseases using the bioenergetic drug, CCrP.

Example 17—the Bioenergetic Drug, Cyclocreatine Phosphate is a "Novel Mechanism" to Prevent the Development of Heart Failure in ISO Rat Model by Preventing Ischemic Injury, Reducing Fibrosis and Remodeling, Resulting in Rejuvenation of Cardiac Function and Restoration of Normal Physical Activities Myocardial infarction is the most common cause of heart failure. The recent improvements in medical and surgical treatments of acute coronary syndrome are leading to an increasing number of "survivors" who are then developing heart failure, which characterized with reduced left ventricular myocardial function, dyspnea (difficulty breathing) and limited exercise tolerance. Depending on the time of onset, HF with reduced ejection fraction (EF) of 40%, is classified as acute or chronic and patients.

Virtually all episodes of ACS, including UA and both STEMI and NSTEMI, are associated with the loss of myocardiocytes, edema, inflammation, fibrosis, and cardiac remodeling, which all together represent the leading pathophysiological mechanisms of HF. A hallmark feature of ventricular remodeling is deposition of excessive extracellular matrix. This surplus extracellular matrix, which constitutes scar or fibrosis, promotes both contractile dysfunction and rhythm disturbances. As a result, cardiac fibrosis contributes to morbidity and mortality in many forms of heart disease. Indeed, the amount of fibrotic scar in the myocardium correlates strongly with the increased incidence of arrhythmias and sudden cardiac death. Extracellular matrix deposition and fibrosis formation occur through the action of cardiac fibroblasts. In the setting of pathological stress, fibroblasts proliferate and differentiate into myofibroblasts, thereby gaining the capacity to contract and secrete collagen I, collagen III, and fibronectine. Both collagenous and myofibroblasts propagate the arrhythmic phenotype of the remodeled heart.

Isoproterenol (ISO) is a beta-adrenergic agonist which in high doses cause pathologic and molecular changes in rat heart that are similar to myocardial injury in humans. It causes coronary vasoconstriction, exaggerates myocardial $Ca^{2+}$ influx and causes shunting of blood away from the subendocardial layer, producing subendocardial ischemia cellular ATP depletion. ISO undergoes autoxidation, generating highly toxic ROS, which activate apoptotic pathways in the myocardium which in turn lead to contractile dysfunction and cardiomyocyte cell death. Therefore, high doses of ISO are used to induce experimental myocardial injury and to validate the effectiveness of test drug against ischemia-induced HF.

Demand ischemia causes irreversible myocardial injury through exhaustion of cellular ATP. It was demonstrated that enhancing myocardial ATP stores during ischemia using Cyclocreatine and its water-soluble salt Cyclocreatine Phosphate, prevents myocardial injury and maintains cardiac contractility in a variety of models. It was therefore tested if the hypothesis that CCrP administration will prevent ischemic injury and the subsequent development of heart failure in standard isoproterenol (ISO) rat model. 25 male Wistar rats (180-220 g) were used: ISO/saline (n=6), ISO/CCrP at three doses, 0.4 gm/kg/day (n=3), 0.8 gm/kg/day (n=5) and 1.2 gm/kg/day (n=2), control/saline (n=5), and control/CCrP 0.8 gm/kg/day (n=4). From our previous studies, CCrP at 0.8 gm/kg/day is the most effective dose to prevent ischemic injury and restores cardiac function. Rats were injected S.C. with ISO for two consecutive days at doses of 85 and 170 mg/kg/day, respectively, then left for 2 weeks. CCrP and saline were injected IP (1 ml) 24 hours and 1 hour before ISO administration, then daily for 2 weeks. Serum CK-MB (U/L) measured 24 hours after last ISO injection. After 14 days, ECHO analysis for Ejection Fraction (EF %) was conducted, as well as heart weight (mg), histologic analysis for fibrosis and deposition of collagen. Mean±S.E.M and one-way ANOVA analysis were used.

FIG. 47B shows evidence of myocardial injury after 24 hours by high elevation of CK-MB in ISO rats (206.20±6.25), while significant protection was seen in ISO/CCrP rats (70.67±5.79) at 0.8 g/kg (p<0.0001). ISO/CCrP rats had CK-MB level comparable to control saline (82.60±5.2), indicating that CCrP treatment prevented myocardial ischemic injury.

FIG. 47A summarizes results of EF % measured in various groups after 14 days using rat ECHO. While ISO rats showed significant drop in EF % of 36 indicative of acute heart failure, ISO/CCrP rats showed normal EF % of 64 at 0.8 g/kg/day (p<0.0001), which was comparable to control saline EF % of also, 64. Furthermore, ISO/CCrP group (n=5) (FIG. 49B) showed "high physical activity" at day 14 before sacrifice; activity which is comparable to control healthy "saline" rats. ISO/saline rats (n=6), on the other hand showed "low physical activity" and rats mainly stayed in place (FIG. 49A). These results indicate that treating ISO rats with CCrP prevented the development of heart failure and restored normal heart function and physical activities. Similarly, treating ISO/saline rats with CCrP at doses of 0.4 g/kg and 1.2 g/kg continued to show good EF % of 54 and 59, respectively, further confirming the cardioprotective benefits of CCrP in preventing the development of acute heart failure. Finally, normal rats treated daily for 14 days with CCrP at 0.8 g/kg also had normal EF % of 61 which was comparable to control saline EF % of 64, suggesting lack of toxicity of CCrP on heart function.

Figure 47C:
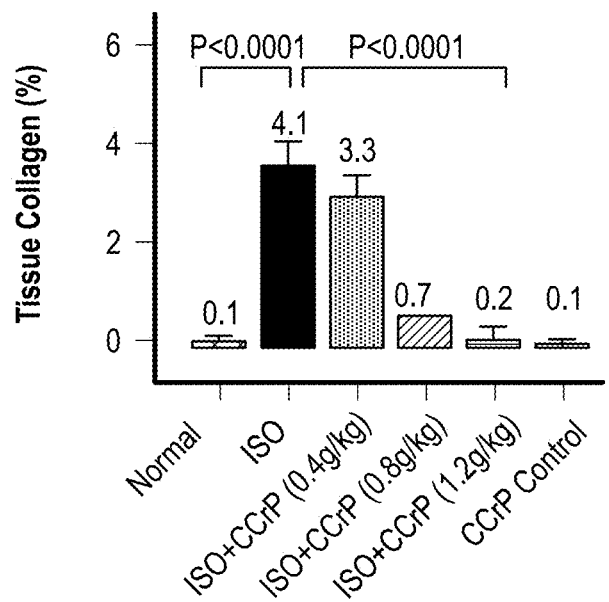

FIG. 47C indicates that while ISO/saline rats showed significant high collagen % of 4.1, ISO/CCrP rats showed low collagen % of 0.7 at 0.8 g/kg/day (p<0.0001), which was comparable to control saline collagen % of 0.1. Furthermore, treating ISO rats with CCrP at 1.2 g/kg continued to show low collagen % of 0.2 compared to ISO/saline rats (4.1) (p<0.0001), further confirming the cardioprotective benefits of CCrP in preventing cardiac remodeling. Only partial reduction of collagen % of 3.3 was seen using CCrP at doses of 0.4 g/kg. Additionally, normal rats treated daily for 14 days with CCrP at 0.8 g/kg also had normal collagen % of 0.1, which was comparable to control saline collagen % of 0.1, suggesting lack of toxicity of CCrP on heart remodeling (FIG. 47C). FIG. 53 describes results of a blinded histopathological study where heart specimens taken at day 14, were stained with Masson's trichrome for estimation of myocardial fibrosis. Normal healthy rats received saline (a) or CCrP (b) for 14 days showed normal delicate fibrous septa between the myocardial bundles. There is a marked increase and extensive fibrous deposition in ISO/saline rat hearts (c), which was not seen in ISO/CCrP rat hearts, and there was a delicate fibrous tissue between the myocardial bundles, almost similar to healthy normal rats (d). In summary, treating ISO rats with CCrP prevented cardiac remodeling. Finally, normal rats treated daily for 14 days with CCrP at 0.8 g/kg also had normal collagen % of 0.1, which was comparable to control saline collagen % of 0.1, suggesting lack of toxicity of CCrP on heart remodeling (FIG. 47C).

Figure 47D:
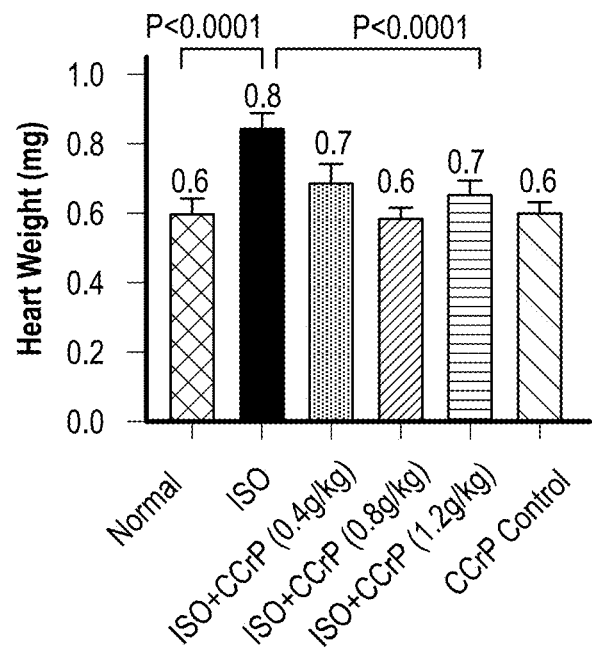

FIG. 47D shows a significant increase in heart weight (0.8 mg) in ISO rats compared to normal saline rats (0.6 mg) (p<0.0001), suggesting heart damage and edema. On the other hand, ISO/CCrP rats showed significantly lower heart weight at doses of 0.4 g/kg (0.7 mg), 0.8 g/kg (0.6 mg), and 1.2 g/kg (0.7 mg) (p<0.0001), confirming the cardioprotective benefits of CCrP in protecting against heart damage and weight gain. Interestingly, the ability of CCrP to prevent heart weight gain in rat model of heart failure supports our previous reporting in FIG. 42B demonstrating that CCrP reduced the gain of heart weight after 6 hours of cold storage. The observed reduction of heart edema in the CCrP hearts is crucial for the restoration of contractile function during reperfusion. Finally, normal rats treated daily for 14 days with CCrP at 0.8 g/kg showed normal heart weight of 0.6 mg, which was comparable to normal saline rats (0.6 mg), suggesting lack of toxicity of CCrP on the heart by maintain normal heart weight.

FIG. 48 indicates the safety of CCrP at a dose of 0.8 g/kg, where healthy rats were treated daily with CCrP for 14 days and showed no toxicity in heart, liver and renal function. There was no significance difference between serum levels of normal rats treated with saline or CCrP for the levels of Nourin gene-based RNA network, liver enzyme ALT, kidney Creatinine and Urea, as well as EF %, collagen % and heart weight.

In summary, this study indicates that:
a. ISO/saline rats showed:
  i. high elevation of CK-MB
  ii. significant drop in EF %
  iii. marked increase in collagen deposition
  iv. marked fibrosis
  v. significant increase in heart weight
  vi. increase in expression level of Nourin gene-based RNA network (miR-137, miRNA-106b, mRNA-FTLH-17, mRNA-ANAPC11, and lncR-CTB89H12.4)
  vii. toxicity of heart
  viii. very low physical activity at day 14.
b. ISO/CCrP rats showed:
  i. no elevation of CK-MB
  ii. no drop in EF %
  iii. no collagen deposition
  iv. no fibrosis
  v. no increase in heart weight
  vi. no increase in expression level of Nourin gene-based RNA network (miR-137, miRNA-106b, mRNA-FTLH-17, mRNA-ANAPC11, and lncR-CTB89H12.4)
  vii. no toxicity in heart
  viii. normal physical activity at day 14.
c. CCrP administration in the ISO rat model of HF likely prevented the development of HF by:
  i. preventing ischemic injury as indicated by normal level of the cardiac biomarker CK-MB;
  ii. preventing cardiac remodeling by reducing fibrosis and collagen deposition;
  iii. preventing cardiac injury and gain in heart weight; and
  iv. restoring normal ejection fraction, cardiac function
  v. restoring organ rejuvenation and physical activities.
d. CCrP not only prevented ischemic injury and the "development" of myocardial injury (MI) by 24 hours after ISO administration, but, also, protected cardiac tissue from remodeling and prevented the "progression" of MI to acute heart failure at day 14.
e. Thus, the bioenergetic CCrP is a promising first-in-class novel mechanism of cardioprotection that prevents ischemic injury, as well as prevents development and progression of heart failure, thus, rejuvenate cardiac function and restores normal physical activity.

Example 18—Clinical Applications of Nourin Protein and its Regulatory RNA Molecular Network as "Diagnostic" and "Prognostic" Biomarkers for Ischemic Heart Diseases, Including CAD, UA, STEMI, NSTEMI and HF The immune system plays a significant role in post-ischemic cardiac inflammation and ventricular remodeling, and its persistent activation may lead to long-term cardiac injury. MicroRNAs are small non-coding RNAs present in circulation and regulate expression of multiple genes involved in atherogenesis and myocardial ischemia. miRNA-expression profiles are novel diagnostic and prognostic biomarkers for multiple human diseases due to their remarkably high stability in body fluids. They are also easy to obtain through non-invasive methods, are highly sensitive to early detection and have high specificity to different disease entities. Both Nourin-related miRNAs have specific roles in myocardial ischemia, where miR-137 is a marker of cell injury and miR-106b is a marker of inflammation. Thus, using both markers with different modes of action increases diagnostic accuracy.

We first determined the expression levels of Nourin RNA molecular network in serum and plasma of patients with stable CAD, UA, STEMI and NSTEMI, as well as healthy individuals. Additionally, using standard rat ISO model of HF, we evaluated: (a) the association between serum Nourin RNA molecular network and, myocardial injury (CK-MB), left ventricle ejection fraction, cardiac fibrosis, remodeling, and heart weight, and (b) whether circulating Nourin level will be reduced by treating ISO rats with the cardioprotective, Cyclocreatine Phosphate (CCrP).

Nourin RNA molecular network was highly expressed in response to ischemic cardiac injury, and were not expressed in healthy hearts. The Nourin-related miR-137 is a marker of cell damage, while miR-106b is a marker of inflammation and their signaling pathways include: mRNA-FTHL-17, mRNA-ANAPC11 and lncR-CTB89H12.4. miR-106b is expressed if ischemic myocardial cell damage is associated with an inflammatory response. miR-137 is first expressed in response to injury followed by the expression of miR-106b for tissue inflammation. miR-137 and miR-106b are not expressed in normal healthy tissues and only baseline values were detected. Fast release of Nourin-related miR-137 and miR-106b which are specific of ischemic injury and inflammation, will allow them to be used as cardiac markers accuracy than each alone. Their circulating level of expression can indicate the degree of myocardial cell damage and inflammation, thus classify the degree of ischemia as: low, medium and severe.

The Nourin RNA molecular network was expressed in ischemic heart diseases, including:
1) CAD—high expression level of miR-137 and miR-106b and their signaling pathways positively correlated with the ECHO/ECG Treadmill stress test results. These results, therefore, suggest the clinical use of the Nourin-related miR-137 and miR-106b as non-invasive quick diagnostic biomarkers in outpatient clinics to diagnose angina patients with chest pain and discriminate them from symptomatic non-cardiac patients and healthy individuals. Furthermore, Nourin can play an important role in identifying stable CAD patients with moderate/severe ischemia, who will benefit from invasive intervention (PCI) procedure and CAD patients with mild/moderate ischemia who will benefit from "medical" therapy.
2) UA—high expression level of Nourin RNA molecular network positively correlated with clinically confirmed UA patients, and they were not expressed in healthy individuals. Nourin RNA molecular network can be used as a non-invasive fast laboratory test to not only diagnose UA patients, but also to differentiate with high confidence, between UA patients and healthy individuals, UA and STEMI, and between STEMI and healthy. As a non invasive blood test, Nourin will provide important information about UA severity and helps in the detection, diagnosis, prognosis, as well as disease management and progression of UA to AMI and HF.

3) STEMI and NSTEMI—high expression level of miR-137 and miR-106b positively correlated with several traditional markers of AMI, including: cardiac Troponin I and CK-MB, with comparable diagnostic accuracy. However, while both miR-137 and miR-106b diagnosed STEMI and NSTEMI patients immediately at presentation to hospital ED, Troponin was not detected in some STEMI patients and, also, NSTEMI patients require additional wait for consecutive blood samples to confirm the diagnosis using cardiac markers. Since, Nourin-related miR-137 and miR-106b are released by "sick, but still alive" myocardial cells before necrosis, they are "earlier" biomarkers than Troponin, which is a marker of necrosis. Very low expression of both miRNAs was detected in healthy individuals.

4) UA & NSTEMI—since changes in the levels of circulating miR-137 and miR-106b were associated with UA and NSTEMI at presentation, it supports a role for Nourin as a novel biomarker to "accelerate" the diagnosis of acute coronary syndrome (ACS) patients.

5) HF—high expression level of miR-137 and miR-106b and signaling pathways in the ISO/HF model was positively associated with: (a) CK-MB as indicative of myocardial injury, (b) echocardiographic LV ejection fraction, (c) cardiac fibrosis and remodeling, and (d) heart weight. Furthermore, since the level of Nourin biomarkers reflects the "severity" of myocardial injury and inflammation, it will accurately predict patients with high risk of developing HF after AMI. High level of Nourin is indicative of high probability of development of HF, while low level of Nourin is indicative of low probability of HF. Thus, Nourin is a new indicator of the degree of LV remodeling after AMI and and can be used as predictive of LV remodeling after AMI. Nourin will have the advantage over BNP of "independently" monitoring the progression of AMI patients for the development of HF without a need of all other clinical and physical assessment. The diagnostic strength of BNP is their high sensitivity for "ruling out" HF; as the value increases, HF becomes more likely. However, defining "rule-in" cutoffs for HF is complicated because multiple factors influence natriuretic peptide levels. Thus, Nourin RNA molecular network: (a) presents a new biomarker for left ventricular remodeling after myocardial infarction to "rule-in" HF patients, (b) prognostic value for "new-onset" HF, (c) risk prediction of progression and deterioration of cardiac function in patients with HF, (c) monitoring response to medical and surgical treatments to determine improvement or deterioration compared to before treatments (disease management), and (d) monitoring patients' hearts in clinical trials to determine drug-induced cardiac toxicity (such in the case of Isoproterenol), as well as drugs that improve and prevent cardiac deterioration (such in the case of Cyclocreatine Phosphate).

6) Cardiac surgery: the release of Nourin by reversible ischemic myocardium and necrotic tissue suggest that circulating Nourin can be useful to identify the extend of perioperative myocardial injury in patients undergoing cardiac procedures and surgeries, and to also monitor heart recovery post-operatively. Thus, Nourin can be a predictive biomarker that gives information about the effect of a therapeutic intervention by determining the benefits of medical and surgical treatments.

7) Serum and plasma samples can be used to evaluate gene expression levels of Nourin RNA molecular network.

8) CCrP treatment prevented ischemic injury and the development of HF in ISO rats by down regulation of gene expression of Nourin RNA network and cardiac inflammation. In several animal models of ischemia/reperfusion, there was, also, a significant reduction in the level of circulating Nourin protein, cardiac inflammation after CCrP treatment.

9) In summary, establishing an accurate, reliable laboratory test to monitor circulating Nourin concentrations in blood samples can provide clinicians information about the diagnosis and severity of myocardial ischemia in CAD, UA, AMI and HF, as well as provide important tools in monitoring and predicting disease progression and therapeutic interventions.

The Nourin family are tissue-derived inflammatory mediators rapidly released by various tissues in response to ischemic injury. Although tissue-derive Nourins share the same molecular weight of 3 KDa, they differ in their isoelectric points. The 3 KDa Nourin protein released by ischemic heart is designated as Nourin-1, while Nourin-2 is for ischemic brain, and Nourin-3 is for ischemic spinal cord. As indicated in this invention, the amino acid sequence of cardiac Nourin-1 and its genetic regulatory pathways, as well as clinical relevance have been determined. The amino acid sequences of brain Nourin-2 and spinal cord Nourin-3 have not determined yet.

Brain inflammation has been shown to play an important role in the development of reperfusion injury in brain ischemia and spinal cord and trauma. Since recruited neutrophils contribute to brain destruction in reperfusion injury, we investigated the release of Nourin-2 by brain tissues. Four pigs were sacrificed and brains were immediately removed, cut and incubated in Hank's Balanced Salt Solution (HBSS) at room temperature (1 gm brain/2 ml HBSS). After 5, 10, 20, 40, 60, and 240 minutes, 100 ul aliquots of supernatant solutions were collected and tested for the level of Nourin-2 using human peripheral neutrophils as indicator cells. Modified Boyden chambers were used to test for Nourin-2 neutrophil chemotactic activity in supernatant solutions (100 ul). The synthetic f-Met-Leu-Phe (fMLP) (10-9 Molar) (SEQ ID NO: 11) was used as positive control for 100% response. HBSS was used as negative control. Results were expressed as maximum chemotactic response of f-MLP. Results indicate significant release of Nourin-2 by ischemic brain tissues as early as 5 minutes (23-55% f-MLP) reaching maximum release by 40 minutes (77-91% f-MLP), then plateau for the remaining 4 hours (80-91% f-MLP). Samples collected from the 2-hour incubation were also processed using size exclusion high performance liquid chromatography (HPLC) using the 1-300 KDa fractionation column. high activity (57-102% f-MLP) was detected in fractions corresponded to fractions below 5 KDa. In conclusion, isolated ischemic pig brains rapidly produce a small molecular weight neutrophil chemotactic factor, Nourin-2, which in-vivo would not only promote inflammation but may also be useful as therapeutic target to reduce brain inflammation in stroke and trauma. Similarly, using pig spinal cord, the 3 KDa Nourin-3 was also rapidly released within 5 minutes of ischemia. Cyclocreatine which crosses blood brain barrier, protected pigs against ischemic injury and showed neuroprotective activity by restoring organ function (unpublished observation).

Example 19—Clinical Applications of Cyclocreatine Phosphate as a Novel "Bioenergetic Therapy" to Prevent and Treat Ischemic and Aging-Related Cardiovascular and Neurodegenerative Diseases Heart and brain are among parts of the body requiring the greatest amounts of energy and they are the most affected during failures of the mitochondria to generate ATP due to ischemia and hypoperfusion. Mitochondrial dysfunction is relevance to aging and aging-related disease such as cardiovascular and Alzheimer's diseases. There is a link between the energy status of the cell and impaired organ function. Reduction of ATP production and the increase of oxidative stress are major triggers of neurons, and cardiac myocytes dysfunction, thereby contributing to the development and progression of age-related disorders. The progression of HF is associated with diminished energy metabolism and a decrease in ATP synthesis capacity and a decrease in overall ATP levels. Age-related changes in mitochondria are associated with decline in mitochondrial function and ATP production. Aging is characterized by a general decrease in O2 supply to tissues and a reduction in tissue pO2. A diminished vascularization (lack of blood flow) in aging alters the diffusion of O2 at the capillary tissue level, and at an advanced stage, this can lead to tissue hypoxia. Preservation of ATP by CCrP treatment prevents ischemic injury, reduces disease progression and restores organ function. It will also slow down the aging process resulting in organ rejuvenation in of the aging-related diseases, HF and Alzheimer.

This example demonstrated that healthy rats treated with CCrP (0.8 gm/kg) for 14 days, showed no toxicity in heart, liver and renal function (Example 16). Since CCrP showed strong cardioprotective activities against ischemic heart diseases (AMI, bypass and HF), CCrP can also be useful to prevent and treat other cardiac ischemic diseases, including: atrial fibrillation, Takotsubo cardiomyopathy and cardiac surgeries, as well as aging-related neurodegenerative diseases, including: cerebral ischemic stroke and Alzheimer.

Despite many therapies for patients with heart failure with reduced ejection fraction, such as angiotensin converting enzyme (ACE) inhibitors, angiotensin receptor blockers (ARBs), β blockers, and mineralocorticoid receptor antagonists, and advanced device therapies, hospital admissions for acute heart failure continue to increase and to date, no new therapies have improved clinical outcomes. Therefore, new drugs with "novel mechanisms of action", such as CCrP which can improve contractile function in patients with reduced left ventricular ejection fraction may likely address these unmet needs for patients with heart failure.

Additionally, although the survival rates for patients with heart failure have improved through current therapies (β-blockers, ACE inhibitors, angiotensin-II receptor blockers, and aldosterone antagonists) to relieve symptoms and reduced left ventricular remodeling and post-MI mortality, they did not result in prevention of the progression of disease. This could be related to complexity of the disease and the involvement of a number of underlying problems with structure or function of heart. Accordingly, heart transplantation is so far the only therapeutic option for end-stage heart failure.

Mitochondrial abnormalities and reduced capacity to generate ATP can have a profound impact in HF. Abnormal mitochondria are also linked to myocyte injury because they are a major source of reactive oxygen species (ROS) production that can induce cellular damage. Abnormal mitochondria also promote programmed cell death through the release of cytochrome c into the cytosolic compartment and activation of caspases. Bendavia was reported to improve cellular ATP levels and prevent pathological ROS formation. However, in the EMBRACE STEMI (Evaluation of Myocardial Effects of Bendavia for Reducing Reperfusion Injury in Patients With Acute Coronary Events—ST-Segment Elevation Myocardial Infarction) trial, elamipretide did not improve the primary or secondary outcomes. In the randomized placebo-controlled trial of elamipretide in HF, the drug was shown to reduce left ventricular volumes; however, the confidence intervals were wide in this small study, and there were no changes in biomarker data. Elamipretide is currently being investigated in larger HF studies to determine its effect on cardiac remodeling and clinical outcomes.

It was shown that depression of myocardial contractility plays an important role in the development of heart failure; therefore, there is a need for cardiotonic agents to improve the contractile function of the failing heart. Additionally, studies indicated that the development and progression to HF are associated with a decline in energy reserve capacity that ultimately reaches a threshold after which compensatory mechanisms can no longer support the decreasing energy supply. Growing evidence indicates that derangements in myocardial fuel metabolism and bioenergetics contribute to the development of heart failure. Stored myocardial high-energy phosphate (phosphocreatine) are reduced in humans with pathological ventricular hypertrophy, with further decline during the transition to heart failure. Notably, the [phosphocreatine]/[ATP] ratio correlates with heart failure severity and is a strong predictor of cardiovascular mortality. Thus, targeting energy metabolic disturbances and corresponding upstream regulatory events occurring during the early stages of HF is an important first step toward the identification of new therapeutic targets to improve the outcomes of current therapies. Mitochondrial energy source could, therefore, be a promising therapeutic target to improve mitochondrial biogenesis. Currently, there are no drugs that specifically target mitochondrial biogenesis in HF patients.

The immune system plays a significant role in ventricular remodeling, and its persistent activation may lead to long-term cardiac injury. Specifically, activation of a variety of inflammatory molecules and pathways, such as the complement system, T cells, and the formation of autoantibodies, have been reported in heart failure patients. Consequently, a number of strategies have been proposed to mitigate the harm caused by these inflammatory events; most have failed. In the 1970s, it became apparent that immunosuppression with glucocorticoids or nonsteroidal anti-inflammatory agents conferred risk in patients with ischemic heart disease. The degree of impaired contractile function after AMI is determined by the scar size: large scars result in progressive chronic heart failure. Furthermore, the influx of large number of neutrophils and inflammatory mediators after an AMI have been proposed as major contributors for microvascular obstruction and post-AMI adverse LV remodeling leading to heart failure.

Although inflammation is an important contributor to the pathogenesis of early and late myocardial reperfusion injury, and it also plays a key role in the "healing" process essential for cardiac repair and scar formation. Therefore, it is critical to achieve the right balance between limiting the early 'harmful' inflammation in the first few minutes to hours after reperfusion and allowing the 'beneficial' inflammation required for tissue repair. Since treating AMI patients with corticosteroids had a serious negative effect because they impaired and retarded wound healing, there is a need for new anti-inflammatory drugs that can control inflammation without affecting the healing process. This invention indicates that experimentally, the administration of Cyclocreatine and Cyclocreatine Phosphate proved to be safe and effective with strong anti-inflammatory activity which protected ischemic hearts against reperfusion injury in 4 different animal models of ischemia/reperfusion: (1) AMI (2 hours reperfusion), (2) bypass surgery (4 hours), (3) heart transplantation (3 days), and (4) HF (14 days).

Since heart and brain are among parts of the body requiring the greatest amounts of energy and they are the most affected during failures of the mitochondria to generate ATP, preservation of the energy source ATP by CCrP will present a promising therapeutic approach as a new "age-modifier therapy" to prevent the development and to treat Alzheimer's disease (AD) similar to HF (described in this invention). Due to the high energy demands of neurons and glia, a considerable amount of ATP is consumed in the brain. Also, because no energy storage (such as fat or glucose) is available in the central nervous system (CNS), brain cells must continually produce ATP to maintain activity and energy homeostasis. With aging, oxygen delivery to cells and tissues is impaired due to diminished vascularization, thereby increasing the susceptibility of neurons to damage. Thus, hypoxic (neuronal) adaptation is significantly compromised during aging. Many neurological diseases, such as stroke and Alzheimer's disease (AD) are characterized by hypoxia, a state that is believed to only exacerbate disease progression. AD is a pressing public health problem with no effective treatment. Existing therapies only provide symptomatic relief without being able to prevent, stop or reverse the pathologic process. While the molecular basis underlying this multifactorial neurodegenerative disorder remains a significant challenge, mitochondrial dysfunction appears to be a critical factor in the pathogenesis of this disease. It is therefore important to target mitochondrial dysfunction in the prodromal phase of AD to slow or prevent the neurodegenerative process and restore neuronal function.

Studies reported mechanisms of action and translational potential of current mitochondrial and bioenergetic therapeutics for AD including: mitochondrial enhancers to potentiate energy production; antioxidants to scavenge reactive oxygen species and reduce oxidative damage; glucose metabolism and substrate supply; and candidates that target apoptotic and mitophagy pathways to remove damaged mitochondria. While mitochondrial therapeutic strategies have shown promise at the preclinical stage, there has been little progress in clinical trials thus far. Current FDA-approved drugs for AD treatment include: N-methyl-D-aspartic acid (NMDA) receptor antagonist memantine and cholinesterase inhibitors donepezil, galantamine, and rivastigmine. These drugs augment cholinergic neurotransmission or attenuate excitotoxic neuronal injury. However, they only provide palliative benefits at best, with limited impact on the underlying disease mechanisms. Therefore, there is an urgent need for interventions that not only impact the aging process in favor of sustained brain health but also promote successful brain aging in the context of neurodegenerative diseases.

The relationship between hypoxia and AD could open the avenue for effective preservation and pharmacological treatments of this neurodegenerative disease by using new therapeutic drugs like the novel bioenergetic drug, CCrP. CCrP provides protection of heart muscle against ischemic injury in CAD, UA, AMI, HF and cardiac surgical patients and thus save ischemic muscles from progressing to necrosis and heart failure, and will be protective against ischemic injury in stroke and AD. It has been previously demonstrated that Cyclocreatine crosses the blood brain barrier and functions as a potent neuroprotective agent by preventing ischemic injury and restoring organ function (unpublished observation). Since paraplegia following surgery of the descending thoracic aorta is a serious complication in adult and pediatric surgery, we tested the neuroprotective effect of Cyclocreatine in Yorkshire pigs which underwent 30 minutes of aortic cross-clamping then left to survive for 4 days. Majority of Cyclocreatine-treated animals were able to stand and walk, while, only few of the saline-treated control pigs were able to stand. This study suggests that Cyclocreatine administration prior to the induction of neural ischemia, protects against tissue injury and the development of paraplegia. As indicated in Example 17, similar to heart tissue (Nourin-1), Nourin protein was quickly released within 5 minutes by brain (Nourin-2) and spinal cord (Nourin-3) in response to ischemia. Because of the great similarities between heart and brain and that they are both require high demand of ATP, CCrP will be as effective in preventing ischemic injury and restoring neurologic function in stroke and AD, similar to HF.

The disclosure according to the invention provides a "novel mechanism of action" for tissue protection against ischemic injury using Cyclocreatine Phosphate to preserve cellular ATP energy source as a promising therapeutic approach to prevent the development and to treat HF patients. CCrP effective therapeutic approache, targeting preservation of ATP in ischemic myocardium, can mitigate the impact of inflammation and apoptosis and help restore post-ischemic cardiac function and normal physical activities.

As a novel mitochondria-targeted protective compound which prevents mitochondrial dysfunction, CCrP can be used for prevention and treatment not only cardiovascular, but also central nervous system diseases, including but not limited to Alzheimer and stroke. Since there is no energy storage (such as fat or glucose) is available in the central nervous system, brain cells must continually produce ATP to maintain activity and energy homeostasis. Additionally, since hypoxia is believed to continue to play a role in disease progression in HF, stroke and AD, continuing production of ATP by CCrP will be crucial for disease treatment by slowing or preventing disease progression and possibly reversing the pathologic process.

In summary, since hypoxia and reduction of ATP production are major triggers of cardiac myocytes and neurons dysfunction and they contribute to the "development" and "progression" of ischemic and aging-related disorders, the below therapeutic strategies summarize a number of clinical protocols for CCrP administration to "prevent" and "treat" ischemic and aging-related cardiovascular and neurodegenerative diseases, including:

1) CAD patients—CCrP can be orally administered prophylactically to stable CAD patients to protect hearts against ischemic injury in case patients are experiencing UA or AMI.
2) UA patients—CCrP can be administered orally to UA patients immediately after an ischemic event to protect hearts against injury in case patients progress to AMI or HF.
3) AMI patients—Although approximately 15 to 20% of the affected area of the heart after an AMI is dead within first few minutes, it takes up to 6 hours for the remaining 80 to 85% of the surrounding areas to progress from ischemic damage to irreversible permanent necrosis which can lead to heart failure. CCrP can be administered intravenously (IV) immediately after AMI is clinically confirm, as well as during the first crucial 6 hours after the ischemic event to control myocardial injury and inflammation without affecting the crucial healing process. To assure the continuation of the beneficial anti-apoptotic activity by CCrP, the drug will be administered orally for an additional 14 days to continue protecting against myocardial injury, save heart muscle, reduce infarction scare size and, thus, reduce the incidence of heart failure. Large scar size after AMI results in progressive chronic heart failure.

4) HF—Since hypoxia and reduction of ATP production are major triggers and contributors not only in the "development" of HF, but also in disease "progression", AMI patients will be treated IV with CCrP immediately after the ischemic event for 6 hours (IV), then orally daily for an additional 14 days to few weeks and months to prevent apoptosis and development of HF particularly for patients with large infarct scar size. CCrP can also be daily administered orally to patients with existing HF to provide the crucial cellular energy needed to prevent disease progression and thus, restore cardiac function and physical activity.

5) AF—CCrP presents a new mechanism with a novel anti-arrhythmic therapeutic approach in AF, by preventing ischemic injury, inflammation, inflammation-induced arrhythmia, and AF-induced cardiac structural remodeling. CCrP can be daily administered orally to high risk aged population to prevent the development of AF, as well as to treat the disease.

6) Takotsubo cardiomyopathy—The administration of CCrP to these patients presented to hospital ED with clinical signs of an AMI triggered by an emotionally or physically stressful event can, therefore, prevent stress-induced ischemic injury and the development of HF. CCrP can be daily administered orally for 7 days and extended as needed.

7) Cardiac procedures and surgeries:
   a) PCI—CCrP can be administered IV 10, 30 to 60 minutes to CAD patients prior to PCI procedure for heart protection during procedure.
   b) Bypass—CCrP can be administered IV 10, 30 to 60 minutes before surgery for heart protection during procedure, then daily for an additional three days.
   c) Valve replacement—CCrP can be administered IV 30 to 60 minutes before surgery for heart protection during procedure, then daily for an additional three days.
   d) Heart transplantation—CCrP can be administered IV to heart donor immediately before removing the heart. Harvested heart will be placed in preserving solution containing CCrP to protect heart during prolong cold storage for 8 to 10 hours. Recipient patient will not receive CCrP.

8) Stroke—CCrP can be orally administered prophylactically to high risk patients of brain stroke and aging population to protect against hypoxia/ischemic injury. CCrP can also be given as a "therapy" immediately after an ischemic event to protect brain tissue against deterioration of areas adjacent to ischemic tissues, thus, minimize cell injury and loss of brain function and disability.

9) Alzheimer—CCrP can be orally administered prophylactically to high risk patients of memory loss and aging population to protect against hypoxia/ischemic injury and, thus, reduces the loss of cognitive functions. CCrP can also be given as a therapy shortly after initiation of reduced cognitive, to prevent progression of tissue damage and loss of functions, thus minimizing severity of Alzheimer disease. By early providing the crucial ATP cellular energy, CCrP treatment may be able to prevent, stop or reverse the pathologic process of AD.

10) Aging—CCrP can function as anti-aging drug due to its ability to preserve mitochondrial function, thus will increase ATP production during the aging process. By decreasing apoptosis and inflammation, CCrP can preserve cognitive and motor functions. As an age-modifier therapy, CCrP can rejuvenation tissue by not only providing cellular energy (ATP), but also by maintaining healthy autophagy by inhibiting gene expression of Nourin-dependent m-R-137 (marker of ischemic injury) and miR-106b (marker of inflammation) with potential of reducing and slow down aging.

11) Based on the fact that CCrP prevented ischemic injury and the development of the aging-related heart failure disease, and since hypoxia/ischemia and reduction of ATP production are major triggers of neurons dysfunction and they contribute to the "development" and "progression" of ischemic and aging-related disorders such as Alzheimer's disease, CCrP will potentially have therapeutic benefits in AD.

12) Cyclocreatine crosses the blood-brain barrier since in the blood, CCrP looses the phosphorous moiety and converts to Cyclocreatine.

13) It can be used in patients who will undergo nerve-related surgery, such as aneurysms, tumor, intracerebral hemorrhage surgery, vascular surgeries, and other similar procedures (neuro muscular diseases), as well as patients who will undergo "non-nerve" related surgery that is capable of causing ischemia of the nervous system.

14) The present invention can be used during many treatment stages:
   a) prophylactically prior to ischemia to protect against heart attack, stroke, peripheral nerve damage in high-risk patients including aging populations, diabetic patients, patients with vascular diseases including CAD, and patients with prior heart attack and transient ischemic attack (TIA).
   b) immediately administered during ischemia to patients experiencing ischemic stroke at presentation to hospital ED, even beyond the three-hour therapeutic time window that often lead to treatment disqualification with thrombolytic therapy such as tPA. Unlike tPA therapy, CCrP would not be expected to have neurotoxic or vasoactive side effects, alter the blood brain barrier, or pose a risk of hemorrhage.

15) CCrP can be administered prophylactically, therapeutically during injury, or post-injury for continued therapy or prophylactically against recurrence.

16) CCrP can be administered by any suitable means, including, but not limited to injection, orally, topically, by inhalation, or by other means to prevent ischemic injury and treat ischemia-relating and aging diseases.

17) Thus, the present invention involves a system that provides for a three-stage treatment of (i) prevention, (ii) immediate therapy during ischemia, and (iii) post-ischemia rehabilitation to preserve, restore, and sustain organ function.

18) When administered shortly after incidence of ischemia it will:
   a) preserve the "salvageable tissue" surrounding the ischemic and necrotic areas, by protecting injured tissues with the goal of preventing them from becoming irreversible damaged, thus, minimize devastating disability.
   b) prevent and slow down disease progression.

It will be apparent to those skilled in the art that various modifications and variations can be made in the practice of the present invention without departing from the scope or spirit of the invention. Other embodiments of the invention will be apparent to those skilled in the art from considering of the specification and practice of the invention. It is intended that the specification and examples be considered as exemplary only, with a true scope and spirit of the invention being indicated by the following claims.

REFERENCES

1. Zhengbing Liu et al., LncRNA GAS5 exacerbates myocardial ischemia-reperfusion injury through regulating serpina3 by targeting miR-137. International Journal of Cardiology (2020) 306: 9
2. M Zhang, D J Ge et al., miR-137 alleviates focal cerebral ischemic injury in rats by regulating JAK1/STAT1 signaling pathway: miR-137 alleviates focal cerebral ischemic injury. Human and Experimental Toxicology. (2020) DOI: 10.1177/0960327119897103
3. Yuuichi Arakawa et al., Transgenic mice overexpressing miR-137 in the brain show schizophrenia-associated behavioral deficits and transcriptome profiles. PLoS ONE (2020) 14 (7): e0220389
4. Haiyan Li et al., MicroRNA-137 regulates hypoxia-induced retinal ganglion cell apoptosis through Notch1. International Journal of Molecular Medicine (2018) 4 1774 1: 1774-1782
5. Fenghui Chen et al., LncRNA GAS5 regulates ischemic stroke as a competing endogenous RNA for miR-137 to regulate the Notch1 signaling pathway. Biochemical and Biophysical Research Communications (2018) 496: 184e190
6. Naveet Pannu et al., Resveratrol: from enhanced biosynthesis and bioavailability to multitargeting chronic diseases. Biomedicine & Pharmacotherapy (2019) 109: 2237-2251
7. Marit Wiersma et al., Mitochondrial Dysfunction Underlies Cardiomyocyte Remodeling in Experimental and Clinical Atrial Fibrillation. Cells. (2019) 8(10): 1202
8. Sufang Li et al., Circulating microRNAs as potential biomarkers for coronary plaque rupture. Oncotarget, (2017) Vol. 8, (No. 29), pp: 48145-48156
9. Jun Liu et al., Circulating microRNAs as potential biomarkers for unstable Angina. Int J Clin Exp Pathol. (2017) 10(8): 9073-9083
10. Alessandro Valli et al., Hypoxia metabolism in ageing. Aging (2015) Vol. 7 No 7
11. O. O. Ogunshola et al., Contribution of hypoxia to Alzheimer's disease: is HIF-1a a mediator of neurodegeneration? Cell. Mol. Life Sci. (2009) 66:3555-3563
12. Muhammad Shahzeb Khan et al., Targeting Mitochondrial Function in Heart Failure—Makes Sense But Will it Work? JACC (2019) VOL. 4, NO. 2
13. Christophe Bauters et al., Circulating miR-133a and miR-423-5p fail as biomarkers for left ventricular remodeling after myocardial infarction. International Journal of Cardiology (2013) 168: 1837-1840
14. E Mahmoudi et al., MiR-137: an important player in neural development and neoplastic transformation. Molecular Psychiatry (2017) 22, 44-55
15. E. Nabialek et al., Circulating microRNAs (miR-423-5p, miR-208a and miR-1) in acute myocardial infarction and stable coronary heart disease. Minerva Cardioangiol (2013) 61:627-37
16. Shan-shan Zhou et al., miRNAS in cardiovascular diseases: potential biomarkers, therapeutic targets and challenges. Acta Pharmacologica Sinica (2018) 39: 1073-1084
17. Christian Mueller et al., Heart Failure Association of the European Society of Cardiology practical guidance on the use of natriuretic peptide concentrations. European Journal of Heart Failure (2019) 21, 715-731
18. Jana S. Burchfield et al., Pathological Ventricular Remodeling. Circulation (2013) 128:388-400
19. Giuseppe Lippi et al., Risk assessment of post-infarction heart failure. Systematic review on the role of emerging biomarkers. Crit Rev Clin Lab Sci (2014) 51(1): 13-29
20. Sheryl L. Chow et al., Role of Biomarkers for the Prevention, Assessment, and Management of Heart Failure: A Scientific Statement From the American Heart Association. Circulation (2017) Volume 135, Issue 22, Pages e1054-e1091
21. Saumya Das et al., Noncoding RNAs in Cardiovascular Disease: Current Knowledge, Tools and Technologies for Investigation, and Future Directions. A Scientific Statement From the American Heart Association. Circ Genom Precis Med. (2020) 13:e000062. DOI: 10.1161/HCG.0000000000000062
22. Yao-Meng Huang et al., The diagnostic value of circulating microRNAs in heart failure. Exp Ther Med (2019) 17(3): 1985-2003
23. D. J. Maron et al., Initial Invasive or Conservative Strategy for Stable Coronary Disease. NEJM (2020) DOI: 10.1056/NEJMoa1915922
24. Salwa A. Elgebaly et al., Methods to prevent and treat diseases. U.S. Pat. No. 8,288,350 B2 (2012)
25. Salwa A. Elgebaly et al., Cyclosporin H: a novel anti-inflammatory therapy for influenza flu patients. J. Egypt. Soc. Parasitol. (2017) 47(1): 25-33
26. S. Nilsson et al., Chest pain and ischaemic heart disease in primary care. British Journal of General Practice (2003) 53, 378-382
27. J. Hector Pope et al., Missed diagnoses of acute cardiac ischemia in the emergency department. NEJM (2020) 342(16):1163-1170
28. Salwa A. Elgebaly et al., Cyclocreatine protects against ischemic injury and enhances cardiac recovery during early reperfusion. Expert Review of Cardiovascular Therapy (2019) 17:9, 683-697
29. Salwa A. Elgebaly et al., A Novel Autophagy-Related Nourin Gene-Based RNA Network as Early Biomarkers for Cardiac Patients. U.S. Ser. No. 16/252,402 (2018)
30. Salwa A. Elgebaly et al., Nourin molecular biomarkers diagnose angina patients with negative Troponin. U.S. Ser. No. 16/719,723 (2018)
31. Zhihua Liu et al., MiR-106b and MiR-15b Modulate Apoptosis and Angiogenesis in Myocardial Infarction. Cell Physiol Biochem (2012) 29:851-862
32. Anke J. Tijsen et al., Circulating microRNAs as diagnostic biomarkers for cardiovascular diseases. Am J Physiol Heart Circ Physiol (2012) 303: H1085-H1095

33. Solenne Paiva et al., MiRroring the Multiple Potentials of MicroRNAs in Acute Myocardial infarction. Front. Cardiovasc. Med. (2017) 4:73
34. Chen Wang et al., Non-coding RNAs as biomarkers for acute myocardial infarction. Acta Pharmacologica Sinica (2018) 39: 1-9
35. Joost Petrus Gerardus Sluijter et al., Extracellular vesicles in diagnostics and therapy of the ischaemic heart: Position Paper from the Working Group on Cellular Biology of the Heart of the European Society of Cardiology. Cardiovascular Research (2018) 114, 19-34
36. J. Bogaert et al., Ischemic Heart Disease. Clinical Cardiac MRI, Medical Radiology. Diagnostic Imaging (2012) DOI: 10.1007/174_2011_336,
37. Zhang, Jing et al., Role of miR-106b-5p in the regulation of gene profiles in endothelial cells. Journal of Peking University (Health Sciences) Vol. 51, No. 2 Apr. 2019.

SEQUENCE LISTING

```
<160> NUMBER OF SEQ ID NOS: 23

<210> SEQ ID NO 1
<211> LENGTH: 88
<212> TYPE: RNA
<213> ORGANISM: Homo sapiens

<400> SEQUENCE: 1
acaaugcuuu gcuagagcug guaaaaugga accaaaucgc cucuucaaug gauuuggucc    60
ccuucaacca gcuguagcua ugcauuga                                      88

<210> SEQ ID NO 2
<211> LENGTH: 22
<212> TYPE: RNA
<213> ORGANISM: Homo sapiens

<400> SEQUENCE: 2
agcugguaaa auggaaccaa au                                            22

<210> SEQ ID NO 3
<211> LENGTH: 830
<212> TYPE: DNA
<213> ORGANISM: Homo sapiens

<400> SEQUENCE: 3
cacccgcctt tcactatccg ccattcttgt cacctcagct gctgccctcg ctaccgcacc    60
gacttcgccc gtgtgctcgc ctgcacttgc gctgcccgcc atggccaccg cccagccgtc   120
gcaggtgcgc cagaagtacg acaccaactg cgacgccgcc atcaacagcc acatcacgct   180
ggagctctac acctcctacc tgtacctgtc tatggccttc tacttcaacc gggacgacgt   240
ggccctggag aacttcttcc gctacttcct gcgcctgtcg gacgacaaaa tggagcatgc   300
ccagaagctg atgaggctgc agaacctgcg cggtggccac atctgccttc acgatatcag   360
gaagccagag tgccaaggct gggagagcgg gctcgtggcc atggagtccg ccttccacct   420
ggagaagaac gtcaaccaga gcctgctgga tctgtaccag ctggccgtgg agaagggcga   480
cccccagctg tgccacttcc tggagagcca ctacctgcac gagcaagtca agaccatcaa   540
agagctgggt ggctacgtga gcaacctgcg caagatttgt tccccggaag ccggcctggc   600
tgagtacctg ttcgacaagc tcaccctggg cggccgcgtc aaagagactt gagcccagat   660
gggccccaca gccacgggt cccttccctg ggtcaggcca ctaggcgggg cgtgcatgtt   720 gcccttttcag aacgttctct tcagttttat ctttcagttt taccattgtt agcaaaaaag   780
ttatctggtt ctcaaagcaa taaggtgtc cataaaaaaa aaaaaaaaaa                830

<210> SEQ ID NO 4
<211> LENGTH: 102
<212> TYPE: RNA
<213> ORGANISM: Homo sapiens

<400> SEQUENCE: 4
```

```
gguccucuga cucucuucgg ugacggguau ucuugggugg auaauacgga uuacguuguu    60
auugcuuaag aauacgcgua gucgaggaga guaccagcgg ca                     102

<210> SEQ ID NO 5
<211> LENGTH: 23
<212> TYPE: RNA
<213> ORGANISM: Homo sapiens

<400> SEQUENCE: 5 acgguauuc uuggguggau aau                                            23

<210> SEQ ID NO 6
<211> LENGTH: 23
<212> TYPE: RNA
<213> ORGANISM: Homo sapiens

<400> SEQUENCE: 6
uuauugcuua agaauacgcg uag                                           23

<210> SEQ ID NO 7
<211> LENGTH: 71
<212> TYPE: RNA
<213> ORGANISM: Homo sapiens

<400> SEQUENCE: 7
ugacgggcga gcuuuuggcc cgguuauac cugaugcuca cguauaagac gagcaaaaag    60
cuuguugguc a                                                        71

<210> SEQ ID NO 8
<211> LENGTH: 22
<212> TYPE: RNA
<213> ORGANISM: Homo sapiens

<400> SEQUENCE: 8
gagcuuuugg cccggguuau ac                                            22

<210> SEQ ID NO 9
<211> LENGTH: 22
<212> TYPE: RNA
<213> ORGANISM: Homo sapiens

<400> SEQUENCE: 9
auaagacgag caaaaagcuu gu                                            22

<210> SEQ ID NO 10
<211> LENGTH: 71
<212> TYPE: RNA
<213> ORGANISM: Homo sapiens

<400> SEQUENCE: 10
ugggaaacau acuucuuuau augcccauau ggaccugcua agcuauggaa uguaagaag    60 uauguaucuc a                                                        71

<210> SEQ ID NO 11
<211> LENGTH: 22
<212> TYPE: RNA
<213> ORGANISM: Homo sapiens

<400> SEQUENCE: 11
acauacuucu uuauaugccc au                                            22
```

```
<210> SEQ ID NO 12
<211> LENGTH: 22
<212> TYPE: RNA
<213> ORGANISM: Homo sapiens

<400> SEQUENCE: 12
uggaauguaa agaaguaugu au                                                  22

<210> SEQ ID NO 13
<211> LENGTH: 21
<212> TYPE: RNA
<213> ORGANISM: Homo sapiens

<400> SEQUENCE: 13
uuaagacuug cagugauguu u                                                   21

<210> SEQ ID NO 14
<211> LENGTH: 22
<212> TYPE: RNA
<213> ORGANISM: Homo sapiens

<400> SEQUENCE: 14
aacaucacag caagucugug cu                                                  22

<210> SEQ ID NO 15
<211> LENGTH: 31
<212> TYPE: PRT
<213> ORGANISM: Homo sapiens

<400> SEQUENCE: 15

Met Ile Ile Asn His Asn Leu Ala Ala Ile Asn Ser His Arg Ser Pro
1               5                   10                  15

Gly Ala Asp Gly Asn Gly Gly Glu Ala Met Pro Gly Gly Gly Arg
            20                  25                  30

<210> SEQ ID NO 16
<211> LENGTH: 14
<212> TYPE: PRT
<213> ORGANISM: Homo sapiens

<400> SEQUENCE: 16

Met Ile Ile Asn His Asn Leu Ala Ala Ile Asn Ser His Arg
1               5                   10

<210> SEQ ID NO 17
<211> LENGTH: 11
<212> TYPE: PRT
<213> ORGANISM: Mus musculus

<400> SEQUENCE: 17

Met Ile Ile Asn His Asp Asp Glu Arg Lys Cys
1               5                   10

<210> SEQ ID NO 18
<211> LENGTH: 11
<212> TYPE: PRT
<213> ORGANISM: Mus musculus

<400> SEQUENCE: 18

Met Ile Ile Asn His Asp Asp Glu Arg Lys Cys
1               5                   10

<210> SEQ ID NO 19
```

<211> LENGTH: 8636
<212> TYPE: DNA
<213> ORGANISM: Homo sapiens

<400> SEQUENCE: 19

```
caaatgccat tgaaaccgct agtcttattt cctttctact tttctttggc actcttactg      60
cctgtaagga gtagaactgt tagggcacac tgttgctata cagtttaact cccatttca     120
tgttttgtct ttcttttccc atttctgggg cttacctcct gatacctgct tactttctgg    180
aagtagtggg caagtaagat ttggctcttg gtttctaatt tttaaatttc tgaatactgc    240
cctagtctga acttggcctt tatagattaa tctttgcttc acattttag tgttgtattt     300
aaactatttt ataatttaaa aatagattct aatctgaaga tacttttcaa gaaatattat    360
taactgatgt catcctcatc ccagcagctc atctgtagg aatgaagttg agatgcttct     420
attccatgtt tttgtatttg ggaaggattc aaagttgaag gtttattgtc gttgggtttt    480
tcagatggtg acatgtaaac tcaggatagc aaaccctaat gttcacacag tgctctgcct    540
ctgcatctca gttgggatag ttgctccttt tgagtgtttt aatcatcgta taactaatca    600
tagtgccaag aagttcataa tgtgttatgt agctaatgtc actgaaaaac agtcctacca    660
ttttaggtaa gaccaaacag agtctctaac ccaaggactt gttacacctg acaacctata    720
gtatatttgc ttttctcac aaaatgaaac caattttgcc gaaagctagc tgggataata     780
ggatcatcac aagttgcagt ttctataact aaaattagat tgaaatctct tctgacctag    840
aacattttac ttcaggcatt cagcagattt cagaagaat taccttattt taagttagtt     900
tctttgttag tttactgtgt gtctcttatt caataaacaa gcagaatttg tgtcctgccc    960
tatccatgtc ttaaagatga gaagttggat ccactgagtt agtttcattg gggcggggga   1020
aagaactgta attaaacttg tttaatcctt attttgtatt gtagctatt tttgtaaaag    1080
caacttaaaa tcttttaaaa attttatagt gacattagag acaatggtca tacaaattat   1140
cacataaaca tggacttgaa aaattaggct tttcataaaa cacatcacat gtcattgact   1200
gcttttaga aatacacttc caaggcagta catctgtatt gctactgaaa agtgccattt    1260
cacagaacac agacttcttt ttgctctttg acatcttgaa aacatctgtt tttcttttt    1320
aatacaaaac tttgtgctca agacaaatct tacatgaaac tctcataaac catgaaaatg   1380
tagctggcct tcgggcctta ggcatgaaat aagcatgagg aacatattcc cctaacttct   1440
accccccagcc cagcaagtta tcctttaaga aatctcctag gaattctgga gtttgaaaac   1500
aattgctcta tgttattcct gcttccagtc tctaagtaac aagggcattt aaaagcatag   1560
tctcttaagg tccactatag tggttcttta tttaaggaat aactcagctg ggtgcagtgg   1620
ctcacgcctg ttatcccagc actttgagag gctgaggcaa gcagatcact tgaggccagg   1680
agttcgagag tctggccaac atggtggaaa cccatctcta caaaaatac aaaaattagc    1740
caggtgtggt ggcgtgcacc tatggtccca gctatttggg aggctgaggc aggagaattg   1800
cttgaacctg ggaggtggag gttgcagtga gccaagattg tgccgctgca ctccagcctg   1860
ggtgacagag tgagactctg tctcaaaaaa aaaaaaaaaa ggaactcata cagctcaatg   1920
attcattgat cccaataata aatcgtttta ataatgatga aaacatccta ctggggtttt   1980
cttgttaaaa actttaggac aggcgcagtg gctcatgcct gttattccaa cacatttggg   2040
aggctgaggt gggagaattg cttgacccta ggagttctag acttgcctgg gccacatagt   2100
aagaccctgt cccagctccc tccaacatcg tccccaaccc cccccccccc aaaaaaaaaa   2160
agcgccaggc gcagtagtga gtgcctgtga tcccagctgt gttgggaggc tgaggtggga   2220
```

```
gtatcacctg agccctggag gttgaggctg caatgagagc tgtgatcatg ccactgcact    2280
ccagcctggg caacagatga daccctgtgt cacaacaagg aatttttaga aggtgctttt    2340
tatattactc ttcacagagt taaattttca gaggatttag tattattgaa ctaagtttca    2400
taagtgtatt ttaagcaagt aaatctctaa tgtaggaaaa tccccaaaat ggtagcattt    2460
actaatgttt tatatggtaa tttttgaaaa atatatctga tatttcttca gtaaaaatgg    2520
tgttgtttta ataacttaat aagaatgttt aaagattctt taagtctggc ttatctagct    2580
aatgtgggcc tattaaataa taggcagact tctgccttcc ttatattctt tagatctttt    2640
caaatactcc attccaatat ccatcaaaag acttctcttt atgccactta ttatctatac    2700 tagttttta tgttcaatta ctacaagatt ataattactg tttttattca tgttcccaag    2760
aaaaatacat aagattcaca cccaacacac ttcgaaattt atttcactcc ctttgactat    2820
atgtgattat caaaaagta ttttcaaga tattaaaaat aagtaaagga aaatgaaata    2880
tttttaggac attcaaaatc taatgaagtt cagtgtttct ttaattgagg gcaggcagag    2940
gtgggggaga atttcagaag gtagtgaacc caaaggtgga ttcttggata attctactat    3000
tctgtactct catcatctta acccatctgt ttactaccct aaccatagtt actaagcaga    3060
gttttatcat aataatatag acagctctca aagtattgac attcagaggg gattacaaat    3120
attatttttc tatcatattg acctaccatg tccacagtct tccttgaatt accttccagt    3180
tttactgggc tgcatctacc gtttatgtct agtttgactt tttctgagtt caccaattgc    3240
tgctaggaat gtgctggtca ctcagcagca cacccacatc acaggggaag attttgaaat    3300
acctggacag tctgaacaca ctgctctgaa tacactcaat tctaagaagt accagggaac    3360
cgcatcttct tgctgaaatc ttgaattttt gtcagctttt tttttactg tggacagtaa    3420 agctggaaag atctaaataa cccaacagga aatgcggatg aaagtgcaag agttggtttg    3480
tggtcatctg gagtccatgt ctccaagact gctggacctt caaattctgc aacttgttag    3540
atcatctgga tgatagcaca actgttagaa gacctagaag aatacagcgt tgctatgact    3600
cagtggtgtt gaatgcagac catctaccag ctgggaaag aatcaattat aaacaggaat    3660
aaagggattc attcctcatt ttaactgatg ttacagtgaa gatgggttct tgaactcttg    3720
gaagcctgga tgagccacct aatctgcaag ataaaaacca aagaccaatg cgtattgggg    3780
aaaagaatgc ttagtactgc aagactgttg aatacctgtt gaatattcct attgaggttt    3840
tttcctaaac atacttcagt aacatcttag gacaattcac tggagaaatg ttgatccctg    3900 gctgaatgt cataccattg acccatttga agagttaaag ctggatttga ctgctctatt    3960
ctaccaggaa tattgttagg gtagcctttt accagtttct aaacaattgt aatcatttat    4020
tgactcagca attcctcaga taacaggtca aaagatgtac agatacattc tgaagttttc    4080
ttgctattaa aggcacaaga gtttccttgt attttgactg acaatgtagc atgtttccat    4140
tttagtttgt tagtgatggt ggttttccct ttgaaagcca tttggtatat tcaccataac    4200
aattagttta atatgattac ataagaaaac tatgataaaa cccagcaatt ttagtagttg    4260
tgaaaatacg ttttttaaat catgtttaag aagaattgca agacttgaaa ccaaatcctg    4320 atggggggaat tctgttaat cctgtttaat ctgtttaatt tctgtttaat ccttagtttc    4380
ttaacctgca tagcttatcc tgtattgtac ttttttttctt ttttaaactc ccaaacaaga    4440
agcttgaaac ttttcctgta ttttaaaatt gaaatttggt cacagggtat agtcagattt    4500
ttattaaggt ttggtttgac aacctttaaa agaaaggttt acctcgctaa tacttcttaa    4560
```

```
taacatgcat caaatgatat tccctatggt gaagtatatt ctcaaagtta tgttatcttt    4620 cattttggc atttggtgct tatggactta gtacccaggc aacaaagatc tattatgcac     4680
ctactctctt gtatgttcgc tattatttcc caaaaaaaaa aaggggcata tatgcataag    4740
aaataaatat tagaattatt ttgtttctcc cacaaagccc atgggagatg cccaacaaa     4800 tgtttaaaaa gtaaagaag ctgggcacgg tggctcccac ctgtaacccc cacactttgg    4860
gaggccatgg cgggtggatc acgaggtcag gagtttgaga ccagcctggc caacacagtg    4920
aaactgtgtc tctactataa atacaaaaat tagccaggca tggtggcagg cacctatagt    4980
cccagctact caggaggctg aggcaggaga atcgcttgaa cccaggaggc agaggttgcg    5040
gtgagccaag atcatgccac tgccctccag cctgggtgac agagcgagac tgtctccaaa    5100
aaaaaagaaa aaagaactaa agaaaagga gcagtttatg attgaagaaa acatgacctg    5160
ggctgaagaa gtgaggattg attggagtgg gctagaatga gctatagttt ctagctcatt    5220
tgtaaggagg tagacaaagg agcattggtg cctcagagtg ggtgtctggt gagaggaaaa    5280
acggtgctta agagattttc aggctattgc tgtgggacag gcatattttc tcccttgcc    5340 tttagctgta gataaagtgt ggttatgacc tgaggcttct tgtattcaaa cttggcctag    5400
ggcctatgta gaggccctag ggtctacttg tggtggagga gggaagtatt tgtagaatgt    5460
gtaggcttga gaagtaaata aagccaaaaa agcatcactt gcttacattt ttaaatgagt    5520
cacaaaacaa tctttctaat gcggccggta aagaagtttt aaaggtctaa ggtttctcta    5580
cagaaattac atgcttctca ggtctttgtt tagtaaaata atacagataa ttatgctttg    5640
aatgcattta ttattaaagc taaccgtttt aatttgtgtc agaataatt tgtgcctatg     5700 gtaggattaa aattgtattc tttagttaaa gcaaagcaat ctgttttca ttgatttgat    5760 aaatatgtga atgcctaata tgttctgcat atgtaaaaat gcagaaacat gctcatttga    5820
attactaata attatttag tatgctgaga ggctttgaat tcactgtacc actccttcct    5880
agagtcattc aaaacagaaa aaattagttt taagtataga ttcatgtttt tctgttttaa    5940
aaagttgagc taatactttt cacaagagac gaaataacat gagccactat aattattggc    6000
tcagttccac ccaatttcca tattttgggt gtaatttaaa attttgact tggaattta    6060 actttttttt tgttttgatt ttttaccagg tttctaagca tgaattgagg aacagaagaa    6120
gcagagcaga tgatcggagc agcatttgtt tctccccaaa tctagaaatt ttagttcata    6180
tgtacactag ccagtggttg tggacaacca tttacttggt gtaaagaact taatttcagt    6240
ataaactgac tctgggcagc attggtgatg ctgtatcctg agttgtagcc tctgtaattg    6300
tgaatattaa ctgagatagt gaaacatggt gtccggtttt ctattgcatt tttttcaagtg    6360 gaaaagttaa ctaaatggtt gacacacaaa aattggtgga gaaattgtgc atatgccaat    6420
tttttgttaa aaccttttgt tttgaactat actgctttga gatctcattt cagaagaacg    6480
gcatgaacag tcttcagcca cagttgtgat ggttgttaaa tgctcacaat gtgcattct    6540 tagggttttt ccatccctgg ggtttgcaag ttgttcactt aaaacattct taaaatggtt    6600
ggcttcttgt ctgcaagcca gctgatatgg tagcaaccaa agattccagt gtttgagcat    6660
atgaaagact ctgcctgctt aattgtgcta gaaataacag catctaaagt gaagacttaa    6720
gaaaaactta gtgactacta gattatcctt aggactctgc attaactcta taatgttctt    6780
ggtattaaaa aaaagcata tttgtcacag aaatttagtt aacatcttac aactgaacat    6840 gtatgtagt tgcttagata aatgtaatca ctgtaaacat ctatatgatc tgggattttg    6900 ttttatttt gaaatgggag cttttttgtt tacaagttca ttaaaaacta aaaactgttt    6960
```

```
ctgtaaggaa atgagatttt ttttaaacaa caaaaaatgc cttgctgact cactattaaa      7020
taaaaatctc cccaattttt tgatagacta cttcaagcca tttgttacat ggtattcctt      7080
tgcaagtcaa tttaggtttc gtgttataac ttttcctctt tttttaagaa aaatgaaaaa      7140
agtaattctt ttgtctgaag gggaaaggca ttctttcatt tttttctttt tttttttttt      7200
tttttatgac ttgcaggcac aatatctagt actgcaactg ccagaacttg gtattgtagc      7260
tgctgcccgc tgactagcag ctggactgat tttgaataaa aatgaaagca ttaaagggtt      7320
tccctacaaa acattttttct ttaaaatact tttgaaatgg ctataagcag ttgactttca      7380
cccttggaga gcatcacact gtgtgaggtt cagtgattgt tgaccctccc cagcccctcc      7440
tgcttcttta agttatctgt gtgcgtgcgc ttcctctcaa tcttctttgc acgctcattt      7500 cttttttctct gacccatgag aaaggaaaac ttactgatga taattttttaa atagtgtaat      7560 ttattcattt atagcatgtc aggataaatt aaaagaacat ttgtctggaa atgctgccgg      7620
gagcctattg tgtaaatgta ggtattttgt aaaataaccct tgaaattgta aattgacacg      7680
tgtttggtca gattgtgtca agtttaattt gttttgtttt cttttttctt tttttttattt      7740 gaaaactact ttagcaataa ttaattccat gattatcaca ttctgccatt aagggatatt      7800
agtaccgtaa tactgaagaa attttattaa gtctgaactt ctggggtagg cagcttcttt      7860
gtttcttttc tatccaccct tgtcggttga ggtatttgtt tcttgactaa taaacccttt      7920
gatactttta gccagaaatc agtctcataa agctattttt gagtatagtt tgtgtaaaat      7980
aaaaatgttt agctttggta ataacttcca agctgaactc cctctagcaa gatatttttc      8040
agtgctttta tttactatgc acttagacta tgcactttt ctgaaatatt tttgtaacac      8100
ttttttgtat ttttgccatt tgaaaaggtt gtggtgtagt tggtctgtaa ttaagttgca      8160
gatttaaaac tgctgttagc tttgtaaatc aaaatatagg tgttttttgt cctggtatat      8220
cgtcattcca tctgcagctg gagctggaat cccattgatc ttctagctac cattcattttt      8280 cttcactgtt cacaaaagaa gagtgtgaaa ttcagtgaat gctgttacta atcctgttac      8340
gagatgaatc tcatttcacc aaaattaaat tatgttttt cgctaaaatg atgatacaag      8400
ttgaagacac atcactctga aattggaaga cctcaccact taaggctcca cagtggctta      8460
ctcagctgaa ctctaggtta ctactcttta cttttgttcac ccattggggg gtgcagtttt      8520
tttaaaatgt tgggagatgg ccattctaac tactgttgaa tgtctctgtt ttgggaaggt      8580
ataacaagaa ataaaaaaga atatatatga agggagagac tggttatctc ctccca        8636
```

<210> SEQ ID NO 20
<211> LENGTH: 892
<212> TYPE: DNA
<213> ORGANISM: Homo sapiens

<400> SEQUENCE: 20

```
gtgcgcactg gcgtgcgaga ctcggcgggc gctgttgagg gagtcgggcc gcgactgtgg        60
tcgtttttat accttcccgc gcggacgccg gcgctgccaa cggaagggcg ggtagggcgg       120
tgcgtgatta ggttggcgaa gagacggagt ttcgtcatgt tggccaggcc catttgagat       180
ctttgaagat atccctcaacg tgaggctctg ctgccatgaa ggtgaagatt aagtgctgga       240
acggcgtggc cacttggctc tgggtggcca acgatgagaa ctgtggcatc tgcaggatgg       300
catttaacgg atgctgccct gactgcaagg tgccggcga cgactgcccg ctggtgtggg       360
gccagtgctc ccactgcttc cacatgcatt gcatcctcaa gtggctgcac gcacagcagg       420
```

```
tgcagcagca ctgccccatg tgccgccagg aatggaagtt caaggagtga ggcccgacct    480
ggctctcgct ggaggggcat cctgagactc cttcctcatg ctggcgccga tggctgctgg    540
ggacagcgcc cctgagctgc aacaaggtgg aaacaagggc tggagctgcg tttgttttgc    600
catcactatg ttgacactttt tatccaataa gtgaaaactc attaaactac tcaaatcttg   660
ctggaggcct ctgggtgcct gtgttctcgg catatagatg tggtctcggt gtgttttgat    720
atgaaaactc tcatgaataa acatctccgt gaaacgccaa ggccctcgtc aaaccctgag    780
tcatgactgg gaggagaagg agcaggatca gacggtagag cctggggcat gctcttcagg    840
catgctcttg cctgctggat tgccggcggc ggccctggga ccctccctca gg            892

<210> SEQ ID NO 21
<211> LENGTH: 21
<212> TYPE: RNA
<213> ORGANISM: Homo sapiens

<400> SEQUENCE: 21
uaaagugcug acagugcaga u                                              21

<210> SEQ ID NO 22
<211> LENGTH: 23
<212> TYPE: RNA
<213> ORGANISM: Homo sapiens

<400> SEQUENCE: 22
uuauugcuua agaauacgcg uag                                            23

<210> SEQ ID NO 23
<211> LENGTH: 3
<212> TYPE: PRT
<213> ORGANISM: Artificial Sequence
<220> FEATURE:
<223> OTHER INFORMATION: OTHER INFORMATION, Synthetic peptide

<400> SEQUENCE: 23

Met Leu Phe
1
```

The invention claimed is:

1. A method for prevention and treatment of ischemic diseases involving ischemia-induced injury, the method comprising administrating a therapeutically effective amount of a bioenergetic agent to a subject in need thereof, wherein the bioenergetic agent is a synthetic analogue that maintains and restores mitochondrial bioenergetics associated with ATP generation disrupted in ischemic events for preventing and treating ischemia-induced injury, wherein the administration of the bioenergetic agent is carried out prophylactically daily, 10, 30 to 60 minutes, or by injection immediately prior to injury to protect against ischemic damage, and to prevent, inhibit or reduce tissue deterioration and disease progression for prevention of ischemic diseases involving ischemia-induced injury, wherein the bioenergetic agent is administered therapeutically during injury or immediately post-injury for few hours, then daily for 1, 7 to 14 days, weeks, months and years to treat disease, to prevent and slowdown tissue deterioration, to inhibit or reduce disease progression, and to stop or reverse the pathologic process for treatment of ischemic diseases involving ischemia-induced injury, and wherein the bioenergetic agent is selected from the group consisting of Cyclocreatine and Cyclocreatine phosphate.

2. The method of claim 1, wherein the therapeutically effective amount of a bioenergetic agent comprises an amount in a range between 0.3 g and 1.2 g per kg of mammalian body weight, administered daily as required.

3. The method of claim 1, wherein the ischemia-induced injury comprises mammalian tissue subject to injury, hypoxia or ischemia.

4. The method of claim 1, wherein the bioenergetic agent is administered intravenously, or intraperitoneally.

5. The method of claim 1, wherein the bioenergetic agent is administered to subjects comprising a group selected from stable coronary artery disease patients, unstable angina patients, acute myocardial infarction patients, hypoxia/ischemia-induced heart failure patients, and hypoxia/ischemia-induced atrial and ventricular fibrillation patients.

6. The method of claim 1, wherein the bioenergetic agent is administered before and after as required to subjects undergoing cardiovascular surgical procedures, wherein the surgical procedures comprising cardiopulmonary bypass surgery, valve replacement, percutaneous coronary intervention and heart transplantation, wherein the bioenergetic agent is carried out by injection immediately prior to harvesting donor hearts and then placed in preservation solutions during transportation, wherein heart recipient patients do not receive the bioenergetic agent.

7. The method of claim 1, wherein the bioenergetic agent is administered to subjects comprising a group selected from hypoxia/ischemia-induced, comprising of coronary artery disease, unstable angina, acute myocardial infarction, atrial and ventricular fibrillation, Takotsubo cardiomyopathy, and hypoxia/ischemia-induced heart failure patients.

8. The method of claim 1, wherein the bioenergetic agent is Cyclocreatine and its water-soluble salt Cyclocreatine Phosphate.

* * * * *